US011439658B2

(12) United States Patent
Kraemer et al.

(10) Patent No.: US 11,439,658 B2
(45) Date of Patent: Sep. 13, 2022

(54) COMPOSITIONS AND METHODS FOR SUPPRESSING MSUT2

(71) Applicants: United States Government As Represented By The Department of Veterans Affairs, Washington, DC (US); University of Washington, Seattle, WA (US)

(72) Inventors: Brian Kraemer, Kent, WA (US); Jeanna M. Wheeler, Seattle, WA (US); Pamela McMillan, Seattle, WA (US); Timothy J. Strovas, Algona, WA (US); Jeremy Baker, Seattle, WA (US)

(73) Assignees: United States Government As Represented By The Department Of Veterans Affairs, Washington, DC (US); University of Washington, Seattle, WA (US)

( * ) Notice: Subject to any disclaimer, the term of this patent is extended or adjusted under 35 U.S.C. 154(b) by 0 days.

(21) Appl. No.: 16/383,178

(22) Filed: Apr. 12, 2019

(65) Prior Publication Data

US 2019/0328766 A1 Oct. 31, 2019

Related U.S. Application Data

(60) Provisional application No. 62/656,900, filed on Apr. 12, 2018.

(51) Int. Cl.

| | | |
|---|---|---|
| *A61K 31/713* | (2006.01) | |
| *A61K 31/7105* | (2006.01) | |
| *A61K 9/00* | (2006.01) | |
| *A61K 31/41* | (2006.01) | |
| *A61K 31/4745* | (2006.01) | |
| *A61K 31/26* | (2006.01) | |
| *C12N 9/22* | (2006.01) | |
| *C12N 15/86* | (2006.01) | |

(52) U.S. Cl.
CPC .......... *A61K 31/713* (2013.01); *A61K 9/0019* (2013.01); *A61K 31/26* (2013.01); *A61K 31/41* (2013.01); *A61K 31/4745* (2013.01); *A61K 31/7105* (2013.01); *C12N 9/22* (2013.01); *C12N 15/86* (2013.01); *C12N 2310/20* (2017.05); *C12N 2740/15043* (2013.01); *C12N 2750/14143* (2013.01)

(58) Field of Classification Search
CPC .............. A61K 31/713; A61K 9/0019; A61K 31/7105; C12N 2310/14; C12N 15/113; A01K 2217/075
See application file for complete search history.

(56) References Cited

PUBLICATIONS

Nishiyama (Neuroscience Research 141 (2019) 4-12) (Year: 2019).*
Lee et al (Nat Biomed Eng. Jul. 2018; 2(7): 497-507) (Year: 2018).*
Myers et al (Current Protocols in Neuroscience, 89, e81. doi: 10.1002/cpns.81, 2019) (Year: 2019).*
Cappa (Front. Neurol. 9:108.doi: 0.3389/fneur.2018.00108) (Year: 2018).*
Cummings et al (Alzheimer's Research & Therapy, 2014, 6:37, 7 pages) (Year: 2014).*
Blanco-Silvente et al. (International Journal of Neuropsychopharmacology (2017) 20(7): 519-528) (Year: 2017).*
Crook et al (Journal of Huntington's Disease 2 (2013) 405-436) (Year: 2013).*
Research Models Tau P301S (Line PS19) retrieved from https://www.alzforum.org/research-models/tau-p301s-line-ps19 (Year: 2018).*
Wilcock et al (J. Neurosci. 26(20):5340-5346, 2005) (Year: 2005).*
Van Dyk (Biological Psychiatry Feb. 15, 2018; 83:311-319) (Year: 2018).*
Rha et al (Human Molecular Genetics, 2017, vol. 26, No. 19 3663-3681) (Year: 2017).*
Juliano (Nucleic Acids Research, 2016, 44(14): 6518-6548) (Year: 2016).*
Ghosh et al. (Alzheimer's Research & Therapy 9(82): 13 pages (2017)) (Year: 2017).*
Zheng et al (Trends in Biotechnology, 36(5): 562-575, May 2018) (Year: 2018).*
Ball et al (Sci Rep 8, 2178, 12 pages (2018). (Year: 2018).*
Guo et al (International Journal of Nanomedicine 2016:11 5287-5310) (Year: 2016).*
Akhtar et al. (Journal of Drug Targeting, 17:7, 491-495, DOI: 10.1080/10611860903057674) (Year: 2009).*
Bruno (Eur Pharm Review, (Jul. 10, 2012), retrieved from https://www.europeanpharmaceuticalreview.com/article/13688/ten-years-of-sirna-a-clinical-overview/) (Year: 2012).*
Anders, S., et al., HTSeq—a Python framework to work with high-throughput sequencing data. Bioinformatics 31, 166-169 (2015).
Anders, S., et al., Detecting differential usage of exons from RNA-seq data. Genome Res 22, 2008-2017(2012).
Ballatore, C., et al., Tau-mediated neurodegeneration in Alzheimer's disease and related disorders. Nat Rev Neurosci 8, 663-672 (2007).
Ballatore, C., et al., Modulation of protein-protein interactions as a therapeutic strategy for the treatment of neurodegenerative tauopathies. Curr Top Med Chem 11, 317-330 (2011).
Banerjee, A., et al., PABPN1: molecular function and muscle disease. FEBS J 280, 4230-4250 (2013).
Barghorn, S., et al., Structure, microtubule interactions, and paired helical filament aggregation by tau mutants of frontotemporal dementias. Biochemistry 39, 11714-11721 (2000).
Barnes, C. A. Memory deficits associated with senescence: a neurophysiological and behavioral study in the rat. Journal of comparative and physiological psychology 93, 74-104 (1979).

(Continued)

*Primary Examiner* — Richard A Schnizer
(74) *Attorney, Agent, or Firm* — Ballard Spahr LLP

(57) ABSTRACT

Described herein are compositions and methods for treating Alzheimer's disease or dementia. The compositions include mammalian suppressor of taupathy 2 inhibitors (MSUT2). The MSUT2 inhibitors can be small interfering RNAs, guide RNAs, or small molecules. The methods include reducing accumulation of phosphorylated and aggregated human tau.

5 Claims, 65 Drawing Sheets

Specification includes a Sequence Listing.

(56) References Cited

PUBLICATIONS

Barten, D. M., et al., Hyperdynamic microtubules, cognitive deficits, and pathology are improved in tau transgenic mice with low doses of the microtubule-stabilizing agent BMS-241027. J Neurosci 32, 7137-7145 (2012).
Bhaskar, K., et al., Regulation of tau pathology by the microglial fractalkine receptor. Neuron 68, 19-31 (2010).
Bierer, L. M., et al., Neocortical neurofibrillary tangles correlate with dementia severity in Alzheimer's disease. Arch Neurol 52, 81-88 (1995).
Braak, H., et al., Staging of Alzheimer's disease-related neurofibrillary changes. Neurobiol Aging 16, 271-278; discussion 278-284 (1995).
Brenner, S., The genetics of Caenorhabditis elegans. Genetics 77, 71-94 (1974).
Brunden, K. R., et al., Epothilone D improves microtubule density, axonal integrity, and cognition in a transgenic mouse model of tauopathy. J Neurosci 30, 13861-13866 (2010).
Bryan, J. B., et al., Inhibition of tubulin assembly by RNA and other polyanions: evidence for a required protein. Proc Natl Acad Sci USA 72, 3570-3574 (1975).
Cappell, K. M., et al., Symplekin specifies mitotic fidelity by supporting microtubule dynamics. Mol Cell Biol 30, 5135-5144 (2010).
Carmel, G., et al., The structural basis of monoclonal antibody Alz50's selectivity for Alzheimer's disease pathology. J Biol Chem 271, 32789-32795 (1996).
Clark, L.N., et al., Pathogenic implications of mutations in the tau gene in pallido-ponto-nigral degeneration and related neurodegenerative disorders linked to chromosome 17. Proc. Natl. Acad. Sci. U.S.A. 95, 13103-13107 (1998).
Clavaguera, F., et al., Transmission and spreading of tauopathy in transgenic mouse brain. Nat Cell Biol 11, 909-913 (2009).
Cunningham, F., et al., Ensembl 2015. Nucleic Acids Res 43, D662-669 (2015).
Du, L., et al., Activity-dependent polyadenylation in neurons. RNA 11, 1340-1347 (2005).
Frangioni, J. V., et al., Solubilization and purification of enzymatically active glutathione S-transferase (pGEX) fusion proteins. Anal Biochem 210, 179-187 (1993).
Goedert, M. The ordered assembly of tau is the gain-of-toxic function that causes human tauopathies. Alzheimers Dement 12, 1040-1050 (2016).
Goedert, M., et al., Epitope mapping of monoclonal antibodies to the paired helical filaments of Alzheimer's disease: identification of phosphorylation sites in tau protein. Biochem J 301 (Pt 3), 871-877 (1994).
Gomez-Isla, T., et al., Neuronal loss correlates with but exceeds neurofibrillary tangles in Alzheimer's disease. Ann Neurol 41, 17-24 (1997).
Guthrie, C. R., et al., SUT-2 potentiates tau-induced neurotoxicity in *Caenorhabditis elegans*. Hum Mol Genet 18, 1825-1838 (2009).
Guthrie, C. R. and Kraemer, B. C. Proteasome inhibition drives HDAC6-dependent recruitment of tau to aggresomes. J Mol Neurosci 45, 32-41 (2011).
Guthrie, C. R., et al., MSUT2 is a determinant of susceptibility to tau neurotoxicity. Hum Mol Genet 20, 1989-1999 (2011).
Harris, J. C., et al., The Cstf2t Polyadenylation Gene Plays a Sex-Specific Role in Learning Behaviors in Mice. PLoS One 11, e0165976 (2016).
Hong, M. et al., Mutation-specific functional impairments in distinct tau isoforms of hereditary FTDP-17. Science 282, 1914-1917 (1998).
Hutton, M., et al., Association of missense and 5'-splice-site mutations in tau with the inherited dementia FTDP-17. Nature 393, 702-705 (1998).
Ishihara, T., et al., Age-dependent induction of congophilic neurofibrillary tau inclusions in tau transgenic mice. American Journal of Pathology 158, 555-562 (2001).
Jenal, M., et al., The poly(A)-binding protein nuclear 1 suppresses alternative cleavage and polyadenylation sites. Cell 149, 538-553 (2012).
Jicha, G. A., et al., Alz-50 and MC-1, a new monoclonal antibody raised to paired helical filaments, recognize conformational epitopes on recombinant tau. J Neurosci Res 48, 128-132 (1997).
Kawakami, A., et al., Identification and functional characterization of a TIA-1-related nucleolysin. Proc Natl Acad Sci USA 89, 8681-8685 (1992).
Kedersha, N., et al., Stress granules and processing bodies are dynamically linked sites of mRNP remodeling. J Cell Biol 169, 871-884 (2005).
Kelly, S. M., et al., A conserved role for the zinc finger polyadenosine RNA binding protein, ZC3H14, in control of poly(A) tail length. RNA 20, 681-688 (2014).
Kelly, S. M., et al., The *Drosophila* ortholog of the Zc3h14 RNA binding protein acts within neurons to pattern axon projection in the developing brain. Dev Neurobiol 76, 93-106 (2016).
Kent, W. J., et al., The human genome browser at UCSC. Genome Res 12, 996-1006 (2002).
Khanna, M. R., et al., Therapeutic strategies for the treatment of tauopathies: Hopes and challenges. Alzheimers Dement 12, 1051-1065 (2016).
Komori, T., Tau-positive glial inclusions in progressive supranuclear palsy, corticobasal degeneration and Pick's disease. Brain Pathology 9, 663-679 (1999).
Kuhn, U., et al., The RNA binding domains of the nuclear poly(A)-binding protein. J Biol Chem 278, 16916-16925 (2003).
Kraemer, B. C., et al., Neurodegeneration and defective neurotransmission in a Caenorhabditis elegans model of tauopathy. Proc Natl Acad Sci USA 100, 9980-9985 (2003).
Kraemer, B. C., et al., SUT-1 enables tau-induced neurotoxicity in C. elegans. Hum Mol Genet 16, 1959-1971 (2007).
Kraemer, B., et al., NANOS-3 and FBF proteins physically interact to control the sperm-oocyte switch in Caenorhabditis elegans. Curr Biol 9, 1009-1018 (1999).
Kwak, J. E., et al., GLD2 poly(A) polymerase is required for long-term memory. Proc Natl Acad Sci USA 105, 14644-14649 (2008).
Lee, V. M., et al., Microtubule stabilizing drugs for the treatment of Alzheimer's disease. Neurobiol Aging 15 Suppl 2, S87-89 (1994).
Lloyd, K. C., A knockout mouse resource for the biomedical research community. Ann N Y Acad Sci 1245, 24-26 (2011).
Love, M. I., et al., Moderated estimation of fold change and dispersion for RNA-seq data with DESeq2. Genome Biol 15, 550 (2014).
Maphis, N., et al., Selective suppression of the α isoform of p38 MAPK rescues late-stage tau pathology. Alzheimer's research & therapy 8, 54 (2016).
Maphis, N., et al., Loss of tau rescues inflammation-mediated neurodegeneration. Frontiers in neuroscience 9, 196 (2015).
Montine, T. J., et al., National Institute on Aging-Alzheimer's Association guidelines for the neuropathologic assessment of Alzheimer's disease: a practical approach. Acta Neuropathol 123, 1-11 (2012).
Naj, A. C., et al., Genomic variants, genes, and pathways of Alzheimer's disease: An overview. Am J Med Genet B Neuropsychiatr Genet 174, 5-26 (2017).
Nelson, P. T., et al., Correlation of Alzheimer disease neuropathologic changes with cognitive status: a review of the literature. J Neuropathol Exp Neurol 71, 362-381 (2012).
Nousch, M., et al., The Ccr4-Not deadenylase complex constitutes the main poly(A) removal activity in C. elegans. J Cell Sci 126, 4274-4285 (2013).
Patterson, K. R. et al., Heat shock protein 70 prevents both tau aggregation and the inhibitory effects of preexisting tau aggregates on fast axonal transport. Biochemistry 50, 10300-10310 (2011).
Poorkaj, P., et al., Tau is a candidate gene for chromosome 17 frontotemporal dementia. Ann. Neurol. 43, 815-825 (1998).

(56) References Cited

PUBLICATIONS

Quinlan, A. R., et al., BEDTools: a flexible suite of utilities for comparing genomic features. Bioinformatics 26, 841-842 (2010).

Rha, J., et al., The RNA-binding protein, ZC3H14, is required for proper poly(A) tail length control, expression of synaptic proteins, and brain function in mice. Hum Mol Genet, (2017).

Rose, K. M., et al., Specific inhibition of chromatin-associated poly(A) synthesis in vitro by cordycepin 5'-triphosphate. Nature 267, 178-180 (1977).

Sahara, N., et al., Tau oligomerization: a role for tau aggregation intermediates linked to neurodegeneration. Curr Alzheimer Res 5, 591-598 (2008).

Schindelin, J., et al., Fiji: an open-source platform for biological-image analysis. Nat Methods 9, 676-682 (2012).

Seki, T., et al., The human Thy-1 gene: structure and chromosomal location. Proc Natl Acad Sci USA 82, 6657-6661 (1985).

Si, K., et al., A neuronal isoform of CPEB regulates local protein synthesis and stabilizes synapse-specific long-term facilitation in aplysia. Cell 115, 893-904 (2003).

Soderberg, O., et al., Characterizing proteins and their interactions in cells and tissues using the in situ proximity ligation assay. Methods 45, 227-232 (2008).

Soucek, S., et al., The long and the short of it: the role of the zinc finger polyadenosine RNA binding protein, Nab2, in control of poly(A) tail length. Biochim Biophys Acta 1819, 546-554 (2012).

Spillantini, M.G., et al., Mutation in the tau gene in familial multiple system tauopathy with presenile dementia. Proc. Natl. Acad. Sci. U.S.A. 95, 7737-7741 (1998).

Sun, A. Y., et al., Comparative analysis of an improved thioflavin-s stain, Galiyas silver stain, and immunohistochemistry for neurofibrillary tangle demonstration on the same sections. Journal of Histochemistry & Cytochemistry 50, 463-472 (2002).

Szot, P., et al., Sequential Loss of LC Noradrenergic and Dopaminergic Neurons Results in a Correlation of Dopaminergic Neuronal Number to Striatal Dopamine Concentration. Frontiers in pharmacology 3, 184 (2012).

Takeuchi, H., et al., P301S mutant human tau transgenic mice manifest early symptoms of human tauopathies with dementia and altered sensorimotor gating. PLoS ONE 6, e21050 (2011).

Tian, Q., et al., A polyadenylate binding protein localized to the granules of cytolytic lymphocytes induces DNA fragmentation in target cells. Cell 67, 629-639 (1991).

Vanderweyde, T., et al., Interaction of tau with the RNA-Binding Protein TIA1 Regulates tau Pathophysiology and Toxicity. Cell reports 15, 1455-1466 (2016).

Vanderweyde, T., et al., Contrasting pathology of the stress granule proteins TIA-1 and G3BP in tauopathies. J Neurosci 32, 8270-8283 (2012).

Wang, Y., et al., Tau in physiology and pathology. Nat Rev Neurosci 17, 5-21 (2016).

Ward, S. M., et al., TOC1: characterization of a selective oligomeric tau antibody. J Alzheimers Dis 37, 593-602 (2013).

Weaver, C. L., et al., Conformational change as one of the earliest alterations of tau in Alzheimer's disease. Neurobiology of Aging 21, 719-727 (2000).

Wegmann, S., et al., Tau protein liquid-liquid phase separation can initiate tau aggregation. EMBO J 37, (2018).

Wheeler, J. M., et al., High copy wildtype human 1N4R tau expression promotes early pathological tauopathy accompanied by cognitive deficits without progressive neurofibrillary degeneration. Acta neuropathologica communications 3, 33 (2015).

Wheeler, J. M., et al., The role of MSUT-2 in tau neurotoxicity: a target for neuroprotection in tauopathy? Biochem Soc Trans 38, 973-976 (2010).

Xia, Z., et al., Dynamic analyses of alternative polyadenylation from RNA-seq reveal a 3'-UTR landscape across seven tumour types. Nat Commun 5, 5274 (2014).

Yoshiyama, Y., et al., Synapse loss and microglial activation precede tangles in a P301S tauopathy mouse model. Neuron 53, 337-351 (2007).

Zhang, B., et al., The microtubule-stabilizing agent, epothilone D, reduces axonal dysfunction, neurotoxicity, cognitive deficits, and Alzheimer-like pathology in an interventional study with aged tau transgenic mice. J Neurosci 32, 3601-3611 (2012).

Zhang, X., et al., RNA stores tau reversibly in complex coacervates. PLoS Biol 15, e2002183 (2017).

U.S. Appl. No. 62/656,900, filed Apr. 12, 2018, Brian Kraemer.
U.S. Appl. No. 63/024,117, filed May 13, 2020, Jeremy D. Baker.
U.S. Appl. No. 17/319,500, filed May 13, 2021, Jeremy D. Baker.
U.S. Appl. No. 63/117,213, filed Nov. 23, 2020, Brian Kraemer.

\* cited by examiner

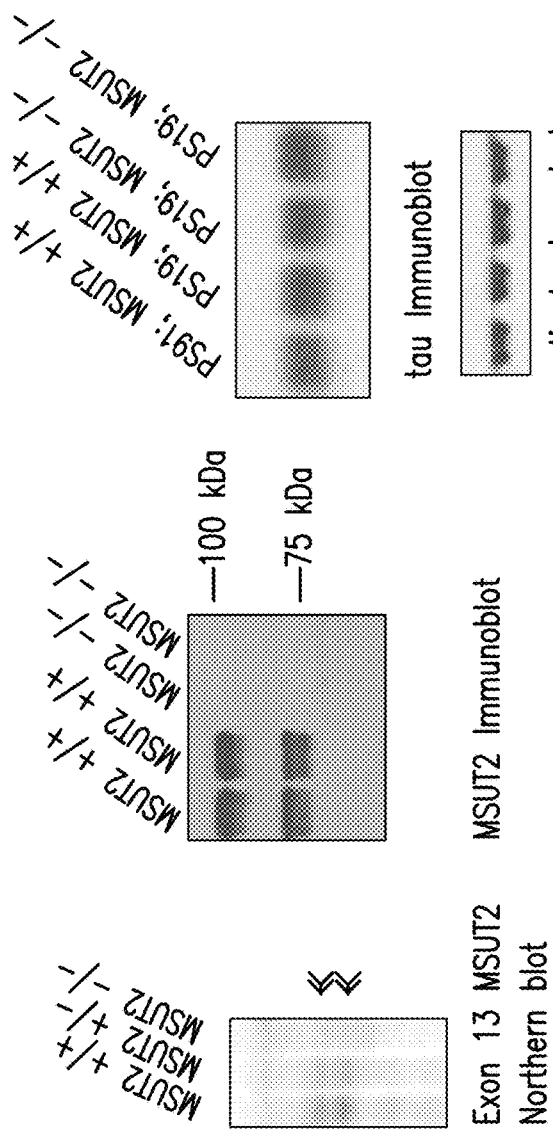
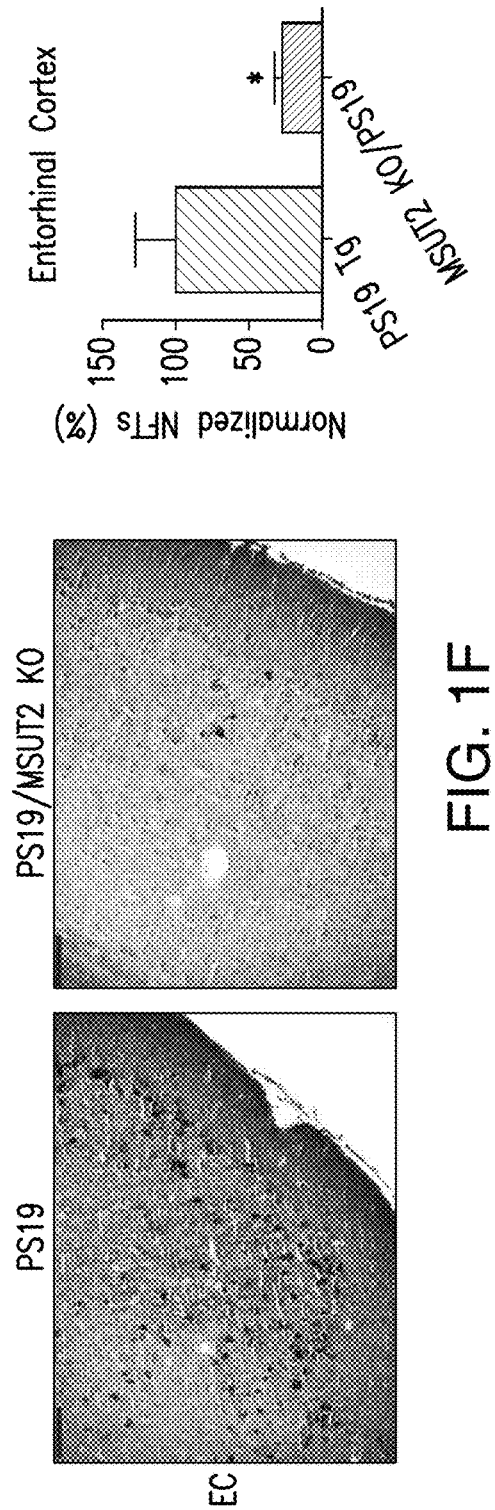
FIG. 1C
FIG. 1D
FIG. 1E
FIG. 1F

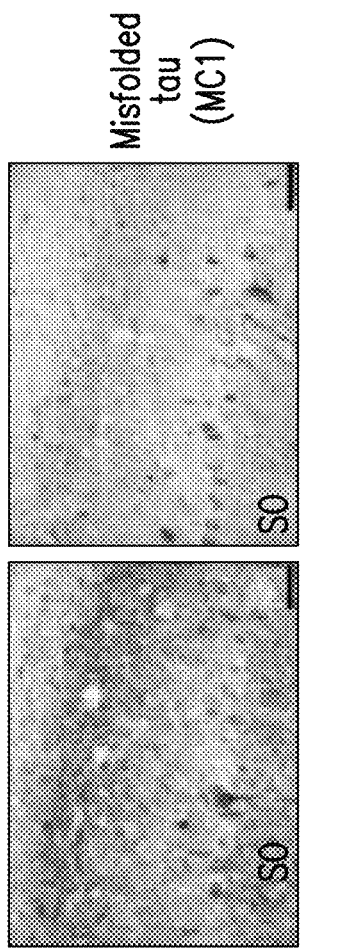
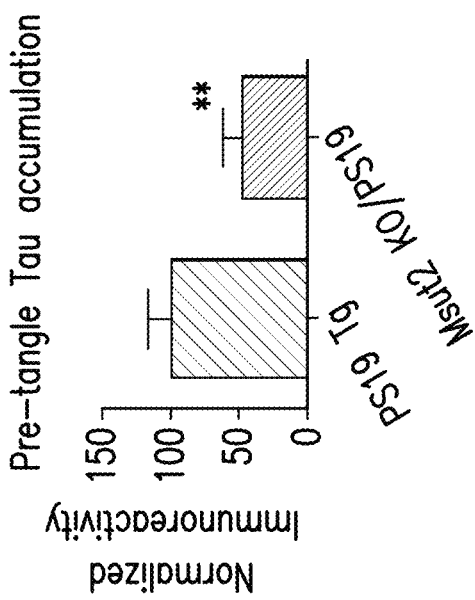
FIG. 2C
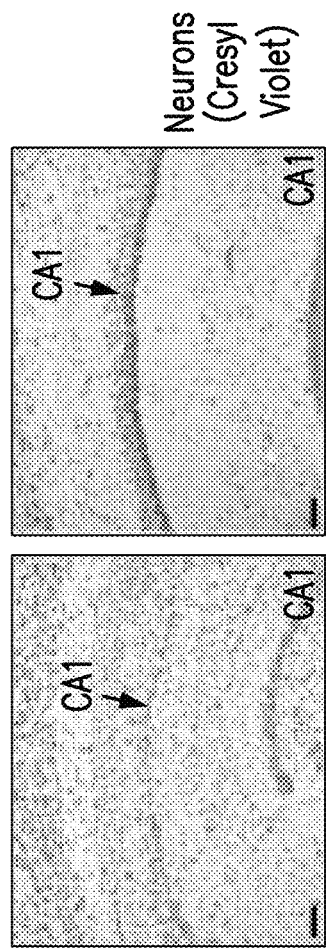
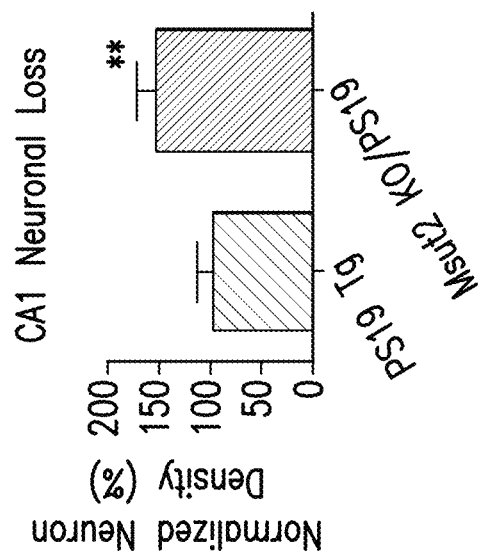
FIG. 2D

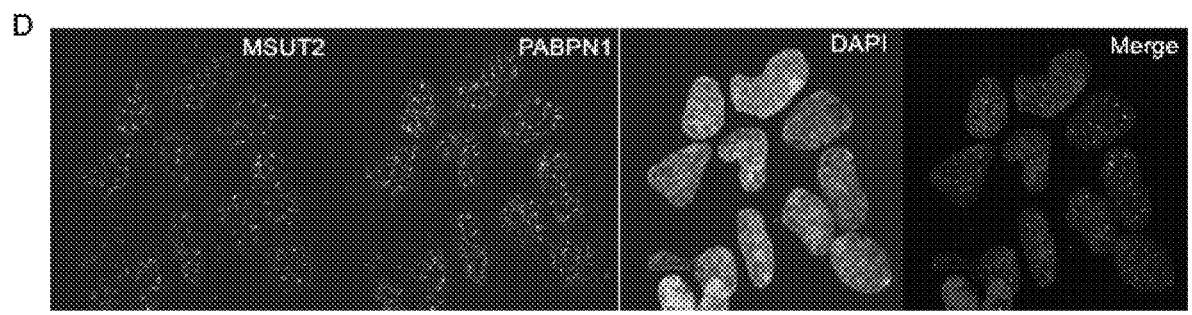
Fig. 5D
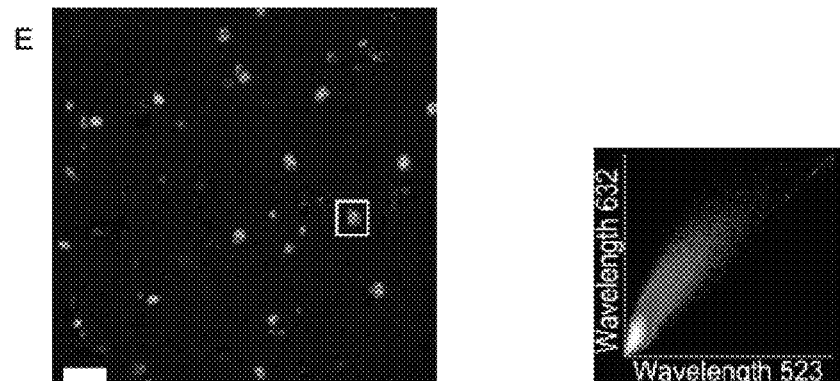
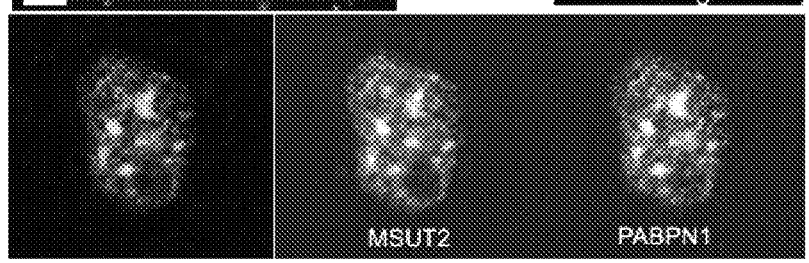
Fig. 5E

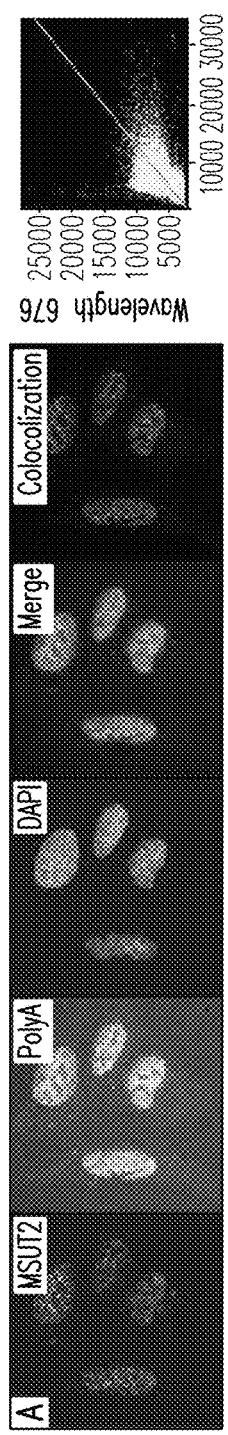
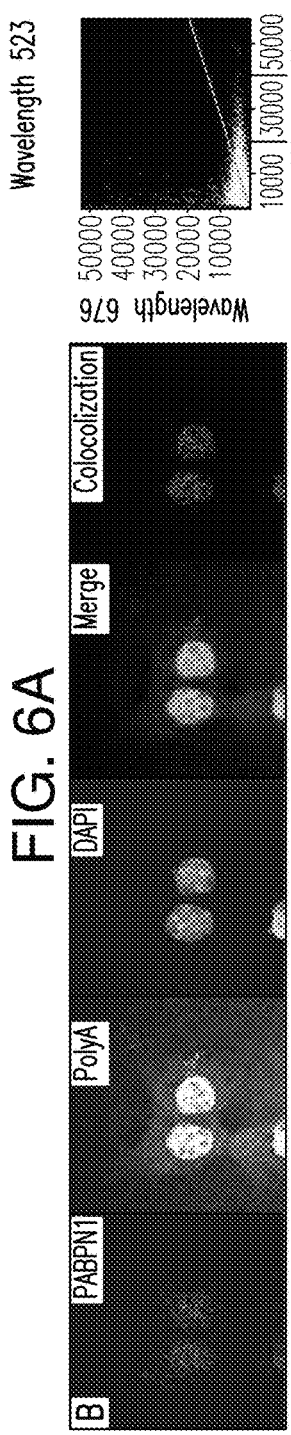
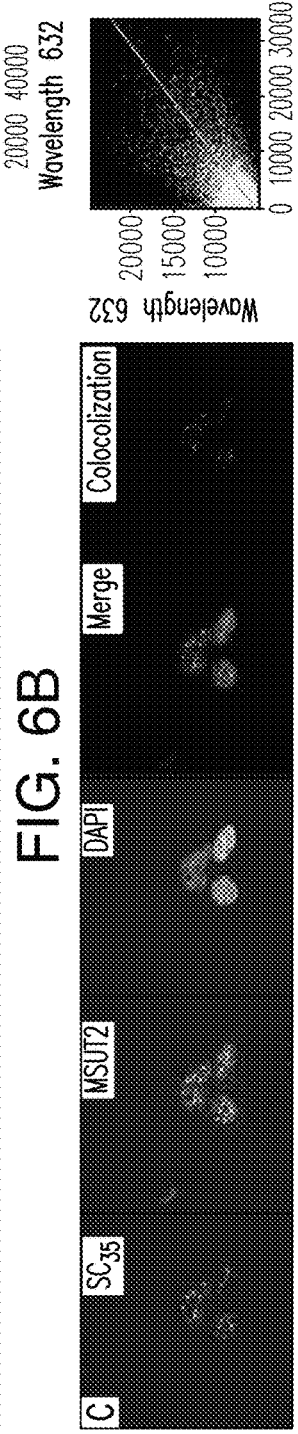
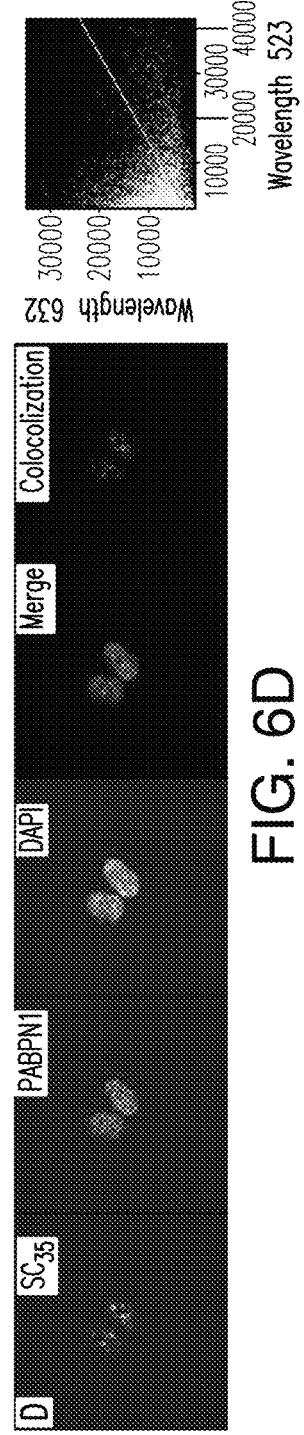
FIG. 6A
FIG. 6B
FIG. 6C
FIG. 6D

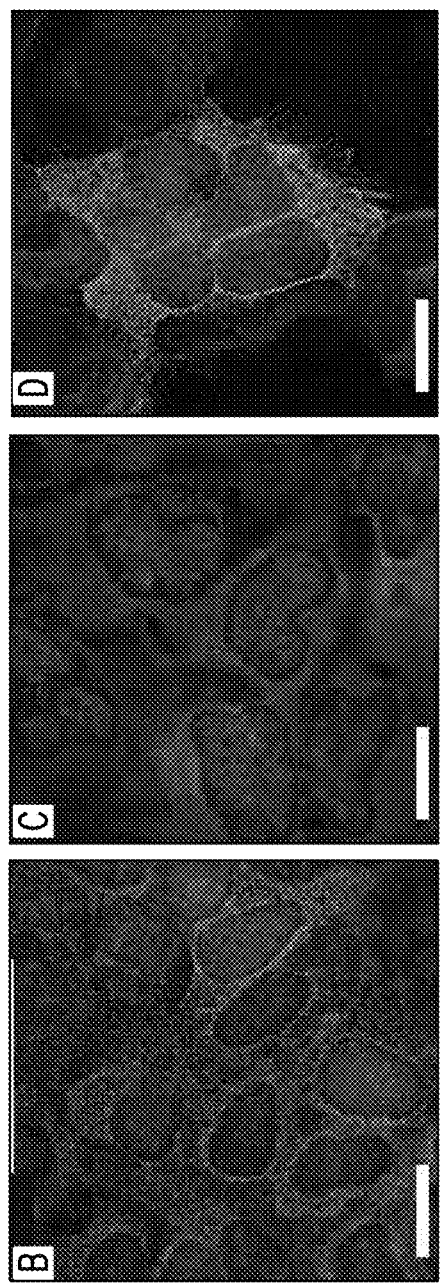
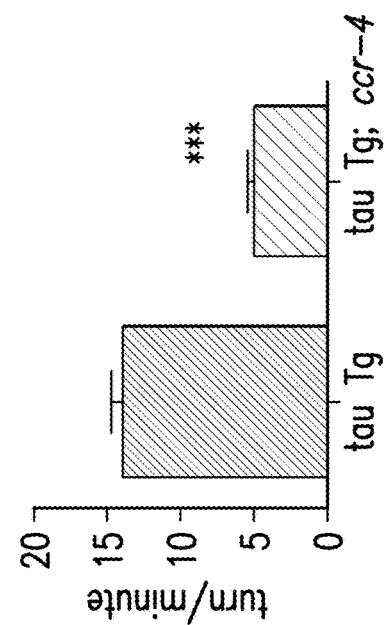
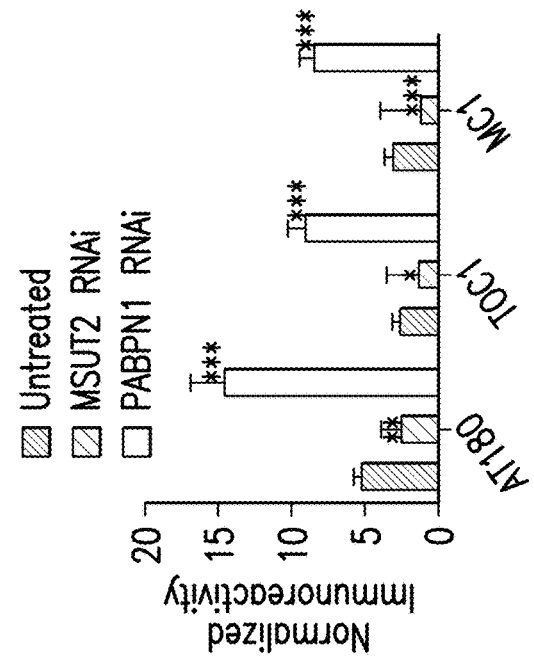

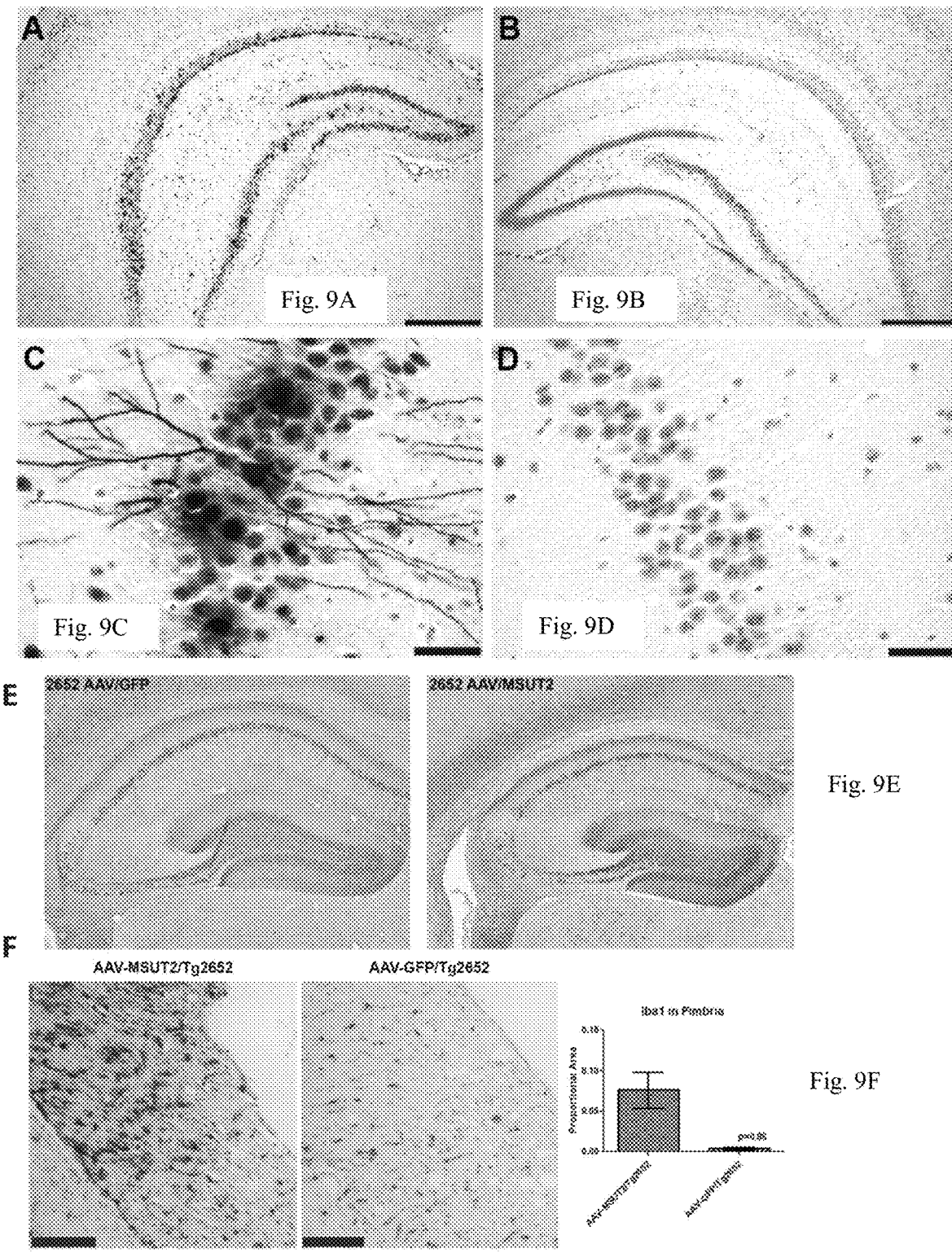

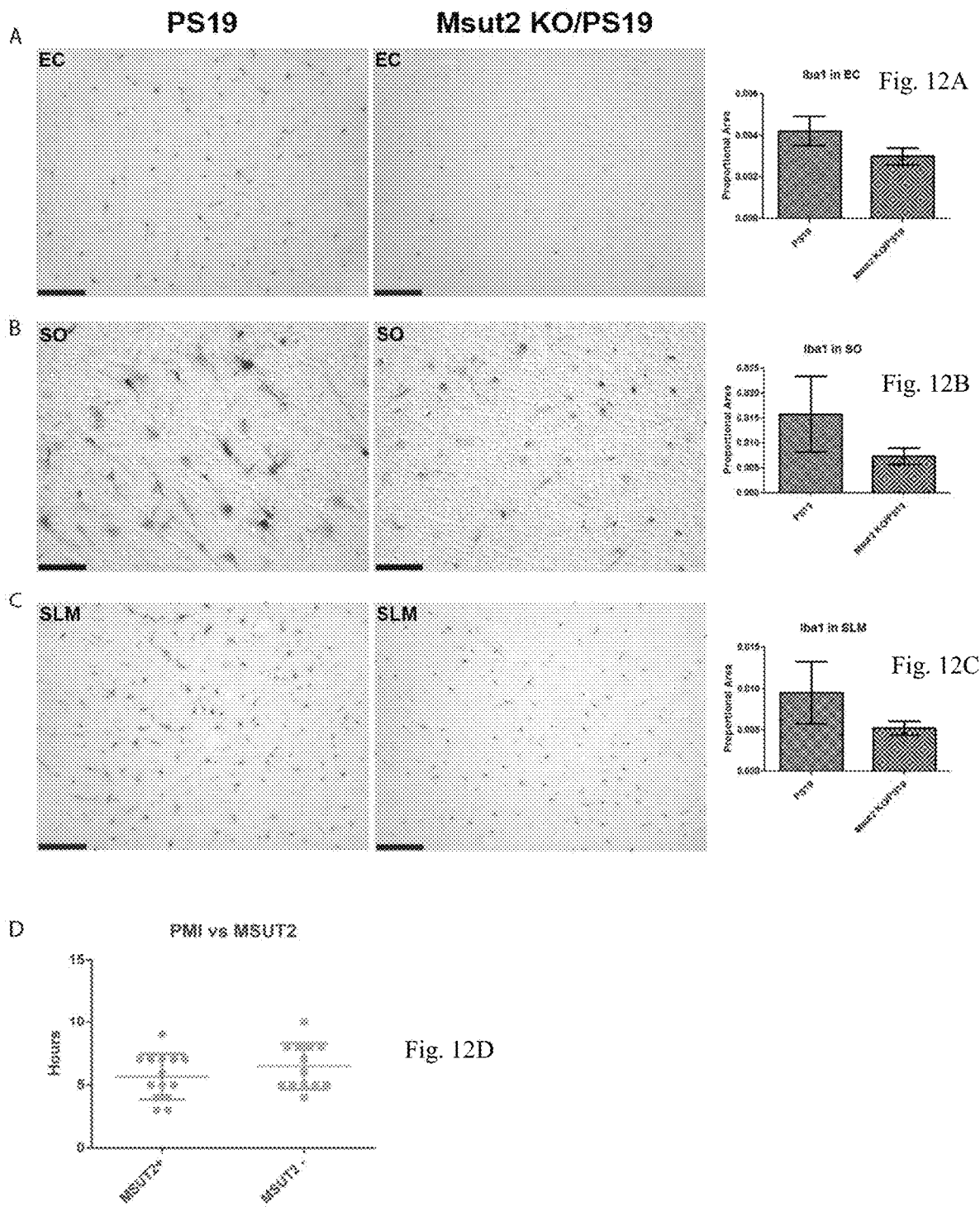

FIG. 16

| | | | | | | | | | | | |
|---|---|---|---|---|---|---|---|---|---|---|---|
| ENSMUSG00000022822.15 | E033 | 548.5462908 | 0.001414344 | 39.79604871 | 2.83E-10 | 2.73E-06 | 20.4161736 | 21.3460945 | 0.0642596 | Abcc5 | chr16 | 20392675 | 20392807 | 133 | a("ENSMUST00000115547.8", "ENSMUST00000077867.9", "ENSMUST00000150340.1", "ENSMUST00000134413.7", "ENSMUST00000079158.12") |
| ENSMUSG00000028165.9 | E002 | 578.0512518 | 0.004035064 | 39.64006394 | 3.05E-10 | 2.81E-06 | 20.6701158 | 21.4536473 | 0.0536776 | Csnk2 | chr3 | 135411012 | 135411010 | 999 | ENSMUST00000129988.1 |
| ENSMUSG00000079657.10+ ENSMUSG00000053752.15 | E088 | 1073.946603 | 0.000264531 | 38.79629372 | 4.70E-10 | 4.12E-06 | 14.69637771 | 12.6034902 | -0.2219317 | NA | chr17 | 24529947 | 24529970 | 24 | a("ENSMUST00000176533.1", "ENSMUST00000177441.1", "ENSMUST00000035797.15") |
| ENSMUSG00000042408.13+ ENSMUSG00000076737.10 | E020 | 443.34246881 | 0.005263573 | 38.58453064 | 5.24E-10 | 4.40E-06 | 11.6821427 | 8.47204914 | -0.4649113 | NA | chr4 | 127105447 | 127106575 | 1129 | ENSMUST00000125160.1 |
| ENSMUSG00000071291.10+ ENSMUSG00000097333.7+ ENSMUSG00000097565.1 | E015 | 1588.413397 | 0.001155438 | 38.30794876 | 6.04E-10 | 4.86E-06 | 25.8587035 | 25.23623715 | -0.035152 | NA | chr13 | 67515781 | 67512575 | 1795 | ENSMUST00000181767.7 |
| ENSMUSG00000045102.11+ ENSMUSG00000079555.2 | E049 | 56.35607205 | 0.003965496 | 37.09457058 | 1.13E-09 | 8.69E-06 | 9.61485075 | 12.07457667 | 0.3286518 | NA | chr5 | 34168568 | 34168770 | 203 | ENSMUST00000201069.1 |
| ENSMUSG00000053297.14 | E005 | 122.68517334 | 0.002345737 | 36.04345762 | 1.93E-09 | 1.43E-05 | 15.3817338 | 16.7323545 | 0.1214207 | A1854703 | chr6 | 48627935 | 48628569 | 635 | ENSMUST00000154570.1 |
| ENSMUSG00000048896.16 | E028 | 246.2261291 | 0.001014648 | 35.96404862 | 2.01E-09 | 1.44E-05 | 16.632442 | 18.04084803 | 0.1122672 | Romad1 | chr3 | 83928049 | 87928258 | 210 | a("ENSMUST00000160074.7", "ENSMUST00000168070.1") |
| ENSMUSG00000069049.11 | E014 | 1511.210912 | 0.000618349 | 34.94254715 | 3.40E-09 | 2.34E-05 | 24.8476509 | 25.42908798 | 0.0310497 | Eif2s3y | chrY | 1016189 | 1016589 | 398 | ENSMUST00000148961.7 |
| ENSMUSG00000093234.16 | E001 | 123.80.6835 | 0.002212857 | 34.11667655 | 5.19E-09 | 3.45E-05 | 35.2516438 | 34.31705974 | -0.0387646 | Hook3 | chr8 | 26032030 | 26032630 | 10610 | ENSMUST00000371782.13 |
| ENSMUSG00000034799.16 | E021 | 445.1740809 | 0.002351985 | 34.02706619 | 5.44E-09 | 3.50E-05 | 19.4367159 | 20.80659166 | 0.09082994 | Unc13a | chr8 | 71642207 | 71642568 | 362 | ENSMUST00000177032.1 |
| ENSMUSG00000015757.10 | E019 | 30.24677713 | 0.006706993 | 33.94042518 | 5.68E-09 | 3.54E-05 | 7.312066846 | 10.09280294 | 0.4649754 | Phf4 | chr10 | 7812112 | 7812874 | 763 | a("ENSMUST00000176025.1", "ENSMUST00000176533.1", "ENSMUST00000177441.1", "ENSMUST00000035797.15") |
| ENSMUSG00000079657.10+ ENSMUSG00000052752.15 | E087 | 119.4744041 | 0.002425494 | 33.7247375 | 6.35E-09 | 3.83E-05 | 15.69770890 | 13.2501667 | -0.1883191 | NA | chr17 | 24529914 | 24529946 | 33 | ENSMUST00000143214.7 |
| ENSMUSG00000041831.16 | E035 | 16.88582204 | 0.006305181 | 33.56559163 | 6.89E-09 | 4.03E-05 | 8.362914427 | 5.009117635 | -0.7394493 | Ibsb | chr5 | 107850070 | 107850304 | 235 | ENSMUST00000133411.1 |
| ENSMUSG00000025495.14 | E014 | 17.93197915 | 0.005622755 | 33.60522048 | 9.19E-09 | 5.22E-05 | 8.625242900 | 5.421494738 | -0.6698744 | Pdss2 | chr7 | 141143347 | 141143642 | 296 | a("ENSMUST00000173721.7", "ENSMUST00000173572.1") |
| ENSMUSG00000035949.15 | E021 | 217.5162297 | 0.009044717 | 32.70893601 | 1.07E-08 | 5.90E-05 | 15.6453104 | 17.93799645 | 0.1972885 | Ehxw2 | chr2 | 34823182 | 34825262 | 2081 | ENSMUST00000201806.1 |
| ENSMUSG00000079657.10+ ENSMUSG00000052752.15 | E089 | 117.6807699 | 0.00513831 | 32.61291807 | 1.12E-08 | 6.03E-05 | 15.6916436 | 12.90389699 | -0.2259431 | NA | chr17 | 24530055 | 24530120 | 66 | a("ENSMUST00000176533.1", "ENSMUST00000177441.1", "ENSMUST00000035797.15") |
| ENSMUSG00000038607.14 | E007 | 565.0807244 | 0.002727766 | 31.6085945 | 1.89E-08 | 9.84E-05 | 20.6717984 | 21.35295697 | 0.046772 | Acer2 | chr4 | 869017394 | 869208875 | 34482 | a("ENSMUST00000045224.13", "ENSMUST00000084433.4") |
| ENSMUSG00000053341.9 | E001 | 190.93631204 | 0.030549786 | 31.413651193 | 2.09E-08 | 0.000105898 | 12.02796679 | 13.81044239 | 0.1993666 | Zfp457 | chr13 | 672292450 | 672942280 | 1831 | ENSMUST00000049705.7 |

| | | | | | | | | | | | |
|---|---|---|---|---|---|---|---|---|---|---|---|
| ENSMUSG00000045348.15 | E009 | 73.30454638 | 0.014349073 | 23.47852046 | 1.26E-06 | 0.003250435 | 11.48667268 | 13.30954837 | 0.2124936 | Nxpd1 | chr5 | 137739803 | 137739998 | 196 | ENSMUST00000183326.7 |
| ENSMUSG00000260034.17 | E001 | 31.68639568 | 0.00439894 | 23.38030231 | 1.33E-06 | 0.003339754 | 9.994936615 | 7.952784769 | -0.3297372 | Clk1 | chr1 | 58410189 | 58411999 | 1811 | ENSMUST00000156931.7 |
| ENSMUSG00000258847.10 | E012 | 13.34299507 | 0.009092293 | 23.37574347 | 1.33E-06 | 0.003339754 | 4.7766215 | 7.539850316 | 0.6585453 | Casp12 | chr9 | 5352846 | 5353445 | 600 | ENSMUST00000149520.7 |
| ENSMUSG00000053477.15 | E025 | 18.40359683 | 0.005713 | 23.23104743 | 1.44E-06 | 0.00353084 | 5.995608535 | 8.472712243 | 0.4989184 | Tcf4 | chr18 | 69348669 | 69348943 | 275 | ENSMUST00000201537.3 |
| ENSMUSG00000366648.17 | E029 | 41.70885762 | 0.008441788 | 23.03439956 | 1.59E-06 | 0.003887457 | 9.169340531 | 11.2801139 | 0.2988918 | BC037034 | chr5 | 138263341 | 138263421 | 81 | ENSMUST00000159514.3 |
| ENSMUSG00000003N14.8 | E011 | 77.10257417 | 0.009261726 | 22.89776721 | 1.71E-06 | 0.00412163 | 11.5614329 | 13.68506661 | 0.2433877 | Cabr | chr8 | 84845750 | 84845861 | 112 | ("ENSMUST00000128028.1", "ENSMUST00000125998.1") |
| ENSMUSG00000046565.7 | E031 | 153.6822935 | 0.00612719F | 22.66693025 | 1.92E-06 | 0.004584577 | 14.85162077 | 15.84336813 | 0.0932587 | Btaf1 | chr19 | 37000092 | 37000233 | 142 | ENSMUST00000099494.3 |
| ENSMUSG00000253550.13 | E002 | 5799.645505 | 0.001247953 | 22.63617232 | 1.96E-06 | 0.0045886249 | 31.77584577 | 31.09118228 | -0.031425 | Sbbsa7 | chr7 | 4825553 | 4828026 | 2474 | ("ENSMUST0000066041.11", "ENSMUST00000117452.7") |
| ENSMUSG00000394586.14 | E028 | 122.24425527 | 0.002095131 | 22.62175426 | 1.97E-06 | 0.004586249 | 14.01069568 | 15.45859788 | 0.1418809 | Hid1 | chr11 | 115359812 | 115360317 | 506 | ENSMUST00000145316.7 |
| ENSMUSG00000289969.10 | E001 | 918.8910982 | 0.006557832 | 22.52076595 | 2.08E-06 | 0.004776237 | 23.4412113 | 23.059868877 | -0.0236741 | Cd65 | chr6 | 24418241 | 24419375 | 1135 | ENSMUST00000030814.10 |
| ENSMUSG00000046565.7 | E025 | 212.99239527 | 0.008941727 | 22.32834846 | 2.30E-06 | 0.005217405 | 16.290863 | 17.358821647 | 0.0995481 | Btaf1 | chr19 | 36992436 | 36992584 | 149 | ENSMUST00000099494.3 |
| ENSMUSG00000053702.16 | E052 | 50.30609447 | 0.003703699 | 22.24710147 | 2.40E-06 | 0.005379604 | 9.81526798 | 11.45166958 | 0.2224584 | Nebl | chr2 | 17528070 | 17528324 | 255 | ENSMUST00000145545.1 |

Fig. 16, Continued

| | | | | | | | | | | | | |
|---|---|---|---|---|---|---|---|---|---|---|---|---|
| ENSMUSG00000103697.1+ | | | | | | | | | | | | |
| ENSMUSG00000023036.14+ | | | | | | | | | | | | |
| ENSMUSG00000103332.1+ | | | | | | | | | | | | |
| ENSMUSG00000102742.1+ | | | | | | | | | | | | |
| ENSMUSG00000102312.1+ | | | | | | | | | | | | |
| ENSMUSG00000104063.1+ | | | | | | | | | | | | |
| ENSMUSG00000103144.1+ | | | | | | | | | | | | |
| ENSMUSG00000102918.1+ | | | | | | | | | | | | |
| ENSMUSG00000104318.1+ | | | | | | | | | | | | |
| ENSMUSG00000102836.1+ | | | | | | | | | | | | |
| ENSMUSG00000103667.1+ | | | | | | | | | | | | |
| ENSMUSG00000104148.5+ | | | | | | | | | | | | |
| ENSMUSG00000102828.5+ | | | | | | | | | | | | |
| ENSMUSG00000102748.1+ | | | | | | | | | | | | |
| ENSMUSG00000103601.1+ | | | | | | | | | | | | |
| ENSMUSG00000104252.5+ | | | | | | | | | | | | |
| ENSMUSG00000102222.1+ | | | | | | | | | | | | |
| ENSMUSG00000103707.5+ | | | | | | | | | | | | |
| ENSMUSG00000103793.1+ | | | | | | | | | | | | |
| ENSMUSG00000102428.1+ | E08.1 | 459.69158885 | 0.00063016 | 22.08136208 | 2.61E-06 | 0.00573137 | 19.9097704 | 20.37326499 | 0.0332054 | NA | chr18 | 37751600 | 37754193 | 2594 | + | ENSMUST00000194928.1 |
| ENSMUSG00000103800.1+ | | | | | | | | | | | | |
| ENSMUSG00000103770.1+ | | | | | | | | | | | | |
| ENSMUSG00000102543.5+ | | | | | | | | | | | | |
| ENSMUSG00000103442.5+ | | | | | | | | | | | | |
| ENSMUSG00000103897.1+ | | | | | | | | | | | | |
| ENSMUSG00000104081.1+ | | | | | | | | | | | | |
| ENSMUSG00000103677.1+ | | | | | | | | | | | | |
| ENSMUSG00000103125.1+ | | | | | | | | | | | | |
| ENSMUSG00000103310.1+ | | | | | | | | | | | | |
| ENSMUSG00000102440.1+ | | | | | | | | | | | | |
| ENSMUSG00000907440.10+ | | | | | | | | | | | | |
| ENSMUSG00000103472.1+ | | | | | | | | | | | | |
| ENSMUSG00000103092.1+ | | | | | | | | | | | | |
| ENSMUSG00000102206.5+ | | | | | | | | | | | | |
| ENSMUSG00000103458.1+ | | | | | | | | | | | | |
| ENSMUSG00000103255.1+ | | | | | | | | | | | | |
| ENSMUSG00000102697.1+ | | | | | | | | | | | | |
| ENSMUSG00000103749.1+ | E08.1 | 459.69158885 | 0.00063016 | 22.08136208 | 2.61E-06 | 0.00573137 | 19.9097704 | 20.37326499 | 0.0332054 | NA | chr18 | 37751600 | 37754193 | 2594 | + | ENSMUST00000194928.1 |

Fig. 16, Continued

| ENSMUSG00000068820.9,1+ ENSMUSG00000068036.13+ | E015 | 201.0008167 | 0.004062573 | 22.08544535 | 2.61E-06 | 0.006573137 | 15.945198 | 17.35311628 | 0.1229728 | NA | chr15 | 80081212 | 80081614 | 403 | | ENSMUST00000187578.1 |
| ENSMUSG00000068022.13 | E029 | 150.9722604 | 0.001527376 | 22.04934036 | 2.66E-06 | 0.005762601 | 15.03756 | 16.06496517 | 0.095342 | Pcnxl2 | chr8 | 125855190 | 125855361 | 172 | | c("ENSMUST00000047239.12", "ENSMUST00000131127.2") |
| ENSMUSG00000097412.1 | E003 | 132.342343 | 0.004923728 | 21.985103.43 | 2.75E-06 | 0.005827462 | 14.2962963 | 15.09254769 | 0.078l9949 | 1810014B01Rik | chr10 | 86688534 | 86689138 | 605 | + | ENSMUST00000181587.1 |
| ENSMUSG00000070056.5 | E004 | 48.0187879 | 0.009814954 | 22.00320252 | 2.72E-06 | 0.005827462 | 9.7337149 | 11.69547182 | 0.2648876 | Mfhas1 | chr8 | 35671722 | 35671831 | 110 | + | ENSMUST00000154989.1 |
| ENSMUSG00000087396.7 | E004 | 80.73430107 | 0.001479974 | 21.81087578 | 3.01E-06 | 0.006177765 | 13.24843869 | 11.76388609 | -0.1714636 | 4933407K13Rik | chrX | 75709407 | 75710630 | 1224 | | ENSMUST00000138943.7 |
| ENSMUSG00000065735.1+ENSMUSG00000080463.1+ENSMUSG00000065160.1+ENSMUSG00000064440.1+ENSMUSG00000105780.1+ENSMUSG00000077220.1+ENSMUSG00000053332.13+ENSMUSG00000064816.1+ENSMUSG00000065228.1+ENSMUSG00000084667.1 | E023 | 206.604476 | 0.001197466 | 21.81407998 | 3.00E-06 | 0.006177765 | 16.0809323 | 17.04707539 | 0.0941732 | NA | chr1 | 161036020 | 161036056 | 37 | + | c("ENSMUST00000162163.7", "ENSMUST00000161229.7", "ENSMUST00000198890.7", "ENSMUST00000160497.1") |
| ENSMUSG00000057364.11+ENSMUSG00000086234.1 | E047 | 98.97472336 | 0.002113799 | 21.81888988 | 3.00E-06 | 0.006177765 | 13.11853693 | 14.56780147 | 0.1526219 | NA | chr5 | 137300414 | 137300731 | 318 | | ENSMUST00000196394.1 |
| ENSMUSG00000056673.14 | E022 | 15.75811486 | 0.008792561 | 21.4722811 | 3.59E-06 | 0.0072927744 | 5.466996734 | 8.9071580829 | 0.5505695 | Kdm5d | chrY | 917331 | 917605 | 275 | + | ENSMUST00000189669.6 |
| ENSMUSG00000052915.14+ENSMUSG00000078676.9 | E008 | 1732.956798 | 0.000719987 | 21.426.33347 | 3.68E-06 | 0.007389397 | 26.2239299 | 25.61839138 | -0.033794 | NA | chr11 | 98800383 | 98801052 | 670 | + | ENSMUST00000107485.7 |
| ENSMUSG00000029544.16 | E013 | 150.88810456 | 0.006615638 | 21.407087.54 | 3.71E-06 | 0.007389397 | 14.74464.51 | 16.235105.16 | 0.1389256 | Cabp1 | chr5 | 1151869972 | 1151811259 | 288 | + | c("ENSMUST00000151775.1", "ENSMUST00000201900.1") |
| ENSMUSG00000026201.12 | E019 | 36.57089384 | 0.005107644 | 21.30960.44 | 3.91E-06 | 0.007695513 | 8.88513257 | 10.8540936 | 0.2887735 | Sik16 | chr1 | 752122.36 | 75212398 | 163 | + | ENSMUST00000186492.1 |
| ENSMUSG00000025937.6 | E001 | 1358.659769 | 0.001691176 | 21.23.395506 | 4.06E-06 | 0.0077667633 | 25.1096763 | 24.55074251 | -0.032494 | Laptm2 | chr1 | 136623330 | 136266.04 | 3535 | | c("ENSMUST00000027071.6", "ENSMUST00000107914.1", "ENSMUST00000171518.7", "ENSMUST00000163534.1", "ENSMUST00000991523.8", "ENSMUST00000076123.11") |
| ENSMUSG00000071291.10+ENSMUSG00000097333.7+ENSMUSG00000097565.1 | E005 | 194.97897257 | 0.001332699 | 21.228478.57 | 4.08E-06 | 0.007867633 | 15.60297319 | 16.82169666 | 0.1685022 | NA | chr13 | 674491862 | 674492150 | 289 | | ENSMUST00000186492.1 |
| ENSMUSG00000074733.14 | E031 | 120.3442646 | 0.007178138 | 21.145601.05 | 4.26E-06 | 0.008133975 | 13.30523459 | 15.054343.21 | 0.178401.5 | Zfp950 | chr19 | 61117625 | 61117727 | 103 | + | ENSMUST00000127117.7 |
| ENSMUSG00000022308.11 | E001 | 1730.202771 | 0.00064116 | 21.06573896 | 4.41E-06 | 0.008396993 | 26.0092148 | 25.84375149 | -0.0082073 | Jph4 | chr14 | 55106830 | 55107276 | 447 | | ENSMUST00000022819.11 |
| ENSMUSG00000055850.12 | E026 | 257.0145171 | 0.006521144 | 20.865606.63 | 4.93E-06 | 0.009234.06 | 16.8983217 | 18.258051.19 | 0.1140214 | Rad18l | chr6 | 72361540 | 72361995 | 456 | | c("ENSMUST00000205399.1", "ENSMUST00000206319.1") |
| ENSMUSG00000038007.14 | E010 | 77.39787796 | 0.004693564 | 20.743041.54 | 5.25E-06 | 0.009562685 | 13.3112537 | 11.66397778 | -0.1987306 | Acer2 | chr4 | 8692492 | 86934822 | 2331 | + | ENSMUST00000135874.1 |

| ENSMUSG00000040565.7 | E013 | 219.4258168 | 0.108368964 | 19.74447641 | 8.85E-06 | 0.013776836 | 19.05404 | 11.29927891 | -0.7538662 | Bbs4l | chr19 | 36969914 | 36969038 | 125 | + | ENSMUST00000094494.3 |
| ENSMUSG00000106621.1 | E012 | 6052.243458 | 0.0001068494 | 19.704158676 | 9.04E-06 | 0.013958007 | 31.69966688 | 13.38515219 | -0.0143856 | Gm37494 | chr7 | 39565211 | 39580589 | 15379 | + | ENSMUST00000188038.2 |
| ENSMUSG00000031600.10 | E009 | 265.8313165 | 0.0001440795 | 19.675936681 | 9.17E-06 | 0.014053225 | 17.32323068 | 17.70232564 | 0.0312246 | Vps37a | chr8 | 40541025 | 40541093 | 69 | - | ENSMUST00000098817.2 |
| ENSMUSG00000053297.14 | E009 | 1208.023541 | 0.0001204065 | 19.49988292 | 1.01E-05 | 0.015289085 | 24.66536574 | 12.21967043 | -0.1262075 | A830035N18 | chr6 | 48633540 | 48633685 | 2146 | - | c("ENSMUST00000095938.9", "ENSMUST00000134570.1") |
| ENSMUSG00000056887.14 | E013 | 551.6115605 | 0.0001217857 | 19.47695692 | 1.02E-05 | 0.015352164 | 29.48741.16 | 21.17416612 | 0.0475673 | Bsxx2 | chr3 | 103174548 | 103175618 | 1071 | - | ENSMUST00000136937.7 |
| ENSMUSG00000087259.7 | E006 | 17.21704738 | 0.0070776082 | 19.24969337 | 1.11E-05 | 0.017158333 | 7.58737522 | 5.462360861 | -0.4740763 | 2610035D17Rik | chr11 | 113172953 | 113173077 | 125 | - | c("ENSMUST00000136438.7", "ENSMUST00000150712.1") |
| ENSMUSG00000035325.16 | E040 | 3872.336882 | 0.0001038036 | 19.17899343 | 1.19E-05 | 0.017668738 | 19.11089602 | 19.77966492 | 0.0496177 | Soc31a | chr5 | 100402215 | 100402355 | 141 | - | c("ENSMUST00000094578.19", "ENSMUST00000182850.1", "ENSMUST00000182886.7") |
| ENSMUSG00000026294.15 | E005 | 263.6464241 | 0.001034735 | 19.078517341 | 1.25E-05 | 0.018484849 | 17.26644442 | 17.96611258 | 0.157227 | Dixnk | chr1 | 93798471 | 93798775 | 305 | + | ENSMUST00000112893.1 |
| ENSMUSG00000029130.12 | E008 | 250.7105347 | 0.002494942 | 18.98635116 | 1.32E-05 | 0.0192795 | 17.7476991 | 16.63983638 | -0.0929925 | Rad32 | chr5 | 29225525 | 29236657 | 2933 | + | ENSMUST00000163050.4 |
| ENSMUSG00000040565.7 | E012 | 153.2793887 | 0.0771011862 | 18.943357062 | 1.35E-05 | 0.019428895 | 17.29553303 | 11.03683261 | -0.648073 | Bbs4l | chr19 | 36969056 | 36969196 | 141 | + | ENSMUST00000094494.3 |
| ENSMUSG00000026034.17 | E015 | 2012.129854 | 0.0018574405 | 18.93993444 | 1.35E-05 | 0.019428895 | 26.9211955 | 26.338603439 | -0.0315446 | C3k1 | chr1 | 58446585 | 58415657 | 973 | + | ENSMUST00000123580.7 |
| ENSMUSG00000013539.13 | E007 | 66.29242304 | 0.003524562 | 18.916450336 | 1.37E-05 | 0.019523633 | 11.37623656 | 12.96472286 | 0.1818696 | Tango2 | chr16 | 18303856 | 18304145 | 290 | + | ENSMUST00000143758.1 |
| ENSMUSG00000034211.14 | E020 | 846.0359472 | 0.0110179071 | 18.789871104 | 1.46E-05 | 0.020709979 | 22.006469 | 23.61010641 | 0.1014769 | Mrps17 | chr5 | 129715942 | 129716726 | 785 | + | c("ENSMUST00000135973.7", "ENSMUST00000121339.1") |
| ENSMUSG00000094638.1, ENSMUSG00000026229.17 | E080 | 203.3649633 | 0.004282901 | 18.69429003 | 1.53E-05 | 0.021615509 | 17.14183961 | 15.93912935 | -0.1049484 | NA | chr1 | 86244566 | 86244670 | 105 | + | c("ENSMUST00000123618.7", "ENSMUST00000156675.7", "ENSMUST00000113309.8", "ENSMUST00000274334.14", "ENSMUST00000126579.1", "ENSMUST00000150859.7", "ENSMUST00000131415.7") |
| ENSMUSG00000062590.13 | E013 | 4762.416931 | 0.0001274927 | 18.625864012 | 1.59E-05 | 0.0722421 | 30.3493691 | 30.71432181 | 0.017245 | Aplp2 | chr9 | 31168708 | 31168916 | 209 | + | ENSMUST00000079758.7, ENSMUST00000072634.13 |
| ENSMUSG00000031996.16 | E037 | 3927.139175 | 0.0001303084 | 18.5433070796 | 1.66E-05 | 0.023037301 | 29.96652269 | 29.23145284 | -0.0358207 | Gibx2 | chr1 | 143747330 | 143749401 | 2092 | + | c("ENSMUST00000129653.2", "ENSMUST00000165362.6") |
| ENSMUSG00000086692.1, ENSMUSG00000057842.13, ENSMUSG00000078595.9, ENSMUSG00000098781.1, ENSMUSG00000098995.1 | E021 | 26.77271316 | 0.0060079972 | 18.53154838 | 1.67E-05 | 0.023037301 | 7.475721083 | 9.505810959 | 0.1469954 | NA | chr13 | 67345350 | 67345445 | 96 | | c("ENSMUST00000170543.1", "ENSMUST00000044819.6", "ENSMUST00000166080.1", "ENSMUST00000181582.6") |

| | | | | | | | | | | | | |
|---|---|---|---|---|---|---|---|---|---|---|---|---|
| ENSMUSG00000025619.15 | E042 | 10855.66617 | 0.001372862 | 17.41710702 | 3.00E-05 | 0.035023036 | 34.48186699 | 33.89684902 | -0.02403868 | Mkln1 | chr6 | 31507969 | 31516811 | 8843 | . | ENSMUST00000026699.14 |
| ENSMUSG00000056486.17 | | | | | | | | | | | | | | | + | c("ENSMUST00000124450.3", "ENSMUST00000166199.7", "ENSMUST00000070579.6", "ENSMUST00000112024.9", "ENSMUST00000180945.7", "ENSMUST00000102677.10") |
| ENSMUSG00000028410.13+ ENSMUSG00000065452.1 | E006 | 7260.843433 | 9.99E-05 | 17.39854115 | 3.01E-05 | 0.035023036 | 32.29796909 | 32.33278737 | 0.0015544 | Cbm1 | chr2 | 736173921 | 73618058 | 138 | . | ENSMUST00000129204.7 |
| ENSMUSG00000033577.18 | E020 | 828.2212294 | 0.003615719 | 17.40286065 | 3.02E-05 | 0.035023036 | 22.22379012 | 23.14741968 | 0.0587464 | NA | chr4 | 40726210 | 40727955 | 1746 | . | c("ENSMUST00000076140.3", "ENSMUST00000133268.7", "ENSMUST00000127779.8", "ENSMUST00000358889.14", "ENSMUST00000113266.7", "ENSMUST00000134489.7") |
| ENSMUSG00000041439.15 | E028 | 218.6574703 | 0.001204117 | 17.43335604 | 3.01E-05 | 0.035023036 | 16.41164148 | 17.16231215 | 0.0645241 | Myo6 | chr9 | 80273923 | 80273961 | 39 | . | ENSMUST00000087901.3 |
| ENSMUSG00000031906.18 | E008 | 111.1206163 | 0.002426345 | 17.47531075 | 2.91E-05 | 0.035023036 | 13.160811 | 14.47471539 | 0.1145863 | Mfsd6 | chr1 | 52660299 | 52664806 | 508 | . | c("ENSMUST00000148600.2", "ENSMUST00000126514.1") |
| ENSMUSG00000000560.9 | E018 | 50.48307062 | 0.002937413 | 17.42314737 | 2.99E-05 | 0.035023036 | 9.99024802 | 11.59811356 | 0.2104384 | Gbrx2 | chr1 | 143741716 | 143741754 | 39 | . | ENSMUST00000030491.10 |
| ENSMUSG00000027361.15 | E011 | 188.440962 | 0.039831595 | 17.43286091 | 2.98E-05 | 0.035023036 | 14.44663151 | 15.05424761 | 0.3176456 | Gabra2 | chr5 | 71012784 | 71013684 | 901 | . | ENSMUST00000197124.4 |
| ENSMUSG00000031600.10 | E019 | 28.47872531 | 0.016117832 | 17.45629317 | 2.94E-05 | 0.035023036 | 7.56240946 | 9.82691629 | 0.3778928 | Golph1 | chr2 | 126663089 | 126663290 | 202 | . | ENSMUST00000137335.1 |
| ENSMUSG00000036052.14 | E012 | 7682.432496 | 0.004161766 | 17.16015611 | 3.09E-05 | 0.035357206 | 33.23534139 | 32.09820238 | -0.05602258 | Vps37a | chr8 | 40306276 | 40551134 | 4859 | . | ENSMUST00000098817.2 |
| ENSMUSG00000058407.12 | E016 | 1727.188795 | 0.00257419 | 17.34990331 | 3.11E-05 | 0.035357206 | 26.2545287 | 25.82563958 | -0.1237622 | Dnajb5 | chr4 | 42957318 | 42958723 | 1406 | . | c("ENSMUST00000107973.2", "ENSMUST00000098112.8", "ENSMUST00000142332.1", "ENSMUST00000084662.11", "ENSMUST00000037672.9") |
| ENSMUSG00000019897.8 | E010 | 419.7108588 | 0.001280861 | 17.34665347 | 3.11E-05 | 0.035357206 | 19.31537708 | 19.94616702 | 0.0463622 | Txndc9 | chr1 | 379943411 | 379936632 | 1522 | . | ENSMUST00000194747.1 |
| ENSMUSG00000085396.7 | E006 | 1578.268322 | 0.001907382 | 17.3276947 | 3.15E-05 | 0.035502859 | 25.389361 | 25.72272141 | 0.0188192 | Ccdc59 | chr19 | 105842983 | 105845349 | 2367 | . | c("ENSMUST00000113538.1", "ENSMUST00000204974.2", "ENSMUST00000204991.2", "ENSMUST00000205059.2") |
| ENSMUSG00000084226.5 | E011 | 136.6176742 | 0.001620027 | 17.25875393 | 3.26E-05 | 0.036388986 | 15.31055511 | 14.26942304 | -0.16115996 | Firre | chrX | 50562872 | 50562954 | 83 | . | ENSMUST00000038574.5 |
| ENSMUSG00000034438.16+ ENSMUSG00000079363.7+ ENSMUSG00000029208.15 | E009 | 129.7763598 | 0.001940226 | 17.268312 | 3.25E-05 | 0.036388986 | 14.16246105 | 15.20293102 | 0.1022776 | Dbx29 | chr13 | 112944494 | 112944639 | 166 | . | ENSMUST00000038574.5 |
| ENSMUSG00000019124.10 | E027 | 74.01353849 | 0.036793364 | 17.15838968 | 3.44E-05 | 0.038142615 | 11.43906901 | 13.0609376 | 0.1846472 | NA | chr5 | 105063911 | 105083572 | 662 | . | ENSMUSG00000196320.4 |
| ENSMUSG00000049933.2 | E003 | 480.250616 | 0.001432054 | 17.078089873 | 3.59E-05 | 0.039562444 | 20.74031652 | 19.828858 | -0.0648397 | Scrn1 | chr6 | 54506265 | 54506322 | 58 | . | c("ENSMUST00000203860.1", "ENSMUST00000199268.10") |
| ENSMUSG00000044933.2 | E001 | 638.1689084 | 0.045904862 | 17.050568376 | 3.64E-05 | 0.039911896 | NA | NA | NA | Sstr3 | chr15 | 78337013 | 78540585 | 3571 | . | ENSMUST00000053239.2 |

| | | | | | | | | | | | |
|---|---|---|---|---|---|---|---|---|---|---|---|
| ENSMUSG00000029366.10 | E007 | 4450.0387612 | 0.0018113994 | 16.499012748 | 4.87E-05 | 0.0484233353 | 19.6629244 | 20.148609645 | 0.0352022 | Dck | chr5 | 88776857 | 88776972 | 116 | + | c("ENSMUST00000182650.7", "ENSMUST00000182174.7", "ENSMUST00000181159.7", "ENSMUST00000180806.8", "ENSMUST00000182758.1") |
| ENSMUSG00000097248.8 | E011 | 193.99663869 | 0.0064369906 | 16.476112246 | 4.93E-05 | 0.0483873328 | 16.9281101 | 15.5591430 | -0.1216583 | Gm2694 | chr8 | 87524296 | 87524427 | 132 | . | c("ENSMUST00000114092.8", "ENSMUST00000135057.1", "ENSMUST00000131983.7", "ENSMUST00000095009.9", "ENSMUST00000114001.7", "ENSMUST00000133999.7", "ENSMUST00000064797.11", "ENSMUST00000133389.1", "ENSMUST00000113996.7", "ENSMUST00000113993.7", "ENSMUST00000956482.13") |
| ENSMUSG00000022957.19 | E014 | 281.5959497 | 0.0019877150 | 16.471315690 | 4.94E-05 | 0.0483873328 | 17.6272495 | 18.4646808 | 0.0669699 | Rsu1 | chr16 | 91793607 | 91793767 | 161 | + | c("ENSMUST00000189327.6", "ENSMUST00000027174.9", "ENSMUST00000189919.6", "ENSMUST00000190759.6", "ENSMUST00000191142.6", "ENSMUST00000185368.1") |
| ENSMUSG00000026020.9 | E026 | 217.0077835 | 0.0020615750 | 16.454481360 | 4.98E-05 | 0.0485562098 | 16.1687122 | 17.088800148 | 0.0798464 | N3 | chr1 | 59696078 | 59696099 | 22 | + | c("ENSMUST00000189542.6", "ENSMUST00000186603.6") |
| ENSMUSG00000026107.11 | E002 | 414.535198 | 0.0031008090 | 16.424448010 | 5.06E-05 | 0.0491080021 | 20.050416 | 18.95336411 | -0.0811782 | Nab1 | chr1 | 51466007 | 51468689 | 2683 | . | |
| ENSMUSG00000077038.5 | E010 | 855.531439 | 0.0016395250 | 16.40444458 | 5.12E-05 | 0.0493772281 | 22.9234153 | 22.84885987 | -0.8046998 | Neat1 | chr17 | 34934605 | 34935921 | 1317 | . | c("ENSMUST00000173269.1", "ENSMUST00000007253.5") |

Fig. 16, Continued

| Gene | fft_value | Predicted_Proximal_APA | Loci | Group_B_Mean_PDUI | PDUI_Group_diff | P_val | adjusted.P_val | Pass_Filter | abs(PDUI_Group_diff) |
|---|---|---|---|---|---|---|---|---|---|
| ENSMUST00000022226\|Ppwd1\|chr13\|- | 502.1 | 104205400 | chr13:104205121-104205647 | 0.47 | 0.3125 | 1.03E-06 | 8.94E-05 | N | 0.3125 |
| ENSMUST00000021836\|Rtok1\|chr13\|+ | 392.4 | 38061181 | chr13:38060755-38161433 | 0.71 | -0.2975 | 0.010023195 | 0.008138768 | N | 0.2975 |
| ENSMUST00000021938\|Aaed1\|chr13\|- | 638.4 | 64291954 | chr13:64291836-64292228 | 0.47 | 0.28 | 0.0004406 | 0.013498347 | N | 0.28 |
| ENSMUST00000132304\|Paip1\|chr13\|- | 252164.2 | 119457189 | chr13:119456988-119457319 | 0.6 | 0.25 | 4.23E-17 | 1.95E-14 | N | 0.25 |
| ENSMUST00000135709\|Arid4a\|chr12\|+ | 514.3 | 71075137 | chr12:71074936-71075405 | 0.83 | -0.2475 | 7.37E-05 | 0.003153758 | N | 0.2475 |
| ENSMUST00000126957\|Paip1\|chr13\|+ | 236610.4 | 119457189 | chr13:119456988-119457357 | 0.574 | 0.246 | 2.48E-14 | 9.04E-12 | N | 0.246 |
| ENSMUST00000153352\|Gm11595\|chr18\|+ | 20.5 | 121198549 | chr18:121198259-121198675 | 0.946 | -0.2235 | 0.00074394 | 0.020499273 | N | 0.2235 |
| ENSMUST00000105867\|Stmn1\|chr4\|+ | 46014.2 | 134473523 | chr4:134473322-134473664 | 0.614 | 0.221 | 7.95E-08 | 8.52E-06 | N | 0.221 |
| ENSMUST00000109203\|Paip1\|chr13\|+ | 215603 | 119457189 | chr13:119456988-119457391 | 0.488 | 0.212 | 3.37E-09 | 5.05E-07 | N | 0.212 |
| ENSMUST00000098317\|Vps37a\|chr8\|+ | 14077.4 | 40546477 | chr8:40546276-40551095 | 0.92 | -0.2 | 1.95E-08 | 2.47E-06 | N | 0.2 |
| ENSMUST00000009774\|Ppp2cb\|chr8\|- | 39449.5 | 33619388 | chr8:33619122-33619586 | 0.932 | -0.1995 | 9.06E-22 | 8.07E-19 | N | 0.1995 |
| ENSMUST00000084436\|Cend1\|chr7\|- | 118670.5 | 141426882 | chr7:141426446-141428003 | 0.696 | -0.191 | 2.95E-10 | 5.67E-08 | N | 0.191 |
| ENSMUST00000162751\|Stau2\|chr1\|- | 8624.7 | 16229117 | chr1:16228674-16229866 | 0.66 | -0.19 | 0.011408553 | 0.027083082 | N | 0.19 |
| ENSMUST00000209048\|Rock2\|chr12\|+ | 42102.6 | 169837212 | chr12:169846638-169883274 | 0.678 | -0.188 | 4.57E-06 | 0.000308513 | N | 0.188 |
| ENSMUST00000137488\|Cend1\|chr7\|- | 118985.7 | 141426886 | chr7:141426451-141428003 | 0.698 | -0.1855 | 1.12E-09 | 1.79E-07 | N | 0.1855 |
| ENSMUST00000088194\|Ndufa9\|chr6\|- | 5917.8 | 126821966 | chr6:126821863-126822189 | 0.706 | 0.1815 | 1.03E-06 | 8.94E-05 | N | 0.1815 |
| ENSMUST00000164966\|Rasgef1a\|chr6\|+ | 61776.8 | 118090966 | chr6:118089816-118091546 | 0.706 | -0.171 | 7.03E-06 | 0.000457433 | N | 0.171 |
| ENSMUST00000144520\|Nsmf\|chr2\|+ | 58261 | 25062258 | chr2:25061672-25062628 | 0.578 | -0.1705 | 2.02E-05 | 0.010086467 | N | 0.1705 |
| ENSMUST00000103079\|Ctnnb\|chr7\|- | 12048.2 | 144436687 | chr7:144435735-144437101 | 0.76 | -0.17 | 0.00044702 | 0.013579679 | N | 0.17 |
| ENSMUST00000033407\|Ctnnb\|chr7\|- | 13942.4 | 144436687 | chr7:144435773-144437101 | 0.76 | -0.17 | 0.00044702 | 0.013579679 | N | 0.17 |
| ENSMUST00000102655\|Pdcla\|chr2\|- | 53762.7 | 79836441 | chr2:79834453-79836924 | 0.814 | -0.169 | 0.000334645 | 0.011242656 | N | 0.169 |
| ENSMUST00000032476\|Slc2a3\|chr6\|+ | 46328.3 | 122728671 | chr6:122727809-122730140 | 0.734 | -0.169 | 6.66E-10 | 1.13E-07 | N | 0.169 |
| ENSMUST00000115365\|Tmem243\|chr8\|+ | 836.8 | 91118663 | chr8:91118454-91118801 | 0.786 | 0.1685 | 0.0020922 | 0.04502338 | N | 0.1685 |
| ENSMUST00000110142\|Grpel1\|chr2\|- | 48882.6 | 132529589 | chr2:132529083-132530742 | 0.5 | -0.1675 | 8.32E-11 | 1.85E-08 | N | 0.1675 |
| ENSMUST00000127712\|Copepd1\|chr2\|- | 48856.7 | 132529589 | chr2:132529082-132530742 | 0.498 | -0.1655 | 5.66E-11 | 1.30E-08 | N | 0.1655 |
| ENSMUST00000168704\|Slc2a3\|chr6\|+ | 46673.8 | 122728671 | chr6:122727826-122730140 | 0.728 | -0.163 | 0.0003546 | 0.011429011 | N | 0.163 |
| ENSMUST00000089018\|Tatdn2\|chr2\|+ | 1751.5 | 113710935 | chr6:113710734-113711069 | 0.81 | 0.1625 | 0.001065267 | 0.026815944 | N | 0.1625 |
| ENSMUST00000153661\|Tatdn2\|chr6\|- | 1759 | 113710935 | chr6:113710734-113711066 | 0.808 | 0.1595 | 0.001044459 | 0.026672883 | N | 0.1595 |
| ENSMUST00000093483\|Pkm\|chr9\|- | 1086852.9 | 59679163 | chr9:59678728-59679375 | 0.558 | 0.158 | 2.32E-22 | 2.36E-19 | N | 0.158 |
| ENSMUST00000132855\|Wipf3\|chr6\|+ | 15990.9 | 54501451 | chr6:54500993-54503765 | 0.834 | -0.154 | 6.09E-05 | 0.002714142 | N | 0.154 |
| ENSMUST00000172046\|Wipf3\|chr6\|+ | 15980.5 | 54501451 | chr6:54500993-54503768 | 0.834 | -0.154 | 6.09E-05 | 0.002714142 | N | 0.154 |
| ENSMUST00000098177\|Nfe2l1\|chr11\|- | 76472.1 | 96820315 | chr11:96817431-96820516 | 0.86 | -0.1525 | 6.44E-07 | 6.00E-05 | N | 0.1525 |
| ENSMUST00000105691\|Clstn1\|chr4\|+ | 168836.1 | 149648145 | chr4:149647373-149648899 | 0.544 | -0.1515 | 1.78E-10 | 3.72E-08 | N | 0.1515 |
| ENSMUST00000107658\|Nfe2l1\|chr11\|- | 67247.9 | 96820315 | chr11:96817431-96820516 | 0.836 | -0.151 | 1.70E-06 | 0.000134645 | N | 0.151 |

Fig. 17

| | | | | | | | | |
|---|---|---|---|---|---|---|---|---|
| ENSMUST00000066041|Shisa7|chr7|- | 31660.5 | 4826924 | chr7:4825553-4830275 | 0.648 | -0.1505 | 0.00132511 | 0.0314101084 | N | 0.1505 |
| ENSMUST00000117452|Stxss7|chr7|- | 31660.5 | 4826924 | chr7:4825552-4830275 | 0.648 | -0.1505 | 0.00132511 | 0.0314101084 | N | 0.1505 |
| ENSMUST00000101509|Ddx|chrX|- | 1047025.2 | 703430695 | chrX:703430169-703746673 | 0.712 | -0.1495 | 4.22E-14 | 1.47E-11 | N | 0.1495 |
| ENSMUST00000200781|Lims1|chr10|+ | 4077.6 | 584234588 | chr10:584214454-584234691 | 0.906 | -0.1485 | 0.00057464 | 0.016372702 | N | 0.1485 |
| ENSMUST00000114178|Raf1|03|chr6|+ | 120026.1 | 715102066 | chr6:715086686-715102883 | 0.838 | -0.148 | 3.13E-05 | 0.001544449 | N | 0.148 |
| ENSMUST00000175647344304402t1Rk|chr19|- | 949.7 | 289001459 | chr19:289012268-289017118 | 0.552 | -0.147 | 0.00173318 | 0.031548898 | N | 0.147 |
| ENSMUST00000065118|Lbe2g1|chr13|- | 172661.9 | 697203355 | chr13:69702835-697041173 | 0.504 | -0.1465 | 2.80E-05 | 0.001413112 | N | 0.1465 |
| ENSMUST00000155237|Nnt|chr9|- | 53627.4 | 28996262 | chr9:28996012-28996634 | 0.574 | -0.1465 | 1.51E-05 | 0.000632671 | N | 0.1465 |
| ENSMUST00000112656it|Asab1|chr8|- | 22096.6 | 413409348 | chr8:413400661-413411685 | 0.806 | -0.146 | 1.14E-05 | 0.000661977 | N | 0.146 |
| ENSMUST00000149234|Aim3|chr16|+ | 16826 | 175048808 | chr16:175013644-175054006 | 0.526 | -0.146 | 0.000772 | 0.021109303 | N | 0.146 |
| ENSMUST00000029727|Fbxw7|chr3|+ | 51037 | 849774474 | chr3:849772773-849777645 | 0.778 | -0.1455 | 1.04E-05 | 0.000614552 | N | 0.1455 |
| ENSMUST00000064184|Cdc42se2|chr11|- | 57193 | 547181477 | chr11:547174566-547197245 | 0.6 | -0.145 | 0.00031034 | 0.010329844 | N | 0.145 |
| ENSMUST00000099547|C78139|chr13|+ | 1474176 | 466758733 | chr13:466755132-466780056 | 0.842 | -0.1445 | 1.33E-11 | 3.33E-09 | N | 0.1445 |
| ENSMUST00000067476|Spcs3|chr8|- | 22971.3 | 545212131 | chr8:545204335-545231995 | 0.644 | -0.1415 | 0.001023056 | 0.008387783 | N | 0.1415 |
| ENSMUST00000153101|Pgp1r12c|chr7|- | 8509.3 | 4481748 | chr7:4481588-4482158 | 0.496 | -0.141 | 0.00074781 | 0.022052655 | N | 0.141 |
| ENSMUST00000127478|Pnpf38b|chr3|- | 9424.9 | 108904561 | chr3:108904476-108904762 | 0.31 | -0.14 | 0.0001344 | 0.0051.66859 | N | 0.14 |
| ENSMUST00000102868|CamkK2a|chr18|+ | 52206962 | 609872122 | chr18:609984777-609988152 | 0.742 | -0.1395 | 3.78E-19 | 2.56E-16 | N | 0.1395 |
| ENSMUST00000131999Hz2|chrX|- | 129.3 | 147075941 | chrX:147075731-147078064 | 0.994 | -0.139 | 5.61E-06 | 0.000372273 | N | 0.139 |
| ENSMUST00000097275|Ptcce|chr17|+ | 466693.4 | 86656972 | chr17:86654541-86657919 | 0.83 | -0.1375 | 2.20E-08 | 2.70E-06 | N | 0.1375 |
| ENSMUST00000182407|Pcloc|chr5|+ | 56601.5 | 147952000 | chr5:147931832-147995993 | 0.79 | -0.1375 | 6.75E-05 | 0.0002931497 | N | 0.1375 |
| ENSMUST00000166597|Opa1|chr16|+ | 62593.7 | 29653891 | chr16:29651754-29654884 | 0.782 | -0.137 | 0.000123475 | 0.004869081 | N | 0.137 |
| ENSMUST00000111115|Bnip3|chr14|- | 108519.7 | 669853949 | chr14:669852239-669877775 | 0.796 | -0.136 | 5.11E-05 | 0.002371129 | N | 0.136 |
| ENSMUST00000019572|Zfp87|chr13|- | 2301.6 | 67473546 | chr13:67471514-67474951 | 0.936 | -0.136 | 0.00125592 | 0.030325139 | N | 0.136 |
| ENSMUST00000064637|Rnf103|chr6|+ | 10547.1 | 715102020 | chr6:715088669-715102881 | 0.868 | -0.1355 | 4.73E-05 | 0.002210255 | N | 0.1355 |
| ENSMUST00000135371|Sc2a|chr3|- | 3206329.9 | 961194702 | chr3:961091733-961195521 | 0.854 | -0.134 | 2.05E-09 | 3.17E-07 | N | 0.134 |
| ENSMUST00000255441|Goaqjchr19|- | 77831.1 | 163861986 | chr19:16383204-163874463 | 0.874 | -0.134 | 7.74E-06 | 0.000489998 | N | 0.134 |
| ENSMUST00000622224|Trappc13|chr13|- | 5342.3 | 104144014 | chr13:104144313-104144245 | 0.976 | -0.1335 | 6.14E-06 | 0.000405214 | N | 0.1335 |
| ENSMUST00000418633|Usp22|chr11|- | 50907.4 | 61152739 | chr11:61151785-61154513 | 0.806 | -0.1335 | 6.44E-06 | 0.000423098 | N | 0.1335 |
| ENSMUST00000012731|Vamp2|chr11|+ | 4138632 | 69091401 | chr11:69090650-69092384 | 0.608 | -0.133 | 3.18E-20 | 2.66E-17 | N | 0.133 |
| ENSMUST00000182915|Pelo|chr5|+ | 57582.5 | 147951192 | chr5:147931832-147960004 | 0.82 | -0.1325 | 5.14E-05 | 0.002378701 | N | 0.1325 |
| ENSMUST00000412855|Sk20at|chr2|- | 8477.5 | 129204786 | chr2:129204246-129205104 | 0.63 | -0.1325 | 4.65E-05 | 0.002184612 | N | 0.1325 |
| ENSMUST00000032216|Prmsk|chr6|- | 162371.9 | 124914031 | chr6:124913681-124914232 | 0.562 | -0.132 | 1.63E-05 | 0.000912555 | N | 0.132 |
| ENSMUST00000151410|Fbxw7|chr3|+ | 469243 | 849774474 | chr3:849772773-849777682 | 0.744 | -0.1315 | 8.23E-05 | 0.003428336 | N | 0.1315 |
| ENSMUST00000415889|Tob1|chr11|+ | 43919.1 | 942113834 | chr11:942113486-942115495 | 0.836 | -0.131 | 0.00233964 | 0.049378637 | N | 0.131 |
| ENSMUST00000416446|Cmg|chr11|- | 95154.1 | 795402004 | chr11:795400982-795403027 | 0.616 | -0.131 | 1.91E-08 | 2.47E-06 | N | 0.131 |

Fig. 17, Continued

| | | | | | | | | |
|---|---|---|---|---|---|---|---|---|
| ENSMUST00000044385|Sgtb|chr1|+ | 65723.1 | 104141069 | chr1:104139740-104141735 | 0.588 | -0.1305 | 0.00047793 | 0.014333803 | N | 0.1305 |
| ENSMUST00000020285|Sar1a|chr10|+ | 34685.1 | 61692732 | chr10:61691285-61693295 | 0.528 | -0.1305 | 0.00173547 | 0.038934741 | N | 0.1305 |
| ENSMUST00000010993.ie9|Nee|chr11|- | 60293.4 | 49411079 | chr11:49387754-49411415 | 0.73 | -0.13 | 6.29E-05 | 0.002766287 | N | 0.13 |
| ENSMUST00000100612|Akap7|chr10|- | 27191.6 | 251691079 | chr10:251691090-251712248 | 0.862 | -0.1295 | 0.0002735 | 0.009321085 | N | 0.1295 |
| ENSMUST00000132551|Degs1|chr1|- | 22008.5 | 182279017 | chr1:182278497-182279718 | 0.542 | -0.1295 | 0.00024081 | 0.018387783 | N | 0.1295 |
| ENSMUST00000047028|Lgals8|chr1|+ | 20688.9 | 208252281 | chr1:208233576-208265515 | 0.822 | -0.1295 | 0.00069132 | 0.019198059 | N | 0.1295 |
| ENSMUST00000025477|Sk8sia3|chr18|+ | 19180.3 | 64272103 | chr18:64271514-64276120 | 0.616 | 0.129 | 6.17E-05 | 0.002728456 | N | 0.129 |
| ENSMUST00000107657|Nfe2l1|chr11|+ | 4013.5 | 96820315 | chr11:96818182-96820516 | 0.704 | -0.129 | 0.000106699 | 0.064293547 | N | 0.129 |
| ENSMUST00000011417|Raf1o3|chr6|-- | 10856.7 | 71510220 | chr6:71508869-71510763 | 0.826 | -0.1285 | 0.00013056 | 0.010775996 | N | 0.1285 |
| ENSMUST00000124722|Tmem260|chr14|+ | 698.2 | 485112542 | chr14:485119903-485112790 | 0.864 | 0.1285 | 0.00233531 | 0.049360213 | N | 0.1285 |
| ENSMUST00000114840|Thy1|chr9|- | 446212.4 | 44047894 | chr9:44047339-44048579 | 0.798 | -0.128 | 3.65E-14 | 1.30E-11 | N | 0.128 |
| ENSMUST00000183756|KCTD12|chr14|- | 8611.2 | 102977767 | chr14:102977537-102978002 | 0.358 | -0.128 | 1.98E-06 | 0.000153136 | N | 0.128 |
| ENSMUST00000116574|Nsml|chr2|- | 47777.7 | 250062260 | chr2:250061672-250062880 | 0.45 | -0.1275 | 0.00097479 | 0.025387413 | N | 0.1275 |
| ENSMUST00000080491|Sptbn2|chr19|- | 958860.6 | 4752041 | chr19:4751501-4752353 | 0.432 | -0.127 | 2.42E-05 | 0.001254766 | N | 0.127 |
| ENSMUST00000049972|Ssg2|chr1|- | 142092.3 | 794353811 | chr1:794346699-794437018 | 0.656 | -0.126 | 1.89E-10 | 3.89E-08 | N | 0.126 |
| ENSMUST00000023024|Te4|chr15|+ | 100870.8 | 818245901 | chr15:818234669-818826698 | 0.918 | -0.1255 | 1.8SE-08 | 2.46E-06 | N | 0.1255 |
| ENSMUST00000100334|Nsm|chr2|+ | 47730.2 | 250062260 | chr2:250061672-250062881 | 0.448 | -0.1255 | 0.00097479 | 0.025387413 | N | 0.1255 |
| ENSMUST00000155349|Zfp943|chr17|+ | 2053.6 | 21993229 | chr17:21992092-219944366 | 0.92 | -0.125 | 0.00029662 | 0.009919223 | N | 0.125 |
| ENSMUST00000067947|Rock1|chr18|+ | 5148.9 | 100065236 | chr18:100064401-100066051 | 0.882 | -0.1245 | 7.45E-05 | 0.003177332 | N | 0.1245 |
| ENSMUST00000109493|Homer1|chr13|+ | 295.2 | 93366711 | chr13:93366278-93367128 | 0.988 | -0.123 | 3.28E-06 | 0.000234747 | N | 0.123 |
| ENSMUST00000177642|Cell1|chr2|+ | 41443.1 | 91017671 | chr2:91013491-910119490 | 0.88 | -0.1225 | 3.80E-05 | 0.011833146 | N | 0.1225 |
| ENSMUST00000115364|Cdk16|chrX|+ | 62143.4 | 20699479 | chrX:20698609-206998811 | 0.63 | -0.1225 | 0.00018254 | 0.006617134 | N | 0.1225 |
| ENSMUST00000113067|Zectic18|chrX|+ | 251707.8 | 136994714 | chrX:136994513-136996378 | 0.93 | -0.1225 | 6.81E-16 | 3.03E-13 | N | 0.1225 |
| ENSMUST00000047534|Fam168b|chr1|- | 224226.5 | 34814675 | chr1:34813309-34817404 | 0.712 | -0.122 | 6.19E-05 | 0.002728456 | N | 0.122 |
| ENSMUST00000170000|Rbm7|chr9|- | 81:10 | 484891928 | chr9:484488709-484489088 | 0.582 | -0.122 | 0.00176903 | 0.039500923 | N | 0.122 |
| ENSMUST00000133156|Dcuo5|chr7|+ | 17474.8 | 122148553 | chr7:122148057-122149044 | 0.562 | -0.122 | 0.0010646 | 0.026842963 | N | 0.122 |
| ENSMUST00000038468|Bag4|chr8|- | 5951.5 | 257653998 | chr8:257764538-257767623 | 0.952 | -0.122 | 1.30E-05 | 0.000743981 | N | 0.122 |
| ENSMUST00000170092|Fam168b|chr1|- | 224226.5 | 348146750 | chr1:348133090-348117404 | 0.712 | -0.122 | 6.19E-05 | 0.002728456 | N | 0.122 |
| ENSMUST00000068747|Cell1|chr2|+ | 41407.4 | 91017671 | chr2:91013491-910119497 | 0.884 | -0.1215 | 3.41E-05 | 0.001662443 | N | 0.1215 |
| ENSMUST00000068726|Cell1|chr2|- | 40576 | 910117672 | chr2:910113238-910119497 | 0.836 | -0.121 | 0.00014914 | 0.005665613 | N | 0.121 |
| ENSMUST00000176675|App12|chr10|- | 48985.6 | 83600840 | chr10:83600742-83601041 | 0.696 | -0.121 | 4.29E-05 | 0.0020030856 | N | 0.121 |
| ENSMUST00000155858|Cers2|chr3|+ | 12921.1 | 95323280 | chr3:953229649-953223525 | 0.756 | -0.121 | 0.0003648 | 0.011704834 | N | 0.121 |
| ENSMUST00000037763|Ythdc2|chr18|- | 7367.8 | 448891791 | chr18:448877789-448897260 | 0.956 | -0.121 | 0.000377893 | 0.000768337 | N | 0.121 |
| ENSMUST00000060687|Mapk10|chr5|- | 259893.9 | 102912778 | chr5:102912369-102913327 | 0.83 | -0.12 | 1.34E-05 | 4.51E-05 | N | 0.12 |
| ENSMUST00000234771|Dnm1l|chr16|- | 154209.1 | 16312983 | chr16:16312235-16314043 | 0.912 | -0.1195 | 7.47E-14 | 2.53E-11 | N | 0.1195 |

Fig. 17, Continued

| | | | | | | | | |
|---|---|---|---|---|---|---|---|---|
| ENSMUST00000060098|Sox1|chr9|- | 92717 | 41966670 | chr9:41964720-41968670 | 0.762 | -0.1195 | 1.5E-05 | 0.000847027 | N | 0.1195 |
| ENSMUST00000177783|Rab11fip4|chr11|+ | 50851.1 | 79695548 | chr11:79692723-79698023 | 0.746 | -0.1185 | 0.00024518 | 0.047667497 | N | 0.1185 |
| ENSMUST00000106690|Oxct1|chr15|+ | 165798.8 | 41544705 | chr15:41537728-41554344 | 0.706 | -0.1185 | 2.27E-08 | 2.77E-06 | N | 0.1185 |
| ENSMUST00000023749|Tmbim6|chr15|- | 73222.1 | 994408749 | chr15:994408475-994410049 | 0.456 | -0.1185 | 0.000413553 | 0.012942208 | N | 0.1185 |
| ENSMUST00000010711|Elavl2|chr4|- | 26762.6 | 91251637 | chr4:91250763-91253570 | 0.81 | -0.1175 | 0.00107557 | 0.027002862 | N | 0.1175 |
| ENSMUST00000099087|Mbnl1|chr3|- | 45085.1 | 606238023 | chr3:606236380-606239748 | 0.912 | -0.117 | 1.16E-07 | 1.19E-05 | N | 0.117 |
| ENSMUST00000103075|Nsd|chr11|- | 2103135.7 | 103822276 | chr11:103821782-103823259 | 0.452 | -0.117 | 2.54E-11 | 6.03E-09 | N | 0.117 |
| ENSMUST00000096084|Cdc136|chr6|+ | 9849.9 | 294268236 | chr6:294266625-294268994 | 0.792 | -0.117 | 0.00206605 | 0.044595372 | N | 0.117 |
| ENSMUST00000146030|Atcay|chr10|- | 33492 | 812052860 | chr10:812048508-812067413 | 0.704 | -0.1165 | 0.00153615 | 0.03518337 | N | 0.1165 |
| ENSMUST00000143599|Cdc136|chr6|+ | 10940.1 | 294268236 | chr6:294266625-294269054 | 0.814 | -0.1165 | 0.00131219 | 0.031312266 | N | 0.1165 |
| ENSMUST00000155275|Cdc136|chr6|+ | 10981.1 | 294268236 | chr6:294266625-294269053 | 0.814 | -0.1165 | 0.00131219 | 0.031312266 | N | 0.1165 |
| ENSMUST00000127611|Cdc136|chr6|+ | 10981.1 | 294268236 | chr6:294266625-294268952 | 0.814 | -0.1165 | 0.00131219 | 0.031312266 | N | 0.1165 |
| ENSMUST00000180829|Cdc136|chr6|+ | 10899.3 | 294268236 | chr6:294266625-294268955 | 0.814 | -0.1165 | 0.00142426 | 0.033099508 | N | 0.1165 |
| ENSMUST00000032065|Pcyox1|chr6|- | 579939.1 | 863689102 | chr6:863686006-863689371 | 0.836 | -0.116 | 0.001011944 | 0.004790372 | N | 0.116 |
| ENSMUST00000025110|Syt4|chr18|- | 249174.7 | 314438559 | chr18:314437808-314440490 | 0.786 | -0.116 | 7.96E-07 | 7.13E-05 | N | 0.116 |
| ENSMUST00000107120|Elavl2|chr4|- | 26728 | 912251637 | chr4:912250763-912253567 | 0.808 | -0.1155 | 0.000080802 | 0.021842653 | N | 0.1155 |
| ENSMUST00000168566|Zfand3|chr3|- | 11551.1 | 323336515 | chr3:323334796-323340423 | 0.95 | -0.115 | 0.001101194 | 0.025667883 | N | 0.115 |
| ENSMUST00000113852|Zmat1|chrX|- | 2072.9 | 1349723234 | chrX:1349721372-1349724026 | 0.99 | -0.115 | 0.00011636 | 0.004604489 | N | 0.115 |
| ENSMUST00000101222|Zcchc18|chrX|- | 110143 | 136994714 | chrX:136694513-136996116 | 0.74 | -0.115 | 1.16E-07 | 1.15E-05 | N | 0.115 |
| ENSMUST00000107124|Elavl2|chr4|- | 26782.2 | 911251637 | chr4:912250769-912253567 | 0.81 | -0.115 | 0.00108058 | 0.027046753 | N | 0.115 |
| ENSMUST00000132969|Snap47|chr11|- | 1110082.4 | 594438253 | chr11:594438034-594438513 | 0.45 | -0.115 | 1.90E-07 | 1.91E-05 | N | 0.115 |
| ENSMUST00000202341|Timp3|chr10|+ | 28082.8 | 863471156 | chr10:863457055-863477774 | 0.752 | -0.1145 | 0.00107663 | 0.027002862 | N | 0.1145 |
| ENSMUST00000102748|March7|chr2|+ | 17264.4 | 602487670 | chr2:602475890-602492911 | 0.622 | -0.1145 | 0.0001816 | 0.006595582 | N | 0.1145 |
| ENSMUST00000181464|Cdc136|chr6|+ | 11147.4 | 294268236 | chr6:294266625-294246948 | 0.812 | -0.1145 | 0.00131219 | 0.031312266 | N | 0.1145 |
| ENSMUST00000081932|Nrut2|chr2|+ | 31529.1 | 3326272 | chr2:3326071-3328877 | 0.822 | -0.1145 | 0.0101488 | 0.00567854 | N | 0.1145 |
| ENSMUST00000045897|Prra|chr1|+ | 122641 | 865330166 | chr1:865329965-865330698 | 0.812 | 0.113 | 8.77E-05 | 0.0036210329 | N | 0.113 |
| ENSMUST00000064659|Zmat1|chrX|- | 2073.9 | 1349723234 | chrX:1349721375-1349974026 | 0.99 | -0.1125 | 0.000011636 | 0.004604489 | N | 0.1125 |
| ENSMUST00000056416|Rfox1|chr16|+ | 287349 | 7411328 | chr16:74096691-74124479 | 0.91 | -0.1125 | 4.97E-10 | 8.96E-08 | N | 0.1125 |
| ENSMUST00000010001|Dak24|chr12|+ | 11681.5 | 103408276 | chr12:103407976-103408477 | 0.89 | -0.1125 | 0.000194687 | 0.042669234 | N | 0.1125 |
| ENSMUST00000156910|Hook1|chr4|- | 17692.9 | 960024257 | chr4:960022167-960025391 | 0.772 | -0.112 | 0.00028132 | 0.009497024 | N | 0.112 |
| ENSMUST00000114321|Kbtbd2|chr6|- | 10749.1 | 56778518 | chr6:56777525-56780413 | 0.892 | -0.112 | 0.001144984 | 0.033475639 | N | 0.112 |
| ENSMUST00000136804|Mrp15|chr6|- | 11743.9 | 125193424 | chr6:125193223-125193558 | 0.638 | -0.112 | 0.00221919 | 0.047186033 | N | 0.112 |
| ENSMUST00000033480|Atp11c|chrX|- | 1864.4 | 602225487 | chrX:602225293-602225793 | 0.962 | 0.112 | 0.0108373 | 0.022463513 | N | 0.112 |
| ENSMUST00000098574|Rap1gds1|chr3|- | 2294887.9 | 1389267530 | chr3:1389259066-1389277712 | 0.764 | -0.115 | 4.43E-10 | 8.09E-08 | N | 0.115 |
| ENSMUST00000114323|Kbtbd2|chr6|- | 10757.3 | 56778518 | chr6:56777524-56780413 | 0.894 | -0.1115 | 0.001144984 | 0.033475639 | N | 0.1115 |

Fig. 17, Continued

| | | | | | | | | |
|---|---|---|---|---|---|---|---|---|
| ENSMUST00000054912|Dync1li1|chr2;- | 313362.5 | 155250122 | chr2:155249921-155250272 | 0.384 | -0.1115 | 1.95E-08 | 2.47E-06 | N | 0.1115 |
| ENSMUST00000054877|Txn2|chr15;- | 218521 | 779915621 | chr15:779915047-779915857 | 0.824 | 0.111 | 0.00069049 | 0.019198059 | N | 0.111 |
| ENSMUST00000011011411|Shroom2|chrX;- | 22878.5 | 1526610494 | chrX:1526609509-1526612794 | 0.866 | -0.111 | 0.010042106 | 0.011309689 | N | 0.111 |
| ENSMUST00000010968|Dync1li1|chr2;- | 309074.6 | 155250122 | chr2:155249921-155250277 | 0.388 | -0.1105 | 2.84E-08 | 3.37E-06 | N | 0.1105 |
| ENSMUST00000034537|St3gal4|chr9;- | 3699.5 | 350047318 | chr9:350046579-350047519 | 0.882 | 0.1105 | 0.000817247 | 0.006181817 | N | 0.1105 |
| ENSMUST00000048092|Prickle1|chr15;- | 29990.4 | 935011102 | chr1:934991114-935011303 | 0.968 | -0.1105 | 1.69E-05 | 0.000941627 | N | 0.1105 |
| ENSMUST00000027020|Gria4|chr9;- | 1319257 | 4418584 | chr9:4417899-4420316 | 0.778 | -0.1105 | 0.00066391 | 0.018581739 | N | 0.1105 |
| ENSMUST00000135269|Cnot7|chr8;- | 34625.7 | 40493286 | chr8:40492547-40494115 | 0.72 | -0.11 | 8.98E-06 | 0.000549517 | N | 0.11 |
| ENSMUST00000102729|Eps15|chr4;+ | 145100.5 | 1093887077 | chr4:1093385319-1093887817 | 0.78 | -0.11 | 2.66E-07 | 2.6E-05 | N | 0.11 |
| ENSMUST00000137363|Clip1|chr5;- | 44365.3 | 123578579 | chr5:1235778707-123579502 | 0.84 | -0.11 | 0.001441089 | 0.032896227 | N | 0.11 |
| ENSMUST00000098266|Arrb1|chr7;- | 335127 | 996604253 | chr7:996601098-996606771 | 0.772 | -0.1095 | 0.001611186 | 0.036681378 | N | 0.1095 |
| ENSMUST00000154051|Arpc1|chr6;+ | 1866.4 | 60225487 | chrX:60223290-60225793 | 0.962 | -0.1095 | 0.0008373 | 0.022463513 | N | 0.1095 |
| ENSMUST00000077853|Prpf4b|chr13;+ | 12450.6 | 349001909 | chr13:349001393-349029877 | 0.772 | -0.1095 | 0.001102592 | 0.026333675 | N | 0.1095 |
| ENSMUST00000032477|Necap1|chr6;+ | 46232 | 122888449 | chr6:122887340-122888934 | 0.672 | -0.1095 | 1.87E-05 | 0.001018635 | N | 0.1095 |
| ENSMUST00000130468|Rab3a|chr8;+ | 18235.6 | 707757339 | chr8:7075713R-707757700 | 0.354 | -0.109 | 1.66E-08 | 2.23E-06 | N | 0.109 |
| ENSMUST00000034012|Cnot7|chr8;- | 34959 | 40493286 | chr8:40492540-40494115 | 0.724 | -0.109 | 8.53E-06 | 0.000535555 | N | 0.109 |
| ENSMUST00000123712|Fbxo18|chr2;- | 1328.4 | 11748476 | chr2:11747850-11749134 | 0.866 | -0.1085 | 0.000861149 | 0.029972274 | N | 0.1085 |
| ENSMUST00000153927|Erbb2ip|chr13;- | 18220.7 | 1038201142 | chr13:10181787-1038208086 | 0.746 | -0.1085 | 0.000706689 | 0.019592123 | N | 0.1085 |
| ENSMUST00000129041|Smg1|chr16;+ | 23813.4 | 909938808 | chr16:909938657-909939034 | 0.556 | -0.1085 | 0.010311814 | 0.010491211 | N | 0.1085 |
| ENSMUST00000025056|Nudt3|chr17;- | 1554842 | 275579835 | chr17:275579382-275580954 | 0.458 | -0.108 | 0.000651836 | 0.015225778 | N | 0.108 |
| ENSMUST00000125340|Clip1|chr5;- | 44624.7 | 123578579 | chr5:1235778818-123579502 | 0.838 | -0.108 | 0.001149439 | 0.032852159 | N | 0.108 |
| ENSMUST00000132032|Cnot7|chr8;- | 34800.3 | 404932867 | chr8:404492542-404948115 | 0.72 | -0.1075 | 8.57E-06 | 0.000535555 | N | 0.1075 |
| ENSMUST00000027495|Sept2|chr1;+ | 42659 | 93508662 | chr1:93507713-93510260 | 0.92 | -0.1075 | 0.0001797 | 0.0065627844 | N | 0.1075 |
| ENSMUST00000062887|Smcd1|chr2;+ | 54388.4 | 1171801484 | chr2:1171177302-1171182279 | 0.84 | -0.1075 | 6.19E-05 | 0.002714142 | N | 0.1075 |
| ENSMUST00000144970|Cnot7|chr8;- | 34800.3 | 40493286 | chr8:404492543-404494115 | 0.72 | -0.1075 | 8.57E-06 | 0.000535555 | N | 0.1075 |
| ENSMUST00000111564|Clip1|chr5;- | 44084.5 | 123578579 | chr5:1235777795-123579502 | 0.84 | -0.1075 | 0.001339933 | 0.031606379 | N | 0.1075 |
| ENSMUST00000134962|Abcc5|chr16;- | 162077 | 204402622 | chr16:204406760-204464713 | 0.972 | -0.107 | 3.67E-06 | 0.0002574405 | N | 0.107 |
| ENSMUST00000021091|Pafah1b1|chr11;+ | 334871.9 | 746755323 | chr11:746673949-746677742 | 0.834 | -0.1065 | 1.70E-11 | 4.18E-09 | N | 0.1065 |
| ENSMUST00000025209|Pafah1b1|chr11;+ | 334871.9 | 746755233 | chr11:1005801347-1006581728 | 0.636 | -0.1065 | 1.70E-11 | 4.18E-09 | N | 0.1065 |
| ENSMUST00000074094|Gnai1|chr5;+ | 114910.4 | 182655716 | chr5:1825665135-18267209 | 0.806 | -0.106 | 1.09E-05 | 0.000638764 | N | 0.106 |
| ENSMUST00000143841|Hrd751c|chr3;+ | 900.8 | 41758018 | chr3:417560049-417593899 | 0.986 | -0.106 | 0.001319957 | 0.031383204 | N | 0.106 |
| ENSMUST00000103120|Capk|chr11;+ | 472873.9 | 1005813411 | chr11:1005801347-1006581728 | 0.636 | -0.106 | 4.19E-05 | 0.0019691155 | N | 0.106 |
| ENSMUST00000091721|Kif5a|chr10;+ | 464413.5 | 1272227985 | chr10:1272225696-1272228421 | 0.918 | -0.1055 | 1.31E-37 | 3.72E-34 | N | 0.1055 |
| ENSMUST00000150826|Cpgl1|chr9;+ | 53695.4 | 730121877 | chr9:7301119350-730113711 | 0.75 | -0.105 | 0.0001966 | 0.004289802 | N | 0.105 |
| ENSMUST00000067635|Dim1|chr2;- | 982498.1 | 323308707 | chr2:32308471-32309064 | 0.39 | -0.105 | 1.30E-08 | 1.81E-06 | N | 0.105 |

Fig. 17, Continued

| | | | | | | | | |
|---|---|---|---|---|---|---|---|---|
| ENSMUST00000102858|Lin7c|cto2|+- | 25852.4 | 1098096678 | chr2:1098697246-1099001003 | 0.96 | 4.56E-06 | 0.000308513 | N | 0.105 |
| ENSMUST00000012400S|Cpg1|chr9|+- | 536954 | 73012187 | chr9:73011930-73013711 | 0.75 | 0.0001066 | 0.0042289802 | N | 0.105 |
| ENSMUST00000112848|Mapk10|chr5|+- | 261823.1 | 102912778 | chr5:1029123S4-102913327 | 0.862 | 1.91E-06 | 0.0001449744 | N | 0.1045 |
| ENSMUST00000009036|Vdac3|chr8|- | 2819559.5 | 22577301 | chr8:22577075-22577602 | 0.792 | 4.15E-05 | 0.001977798 | N | 0.1045 |
| ENSMUST00000155363|Igsf8|chr1|+ | 18664.3 | 172291306 | chr1:172290232-172292725 | 0.562 | 2.52E-05 | 0.0012292685 | N | 0.1045 |
| ENSMUST00000146659|Ssbp3|chr4|+ | 1048242 | 107048377 | chr4:107048024-107048515 | 0.836 | 2.21E-05 | 0.001169119 | N | 0.104 |
| ENSMUST00000129156|Dnm1|chr2|-. | 1020583.2 | 32308708 | chr2:32308497-32309064 | 0.434 | 1.53E-08 | 2.07E-06 | N | 0.104 |
| ENSMUST00000133827|Ssbp3|chr4|+ | 103732.1 | 107048380 | chr4:1070480024-107048519 | 0.824 | 3.23E-05 | 0.001579352 | N | 0.1035 |
| ENSMUST00000113316S|Dnm1|chr2|- | 988044.2 | 323308707 | chr2:32308475-32309064 | 0.398 | 1.18E-08 | 1.66E-06 | N | 0.103 |
| ENSMUST00000046587|Acox1|chr11|- | 952405 | 116172463 | chr11:116171888-116173598 | 0.498 | 0.00169957 | 0.038343405 | N | 0.103 |
| ENSMUST00000102632|Sort1|chr3|+ | 11646 | 108359266 | chr3:108357229-108361511 | 0.778 | 0.00035908 | 0.011547409 | N | 0.103 |
| ENSMUST000000884528|Slc38a1|chr15|- | 655426 | 96573911 | chr15:96571418-96576812 | 0.86 | 0.00180916 | 0.040230241 | N | 0.1025 |
| ENSMUST00000028854|Malt|chr2|- | 2692142 | 127634404 | chr2:127633226-127635054 | 0.94 | 1.09E-19 | 7.85E-17 | N | 0.1025 |
| ENSMUST00000062673|Stx1b|chr7|- | 260019.8 | 127805148 | chr7:127803060-127807389 | 0.19 | 5.62E-06 | 0.000372273 | N | 0.1025 |
| ENSMUST00000105660S|Camta1|chr4|- | 207324.6 | 151060666 | chr4:151059814-151062855 | 0.852 | 2.78E-05 | 0.00140799 | N | 0.102 |
| ENSMUST00000114666|Atpov1a|chr16|+ | 5056814 | 440865S2 | chr16:44085402-44087516 | 0.802 | 5.76E-10 | 1.00E-07 | N | 0.102 |
| ENSMUST00000014221|Clip1|chr2|+ | 385435 | 119586436 | chr2:119585107-119587027 | 0.742 | 0.00131894 | 0.031383204 | N | 0.102 |
| ENSMUST00000003069|Hook3|chr8|+ | 18577.5 | 966024258 | chr8:4960221167-960025413 | 0.802 | 0.00068626 | 0.019131899 | N | 0.102 |
| ENSMUST000000377441|C0N1|chr7|+ | 545520.3 | 143067605 | chr7:143067312-143067934 | 0.514 | 1.51E-06 | 0.000124161 | N | 0.1015 |
| ENSMUST000000431138|Inpp5|chr7|+- | 166638.5 | 128694574 | chr7:128694176-128696425 | 0.814 | 2.10E-05 | 0.001123025 | N | 0.1015 |
| ENSMUST00000168077|Fads1|chr19|- | 122805.3 | 101963100 | chr19:101194871-101196870 | 0.626 | 0.0007967 | 0.0216183539 | N | 0.101 |
| ENSMUST000000423341|Ugcris1|chr13|- | 1674429 | 305403867 | chr13:305403108-30541341 | 0.886 | 2.17E-08 | 2.69E-06 | N | 0.101 |
| ENSMUST00000217501Rty2|chr13|+ | 77407 | 11554410 | chr13:11553103-11554611 | 0.898 | 9.56E-05 | 0.0038922S2 | N | 0.1005 |
| ENSMUST00000822905|Slc39a12|chr2|+ | 107412 | 14494649 | chr2:1449421-14494977 | 0.618 | 0.00109625 | 0.027160357 | N | 0.1005 |
| ENSMUST00000114731|Slc39a12|chr2|+ | 107861 | 14494649 | chr2:1449421-14494975 | 0.618 | 0.0011096S | 0.027160357 | N | 0.1005 |
| ENSMUST00000039O5|Clip1|chr5|- | 248654 | 123579301 | chr5:123578833-123579502 | 0.822 | 0.0020525 | 0.044437489 | N | 0.1005 |
| ENSMUST00000108377|Zfand1|chr3|- | 3276 | 103400699 | chr3:103340619-103440905 | 0.9 | 0.00163S83 | 0.037176415 | N | 0.1 |
| ENSMUST00000344740|Ncdd4|chr9|+ | 231269.6 | 727477874 | chr9:727471226-727498S2 | 0.72 | 4.10E-08 | 4.67E-06 | N | 0.1 |
| ENSMUST00000105447|Vps26a|chr10|+ | 252945 | 624557229 | chr10:62454843-624568S8 | 0.89 | 0.00169329 | 0.038289893 | N | 0.1 |
| ENSMUST00000015719|Atp6v0e|chr17|+ | 4156 | 266999S23 | chr17:266699212-266999644 | 0.922 | 0.00168098 | 0.038071852 | N | 0.0995 |
| ENSMUST000001098381NnK2|chr13|- | 41943 | 589935035 | chr13:589932023-589937030 | 0.772 | 0.00128442 | 0.030908643 | N | 0.0995 |
| ENSMUST000000120746|Ncald|chr15|- | 6549281 | 373367851 | chr15:373660218-37368925 | 0.912 | 6.12E-10 | 1.05E-07 | N | 0.0995 |
| ENSMUST000000203161|Tbk1|chr10|- | 113395.7 | 1215469087 | chr10:1215469S5-121547188 | 0.884 | 0.00082258 | 0.022152905 | N | 0.099 |
| ENSMUST000000034738|Rsa2a0|chr9|+ | 1750S2 | 731223013 | chr9:2311222647-31213333 | 0.896 | 4.75E-05 | 0.00221366S | N | 0.099 |
| ENSMUST000000031423|Atp2a2|chr5|- | 3342153 | 122456661 | chr5:122456335-12245762 | 0.524 | 9.21E-09 | 1.32E-06 | N | 0.099 |

Fig. 17, Continued

| | | | | | | | | |
|---|---|---|---|---|---|---|---|---|
| ENSMUST00000112182005pock2jchr10+ | 5193662.7 | 60132455 | chr10:60113336-60135198 | 0.494 | -0.099 | 1.05E-05 | 0.000618454 | N | 0.099 |
| ENSMUST00000080411tMorf4l2jchrX|- | 923337.1 | 136734300 | chrX:136732953-136734501 | 0.814 | -0.099 | 1.89E-09 | 2.97E-07 | N | 0.099 |
| ENSMUST00000159220jArpp21jchr9|- | 1551106.4 | 112181791 | chr9:112181007-112182820 | 0.864 | -0.099 | 1.41E-08 | 1.93E-06 | N | 0.099 |
| ENSMUST00000065304jRtn3jchr19|- | 4500479 | 7427460 | chr19:7425904-7427875 | 0.664 | -0.099 | 7.61E-24 | 1.01E-20 | N | 0.099 |
| ENSMUST00000041468jNsp3jchr7|- | 43147.1 | 109759713 | chr7:109758055-109761189 | 0.984 | -0.099 | 2.16E-08 | 2.69E-06 | N | 0.099 |
| ENSMUST00000072634jAph2jchr9|- | 20916159 | 311500352 | chr9:311499557-311500972 | 0.786 | -0.0985 | 4.17E-08 | 4.72E-06 | N | 0.0985 |
| ENSMUST00000112691jGnl3ljchrX|- | 105832.6 | 150084631 | chrX:150083141-150086186 | 0.586 | -0.0985 | 0.00028438 | 0.00955475 | N | 0.0985 |
| ENSMUST00000119730jNcald|chr15|- | 665381.7 | 373367851 | chr15:373366267-373368925 | 0.906 | -0.0965 | 5.64E-10 | 9.92E-08 | N | 0.0985 |
| ENSMUST00000289236jNuptjchr2|- | 271748.3 | 148696265 | chr2:148693985-148697506 | 0.888 | -0.098 | 7.57E-12 | 1.96E-09 | N | 0.098 |
| ENSMUST00000151237jhppp5jchr7|+ | 1595988 | 128694575 | chr7:128694176-128696359 | 0.788 | -0.098 | 7.80E-05 | 0.0013287357 | N | 0.098 |
| ENSMUST00000143402jPrdx2jchr8|+ | 11277 | 849971763 | chr8:849971562-849972103 | 0.89 | -0.0975 | 0.00080737 | 0.021842653 | N | 0.0975 |
| ENSMUST00000079491jSez6|chr5|- | 818207 | 112421234 | chr5:112419151-112422038 | 0.912 | -0.097 | 0.000234889 | 0.008062696 | N | 0.097 |
| ENSMUST00000042766jPpm1kjchr6|- | 97777 | 57508816 | chr6:57506502-57510849 | 0.952 | -0.097 | 0.00123919 | 0.030125347 | N | 0.097 |
| ENSMUST00000115230jApod|chr16|- | 369688.1 | 312975351 | chr16:312971223-312975576 | 0.542 | -0.097 | 9.29E-09 | 1.32E-06 | N | 0.097 |
| ENSMUST00000162772jLmco3jchr6|- | 253101 | 138364973 | chr6:138362918-138366047 | 0.942 | -0.097 | 5.02E-06 | 0.000337361 | N | 0.097 |
| ENSMUST00000162544jWnk1|chr6|- | 51205 | 119937807 | chr6:119937460-119938018 | 0.782 | -0.097 | 0.00112146 | 0.027688582 | N | 0.097 |
| ENSMUST00000142075jtuppp5jchr7|- | 134248.9 | 128694576 | chr7:128694176-128696274 | 0.742 | -0.097 | 0.00020882 | 0.007474189 | N | 0.097 |
| ENSMUST00000119158430419109Rikjchr6|+ | 220343.1 | 135235538 | chr5:135239979-135236242 | 0.694 | -0.0965 | 0.008096196 | 0.035904121 | N | 0.0965 |
| ENSMUST00000113885jArhgePjchrX|- | 78435.1 | 95049991 | chrX:95049938-95051199 | 0.736 | -0.096 | 1.13E-17 | 6.18E-15 | N | 0.096 |
| ENSMUST00000020741jDrgljchr11|- | 27083.9 | 3250112 | chr1:32496907-3250365 | 0.486 | -0.096 | 9.74E-06 | 0.00058065 | N | 0.096 |
| ENSMUST00000072376jRnfl4jchr18|+ | 3426941 | 383169604 | chr18:38316625-38317847 | 0.736 | -0.096 | 0.00124914 | 0.0302507999 | N | 0.096 |
| ENSMUST00000126242jArpe3jchr5|- | 380661.6 | 122404325 | chr5:122404124-122404781 | 0.388 | -0.0955 | 3.78E-07 | 3.68E-05 | N | 0.0955 |
| ENSMUST00000059680jGolph3jchr13|+ | 57441.4 | 123499568 | chr15:123499368-123512165 | 0.878 | -0.0955 | 0.00025172 | 0.008703863 | N | 0.0955 |
| ENSMUST00000112200jCadm3|chr1|- | 2462091.2 | 173335604 | chr1:173334254-173337139 | 0.468 | -0.0955 | 5.63E-05 | 0.002594175 | N | 0.0955 |
| ENSMUST00000102800jPpp3r1|chr1|+ | 2606684 | 171199735 | chr1:171198259-17200375 | 0.608 | -0.0955 | 0.008096196 | 0.025144991 | N | 0.0955 |
| ENSMUST00000113097jMorf4l2|chrX|- | 9215779 | 136734300 | chrX:136732942-136734501 | 0.818 | -0.0955 | 1.13E-17 | 6.18E-15 | N | 0.0955 |
| ENSMUST00000064651jPhyhipljchr10|- | 164355.5 | 70559422 | chr10:70558731-70559781 | 0.548 | -0.0955 | 1.09E-09 | 1.77E-07 | N | 0.0955 |
| ENSMUST00000023207jApod|chr16|- | 3976543 | 312297351 | chr16:312297156-312297576 | 0.56 | -0.095 | 3.42E-05 | 0.0016664375 | N | 0.095 |
| ENSMUST00000033331jNsp3jchr7|- | 43123.8 | 109759713 | chr7:109758059-109761189 | 0.98 | -0.095 | 3.11E-08 | 3.66E-06 | N | 0.095 |
| ENSMUST00000440334djFcho2|chr13|- | 8953.2 | 987243099 | chr13:98722340-98725776 | 0.902 | -0.0945 | 2.11E-08 | 2.65E-06 | N | 0.0945 |
| ENSMUST00000132443jPpp1r1bjchr11|+ | 73431.4 | 98357444 | chr11:98357033-98357788 | 0.562 | -0.0945 | 0.00019031 | 0.0124392282 | N | 0.0945 |
| ENSMUST00000161434jSdhajchr13|- | 1065594.3 | 74322856 | chr13:74322732-74323173 | 0.858 | -0.0945 | 0.00048888 | 0.014570322 | N | 0.0945 |
| ENSMUST00000150762jPpp1r1bjchr11|+ | 72834.1 | 98357444 | chr11:98357033-98357794 | 0.562 | -0.0945 | 8.35E-27 | 1.76E-23 | N | 0.0945 |
| ENSMUST00000080536jAbcc11chr8|- | 19831.6 | 79684776 | chr8:79683442-79685277 | 0.862 | -0.0945 | 0.00019997 | 0.012634041 | N | 0.0945 |
| ENSMUST00000090150jNcald|chr15|- | 6466066.7 | 373667851 | chr15:373666175-373668925 | 0.914 | -0.094 | 0.00051323 | 0.015137557 | N | 0.0945 |
| | | | | | | 1.98E-09 | 2.97E-07 | | 0.094 |

Fig. 17, Continued

| | | | | | | | | |
|---|---|---|---|---|---|---|---|---|
| ENSMUST00000114924{CsfI2{chr2{- | 167968.9 | 65441686 | chr2:65439705-65467779 | 0.856 | -0.0935 | 0.010227846 | 0.009422643 | N | 0.0935 |
| ENSMUST00000136340{Atp1a1{chr3{- | 119807 | 1011586118 | chr3:1011585788-1011586319 | 0.508 | -0.093 | 0.000065394 | 0.018374688 | N | 0.093 |
| ENSMUST00000098275{Aspb{chr4{- | 30250.6 | 96306596 | chr4:96306547-96309252 | 0.52 | -0.0925 | 0.010073943 | 0.020414665 | N | 0.0925 |
| ENSMUST00000009255{Smarcb1{chr10{- | 1371.5 | 758968859 | chr10:758967769-75897088 | 0.88 | 0.0925 | 0.001907645 | 0.04305278 | N | 0.0925 |
| ENSMUST00000102817{Gap43{chr16{- | 993596.2 | 422348630 | chr16:422348443-422491114 | 0.88 | 0.0925 | 4.24E-19 | 2.75E-16 | N | 0.0925 |
| ENSMUST00000107289{Ptprd{chr4{- | 90318.6 | 759431026 | chr4:759412138-759458026 | 0.94 | -0.0925 | 4.33E-06 | 0.000295364 | N | 0.0925 |
| ENSMUST00000078694{Ppp1r1b{chr11{- | 72716 | 983357444 | chr11:983357033-983357796 | 0.56 | -0.0925 | 0.000339997 | 0.012634041 | N | 0.0925 |
| ENSMUST00000102834{Ptprd{chr4{- | 90318.6 | 759431026 | chr4:759431239-759458026 | 0.94 | -0.0925 | 4.33E-06 | 0.000295364 | N | 0.0925 |
| ENSMUST00000113189{Smarcb1{chr10{- | 1412.1 | 758968562 | chr10:758968773-75897088 | 0.898 | 0.092 | 6.35E-05 | 0.002782878 | N | 0.092 |
| ENSMUST00000110664{Nrsr2{chr12{- | 17085.4 | 166604056 | chr12:166597709-166660236 | 0.622 | -0.092 | 0.000146363 | 0.013934435 | N | 0.092 |
| ENSMUST00000026243{Mgea5{chr19{- | 146820.4 | 457507082 | chr19:457576261-457517130 | 0.534 | -0.0915 | 0.000019949 | 0.007176648 | N | 0.0915 |
| ENSMUST00000087600{Gdal{chr19{- | 85082.1 | 213792804 | chr19:213913907-213395258 | 0.964 | -0.0915 | 6.47E-13 | 1.96E-10 | N | 0.0915 |
| ENSMUST00000109605{Atf4{chr15{- | 74843.7 | 802570155 | chr15:802566344-802575440 | 0.474 | -0.0915 | 0.000095057 | 0.024921498 | N | 0.0915 |
| ENSMUST00000131866{Mrpe{chr6{- | 276634.3 | 355609686 | chr6:355608906-355612317 | 0.926 | -0.091 | 1.49E-17 | 7.33E-15 | N | 0.091 |
| ENSMUST00000064062{mmp{chr6{- | 15122.8 | 71874751 | chr6:71874317-71875244 | 0.996 | -0.091 | 2.28E-12 | 6.76E-10 | N | 0.091 |
| ENSMUST00000148591{Phactr1{chr13{- | 168368.4 | 431135375 | chr13:431351174-431138526 | 0.85 | -0.09 | 0.000400866 | 0.012631621 | N | 0.09 |
| ENSMUST00000014913{Fsmb1{chr17{- | 26153.3 | 154475993 | chr17:154475721-154476205 | 0.75 | -0.09 | 7.35E-05 | 0.003153258 | N | 0.09 |
| ENSMUST00000118398{Symj{chr16{- | 26564.5 | 909938822 | chr16:909938240-909939034 | 0.8 | -0.09 | 0.000039326 | 0.012505442 | N | 0.09 |
| ENSMUST00000128646{Phactr1{chr13{- | 168306.7 | 431135375 | chr13:431131174-431138524 | 0.85 | -0.09 | 0.000054652 | 0.015910537 | N | 0.09 |
| ENSMUST00000140408{Smarcb1{chr10{- | 1442.6 | 758968638 | chr10:758968775-758897088 | 0.91 | 0.09 | 0.000025358 | 0.008747014 | N | 0.09 |
| ENSMUST00000182010{Gm26924{chr17{- | 108858171.1 | 398477782 | chr17:398468958-398481103 | 0.7 | -0.09 | 9.26E-54 | 4.40E-50 | N | 0.09 |
| ENSMUST00000182006{Scbip{chr3{- | 284939.3 | 686266008 | chr3:686255807-686262631 | 0.888 | -0.0895 | 4.26E-13 | 1.41E-10 | N | 0.0895 |
| ENSMUST00000225629{Band5{chr19{- | 132635.1 | 212281577 | chr19:212280423-212282289 | 0.902 | -0.0895 | 5.86E-13 | 1.81E-10 | N | 0.0895 |
| ENSMUST00000049152{Snx10{chr6{- | 85522.7 | 51590055 | chr6:515888881-515906792 | 0.864 | -0.089 | 0.000171148 | 0.006381811 | N | 0.089 |
| ENSMUST00000105499{Snx3{chr10{- | 56473.5 | 425345854 | chr10:425346553-425353538 | 0.504 | -0.089 | 0.0104285 | 0.013184327 | N | 0.089 |
| ENSMUST00000093773{Mobp{chr9{- | 139860.7 | 1201733152 | chr9:1201733151-120176091 | 0.764 | -0.089 | 2.32E-06 | 0.000175078 | N | 0.089 |
| ENSMUST00000025083{Kif5b{chr18{- | 147621.2 | 6202635 | chr18:6201002-6203707 | 0.726 | -0.0885 | 0.001212521 | 0.045960052 | N | 0.0885 |
| ENSMUST00000145205{Hsp90ab1{chr17{- | 154404.6 | 455669104 | chr17:455668584-455669387 | 0.516 | -0.0885 | 8.95E-16 | 3.75E-13 | N | 0.0885 |
| ENSMUST00000113920{Ohfnl{chr3{- | 138120.5 | 282239919 | chr3:282239054-282230462 | 0.626 | -0.0885 | 0.000400259 | 0.012688843 | N | 0.0885 |
| ENSMUST00000068275{Bdhb9{chrX{+ | 34980.9 | 135889061 | chrX:135888751-135891081 | 0.876 | -0.0885 | 0.001113064 | 0.027770883 | N | 0.0885 |
| ENSMUST00000088419{Mbnl2{chr14{- | 387695.3 | 1204294330 | chr14:1204280935-120431697 | 0.886 | -0.0885 | 6.38E-11 | 1.44E-08 | N | 0.0885 |
| ENSMUST00000449681{Hzbi1{chr14{+ | 3407.9 | 123974964 | chr14:123973285-123975618 | 0.912 | 0.088 | 0.000173332 | 0.006392853 | N | 0.088 |
| ENSMUST00000098236{Suka4{chr15{- | 94460.2 | 840765918 | chr15:840760907-840775822 | 0.358 | -0.088 | 0.002659 | 0.009103584 | N | 0.088 |
| ENSMUST00000046963{Map2k4{chr11{- | 42963.8 | 656902756 | chr11:656888243-656690804 | 0.832 | -0.087 | 0.000025753 | 0.018840384 | N | 0.087 |
| ENSMUST00000316697{Cal1{chr6{- | 11461 | 475257555 | chr6:475255554-475261339 | 0.592 | -0.087 | 0.00234484 | 0.049490062 | N | 0.087 |

Fig. 17, Continued

| | | | | | | | |
|---|---|---|---|---|---|---|---|
| ENSMUST00000106226|Tial1|chr7|- | 38204.4 | 1284405584 | chr7:128439277-128442659 | 0.682 | -0.087 | 0.0107853 | 0.021348108 | N | 0.087 |
| ENSMUST00000172956|Cobl|chr11|- | 5293.8 | 122373844 | chr11:122371111-122380059 | 0.994 | -0.0865 | 3.03E-06 | 0.000218771 | N | 0.0865 |
| ENSMUST00000109939|Snx3|chr10|+ | 55361.6 | 42534854 | chr10:42534653-42535370 | 0.494 | -0.0865 | 0.00057155 | 0.016317222 | N | 0.0865 |
| ENSMUST00000060431|Dcaf12l1|chrX|- | 25326.4 | 447870771 | chrX:447865170-447882093 | 0.954 | -0.0865 | 9.49E-06 | 0.000568308 | N | 0.0865 |
| ENSMUST00000162251|Phyhipl|chr10|- | 136864.1 | 705594408 | chr10:705588477-705597819 | 0.434 | -0.0865 | 0.000117366 | 0.006639283 | N | 0.0865 |
| ENSMUST00000040284|HC031181l|chr18|+ | 56405 | 750097271 | chr18:750092278-751099933 | 0.294 | -0.0865 | 0.012173231 | 0.646416507 | N | 0.0865 |
| ENSMUST00000180025|Bhlhe40|chrX|+ | 34865.3 | 1358890611 | chrX:1358887511-13589310781 | 0.874 | -0.0865 | 0.001128691 | 0.027770083 | N | 0.0865 |
| ENSMUST00000041769|Dync1h2|chr8|- | 163570.4 | 1044204261 | chr8:1044176741-10442068211 | 0.766 | -0.086 | 7.56E-05 | 0.006321353591 | N | 0.086 |
| ENSMUST00000151068|Ssk25|chr1|- | 357225.7 | 936223116 | chr1:936219761-936225261 | 0.766 | -0.086 | 0.011611244 | 0.0262198351 | N | 0.086 |
| ENSMUST00000127496|Ssk25|chr1|- | 35725.7 | 936223116 | chr1:936219761-936225261 | 0.766 | -0.086 | 0.01101244 | 0.026219835 | N | 0.086 |
| ENSMUST00000179365|Snx19|chr6|+ | 857769.4 | 515906055 | chr6:515888831-515906670 | 0.886 | -0.086 | 0.00024267 | 0.008431746 | N | 0.086 |
| ENSMUST00000166975|Immp|chr6|+ | 15391.5 | 71874751 | chr6:71874317-71875250 | 0.996 | -0.086 | 2.64E-12 | 7.52E-10 | N | 0.086 |
| ENSMUST00000161467|Appp2|chr9|- | 169025.8 | 1121817911 | chr9:1121809781-11218282011 | 0.886 | -0.086 | 1.90E-08 | 2.47E-06 | N | 0.086 |
| ENSMUST00000108425|Ctk|chr11|- | 85023.5 | 757658111 | chr1:757603661-757066908 | 0.466 | -0.086 | 9.85E-05 | 0.003997172 | N | 0.086 |
| ENSMUST00000025774|Sf3b2|chr19|- | 114393.3 | 52274094 | chr19:5273923-5274527 | 0.786 | -0.086 | 0.001342841 | 0.0301623584 | N | 0.086 |
| ENSMUST00000162082|Appp2|chr9|- | 1706119.6 | 1121817911 | chr9:1121809721-11218282011 | 0.888 | -0.0855 | 1.93E-08 | 2.47E-06 | N | 0.0855 |
| ENSMUST00000027451|Epha4|chr1|- | 52221.6 | 773368103 | chr1:773671851-773699671 | 0.948 | -0.0855 | 4.41E-05 | 0.0020819621 | N | 0.0855 |
| ENSMUST00000105470|Man1a|chr10|- | 1006.3 | 539907202 | chr10:539070151-53907756311 | 0.988 | -0.0855 | 0.00042232 | 0.013107527 | N | 0.0855 |
| ENSMUST00000121990|Sva2|chr1|+ | 30601.8 | 134751560 | chr1:134747475-134753149 | 0.97 | -0.085 | 0.000811161 | 0.02188587611 | N | 0.085 |
| ENSMUST00000028386|Nckap1|chr2|- | 919589 | 80500784 | chr2:80500512-805014111 | 0.34 | -0.085 | 5.02E-07 | 4.80E-05 | N | 0.085 |
| ENSMUST00000060553|Ksr1|chr4|- | 66292.4.9 | 1491179936 | chr4:1491763191-1491808101 | 0.892 | -0.0845 | 2.62E-10 | 5.18E-08 | N | 0.0845 |
| ENSMUST00000141416|Hars|chr18|- | 24523.4 | 367666752 | chr18:367665301-367666953 | 0.898 | 0.0845 | 5.41E-06 | 0.00036158611 | N | 0.0845 |
| ENSMUST00000069187|Trim23|chr13|+ | 33868.3 | 104202616 | chr13:1042012311-1042033721 | 0.632 | -0.0845 | 0.00044706 | 0.013579679 | N | 0.0845 |
| ENSMUST00000085904|Irc4c|chr2|+ | 26625.2 | 976299054 | chr2:976288989-97631664 | 0.954 | -0.084 | 0.000161421 | 0.00060355471 | N | 0.084 |
| ENSMUST00000059667|Hpca14|chr4|+ | 429045.3 | 1231193568 | chr4:1231190658-123119470111 | 0.954 | -0.084 | 6.64E-09 | 9.75E-07 | N | 0.084 |
| ENSMUST00000033933|Tmem66|chr8|+ | 146350.2 | 341703346 | chr8:341170096-341708451 | 0.674 | -0.084 | 1.76E-05 | 0.000968071 | N | 0.084 |
| ENSMUST00000135431|Irc4c|chr2|+ | 266121.1 | 976299054 | chr2:976288989-976316661 | 0.954 | -0.084 | 0.0001614211 | 0.00060355471 | N | 0.084 |
| ENSMUST00000042934|Car10|chr11|+ | 54556 | 936008171 | chr11:936600316-93601745 | 0.676 | -0.0835 | 0.00115992 | 0.02839211 | N | 0.0835 |
| ENSMUST00000107863|Car10|chr11|+ | 54514.4 | 936008171 | chr11:936006316-936601749 | 0.676 | -0.0835 | 0.00143185 | 0.03322177 | N | 0.0835 |
| ENSMUST00000108308|Nfig1|chr3|- | 11111 | 254342591 | chr3:2543181,1-254344460 | 0.966 | -0.0835 | 0.000311204 | 0.010362164 | N | 0.0835 |
| ENSMUST00000029788|Ptbp2|chr3|- | 55875.5 | 119719231 | chr3:1197187421-1197204601 | 0.668 | -0.083 | 2.41E-06 | 0.000180038 | N | 0.083 |
| ENSMUST00000062288|Bend6|chr1|- | 194450.5 | 338524211 | chr1:338525921-338533671 | 0.62 | -0.0825 | 0.00045771 | 0.013798339 | N | 0.0825 |
| ENSMUST00000093661|Pepiad1|chr9|- | 52920.2 | 649878671 | chr9:649869851-649988529 | 0.81 | -0.0825 | 0.000161421 | 0.006547172 | N | 0.0825 |
| ENSMUST00000064503|Lap|chr2|- | 8142.3 | 745208991 | chr2:7452033,1-745222971 | 0.88 | -0.0825 | 8.87E-06 | 0.013398219 | N | 0.0825 |
| ENSMUST00000131214|Sqstm1|chr11|- | 61182.9 | 502202393 | chr11:502203121-502202594 | 0.56 | -0.0825 | 2.52E-05 | 0.0012926851 | N | 0.0825 |

Fig. 17, Continued

| | | | | | | | |
|---|---|---|---|---|---|---|---|
| ENSMUST00000102180;Dok;chr13;- | 12540.5 | 470858738 | chr13:470847482-470846029 | 0.872 | 0.0011298968 | 0.0311990024 | N | 0.082 |
| ENSMUST00000106598;Elav14;chr4;- | 63412.6 | 110294544 | chr4:110203722-110206659 | 0.962 | 1.51E-07 | 1.55E-05 | N | 0.082 |
| ENSMUST00000030578;Ptp4a2;chr4;- | 91172.1 | 129848982 | chr4:129847714-129849978 | 0.922 | 0.010011883 | 0.0046189369 | N | 0.082 |
| ENSMUST00000138401;Dok;chr13;- | 12607.7 | 470858738 | chr13:470847475-470846079 | 0.872 | 0.001135939 | 0.031956986 | N | 0.082 |
| ENSMUST00000103552;Sesf5;chr12;+ | 477404.5 | 809850028 | chr12:809449726-809950503 | 0.858 | 3.40E-06 | 0.000241868 | N | 0.082 |
| ENSMUST00000051454;Fam117b;chr2;+ | 201059.6 | 838794633 | chr2:838791110-838813486 | 0.952 | 2.63E-08 | 3.15E-06 | N | 0.082 |
| ENSMUST00000111760;Nckap1;chr2;- | 925713.8 | 805007844 | chr2:805050518-805501411 | 0.344 | 6.53E-07 | 6.04E-05 | N | 0.0815 |
| ENSMUST00000165853;Ptp4a2;chr4;+ | 922771.6 | 129848982 | chr4:129847714-129850003 | 0.946 | 1.70E-05 | 0.000941627 | N | 0.081 |
| ENSMUST00000321196;Ari88b;chr6;+ | 146694.8 | 108822157 | chr6:108821503-108823723 | 0.926 | 2.53E-10 | 5.16E-08 | N | 0.081 |
| ENSMUST00000058499;Sync1;chr10;- | 559210.1 | 5021374 | chr10:5020203-5022247 | 0.688 | 0.000028766 | 0.019664237 | N | 0.0805 |
| ENSMUST00000021001;Rab10;chr12;+ | 942269.7 | 3249150 | chr12:3247430-3249739 | 0.928 | 1.03E-05 | 0.000611825 | N | 0.0805 |
| ENSMUST00000117377;Spock3;chr8;+ | 116308.8 | 63355964 | chr8:63355212-63356852 | 0.938 | 3.55E-10 | 6.6E-08 | N | 0.0805 |
| ENSMUST00000026221;Scd2;chr19;- | 4706292.3 | 44305782 | chr19:44103001-44306864 | 0.98 | 5.19E-39 | 1.85E-35 | N | 0.08 |
| ENSMUST00000166680;Cul4a;chr8;- | 17088.7 | 131146733 | chr8:131146532-131147940 | 0.98 | 0.0010388835 | 0.012404692 | N | 0.08 |
| ENSMUST00000125187;Gap43;chr16;- | 1024643.1 | 42248642 | chr16:42224858-42249114 | 0.92 | 4.12E-32 | 9.79E-29 | N | 0.08 |
| ENSMUST00000121304;Smarcb1;chr10;- | 1469.6 | 758906864 | chr10:758967777-758907088 | 0.92 | 0.000042368 | 0.013121052 | N | 0.08 |
| ENSMUST00000162858;Ipo9;chr1;- | 119.4 | 1353866605 | chr1:1353862588-1353860806 | 0.918 | 0.000017676 | 0.006473392 | N | 0.0795 |
| ENSMUST00000120959;Sept3;chr15;+ | 1498449.1 | 822993002 | chr15:822960738-822964442 | 0.302 | 0.000037695 | 0.012106762 | N | 0.0795 |
| ENSMUST00000020537;Nsg2;chr11;+ | 1474591.3 | 320580633 | chr11:320574443-320459202 | 0.834 | 7.63E-05 | 0.003226017 | N | 0.079 |
| ENSMUST00000105616;Gnb1;chr4;+ | 1420381.9 | 155558018 | chr4:155557471-155559269 | 0.684 | 7.05E-07 | 6.43E-05 | N | 0.079 |
| ENSMUST00000063661;Atpev1a;chr16;- | 3862473 | 440865579 | chr16:440856c5-440875516 | 0.654 | 1.91E-05 | 0.0011034677 | N | 0.079 |
| ENSMUST00000150516;Nsf;chr11;- | 114718.3 | 103861848 | chr11:103861639-1038662049 | 0.454 | 8.22E-05 | 0.003428336 | N | 0.079 |
| ENSMUST00000024959;Cript;chr17;+ | 8371 | 87035514 | chr17:87034978-87035810 | 0.816 | 0.00104498 | 0.026667883 | N | 0.0785 |
| ENSMUST00000079086;Homer1;chr13;+ | 10601.8 | 934403059 | chr13:934402041-934004129 | 0.996 | 3.72E-08 | 4.28E-06 | N | 0.0785 |
| ENSMUST00000127168;Lnp;chr2;- | 8145.6 | 745200899 | chr2:745200341-745222997 | 0.868 | 0.001198458 | 0.043163848 | N | 0.078 |
| ENSMUST00000067664;Yobsae;chr13;+ | 4388250.8 | 757765269 | chr13:757764620-757651845 | 0.448 | 3.26E-09 | 4.94E-07 | N | 0.078 |
| ENSMUST00000106603;Elav14;chr4;- | 65781.8 | 110294555 | chr4:110203737-110206659 | 0.968 | 6.21E-08 | 6.86E-06 | N | 0.078 |
| ENSMUST00000135807;Epna2api;chr9;+ | 46120.6 | 111278125 | chr9:111277444-111279089 | 0.808 | 0.000078259 | 0.021316943 | N | 0.078 |
| ENSMUST00000227209;Ptcd3;chr14;- | 60406.1 | 103081181 | chr14:103080239-103083510 | 0.21 | 0.000818439 | 0.00665144 | N | 0.0775 |
| ENSMUST00000041282;Trim37;chr11;+ | 145957.3 | 87219308 | chr11:87218252-87229683 | 0.69 | 0.0010 13976 | 0.005352135 | N | 0.0775 |
| ENSMUST00000146441;Asph;chr4;- | 380823.9 | 9630743 | chr4:9629023-9630952 | 0.61 | 0.000094535 | 0.024847828 | N | 0.0775 |
| ENSMUST00000595 15;Gdi2;chr13;+ | 436816.6 | 3565675 | chr13:3564996-3566936 | 0.54 | 8.14E-05 | 0.003415919 | N | 0.0775 |
| ENSMUST00000111993;Lnp;chr2;- | 8176.1 | 745209900 | chr2:745209291-745222297 | 0.94 | 0.000056394 | 0.016230034 | N | 0.077 |
| ENSMUST00000493859;Eif1;chr11;+ | 82617.1 | 100321642 | chr11:100321317-100322096 | 0.482 | 1.39E-05 | 0.000793806 | N | 0.077 |
| ENSMUST00000064355;Atp6v1b2;chr8;+ | 1017400 | 69112963 | chr8:69112430-69113711 | 0.432 | 1.86E-07 | 1.88E-05 | N | 0.077 |

Fig. 17, Continued

| | | | | | | | | |
|---|---|---|---|---|---|---|---|---|
| ENSMUST00000018250 | Cbordc1 chr9 + | 21362.3 | 18313491 | chr9:18312778-18314000 | 0.802 | -0.077 | 0.010076612 | 0.020988621 | N | 0.077 |
| ENSMUST00000108345 | Yrhdf3 chr3 + | 17888.1 | 16215042 | chr3:16213955-16217035 | 0.952 | -0.077 | 1.83E-06 | 0.00014411 | N | 0.077 |
| ENSMUST00000140065 | Clip3 chr7 + | 323880.3 | 30307452 | chr7:30306806-30308367 | 0.892 | -0.077 | 3.30E-10 | 6.27E-08 | N | 0.077 |
| ENSMUST00000050511 | Lhq chr7 + | 55278.7 | 468855178 | chr7:468854977-468855626 | 0.434 | -0.0765 | 0.001090085 | 0.027160357 | N | 0.0765 |
| ENSMUST00000176637 | Gnb4 chr4 + | 1430764.1 | 155558018 | chr4:155557468-155559267 | 0.684 | -0.0765 | 7.33E-07 | 6.65E-05 | N | 0.0765 |
| ENSMUST00000165335 | Cnnb1 chr4 + | 1429846.4 | 155558018 | chr4:155557468-155559269 | 0.684 | -0.0765 | 6.43E-07 | 6.00E-05 | N | 0.0765 |
| ENSMUST00000163205 | Cstk1u1 chr18 + | 3972.5 | 615805540 | chr18:615803339-615823262 | 0.966 | -0.076 | 1.87E-05 | 0.001018635 | N | 0.076 |
| ENSMUST00000048209 | Ldhq chr7 + | 55779.2 | 468855178 | chr7:468854977-468855627 | 0.436 | -0.076 | 0.001093303 | 0.027160357 | N | 0.076 |
| ENSMUST00000113909 | Copa chr1 + | 1693.4 | 1721148603 | chr1:1721113334-1721115568 | 0.706 | -0.076 | 0.001193048 | 0.042440822 | N | 0.076 |
| ENSMUST00000107396 | Sccint1 chr11 + | 51659.4 | 975121104 | chr11:975093340-975112648 | 0.986 | -0.076 | 0.000023501 | 0.008226058 | N | 0.076 |
| ENSMUST00000089912 | Casc4 chr2 + | 33814.8 | 121935061 | chr2:121933478-121935866 | 0.896 | -0.076 | 0.00175438 | 0.039222386 | N | 0.076 |
| ENSMUST00000029558 | Eif3ak chr19 - | 122942.2 | 607611529 | chr19:60761116-60762304 | 0.988 | -0.0755 | 1.07E-09 | 1.74E-07 | N | 0.0755 |
| ENSMUST00000077458 | Sxthp1 chr2 + | 1685028.6 | 327885824 | chr2:327878962-327890637 | 0.268 | -0.0755 | 1.10E-06 | 9.46E-05 | N | 0.0755 |
| ENSMUST00000196496 | b6s chr11 + | 600268.4 | 62552341 | chr1:1625521400-625532133 | 0.368 | -0.0755 | 2.02E-05 | 0.001085465 | N | 0.0755 |
| ENSMUST00000146775 | Cttnbp2 chr6 - | 34321.4 | 183668859 | chr6:183668565-183668616 | 0.818 | -0.0755 | 0.00028262 | 0.009518369 | N | 0.0755 |
| ENSMUST00000023827 | Psmd14 chr2 + | 52682.6 | 61800183 | chr2:617990082-61800376 | 0.948 | -0.0755 | 2.23E-05 | 0.001173985 | N | 0.0755 |
| ENSMUST00000106063 | Zranb2 chr3 + | 2332887 | 157547873 | chr3:157547466754-157548339 | 0.718 | -0.0755 | 2.29E-06 | 0.000174627 | N | 0.0755 |
| ENSMUST00000123918 | vos1abp chr1 + | 129917.8 | 1513637968 | chr1:151363112-1513644445 | 0.8 | -0.075 | 3.82E-06 | 0.0010266946 | N | 0.075 |
| ENSMUST00000013714 | Actr2 chr1 + | 493984310 | 2000633362 | chr1:120063230-20064859 | 0.54 | -0.075 | 9.94E-05 | 0.004022464 | N | 0.075 |
| ENSMUST00000332264 | Gabarap1 chr6 + | 619872.3 | 1295419300 | chr6:1295411002-129542331 | 0.302 | -0.0745 | 1.08E-07 | 1.14E-05 | N | 0.0745 |
| ENSMUST00000031536 | Trucm106 chr6 + | 63055.4 | 130844268 | chr6:130841488-130889269 | 0.902 | -0.0745 | 0.000157490 | 0.015935297 | N | 0.0745 |
| ENSMUST00000099329 | Lbc2 chr10 + | 85112.4 | 95542590 | chr10:955422272-955445658 | 0.872 | -0.0745 | 0.000254880 | 0.008770675 | N | 0.0745 |
| ENSMUST00000106058 | Zranb2 chr3 + | 2263789 | 157547893 | chr3:157547466675-15754839 | 0.732 | -0.0745 | 2.29E-06 | 0.000174627 | N | 0.0745 |
| ENSMUST00000118003 | Snock3 chr8 + | 1168509 | 63355955 | chr8:633552122-633356860 | 0.942 | -0.0745 | 3.62E-10 | 6.70E-08 | N | 0.0745 |
| ENSMUST00000136835 | Micu3 chr8 + | 90671 | 40384810 | chr8:403846409-40386308 | 0.774 | -0.074 | 0.000071561 | 0.019795362 | N | 0.074 |
| ENSMUST00000156566 | Tubb5 chr17 - | 85442 | 358348868 | chr7:35833926-358360339 | 0.546 | -0.074 | 0.00022813 | 0.018084541 | N | 0.074 |
| ENSMUST00000063354 | Vbp1 chrX + | 102751.5 | 755341099 | chrX:75553909-755534942 | 0.994 | 0.074 | 1.14E-18 | 7.07E-16 | N | 0.074 |
| ENSMUST00000159837 | Cobs chr18 + | 64359 | 848799763 | chr18:84879503-848798864 | 0.924 | 0.0735 | 1.54E-10 | 3.27E-08 | N | 0.0735 |
| ENSMUST00000176430 | Ap2b1 chr11 + | 6289.5 | 83397956 | chr11:833977755-833908597 | 0.936 | -0.0735 | 7.06E-05 | 0.003046855 | N | 0.0735 |
| ENSMUST00000114151 | ftmm chr6 - | 15786.8 | 71874738 | chr6:718743177-71875257 | 0.998 | -0.073 | 2.97E-12 | 8.14E-10 | N | 0.073 |
| ENSMUST00000185148 | Mrp120 chr4 + | 8737.6 | 1558087066 | chr4:155808479-155808798 | 0.83 | 0.0725 | 0.001701004 | 0.038343405 | N | 0.0725 |
| ENSMUST00000179857 | Tomm20 chrN + | 1592107 | 126932112 | chr8:126930664-126935059 | 0.94 | -0.0725 | 4.05E-05 | 0.0019422552 | N | 0.0725 |
| ENSMUST00000173253 | Tubb5 chr17 - | 56265.4 | 158355727 | chr7:358315605-358336039 | 0.802 | -0.072 | 0.001011032 | 0.004402278 | N | 0.072 |
| ENSMUST00000232256 | Gcmalchr15 + | 407788.7 | 762349418 | chr5:762492176-26249904 | 0.322 | -0.072 | 0.000091747 | 0.024439526 | N | 0.072 |
| ENSMUST00000029831 | Zranb2 chr3 + | 234048.8 | 157547871 | chr3:157547466675-157548336 | 0.722 | -0.072 | 2.54E-06 | 0.000188327 | N | 0.072 |

Fig. 17, Continued

| | | | | | | | | |
|---|---|---|---|---|---|---|---|---|
| ENSMUST00000106057|Zranb2|chr3|+ | 225756.4 | 157547894 | chr3:157546675-157548376 | 0.702 | -0.072 | 4.04E-06 | 0.000279514 | N | 0.072 |
| ENSMUST00000106933|Dnajc6|chr4|- | 305475.4 | 101641566 | chr4:101640472-101642782 | 0.622 | -0.072 | 0.00045815 | 0.013798839 | N | 0.072 |
| ENSMUST00000099458|Sve1|chr8|- | 607592.3 | 887746991 | chr8:887744701-887748010 | 0.402 | -0.072 | 3.13E-05 | 0.00154449 | N | 0.072 |
| ENSMUST00000038027|Gpi1|chr7|- | 36626.9 | 34202348 | chr7:34202122-34202549 | 0.788 | -0.072 | 0.000351S3 | 0.011379637 | N | 0.072 |
| ENSMUST00000107503|Svt1|chr8|- | 607451.7 | 887746991 | chr8:887744700-887748010 | 0.402 | -0.072 | 3.13E-05 | 0.00154449 | N | 0.072 |
| ENSMUST00000030042|Mrp120|chr4|- | 8299 | 155808706 | chr4:155808479-155808831 | 0.818 | 0.072 | 0.01232214 | 0.64915489 | N | 0.072 |
| ENSMUST00000072113|Tmem65|chr15|- | 58827.3 | 587840G3 | chr15:58782269-58785010 | 0.932 | -0.072 | 0.00048341 | 0.01437362 | N | 0.072 |
| ENSMUST00000107691|Trim2|chr3|- | 124813.3 | 841G4503 | chr3:841G0440-841G5249 | 0.974 | -0.0715 | 6.45E-08 | 6.96E-06 | N | 0.0715 |
| ENSMUST00000142017|Cysltp2|chr11|+ | 67626 | 46196266 | chr11:46196071-46196467 | 0.514 | -0.0715 | 0.00115494 | 0.02681S044 | N | 0.0715 |
| ENSMUST00000107695|Trim2|chr3|- | 124839.6 | 84164503 | chr3:841G0441-84165249 | 0.974 | -0.0715 | 6.45E-08 | 6.96E-06 | N | 0.0715 |
| ENSMUST00000114513|Gls|chr1|- | 149343.2 | 521G4960 | chr1:521G3448-521G6314 | 0.604 | -0.0715 | 0.0016167 | 0.036732931 | N | 0.0715 |
| ENSMUST00000107692|Trim2|chr3|- | 124787.3 | 841G4503 | chr3:841G0439-841G5249 | 0.974 | -0.0715 | 6.45E-08 | 6.96E-06 | N | 0.0715 |
| ENSMUST00000129999|Rbm4_111|chr2|+ | 167207.6 | 156540911 | chr2:156539810-156540326 | 0.906 | -0.0715 | 5.6-E-10 | 9.92E-08 | N | 0.0715 |
| ENSMUST00000121334|Sept8|chr11|+ | 606754.4 | 53549208 | chr11:53548291-53549565 | 0.894 | -0.0715 | 7.58E-05 | 0.003215181 | N | 0.0715 |
| ENSMUST00000172107|St813|chr15- | 93798.4 | 81364222 | chr15:81363669-81365578 | 0.986 | -0.071 | 7.25E-10 | 1.21E-07 | N | 0.071 |
| ENSMUST00000146259|Cdk16|chrX|- | 118839.9 | 206096039 | chrX:206095699-206096285 | 0.386 | -0.071 | 0.00221117 | 0.047085618 | N | 0.071 |
| ENSMUST00000139623|H3G3b|chr11|- | 193175.3 | 116023334 | chr11:116023193-116023535 | 0.914 | 0.071 | 4.06E-15 | 1.56E-12 | N | 0.071 |
| ENSMUST00000159487|Ipo8|chr11|+ | 147.1 | 135386605 | chr11:135386393-135386806 | 0.922 | 0.0705 | 0.00117101 | 0.028614494 | N | 0.0705 |
| ENSMUST00000150565|Rpl11|chr4|- | 174764.7 | 136051222 | chr4:136051028-136051720 | 0.798 | -0.0705 | 8.65E-07 | 7.69E-05 | N | 0.0705 |
| ENSMUST00000104498|Hsph1|chr5|+ | 246912.5 | 1496175G9 | chr5:1496171G9-149617710 | 0.688 | -0.0705 | 7.60E-05 | 0.0030299557 | N | 0.0705 |
| ENSMUST00000044369|Atpov1h|chr1|+ | 108755 | 5162368 | chr1:5162105-5162549 | 0.298 | -0.0705 | 0.00125072 | 0.0312560799 | N | 0.0705 |
| ENSMUST00000049937|Ostc|chr3|- | 240047.4 | 1306096277 | chr3:1306095921-1306096478 | 0.93 | 0.07 | 1.56E-06 | 0.000127347 | N | 0.07 |
| ENSMUST00000106552|S030306124102Rik|chr7|+ | 5820.4 | 118841399 | chr7:1188411396-118841479 | 0.93 | 0.07 | 0.000074572 | 0.020508643 | N | 0.07 |
| ENSMUST00000106930|Dnajc6|chr4|+ | 314729.1 | 101641566 | chr4:101640472-101642799 | 0.64 | -0.07 | 0.000035227 | 0.011379637 | N | 0.07 |
| ENSMUST00000019931|Lrp1|chr10|+ | 172475.6 | 7624245 | chr10:7623630-7625483 | 0.932 | -0.0695 | 0.00012379 | 0.004844768 | N | 0.0695 |
| ENSMUST00000034348|Hrfg|chr8|- | 148278.4 | 85718566 | chr8:85717557-85718927 | 0.882 | -0.0695 | 2.16E-05 | 0.0011146754 | N | 0.0695 |
| ENSMUST00000184707|Ywbab|chr2|+ | 1305972.8 | 1640617515 | chr2:1640616699-1640618588 | 0.682 | -0.0695 | 9.62E-07 | 8.46E-05 | N | 0.0695 |
| ENSMUST00000020775|Dynll1|chr11|+ | 4123785 | 879801169 | chr11:879799525-879815570 | 0.672 | -0.0695 | 1.14E-06 | 9.71E-05 | N | 0.0695 |
| ENSMUST00000143503|Mrpl20|chr4|+ | 8518.4 | 155808705 | chr4:155808479-155808794 | 0.828 | 0.0695 | 0.0018238 | 0.040046998 | N | 0.0695 |
| ENSMUST00000038791|Gde1|chr7|- | 500S8.2 | 118688949 | chr7:118688545-118689150 | 0.326 | -0.0685 | 0.012016429 | 0.044595372 | N | 0.0685 |
| ENSMUST00000106929|Dnajc6|chr4|+ | 313743.6 | 101641566 | chr4:101640472-101642798 | 0.636 | -0.0685 | 0.000441765 | 0.013010214 | N | 0.0685 |
| ENSMUST00000079324|Ub13|chr5|- | 267554.1 | 148505965 | chr5:148504631-148506187 | 0.912 | 0.068 | 1.55E-06 | 0.000126706 | N | 0.068 |
| ENSMUST00000092153|Atp6v1d|chr12- | 458260 | 788433172 | chr12:788442989-788434610 | 0.848 | -0.068 | 0.00018443 | 0.00665144 | N | 0.068 |
| ENSMUST00000092678|Bc1af1|chr10|- | 59991.8 | 203411140 | chr10:203400052-203442501 | 0.88 | -0.0675 | 0.00061524 | 0.017390233 | N | 0.0675 |
| ENSMUST00000102723|Elavl4|chr4|- | 67800.3 | 110204567 | chr4:110203737-110206701 | 0.99 | -0.0675 | 1.35E-08 | 1.87E-06 | N | 0.0675 |

Fig. 17, Continued

| | | | | | | | |
|---|---|---|---|---|---|---|---|
| ENSMUST00000176291Top2b]chr14]- | 21959.6 | 16430593 | chr14:164302991-64307873 | 0.61 | -0.0675 | 0.010311362 | 0.0103904333 | N | 0.0675 |
| ENSMUST00000032838:Arl6ip1]chr7]- | 344729 | 118119398 | chr7:118118891-118120410 | 0.842 | -0.067 | 0.00014041 | 0.005362638 | N | 0.067 |
| ENSMUST00000113025:Rab14]chr2]- | 1909234 | 351824444 | chr2:351802205-351813331 | 0.922 | -0.067 | 1.14E-07 | 1.19E-05 | N | 0.067 |
| ENSMUST00000120349:Aktip]chr8]- | 49528.7 | 911234078 | chr8:911234844-911234678 | 0.894 | -0.0665 | 2.78E-05 | 0.001140799 | N | 0.0665 |
| ENSMUST00000037850:Sox2]chr18]+ | 16995.1 | 53220573 | chr18:532203721-5322080860 | 0.814 | -0.0665 | 0.000138005 | 0.032335836 | N | 0.0665 |
| ENSMUST00000070080:B4galt6]chr18]+ | 67797 | 206985683 | chr18:206845991-206883468 | 0.964 | -0.0665 | 9.08E-05 | 0.003715113 | N | 0.0665 |
| ENSMUST00000045180:Tardbp]chr4]- | 30392.4 | 148616254 | chr4:148615919-148616844 | 0.954 | -0.0665 | 3.22E-06 | 0.000231955 | N | 0.0665 |
| ENSMUST00000156000:Mib1]chr18]+ | 68135.1 | 10817098 | chr18:108157361-108117628 | 0.894 | -0.0665 | 5.72E-05 | 0.002621429 | N | 0.0665 |
| ENSMUST00000104848:Pnf20l1]chr15]+ | 11390 | 666422660 | chr15:666417981-666645255 | 0.994 | -0.0665 | 7.27E-06 | 0.000470497 | N | 0.0665 |
| ENSMUST00000114276:Rcn2]chr9]+ | 436542.1 | 560586836 | chr9:560580391-560590077 | 0.554 | -0.0665 | 0.000328731 | 0.010748501 | N | 0.0665 |
| ENSMUST00000064490:Homer1]chr13]+ | 11253.3 | 934403059 | chr13:934020411-934037901 | 0.996 | -0.066 | 2.04E-06 | 0.000157067 | N | 0.066 |
| ENSMUST00000065308:Azin1]chr15]- | 43646.1 | 384884021 | chr15:384874301-3849094721 | 0.406 | -0.066 | 0.001951771 | 0.042711173 | N | 0.066 |
| ENSMUST00000068137:Bcas1]chr2]- | 228686.8 | 170347426 | chr2:170347144-170348148 | 0.786 | -0.066 | 0.000027621 | 0.009368478 | N | 0.066 |
| ENSMUST00000088615:Arfgef1]chr1]+ | 339963.1 | 101138795 | chr1:101375711-101138996 | 0.938 | -0.0655 | 0.001192921 | 0.042440822 | N | 0.0655 |
| ENSMUST00000050000:Stxbp1]chr2]- | 19996121 | 327589112 | chr2:327876021-327899637 | 0.98 | -0.065 | 2.93E-18 | 1.74E-15 | N | 0.065 |
| ENSMUST00000115345:Syn1]chrX]- | 206254091 | 208608141 | chrX:208605191-208861571 | 0.86 | -0.065 | 3.31E-08 | 3.86E-06 | N | 0.065 |
| ENSMUST00000113222:Stxbp1]chr2]- | 2003849.2 | 327589112 | chr2:327876071-327899637 | 0.98 | -0.065 | 4.83E-18 | 2.75E-15 | N | 0.065 |
| ENSMUST00000139123:Ksf1]chr4]- | 463458.8 | 149179932 | chr4:149178863-149180810 | 0.8 | -0.065 | 0.000499883 | 0.014831681 | N | 0.065 |
| ENSMUST00000067491:Cadps]chr14]- | 1895983 | 123729081 | chr14:123725631-123737931 | 0.752 | -0.0645 | 2.33E-05 | 0.001214347 | N | 0.0645 |
| ENSMUST00000151120:Clsd]chr7]- | 179054 | 142376497 | chr7:142375910-142376738 | 0.272 | -0.0645 | 0.000329261 | 0.010748501 | N | 0.0645 |
| ENSMUST00000106211:Sep15]chr3]- | 1295495 | 144597284 | chr3:144596823-144597661 | 0.532 | -0.0645 | 0.001063611 | 0.026842963 | N | 0.0645 |
| ENSMUST00000163083:Cyb5]chr18]- | 60891 | 84879761 | chr18:848793503-848798621 | 0.936 | -0.064 | 8.46E-11 | 1.85E-08 | N | 0.064 |
| ENSMUST00000130394:Atp1b2]chr11]- | 7638254 | 69600340 | chr11:695999741-69601412 | 0.434 | -0.064 | 8.89E-05 | 0.003663971 | N | 0.064 |
| ENSMUST00000118878:vsnlabp]chr11]- | 97117 | 151356053 | chr11:151355167-151356798 | 0.954 | -0.064 | 0.008099119 | 0.025767265 | N | 0.064 |
| ENSMUST00000144645:Fam18a]chr2]- | 4710 | 12348100 | chr2:12347920-12348203 | 0.964 | -0.064 | 8.15E-05 | 0.003415919 | N | 0.064 |
| ENSMUST00000041723:Ztbhc17]chr10]- | 48334.2 | 109443202 | chr10:110943782-110944531 | 0.946 | -0.0635 | 0.000779471 | 0.021272664 | N | 0.0635 |
| ENSMUST00000136671:Bcas1]chr2]- | 229427.7 | 170347428 | chr2:170347148-170348148 | 0.798 | -0.063 | 0.000180121 | 0.006562784 | N | 0.063 |
| ENSMUST00000129589:Azin1]chr15]- | 357116 | 384897221 | chr15:384848241-384904721 | 0.848 | -0.063 | 0.000566387 | 0.016230034 | N | 0.063 |
| ENSMUST00000040109:Cnta]chr15]+ | 431578.2 | 923407471 | chr15:923395113-923341953 | 0.998 | -0.063 | 4.59E-24 | 7.27E-21 | N | 0.063 |
| ENSMUST00000110329:Azin1]chr15]- | 35721 | 384897221 | chr15:384848238-384904721 | 0.848 | -0.063 | 0.000448641 | 0.013598689 | N | 0.063 |
| ENSMUST00000134536:Tryb1]chr7]+ | 180386013 | 41349381 | chr7:41343511-41354071 | 0.38 | -0.0625 | 8.67E-05 | 0.003600136 | N | 0.0625 |
| ENSMUST00000136936:Segsm1]chr11]- | 407157 | 502000601 | chr11:502006167-502009471 | 0.89 | -0.0625 | 6.21E-07 | 5.86E-05 | N | 0.0625 |
| ENSMUST00000177814:Cadps]chr14]- | 190023.7 | 123729101 | chr14:123725651-123737931 | 0.76 | -0.0625 | 2.28E-05 | 0.001194886 | N | 0.0625 |
| ENSMUST00000066401:Ctsd]chr7]- | 183009 | 142376497 | chr7:142375929-142376738 | 0.272 | -0.062 | 0.000501529 | 0.014965431 | N | 0.062 |
| ENSMUST00000047899:Atp1b2]chr1]- | 7679756 | 696003401 | chr1:6959997361-69601412 | 0.444 | -0.0615 | 0.00301096 | 0.0043857341 | N | 0.0615 |

Fig. 17, Continued

| | | | | | | | | |
|---|---|---|---|---|---|---|---|---|
| ENSMUST00000107052 4|Tgtp|chr6|- | 48437.2 | 72610643 | chr6:72608432-72612110 | 0.974 | -0.0615 | 2.93E-06 | 0.00021637 | N | 0.0615 |
| ENSMUST00000148750|Sk4a4|chr5|+ | 110205.1 | 89238339 | chr5:89235507-89239653 | 0.944 | -0.0615 | 0.00016078 | 0.0016035547 | N | 0.0615 |
| ENSMUST00000049357|Pnrc1|chr4|- | 42383.8 | 332246219 | chr4:332245423-332246507 | 0.996 | -0.061 | 1.24E-06 | 0.0001105408 | N | 0.061 |
| ENSMUST00000039121|Calr|chr8|- | 480792.3 | 84842231 | chr8:84841850-84842844 | 0.166 | -0.061 | 8.98E-05 | 0.003688338 | N | 0.061 |
| ENSMUST00000033734|Ap1s2|chrX|+ | 31563.4 | 163933016 | chrX:163932133-163933359 | 0.948 | -0.0605 | 0.0008065839 | 0.018463354 | N | 0.0605 |
| ENSMUST00000150853|Kif1b|chr4|- | 727121.9 | 149179936 | chr4:149178018-149180810 | 0.818 | -0.0605 | 0.0010128826 | 0.0049951845 | N | 0.0605 |
| ENSMUST00000174193|Mob|p|chr9|+ | 380045.76 | 120180538 | chr9:120179525-120181484 | 0.238 | -0.0605 | 3.64E-15 | 1.44E-12 | N | 0.0605 |
| ENSMUST00000126094|Rpl0|chr5|- | 2965072 | 65388478 | chr5:65388365-65388679 | 0.54 | -0.06 | 5.67E-05 | 0.002605198 | N | 0.06 |
| ENSMUST00000140845|Ap1s2|chrX|+ | 31670 | 163933013 | chrX:163932133-163933356 | 0.952 | -0.0595 | 0.0001061207 | 0.0173334999 | N | 0.0595 |
| ENSMUST00000136455|Uhe2w|chr1|- | 729.7 | 16585230 | chr1:16584158-16585431 | 0.898 | -0.0595 | 0.0015408 | 0.03523321 | N | 0.0595 |
| ENSMUST00000191109|Ywhah|chr5|+ | 4851871.2 | 330226863 | chr5:330226542-330227966 | 0.452 | -0.0595 | 5.46E-07 | 5.18E-05 | N | 0.0595 |
| ENSMUST00000102774|Sgsm1|chr1|- | 438502.8 | 50200609 | chr1:50200152-50200947 | 0.918 | 0.0595 | 2.73E-10 | 5.33E-08 | N | 0.0595 |
| ENSMUST00000035295|Dgg1|chr1|- | 182255.3 | 182276692 | chr1:182275772-182276893 | 0.878 | -0.0595 | 0.00209907 | 0.045103112 | N | 0.0595 |
| ENSMUST00000082437|Sep15|chr3|- | 128042.9 | 144597283 | chr3:144596823-144597680 | 0.532 | -0.0595 | 0.00134226 | 0.031606379 | N | 0.0595 |
| ENSMUST00000052798|Pages3|chr10|+ | 245986 | 1280076934 | chr10:1280076067-1280077272 | 0.934 | -0.059 | 0.00045314 | 0.0137056689 | N | 0.059 |
| ENSMUST00000151045|Gna1|chr11|+ | 324607.1 | 57329091 | chr11:57327443-57330240 | 0.884 | -0.059 | 0.00105908 | 0.026838694 | N | 0.059 |
| ENSMUST00000036315|Grla1|chr11|+ | 324287.8 | 573929091 | chr11:57327443-57330244 | 0.884 | -0.059 | 0.00106066 | 0.0268386694 | N | 0.059 |
| ENSMUST00000094179|Gna1|chr11|+ | 324394.6 | 57329091 | chr11:57327443-57330243 | 0.884 | -0.059 | 0.00105596 | 0.0268815044 | N | 0.059 |
| ENSMUST00000049941|Scn3b|chr9|+ | 9819.9 | 402389819 | chr9:402288544-402291618 | 0.994 | -0.059 | 8.99E-06 | 0.000549517 | N | 0.059 |
| ENSMUST00000149656|Scn3b|chr9|+ | 9811.1 | 402389819 | chr9:402288544-402291617 | 0.994 | -0.059 | 8.85E-06 | 0.000547172 | N | 0.059 |
| ENSMUST00000102751|Vdac1|chr11|- | 7136755.6 | 52389035 | chr11:52189432-52389397 | 0.654 | 0.0585 | 4.17E-05 | 0.0019981721 | N | 0.0585 |
| ENSMUST00000125295|Sorbs2|chr8|+ | 107768.8 | 458227296 | chr8:458825745-458227904 | 0.848 | -0.058 | 0.00055849 | 0.0161383111 | N | 0.058 |
| ENSMUST00000262270|Sacm1|chr9|- | 45424.1 | 1235911002 | chr9:1235590801-1235592598 | 0.968 | -0.058 | 5.76E-05 | 0.0026632025 | N | 0.058 |
| ENSMUST00000139869|Sorbs2|chr8|+ | 107707.5 | 458277296 | chr8:458825745-458277903 | 0.848 | -0.058 | 0.00058931 | 0.016723797 | N | 0.058 |
| ENSMUST00000135336|Sorbs2|chr8|+ | 108226.3 | 458227276 | chr8:458825745-458227873 | 0.84 | -0.0575 | 0.0004296 | 0.013189976 | N | 0.0575 |
| ENSMUST00000139965|Gna3|chrX|+ | 109681 | 416771149 | chrX:416763440-416788598 | 0.952 | -0.057 | 1.04E-05 | 0.000614522 | N | 0.057 |
| ENSMUST00000166704|Sorbs2|chr8|+ | 107905.9 | 458227296 | chr8:458825745-458227906 | 0.854 | -0.0565 | 0.00049973 | 0.0148316811 | N | 0.0565 |
| ENSMUST00000107048|Rab6|chr7|+ | 25498809.8 | 1006640563 | chr7:1006139255-100641268 | 0.834 | -0.0565 | 6.17E-12 | 1.63E-09 | N | 0.0565 |
| ENSMUST00000141192|Ttc3|chr16|+ | 1279262 | 944599963 | chr16:944459762-944460077 | 0.754 | -0.0565 | 0.00134045 | 0.031606379 | N | 0.0565 |
| ENSMUST00000048976|Gucy1a3|chr3|- | 27279.8 | 820946983 | chr3:820922428-820944899 | 0.914 | 0.056 | 0.00195593 | 0.042736401 | N | 0.056 |
| ENSMUST00000066652|Kaltius220|chr12|+ | 232566.7 | 250506823 | chr12:250566582-250596697 | 0.988 | -0.0555 | 1.63E-07 | 1.65E-05 | N | 0.0555 |
| ENSMUST00000174606|Ugerb|chr13|- | 34285.3 | 669901367 | chr13:669001061-669901568 | 0.948 | -0.0555 | 2.75E-12 | 7.68E-10 | N | 0.0555 |
| ENSMUST00000169825|Cntnl|chr15|- | 4376569 | 923340747 | chr15:923339513-923411967 | 1 | -0.055 | 4.95E-22 | 4.70E-19 | N | 0.055 |
| ENSMUST00000109686|Neto2|chr8|- | 25747.2 | 856640915 | chr8:856365688-456641116 | 0.98 | -0.055 | 0.00058037 | 0.016502758 | N | 0.055 |
| ENSMUST00000159078|Spp|cap|chr1|- | 111372.6 | 832256028 | chr18:83255442-832257270 | 0.85 | -0.055 | 0.00013456 | 0.0051166852 | N | 0.055 |

Fig. 17, Continued

| | | | | | | | |
|---|---|---|---|---|---|---|---|
| ENSMUST00000048309|Camsap2|chr1|- | 70203.2 | 1362270876 | chr1:136268123-136271147 | 0.98 | -0.055 | 9.47E-06 | 0.000568308 | N | 0.055 |
| ENSMUST00000085374|Ska17a7|chr7|+ | 1935374.5 | 45175749 | chr7:45174751-45176138 | 0.262 | -0.0545 | 0.00173005 | 0.038874389 | N | 0.0545 |
| ENSMUST00000076349|Gria3|chrX|+ | 110103.9 | 41677149 | chrX:41676340-41678601 | 0.952 | -0.0545 | 9.24E-06 | 0.000562289 | N | 0.0545 |
| ENSMUST00000184200|Ncdd4|chr9|+ | 167791.9 | 727473863 | chr9:727471126-727448158 | 0.834 | -0.054 | 0.0008498 | 0.022756116 | N | 0.054 |
| ENSMUST00000075312|Trick|chr18|+ | 7736358.2 | 206673865 | chr18:206673631-206674324 | 0.226 | 0.054 | 5.65E-08 | 6.28E-06 | N | 0.054 |
| ENSMUST00000070112|Ndufa8|chr2|- | 8771.9 | 36036415 | chr2:36036320-36036641 | 0.946 | -0.054 | 6.65E-05 | 0.0029072278 | N | 0.054 |
| ENSMUST00000025563|Fth1|chr19|- | 20429803 | 9984082 | chr19:9984781-9985092 | 0.474 | -0.054 | 7.86E-20 | 6.08E-17 | N | 0.054 |
| ENSMUST00000063301|Far1|chr7|+ | 437716.9 | 1135609211 | chr7:1135689995-113571511 | 0.934 | -0.054 | 0.00170249 | 0.029283177 | N | 0.054 |
| ENSMUST00000127652|Tmem59|chr4|+ | 2472281.7 | 1072200706 | chr4:1072200168-107200994 | 0.794 | -0.054 | 0.0117866 | 0.039830727 | N | 0.054 |
| ENSMUST00000138240|asmp1|chr8|+ | 1310559.5 | 131174930 | chr8:131174419-131175338 | 0.276 | -0.0535 | 0.000994458 | 0.024847828 | N | 0.0535 |
| ENSMUST00000154650|Beast1|chr2|- | 203724 | 170347393 | chr2:170346991-170348148 | 0.796 | -0.0535 | 0.00101412 | 0.0262219835 | N | 0.0535 |
| ENSMUST00000145806|Atp6ap1|chrX|+ | 53882.1 | 74303559 | chrX:74303358-74304013 | 0.726 | -0.0535 | 0.00146233 | 0.0337093397 | N | 0.0535 |
| ENSMUST00000122941|Zf|chr15|+ | 243444.2 | 121841160 | chr15:121839959-121185683 | 0.906 | -0.0535 | 3.73E-08 | 4.24E-06 | N | 0.0535 |
| ENSMUST00000025290|fnpact|chr18|- | 40268.8 | 129908922 | chr18:129904933-129932948 | 0.948 | -0.053 | 3.11E-07 | 3.05E-05 | N | 0.053 |
| ENSMUST00000109815|Camk2b|chr11|- | 124180.7 | 5969831 | chr11:5969672-5970131 | 0.84 | -0.0525 | 0.00020261 | 0.007270489 | N | 0.0525 |
| ENSMUST00000069600|Ndrg3|chr2|- | 9579965.2 | 156028106 | chr2:156027345-156028881 | 0.962 | -0.052 | 3.48E-12 | 9.36E-10 | N | 0.052 |
| ENSMUST00000031138|Ran|chr5|+ | 1564886.6 | 129023505 | chr5:129022774-129024323 | 0.972 | -0.052 | 0.000425653 | 0.0131248 | N | 0.052 |
| ENSMUST00000081104|Timm17a|chr1|- | 61821.7 | 1353011757 | chr1:135301532-135302003 | 0.948 | 0.052 | 4.38E-07 | 4.24E-05 | N | 0.052 |
| ENSMUST00000034965|Snapc5|chr9|+ | 6295.8 | 641182507 | chr9:641182142-641N2684 | 0.984 | -0.0515 | 0.00092088 | 0.0243N4545 | N | 0.0515 |
| ENSMUST00000154358|Gdi1|chrX|+ | 599140.5 | 74311200 | chrX:74310787-74311862 | 0.354 | -0.0515 | 0.00023129 | 0.0081358839 | N | 0.0515 |
| ENSMUST00000107924|Se|chr3|- | 40452.4 | 585924550 | chr3:585909595-58593113 | 0.794 | -0.0515 | 0.00194196 | 0.042627329 | N | 0.0515 |
| ENSMUST00000149391|Gdi1|chrX|+ | 5531837.8 | 74311201 | chrX:74310638-74311858 | 0.354 | -0.0515 | 0.00027109 | 0.0092261389 | N | 0.0515 |
| ENSMUST00000146613|Gdi1|chrX|+ | 600181.9 | 74311200 | chrX:74310787-74311800 | 0.354 | -0.0515 | 0.00023064 | 0.0081333008 | N | 0.0515 |
| ENSMUST00000083036|Tmem59|chr4|+ | 2469312 | 1072007006 | chr4:1072200368-107220996 | 0.794 | -0.0515 | 0.001531199 | 0.035144531 | N | 0.0515 |
| ENSMUST00000206657|Hpc2|chr11|- | 1520473 | 519856421 | chr11:51985497-519868810 | 0.494 | -0.0515 | 0.00220661 | 0.047059021 | N | 0.0515 |
| ENSMUST00000188666|310035E148Rik|chr3|+ | 217022.5 | 96265372 | chr1:96624713-9627143 | 0.956 | -0.051 | 3.52E-06 | 0.0002248566 | N | 0.053 |
| ENSMUST00000132139|Sorbs2|chr8|+ | 1078344 | 458272596 | chr8:45825745-458237905 | 0.848 | -0.0505 | 0.000532863 | 0.01545964 | N | 0.0505 |
| ENSMUST00000147307|Eno2|chr6|- | 2792224.7 | 1247600535 | chr6:1247600653-1247617006 | 0.168 | -0.0505 | 1.78E-05 | 0.0009074927 | N | 0.0505 |
| ENSMUST00000119661|Txyh1|chr7|+ | 1943194.7 | 4134938 | chr7:4134351-4135330 | 0.34 | -0.05 | 0.000886353 | 0.0229972274 | N | 0.05 |
| ENSMUST00000113876|Arhgef9|chrX|- | 275573.7 | 950499844 | chrX:95048935-95052154 | 0.94 | -0.05 | 7.4E-06 | 0.0004475626 | N | 0.05 |
| ENSMUST00000113833|Arhgef9|chrX|- | 275790 | 950499844 | chrX:950489930-95052154 | 0.94 | -0.05 | 7.41E-06 | 0.0004475626 | N | 0.05 |
| ENSMUST000000013883|Gltb|chr10|+ | 10552.4 | 799910321 | chr10:799910238-799910532 | 0.95 | 0.05 | 1.66E-06 | 0.00013334 | N | 0.05 |
| ENSMUST00000029654|Gltb|chr3|- | 548077.7 | 808444064 | chr3:808443599-808845257 | 0.61 | -0.05 | 0.010088509 | 0.0235244245 | N | 0.05 |
| ENSMUST00000200831|Zxint|chr10|+ | 3271561.1 | 726742223 | chr10:7267396662-26674964 | 0.76 | -0.05 | 8.69E-07 | 7.69E-05 | N | 0.05 |
| ENSMUST00000113820|Arhgef9|chrX|- | 2760574 | 950499844 | chrX:950489944-950502154 | 0.94 | -0.05 | 6.93E-06 | 0.0004453163 | N | 0.05 |

Fig. 17, Continued

| | | | | | | | | |
|---|---|---|---|---|---|---|---|---|
| ENSMUST00000110329:Oxr1|chr1:5|+ | 252392.6 | 418594407 | chr15:41859158-41861045 | 0.882 | -0.0495 | 1.95E-06 | 0.0001152136 | N | 0.0495 |
| ENSMUST00000134496:Cank2a|chr18|- | 292.2 | 609941488 | chr18:609941287-609943378 | 0.942 | -0.0495 | 0.00017231 | 0.00638181 | N | 0.0495 |
| ENSMUST00000022918:Oxr1|chr15|+ | 252143.4 | 418594407 | chr15:41859158-41861048 | 0.882 | -0.0495 | 2.57E-06 | 0.0001189082 | N | 0.0495 |
| ENSMUST00000088169:Rbn3|chr19|- | 4640171.2 | 7427473 | chr19:7427028-7427875 | 0.612 | -0.0495 | 5.65E-08 | 6.28E-06 | N | 0.0495 |
| ENSMUST00000165629:Acsbl|chr5|- | 72131.6 | 1429052275 | chr5:142904766-142905476 | 0.754 | -0.049 | 0.00022935 | 0.008107343 | N | 0.049 |
| ENSMUST00000193448:P62|chr3|- | 496981.4 | 578842882 | chr3:578419105-57843314 | 0.974 | -0.049 | 3.62E-15 | 1.44E-12 | N | 0.049 |
| ENSMUST00000158201:Cux1|chr11|- | 194409.3 | 502901143 | chr1:502983838-50299344 | 0.164 | -0.049 | 5.98E-05 | 0.002687973 | N | 0.049 |
| ENSMUST00000148295:Fbxp1a|chr2|- | 44903.1 | 1515596559 | chr2:151559458-151559828 | 0.784 | -0.049 | 0.00027574 | 0.048244283 | N | 0.049 |
| ENSMUST00000116403:Hmpki|chr13|- | 824391.5 | 583915.16 | chr3:583912142-58392476 | 0.796 | -0.0485 | 2.52E-05 | 0.0012926685 | N | 0.0485 |
| ENSMUST00000019344:Ssbp3|chr4|+ | 1226268 | 1070048365 | chr4:1070480024-1070048498 | 0.952 | -0.048 | 7.64E-06 | 0.000486207 | N | 0.048 |
| ENSMUST00000206576:Cong1|chr11|- | 22818.6 | 40750412 | chr11:40748552-40751059 | 1 | -0.0475 | 1.29E-05 | 0.000743981 | N | 0.0475 |
| ENSMUST00000199533:Rsf1d1|chr16|- | 14962 | 111193252 | chr16:11192970-11193737 | 0.98 | -0.0475 | 0.00054725 | 0.0159100537 | N | 0.0475 |
| ENSMUST00000132017:Vps54|chr11|- | 2884.5 | 213199054 | chr1:211319753-21320324 | 1 | -0.0475 | 0.00086365 | 0.022997274 | N | 0.0475 |
| ENSMUST00000221975:Scamp1|chr13|- | 337421.2 | 942025.42 | chr1:94201310-94204163 | 0.97 | -0.0475 | 7.5E-07 | 6.83E-05 | N | 0.0475 |
| ENSMUST00000182213:Arhgap12|chr18|- | 4876.9 | 60264.70 | chr18:60254197-6026730 | 0.992 | -0.047 | 0.00173958 | 0.038965389 | N | 0.047 |
| ENSMUST00000067602:Nenm2|chr16|+ | 2731.3 | 816233747 | chr16:816233342-816242285 | 0.992 | -0.047 | 0.00039612 | 0.012568164 | N | 0.047 |
| ENSMUST00000033040:Pak1|chr7|- | 4692833.1 | 979111646 | chr7:979110962-97912381 | 0.982 | -0.047 | 5.20E-13 | 1.64E-10 | N | 0.047 |
| ENSMUST00000142939:Ppp2cα|chr11|- | 8460 | 522119344 | chr2:521191432-52119692 | 0.946 | -0.0465 | 4.40E-13 | 1.41E-10 | N | 0.0465 |
| ENSMUST00000029299:Rumd3a|chr6|- | 55908.6 | 713911667 | chr6:71388634-71393188 | 0.974 | -0.0465 | 0.010315461 | 0.010431823 | N | 0.0465 |
| ENSMUST00000130606:Capza2|chr6|+ | 26174.9 | 176655505 | chr6:176655295-17665588 | 0.788 | -0.0455 | 0.00051602 | 0.015188617 | N | 0.0455 |
| ENSMUST00000025117:Cetl6|chr18|- | 12376558 | 25479428 | chr18:25477632-25479711 | 0.82 | -0.045 | 0.00112608 | 0.027770883 | N | 0.045 |
| ENSMUST00000033519:DynlH3|chrX|- | 154236.4 | 9655300 | chrX:9654267-9656063 | 0.99 | -0.045 | 4.74E-09 | 7.03E-07 | N | 0.045 |
| ENSMUST00000200027:Serinc1|chr10|- | 4216820.6 | 575516212 | chr10:575515774-575517292 | 0.8 | -0.045 | 1.28E-17 | 6.50E-15 | N | 0.045 |
| ENSMUST00000066958:205pp|chrX|- | 836550.8 | 76529.59 | chrX:76527.11-7653256 | 0.212 | -0.0445 | 2.67E-07 | 2.64E-05 | N | 0.0445 |
| ENSMUST00000032413:Ebnk1|chr6|- | 323835 | 143205265 | chr6:143203384-143208542 | 0.922 | -0.0445 | 0.001151278 | 0.034791139 | N | 0.0445 |
| ENSMUST00000028266:Chgb|chr2|+ | 7356768.4 | 1327944987 | chr2:1327947521-132795079 | 0.858 | -0.0445 | 0.00012085 | 0.0047429692 | N | 0.0445 |
| ENSMUST00000146178:Humpnk|chr17|- | 91387.7 | 336646416 | chr17:336646233-336646659 | 0.956 | 0.044 | 3.05E-05 | 0.001524453 | N | 0.044 |
| ENSMUST00000152831:Arp2b2|chr6|- | 859125.5 | 113746669 | chr6:113745670-113748848 | 0.864 | -0.044 | 0.00181016 | 0.040230241 | N | 0.044 |
| ENSMUST00000089003:Arp2b2|chr6|- | 8589663 | 113746669 | chr6:1137456069-11374848 | 0.864 | -0.044 | 0.00216064 | 0.046216689 | N | 0.044 |
| ENSMUST00000045054:Fam115a|chr6|- | 110717.1 | 42669435 | chr6:42668002-42670323 | 0.984 | -0.044 | 1.46E-06 | 0.000121145 | N | 0.044 |
| ENSMUST00000029271:Trpc3|chr3|- | 48173.7 | 50822322 | chr3:50820482-50822433 | 0.956 | 0.044 | 0.00022008 | 0.0097857778 | N | 0.044 |
| ENSMUST00000100824:Calm1|chr12|+ | 11675216.7 | 1002069963 | chr12:100206400-100208988 | 0.448 | -0.0435 | 0.00191539 | 0.0422394494 | N | 0.0435 |
| ENSMUST00000004965:Chmp2b|chr16|- | 29544 | 65539991 | chr16:65539133-65540250 | 0.988 | -0.043 | 7.48E-06 | 0.0004779787 | N | 0.043 |
| ENSMUST00000169034:Tnk|chr2|+ | 27105.8 | 286668117 | chr3:28667899-28670585 | 1 | -0.0425 | 0.0002984 | 0.0099555515 | N | 0.043 |

Fig. 17, Continued

| | | | | | | | | |
|---|---|---|---|---|---|---|---|---|
| ENSMUST00000101045|Atp2b2|chr6;- | 8594470.5 | 113746669 | chr6:113746675-113748848 | 0.86 | -0.0425 | 0.001157518 | 0.03594121 | N | 0.0425 |
| ENSMUST00000066882|Pfn2|chr3;- | 547702.7 | 578428832 | chr3:578418195-578443314 | 0.98 | -0.0425 | 3.85E-17 | 1.83E-14 | N | 0.0425 |
| ENSMUST00000078528|C1qtnp|chr11;- | 64229.2 | 709977951 | chr1:709977836-709978244 | 0.94 | 0.0425 | 0.010067609 | 0.018883412 | N | 0.0425 |
| ENSMUST00000130946|Hnrnph|chr17;- | 92800.7 | 336446416 | chr17:336462339-336446659 | 0.958 | 0.042 | 3.06E-05 | 0.001524453 | N | 0.042 |
| ENSMUST00000050552|Bzw1|chr1;+ | 145936.5 | 584059905 | chr1:584056035-58406548 | 0.954 | -0.0415 | 5.87E-05 | 0.002653579 | N | 0.0415 |
| ENSMUST00000226939|Nef|chr14;+ | 409306.8 | 680088044 | chr14:680087308-680189095 | 0.786 | -0.041 | 0.000062224 | 0.017518501 | N | 0.041 |
| ENSMUST00000141446|Pahpnt1|chr14;+ | 23554.6 | 548897322 | chr14:548897121-548977557 | 0.952 | 0.0405 | 9.34E-06 | 0.000566043 | N | 0.0405 |
| ENSMUST00000149968|Usp11|chrX;+ | 668868.7 | 207119967 | chrX:207119766-20720537 | 0.96 | 0.04 | 2.35E-06 | 0.000176277 | N | 0.04 |
| ENSMUST00000103838|Usp11|chrX;+ | 673879 | 207119967 | chrX:207119766-20720539 | 0.96 | 0.04 | 2.32E-06 | 0.000175078 | N | 0.04 |
| ENSMUST00000132300|Prmt6|chr6;- | 350099.9 | 127689707 | chr6:127689011-127689908 | 0.96 | 0.04 | 0.00202874 | 0.044057087 | N | 0.04 |
| ENSMUST00000149393|Snhg1|chr2;+ | 584354.7 | 158381339 | chr2:158380939-158381590 | 0.89 | 0.04 | 8.75E-05 | 0.003620329 | N | 0.04 |
| ENSMUST00000111212|Slc1a2|chr2;- | 19558.7 | 102781664 | chr2:102781463-102781743 | 0.948 | 0.0395 | 0.001141743 | 0.032994566 | N | 0.0395 |
| ENSMUST00000144978|Mdh1|chr11;- | 4076981.7 | 21559674 | chr11:21559522-21559875 | 0.152 | -0.0395 | 2.51E-09 | 3.84E-07 | N | 0.0395 |
| ENSMUST00000042564|Gfm|chr14;- | 746748.6 | 371209343 | chr14:371209443-371122226 | 0.344 | -0.039 | 0.001140675 | 0.032853302 | N | 0.039 |
| ENSMUST00000092777|Spag9|chr11;+ | 255069.4 | 941236822 | chr11:941227222-94126080 | 0.964 | 0.04 | 0.000012631 | 0.004889714 | N | 0.039 |
| ENSMUST00000174526|Hnrnp|chr7;+ | 220551.8 | 208221330 | chr7:288221848-288222244 | 0.946 | 0.04 | 0.00041427 | 0.012942208 | N | 0.039 |
| ENSMUST00000041956|Spag9|chr11;+ | 254819.1 | 941236822 | chr11:941227222-94126085 | 0.964 | -0.039 | 0.000126 | 0.004889714 | N | 0.039 |
| ENSMUST00000249979|Spag9|chr11;+ | 254882.5 | 941236822 | chr11:941227222-94126083 | 0.964 | -0.039 | 0.000126 | 0.004889714 | N | 0.039 |
| ENSMUST00000193299|Srp19|chr18;+ | 20148.7 | 343363000 | chr18:343369099-34336421 | 0.962 | 0.038 | 3.18E-05 | 0.001562268 | N | 0.038 |
| ENSMUST00000124047|Gm12234|chr11;- | 1446.5 | 543404483 | chr1:543340369-54340684 | 0.962 | 0.038 | 0.00092905 | 0.024555302 | N | 0.038 |
| ENSMUST00000348787|Tmcm30a|chr9;+ | 7291881 | 797711144 | chr9:797768943-79771479 | 1 | -0.0375 | 3.77E-24 | 6.72E-21 | N | 0.0375 |
| ENSMUST00000133567|Ptrk|chr4;- | 80267 | 4134236 | chr4:4134112-4134507 | 0.932 | -0.037 | 0.00151414 | 0.034793139 | N | 0.037 |
| ENSMUST00000138968|Chd4|chr6;+ | 14843.6 | 1251144692 | chr6:1251142291-125114621 | 0.956 | 0.0365 | 0.000034598 | 0.01124565 | N | 0.0365 |
| ENSMUST00000127286|Ndfip2|chr14;+ | 218455.8 | 105308317 | chr14:105308116-105308803 | 0.964 | 0.036 | 2.92E-05 | 0.001463204 | N | 0.036 |
| ENSMUST00000163246|Slc25a3|chr10;- | 2473519 | 911116885 | chr10:911116791-911117124 | 0.964 | 0.036 | 8.51E-24 | 1.01E-20 | N | 0.036 |
| ENSMUST00000074477|Bsrp|chr7;- | 2255904 | 288221130 | chr7:288221848-288222240 | 0.954 | 0.036 | 3.94E-05 | 0.0013895622 | N | 0.036 |
| ENSMUST00000029414|Ses3|chr3;- | 1063611 | 653181556 | chr3:653379655-653182034 | 0.986 | -0.036 | 1.48E-05 | 0.000839566 | N | 0.036 |
| ENSMUST00000170810|Slc25a3|chr10;- | 2473519 | 911116885 | chr10:911116792-911117124 | 0.964 | 0.036 | 8.51E-24 | 1.01E-20 | N | 0.036 |
| ENSMUST00000121138|Dync112|chr2;- | 238814.2 | 712631004 | chr2:712632648-712631293 | 0.952 | -0.0355 | 0.000661727 | 0.017413173 | N | 0.0355 |
| ENSMUST00000182112|Ank2|chr3;- | 713485.5 | 1269231165 | chr3:1269221612-126923971 | 0.968 | -0.0355 | 1.61E-05 | 0.000901504 | N | 0.0355 |
| ENSMUST00000120164|Atf2|chr2;- | 558461 | 738177797 | chr2:738816509-73819148 | 1 | -0.035 | 6.99E-07 | 6.43E-05 | N | 0.035 |
| ENSMUST00000152728|Sept7|chr9;+ | 9208754 | 253077144 | chr9:253075513-25308571 | 0.712 | -0.0345 | 3.53E-05 | 0.001708403 | N | 0.0345 |
| ENSMUST00000136788|Atp5a1|chr18;+ | 1707156.1 | 777825002 | chr18:777823101-77782655 | 0.604 | -0.034 | 0.000566652 | 0.016271404 | N | 0.034 |
| ENSMUST00000123803|Atp5b|chr10;+ | 1920398 | 128089158 | chr10:128089057-128089681 | 0.954 | -0.034 | 2.62E-12 | 7.52E-10 | N | 0.034 |
| ENSMUST00000124760|Eno2|chr6;- | 26960992 | 124761036 | chr6:124760055-124761362 | 0.144 | -0.034 | 0.00022746 | 0.0080869 | N | 0.034 |

Fig. 17, Continued

| | | | | | | | |
|---|---|---|---|---|---|---|---|
| ENSMUST00000118258|Anok2|chr3|- | 7134412.7 | 126923165 | chr3:126921608-126923971 | 0.968 | -0.033 | 1.96E-05 | 0.0010055002 | N | 0.033 |
| ENSMUST00000182704|Ank2|chr3|- | 7134467.7 | 126923165 | chr3:126921606-126923971 | 0.968 | -0.033 | 2.37E-05 | 0.0012134314 | N | 0.033 |
| ENSMUST00000112144|Dync1i2|chr2|- | 258031.2 | 71263004 | chr2:71262648-71263297 | 0.96 | -0.0325 | 0.00027443 | 0.009330478 | N | 0.0325 |
| ENSMUST00000027863|Atp1b1|chr1|- | 3106784.1 | 164437717 | chr1:164437267-164438539 | 0.22 | -0.0325 | 2.57E-06 | 0.0001890082 | N | 0.0325 |
| ENSMUST00000026495|Atp5al|chr18|- | 1278792 | 77782502 | chr18:77782301-77782869 | 0.54 | -0.0325 | 0.00047985 | 0.01436118 | N | 0.0325 |
| ENSMUST00000176191|Kcnip4|chr5|- | 4522.8.7 | 483903.57 | chr5:48389504-483909.56 | 1 | -0.0325 | 1.69E-06 | 0.000134112 | N | 0.0325 |
| ENSMUST00000087395|Kcnip4|chr5|- | 45304.3 | 483903.57 | chr5:48389502-483909.56 | 1 | -0.0325 | 3.41E-06 | 0.000241868 | N | 0.0325 |
| ENSMUST00000364551|Atf2|chr2|- | 56676.2 | 73817797 | chr2:73816520-73819148 | 1 | -0.0325 | 1.41E-06 | 0.000117971 | N | 0.0325 |
| ENSMUST00000147148|Atp5a|chr18|- | 1283925.3 | 777825.02 | chr18:77782301-77782866 | 0.54 | -0.0325 | 0.00051006 | 0.015075355 | N | 0.0325 |
| ENSMUST00000175660|Kcnip4|chr5|- | 45228.7 | 483903.57 | chr5:48389503-483909.56 | 1 | -0.0325 | 1.69E-06 | 0.000134112 | N | 0.0325 |
| ENSMUST00000106099|Atf2|chr2|- | 56153 | 73817797 | chr2:73816524-73819148 | 1 | -0.0325 | 1.41E-06 | 0.000117971 | N | 0.0325 |
| ENSMUST00000145364|D4Wsu53e|chr4|+ | 2279959.1 | 134927248 | chr4:134926931-134927372 | 0.602 | -0.032 | 0.00041149 | 0.01291194 | N | 0.032 |
| ENSMUST00000138283|Ndfip2|chr14|- | 1999991.2 | 105308117 | chr14:105308116-105308871 | 0.968 | 0.032 | 5.87E-05 | 0.002653579 | N | 0.032 |
| ENSMUST00000112139|Dync1i2|chr2|- | 2577786.4 | 71263004 | chr2:71262651-71263294 | 0.958 | 0.032 | 0.00044183 | 0.0115071113 | N | 0.032 |
| ENSMUST00000149781|Ndfip2|chr14|- | 200638 | 105308317 | chr14:105308116-105308869 | 0.968 | 0.032 | 5.87E-05 | 0.002653579 | N | 0.032 |
| ENSMUST00000115361|Cadps2|chr6|- | 697404.7 | 232623839 | chr6:232623839-23263716 | 0.968 | 0.032 | 0.000355329 | 0.01602066 | N | 0.032 |
| ENSMUST00000142913|Cadps2|chr6|- | 697404.7 | 232623515 | chr6:232623838-232623716 | 0.968 | 0.032 | 0.000553.29 | 0.01602066 | N | 0.032 |
| ENSMUST00000102592|Tjp1|chr7|- | 3483.5.3 | 652997093 | chr7:652961.65-652977667 | 0.994 | -0.0315 | 0.00171438 | 0.03858309 | N | 0.0315 |
| ENSMUST00000086526|Htatsf1|chrX|- | 668.71.4 | 570667753 | chrX:570656.46-570671.83 | 0.976 | -0.031 | 0.01207.307 | 0.146679285 | N | 0.031 |
| ENSMUST00000028938|Cst3|chr2|- | 1766295.7 | 148871842 | chr2:148871722-1488720.43 | 0.146 | -0.031 | 1.44E-06 | 0.000120658 | N | 0.031 |
| ENSMUST00000143570|Eef1a1|chr9|- | 304017 | 78478991 | chr9:78478912-78479192 | 0.886 | -0.031 | 7.39E-09 | 1.07E-06 | N | 0.031 |
| ENSMUST00000061158|Commd3|chr2|+ | 527807 | 18676063 | chr2:186758.67-18676231 | 0.964 | 0.031 | 0.000529.57 | 0.015459564 | N | 0.031 |
| ENSMUST00000171845|Commd3|chr2|+ | 529636 | 186760.68 | chr2:186758.67-186760230 | 0.964 | 0.031 | 0.000529.57 | 0.015459564 | N | 0.031 |
| ENSMUST00000138413|Mapk1|chr16|- | 45145 | 170236.53 | chr16:170234.52-17024055 | 0.962 | 0.0305 | 7.19E-05 | 0.003057631 | N | 0.0305 |
| ENSMUST00000102735|Slc4a10|chr2|- | 2900086.7 | 623255.48 | chr2:623247.25-62326730 | 0.98 | -0.03 | 4.70E-05 | 0.002201395 | N | 0.03 |
| ENSMUST00000159815|Sgsm1|chr1|- | 5729865 | 50200619 | chr1:50200115-502009.47 | 0.97 | 0.03 | 9.51E-10 | 1.58E-07 | N | 0.03 |
| ENSMUST00000040766|Tmed10|chr14|- | 1236640.6 | 853433.48 | chr14:853406.14-853443549 | 0.97 | 0.03 | 0.00095166 | 0.024921498 | N | 0.03 |
| ENSMUST00000181221|Cadps2|chr6|- | 708011 | 232623515 | chr6:232623.23-23263716 | 0.97 | 0.03 | 0.00108217 | 0.027046753 | N | 0.03 |
| ENSMUST00000165134|Sec23o|chr12|- | 51677 | 58995981 | chr12:589593.704-58960086 | 0.97 | 0.03 | 6.70E-05 | 0.0029209.67 | N | 0.03 |
| ENSMUST00000156135|Stx1b|chr7|- | 3097 | 127807565 | chr7:127807.372-127807766 | 0.97 | 0.03 | 1.03E-07 | 1.14E-05 | N | 0.03 |
| ENSMUST00000112146|Dync1i2|chr2|- | 256619.2 | 71263004 | chr2:712626.48-712613.03 | 0.968 | 0.0295 | 9.56E-05 | 0.003892452 | N | 0.0295 |
| ENSMUST00000121142|Dync1i2|chr2|- | 257760.5 | 712613.04 | chr2:71262648-712632.98 | 0.964 | 0.0285 | 0.000114889 | 0.005665613 | N | 0.0285 |
| ENSMUST00000092292|Rad21|chr15|- | 1472645 | 519636.64 | chr15:519626.05-519642.47 | 0.988 | -0.028 | 0.00111118 | 0.027497.65 | N | 0.028 |
| ENSMUST00000168211|Slc6a17|chr3|- | 1872908 | 107468154 | chr3:107467549-107468555 | 0.972 | 0.028 | 0.000224.53 | 0.007999649 | N | 0.028 |
| ENSMUST00000112136|Dync1i2|chr2|- | 255660.2 | 712613.04 | chr2:71262651-71263.03 | 0.97 | 0.0275 | 0.00017221 | 0.006638181 | N | 0.0275 |

Fig. 17, Continued

| | | | | | | | |
|---|---|---|---|---|---|---|---|
| ENSMUST00000115231|Mapk3|chr16|- | 11795.5 | 17038515 | chr16:17038314-17039040 | 0.954 | -0.0265 | 0.00137776 | 0.032335433 | N | 0.0265 |
| ENSMUST00000093201|Npm1|chr11|- | 91920.2 | 33152606 | chr11:33152510-33152832 | 0.966 | -0.026 | 0.00182663 | 0.040046998 | N | 0.026 |
| ENSMUST00000011104t5|Zscan26|chr13|- | 22710 | 21444721 | chr13:21444534-21444922 | 0.974 | 0.026 | 0.011391244 | 0.042359494 | N | 0.026 |
| ENSMUST00000141152|Clhc|chr1|- | 10720.5 | 867252070 | chr1:867232278-867252271 | 0.974 | 0.026 | 1.03E-06 | 8.94E-05 | N | 0.026 |
| ENSMUST00000027111|Ndufs1|chr1|- | 209230.5 | 631443637 | chr1:631443596-631443922 | 0.972 | 0.0255 | 0.000042564 | 0.0131248 | N | 0.0255 |
| ENSMUST00000087689|Prune2|chr19|+ | 41097.9 | 17222370 | chr19:17220784-17223932 | 0.998 | -0.0255 | 0.00093838 | 0.024755822 | N | 0.0255 |
| ENSMUST00000119068|Spock3|chr8|+ | 173411.2 | 63355413 | chr8:63355212-63357103 | 1 | -0.025 | 1.72E-05 | 0.000095163 | N | 0.025 |
| ENSMUST00000093480|Spock3|chr8|+ | 173626.9 | 63355413 | chr8:63355212-63357094 | 1 | -0.025 | 8.84E-06 | 0.000547172 | N | 0.025 |
| ENSMUST00000142704|Acss1|chr1|- | 75211.9 | 78706521 | chr1:78706258-78706967 | 0.958 | 0.0245 | 0.00126414 | 0.030472063 | N | 0.0245 |
| ENSMUST00000210062|Ddx5|chr11|- | 33172160.8 | 106781926 | chr11:106780355-106782256 | 0.864 | -0.024 | 9.46E-06 | 0.000568308 | N | 0.024 |
| ENSMUST00000082390|mt-Rnr2|chrM|+ | 17644116017 | 1678 | chrM:1094-2675 | 0.7 | -0.0225 | 2.57E-10 | 5.16E-08 | N | 0.0225 |
| ENSMUST00000026989|Hs48334391.19Rik|chr13|- | 46119 | 54552314 | chr13:54551290-54552817 | 1 | -0.0225 | 0.000057119 | 0.016317222 | N | 0.0225 |
| ENSMUST00000153065|Hs48334391.19Rik|chr13|- | 46119 | 54552314 | chr13:54551290-54552817 | 1 | -0.0225 | 0.000057119 | 0.016317222 | N | 0.0225 |
| ENSMUST00000150137|Calm2|chr17|- | 20475148 | 874345010 | chr17:874344894-874345211 | 0.88 | -0.0225 | 1.63E-06 | 0.000132337 | N | 0.0225 |
| ENSMUST00000109290|Gabrg2|chr11|+ | 2860.6 | 419146282 | chr11:419145467-419146489 | 0.978 | 0.022 | 4.03E-06 | 0.000279514 | N | 0.022 |
| ENSMUST00000030417|Ccdc42|chr4|- | 166103.5 | 137322418 | chr4:137321762-137322619 | 0.978 | 0.022 | 4.89E-11 | 1.14E-08 | N | 0.022 |
| ENSMUST00000172233|Becn|chr1|- | 29610.6 | 101288780 | chr1:101288701-101288981 | 0.978 | 0.022 | 0.00102191 | 0.026278191 | N | 0.022 |
| ENSMUST00000139997|Becn1|chr1|- | 29610.6 | 101288780 | chr1:101288701-101288981 | 0.978 | 0.022 | 0.00102191 | 0.026278191 | N | 0.022 |
| ENSMUST00000125909|Eif4a2|chr16|+ | 5613865.7 | 23111327 | chr16:23111126-23111626 | 0.982 | -0.022 | 2.69E-06 | 0.000196183 | N | 0.022 |
| ENSMUST00000130916|Becn1|chr1|- | 29610.6 | 101288780 | chr1:101288701-101288981 | 0.978 | 0.022 | 0.00102191 | 0.026278191 | N | 0.022 |
| ENSMUST00000086199|Gnb|chr1|- | 73906606.1 | 1539408977 | chr1:1539407864-1539409723 | 1 | -0.0215 | 4.18E-06 | 0.000287847 | N | 0.0215 |
| ENSMUST00000104497|Actb|chr5|+ | 27178812 | 142903417 | chr5:142903115-142903941 | 0.974 | -0.021 | 0.00017644 | 0.006473392 | N | 0.021 |
| ENSMUST00000029002|Stmm2|chr2|- | 4852220.9 | 85604528 | chr3:85602266-85661604 | 0.976 | -0.021 | 0.00032197 | 0.010593175 | N | 0.021 |
| ENSMUST00000144016|Ptgds|chr2|- | 158270 | 254467144 | chr2:254466711-254467345 | 0.856 | -0.0205 | 0.02039964 | 0.044226369 | N | 0.0205 |
| ENSMUST00000146280|Cnot7|chr8|- | 9703.9 | 405507411 | chr8:405507318-405507648 | 0.998 | -0.0205 | 1.30E-10 | 2.83E-08 | N | 0.0205 |
| ENSMUST00000102843|Rbn4|chr11|- | 5762062.8 | 297424243 | chr11:297419875-297429916 | 0.978 | -0.02 | 1.39E-19 | 9.92E-17 | N | 0.02 |
| ENSMUST00000086199|Gnb|chr1|- | 73906606.1 | 1539408977 | chr1:1539407864-1539409723 | 1 | 0.02 | 1.79E-11 | 4.31E-09 | N | 0.02 |
| ENSMUST00000167721|Actb|chr5|+ | 28174758 | 1429037400 | chr5:1429035614-1429039411 | 0.98 | -0.02 | 5.90E-05 | 0.002660202 | N | 0.02 |
| ENSMUST00000130450|Pdia3|chr2|+ | 12919 | 1214431853 | chr2:1214316525-1214432136 | 0.98 | -0.02 | 7.17E-196 | 5.10E-192 | N | 0.02 |
| ENSMUST00000082421|mt-Cytb|chrM|+ | 11780558x62 | 14588 | chrM:14145-15288 | 0.98 | -0.02 | 2.90E-05 | 0.00145917 | N | 0.02 |
| ENSMUST00000100608|110004F10Rik|chr7|+ | 2272209.9 | 1161046657 | chr7:1161042212-1161104831 | 0.98 | 0.02 | 0.00015614 | 0.005900224 | N | 0.019 |
| ENSMUST00000031249|Spatc3|chr5|- | 77238313 | 1040709135 | chr5:1040709113-1040709577 | 0.504 | -0.019 | 0.00021267 | 0.045901489 | N | 0.019 |
| ENSMUST00000133104|Apev6d1|chr8|- | 125439.8 | 1055248e3 | chr8:1055234465-1055225064 | 0.994 | -0.019 | 0.00214267 | 0.045901489 | N | 0.019 |
| ENSMUST00000137990|Rtn1|chr12|- | 181119522 | 722123370 | chr12:7221222A9-722133577 | 0.984 | 0.016 | 1.18E-17 | 6.23E-15 | N | 0.016 |
| ENSMUST00000085653|Npm|chr9|+ | 141411.2 | 586652060 | chr9:586651859-58652856 | 0.806 | -0.016 | 0.00107107 | 0.026958442 | N | 0.016 |
| ENSMUST00000205041|Hint1|chr11|+ | 3572672 | 548704414 | chr11:548761189-548705011 | 0.986 | 0.014 | 2.27E-05 | 0.001191047 | N | 0.014 |

Fig. 17, Continued

| ENSMUST00000112268;Sefk;chr14;+ | 318302.7 | 299746477 | chr14:299744476-299750074 | 0.986 | 0.014 | 0.00196648 | 0.042901235 | N | 0.014 |
| ENSMUST00000133325;Gm1;chr19;- | 60417.9 | 43500356 | chr19:43500021-43500557 | 0.986 | 0.014 | 1.19E-05 | 0.00068706 | N | 0.014 |
| ENSMUST00000133067;Eif4a1;chr11;- | 10630.8 | 69667910 | chr11:69667453-69668111 | 1 | -0.01 | 0.00118761 | 0.028970336 | N | 0.01 |
| ENSMUST00000139295;Atp5b;chr10;+ | 537835.9 | 128085643 | chr10:128085442-128085949 | 0.988 | -0.008 | 0.00011471 | 0.004564732 | N | 0.008 |
| ENSMUST00000115736;Paip2;chr18;+ | 1331114.5 | 35616400 | chr18:35616199-35616519 | 0.992 | 0.008 | 0.00187951 | 0.041576912 | N | 0.008 |
| ENSMUST00000082388;mt-Rnr1;chrM;+ | 2222396174.5 | 756 | chrM:70-1024 | 0.904 | -0.0065 | 7.44E-16 | 3.21E-13 | N | 0.0065 |
| ENSMUST00000078830;Rtm4;chr11;+ | 5467230.3 | 29742442 | chr11:29741987-29743048 | 0.996 | -0.006 | 2.32E-08 | 2.80E-06 | N | 0.006 |
| ENSMUST00000404408;Calm2;chr17;- | 190308816.8 | 874433732 | chr17:874334412-874134055 | 0.998 | -0.0055 | 2.23E-22 | 2.36E-19 | N | 0.0055 |
| ENSMUST00000054066;Appl;chr16; | 172113562.2 | 84954734 | chr16:84954440-84954432 | 0.814 | -0.004 | 0.00115544 | 0.028331063 | N | 0.004 |
| ENSMUST00000148085;Eif4a2;chr16;+ | 122812.5 | 23112243 | chr16:23111817-23112409 | 0.994 | 0.0035 | 0.00032532 | 0.010678692 | N | 0.0035 |
| ENSMUST00000082419;mt-Nd6;chrM;- | 8393274e.5 | 13707 | chrM:13565-14070 | 1 | 0 | 1.65E-14 | 6.18E-12 | N | 0 |

Fig. 17, Continued

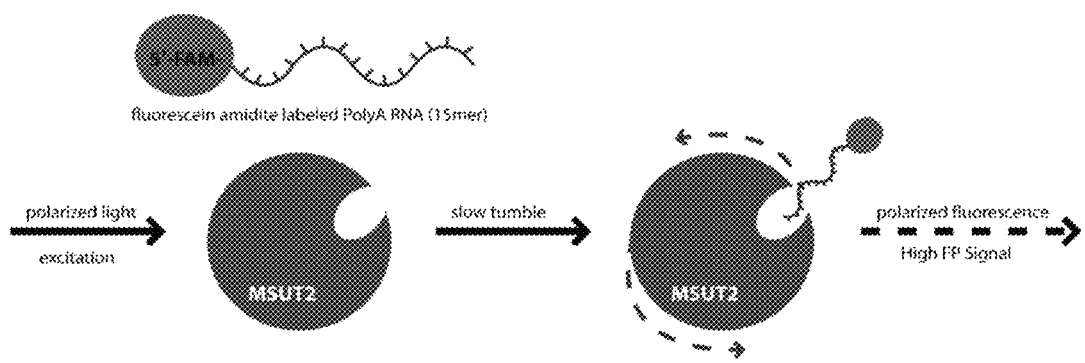
Fig. 23
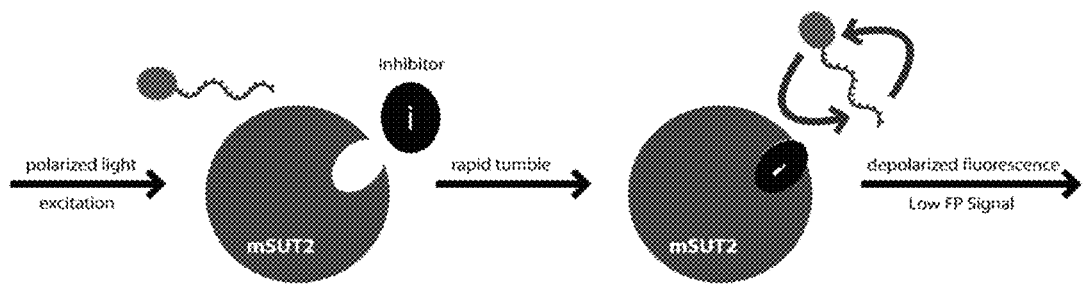

SEQUENCE LISTING

<160> NUMBER OF SEQ ID NOS: 33

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
aatttatcga ccacctgcaa g                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic construct

<400> SEQUENCE: 2
tactggcctg cctgtaaaaa t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic construct

<400> SEQUENCE: 3
ggcctgcctg taaaaatggg g                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
gccaccaaga cacgccttga a                                              21

<210> SEQ ID NO 5
<211> LENGTH: 20
<212> TYPE: DNA
<213> ORGANISM: Artificial Sequence
<220> FEATURE:
<223> OTHER INFORMATION: Synthetic construct

<400> SEQUENCE: 5
attagacact tcagatagat                                                20

<210> SEQ ID NO 6
<211> LENGTH: 107
<212> TYPE: RNA
<213> ORGANISM: Artificial Sequence
<220> FEATURE:
<223> OTHER INFORMATION: Synthetic construct

<400> SEQUENCE: 6
gaauuuaucg accaccugca agcaaaguuu uaguacucug gaaacagaau cuacuaaaac    60
aaggcaaaau gccguguuua ucucgucaac uuguuggcga gauuuuu                 107

```
<210> SEQ ID NO 7
<211> LENGTH: 106
<212> TYPE: RNA
<213> ORGANISM: Artificial Sequence
<220> FEATURE:
<223> OTHER INFORMATION: Synthetic construct

<400> SEQUENCE: 7
ggccugccug uaaaaauggg gcaaaguuuu aguacucugg aaacagaauc uacuaaaaca    60
aggcaaaaug ccguguuuau cucgucaacu uguuggcgag auuuuu                 106

<210> SEQ ID NO 8
<211> LENGTH: 106
<212> TYPE: RNA
<213> ORGANISM: Artificial Sequence
<220> FEATURE:
<223> OTHER INFORMATION: Synthetic construct

<400> SEQUENCE: 8
gccaccaaga cacgccuuga acaaaguuuu aguacucugg aaacagaauc uacuaaaaca    60
aggcaaaaug ccguguuuau cucgucaacu uguuggcgag auuuuu                 106

<210> SEQ ID NO 9
<211> LENGTH: 102
<212> TYPE: RNA
<213> ORGANISM: Artificial sequence
<220> FEATURE:
<223> OTHER INFORMATION: Synthetic construct

<400> SEQUENCE: 9
auuagacacu ucagauagau cuguuuuaga gcuagaaaua gcaaguuaaa auaaggcuag    60
uccguuauca acuugaaaaa guggcaccga gucggugcuu uu                     102

<210> SEQ ID NO 10
<211> LENGTH: 24
<212> TYPE: RNA
<213> ORGANISM: Artificial Sequence
<220> FEATURE:
<223> OTHER INFORMATION: Synthetic construct

<400> SEQUENCE: 10
augaugcaaa guguacuaaa ccag                                          24

<210> SEQ ID NO 11
<211> LENGTH: 27
<212> TYPE: RNA
<213> ORGANISM: Artificial Sequence
<220> FEATURE:
<223> OTHER INFORMATION: Synthetic construct

<400> SEQUENCE: 11
augaugcaaa guguacuaaa ccagauu                                       27

<210> SEQ ID NO 12
<211> LENGTH: 26
<212> TYPE: RNA
<213> ORGANISM: Artificial Sequence
<220> FEATURE:
<223> OTHER INFORMATION: Synthetic construct

<400> SEQUENCE: 12
augaugcaaa guguacuaaa ccagau                                        26
```

```
<210> SEQ ID NO 13
<211> LENGTH: 23
<212> TYPE: RNA
<213> ORGANISM: Artificial Sequence
<220> FEATURE:
<223> OTHER INFORMATION: Synthetic construct

<400> SEQUENCE: 13
augaugcaaa guguacuaaa cca                                              23

<210> SEQ ID NO 14
<211> LENGTH: 26
<212> TYPE: RNA
<213> ORGANISM: Artificial Sequence
<220> FEATURE:
<223> OTHER INFORMATION: Synthetic construct

<400> SEQUENCE: 14
auaugaugca aaguguacua aaccag                                           26

<210> SEQ ID NO 15
<211> LENGTH: 25
<212> TYPE: RNA
<213> ORGANISM: Artificial Sequence
<220> FEATURE:
<223> OTHER INFORMATION: Synthetic construct

<400> SEQUENCE: 15
uaugaugcaa aguguacuaa accag                                            25

<210> SEQ ID NO 16
<211> LENGTH: 24
<212> TYPE: DNA
<213> ORGANISM: Artificial Sequence
<220> FEATURE:
<223> OTHER INFORMATION: Synthetic construct

<400> SEQUENCE: 16
atgatgcaaa gtgtactaaa ccag                                             24

<210> SEQ ID NO 17
<211> LENGTH: 25
<212> TYPE: DNA
<213> ORGANISM: Artificial Sequence
<220> FEATURE:
<223> OTHER INFORMATION: Synthetic construct

<400> SEQUENCE: 17
atgatgcaaa gtgtactaaa ccaga                                            25

<210> SEQ ID NO 18
<211> LENGTH: 27
<212> TYPE: DNA
<213> ORGANISM: Artificial Sequence
<220> FEATURE:
<223> OTHER INFORMATION: Synthetic construct

<400> SEQUENCE: 18
atgatgcaaa gtgtactaaa ccagatt                                          27

<210> SEQ ID NO 19
<211> LENGTH: 24
<212> TYPE: DNA
<213> ORGANISM: Artificial Sequence
<220> FEATURE:
<223> OTHER INFORMATION: Synthetic construct
```

<400> SEQUENCE: 19
atgatgcaaa gtgtactaaa ccag    24

<210> SEQ ID NO 20
<211> LENGTH: 24
<212> TYPE: DNA
<213> ORGANISM: Artificial Sequence
<220> FEATURE:
<223> OTHER INFORMATION: Synthetic construct

<400> SEQUENCE: 20
aatatgatgc aaagtgtact aaac    24

<210> SEQ ID NO 21
<211> LENGTH: 26
<212> TYPE: DNA
<213> ORGANISM: Artificial Sequence
<220> FEATURE:
<223> OTHER INFORMATION: Synthetic construct

<400> SEQUENCE: 21
atatgatgca aagtgtacta aaccag    26

<210> SEQ ID NO 22
<211> LENGTH: 4
<212> TYPE: PRT
<213> ORGANISM: Artificial Sequence
<220> FEATURE:
<223> OTHER INFORMATION: Synthetic construct

<400> SEQUENCE: 22

Cys Cys Cys His
1

<210> SEQ ID NO 23
<211> LENGTH: 43
<212> TYPE: DNA
<213> ORGANISM: Artificial Sequence
<220> FEATURE:
<223> OTHER INFORMATION: Synthetic construct

<400> SEQUENCE: 23
tttttttttt tttttttttt tttttttttt tttttttttt ttt    43

<210> SEQ ID NO 24
<211> LENGTH: 34
<212> TYPE: DNA
<213> ORGANISM: Artificial Sequence
<220> FEATURE:
<223> OTHER INFORMATION: Synthetic construct

<400> SEQUENCE: 24
agatcggaag agcacacgtc tgaactccag tcac    34

<210> SEQ ID NO 25
<211> LENGTH: 15
<212> TYPE: DNA
<213> ORGANISM: Artificial Sequence
<220> FEATURE:
<223> OTHER INFORMATION: Synthetic construct

<400> SEQUENCE: 25
aaaaaaaaaa aaaaa    15

```
<210> SEQ ID NO 26
<211> LENGTH: 3556
<212> TYPE: DNA
<213> ORGANISM: Mus musculus

<400> SEQUENCE: 26
```

| | | | | | |
|---|---|---|---|---|---|
| ggggacgcgc | acggcggagg | cggagcggcg | gcggcagcgg | cggcagcggc | agcggcagcg | 60 |
| gcgtagggg | cccaggctgc | agggtggcag | cccgcggcgg | gctccaggta | accgaggcgc | 120 |
| cgcgcagtgc | cgagccggcc | gcccgccgcc | gagccatgga | aatcggcacc | gagatcagcc | 180 |
| gcaagatccg | gagtgccatt | aaggggaaat | tacaagaatt | aggagcttac | gtagatgaag | 240 |
| aacttcctga | ttacattatg | gtgatggtgg | ccaacaagaa | aagtcaggac | caaatgacag | 300 |
| aggacctgtc | cctgtttcta | gggaacaaca | caattcgatt | caccgtatgg | ctccatggtg | 360 |
| tattagataa | actgcgctct | gtcacgactg | agccctctag | tctaaagtct | cctgacgcca | 420 |
| gcatcttcga | tagtcacgtg | ccttcaaaca | agagcagttt | cagtcgggga | gatgagagaa | 480 |
| ggcacgaagc | tgccgtccct | ccccttgctg | tttctagttc | tagacctgaa | agagggatt | 540 |
| ccagagtttc | tacaagttca | caggagcaga | aatccactaa | tgtcagacat | tcatatgatg | 600 |
| atggagcttc | cacccggcta | atgtcaacag | tgaaacctct | gagggaacca | gcaccctctg | 660 |
| aagatgtgat | tgatatcaag | ccagaaccag | atgatctcat | tgatgaagac | ctcaattttg | 720 |
| tgcaggagaa | tccctatctc | agaaaaaac | ctacagtgac | acttacatac | ggttcttctc | 780 |
| gcccttctat | tgaaatttat | cgaccacctg | caagtagaaa | tgcagacact | ggtactcact | 840 |
| taaacaggct | gcaacttcat | ccgcagcaaa | gcagtgctca | cgctgccaag | cagctggatg | 900 |
| tacaaagcag | ccaggtatcc | gaagcaggac | ggttgtgtga | gccaccagtg | cttagcagcg | 960 |
| tagaagacac | ttatagcccc | ttcttcagaa | acaacttgga | taaatgagt | attgaggacg | 1020 |
| aaaactttcg | aaagagaaaa | ttgcctgtgg | taagttcggt | tgttaaagta | aaaagattta | 1080 |
| gccatgatgg | agaagaggag | gaagaagatg | aggattatgg | gacccgcata | ggaagcttgt | 1140 |
| ccagcagcgt | gtcagtacca | gcaaagcctg | agaggagacc | ttctcttcca | ccttctaaac | 1200 |
| aagctaacaa | gaatctaatt | ttgaaggcta | tctctgaagc | tcaagagtct | gtaacaaaga | 1260 |
| caactaacta | ttctgcagtt | ccacagaaac | agacacttcc | agttgctccc | agaactcgaa | 1320 |
| cttctcaaga | agaattgcta | gcagaaatgg | tccaggggca | aaacagggcc | cccagaataa | 1380 |
| gtccccctgt | taaagaagag | gaagcaaaag | gagataatac | aggaaaaagt | caaggaactc | 1440 |
| aacagaggca | attgttatcc | cgactgcaaa | ttgatccagt | aatggtagaa | acaatggaga | 1500 |
| tgagtcaaga | ttactatgac | atggaatcca | tggtccatgc | agacacaaga | tcatttattc | 1560 |
| tgaagaagcc | aaagctgtct | gaggaaatag | tagtgacacc | caaccaggat | tcggggatga | 1620 |
| agactgcaga | tgcccttcgg | gtcctttcag | gacaccttat | gcagacacga | gatcttgtac | 1680 |
| aaccagataa | acctgcaagt | cccaagttta | tagtgacgct | ggatggtgtc | cccagccccc | 1740 |
| caggatacat | gtcagatcaa | gaggaggaga | tgtgctttga | aggaatgaaa | cccgtaaacc | 1800 |
| aaacttcagc | ctcaaacaag | ggactcagag | gtctcctcca | cccacagcag | ttgcatttgc | 1860 |
| tgagcaggca | gcttgaggac | ccagatggta | gcttttccaa | cgccgagatg | actgacctga | 1920 |
| gtgtggcaca | gaaaccagaa | aaacttctgg | agcgctgcaa | gtactggcct | gcctgtaaaa | 1980 |
| atggggatga | gtgtgtatac | catcatccca | tttcaccttg | caaagccttt | cccaactgta | 2040 |
| aatttgctga | gaaatgtttg | tttgtgcatc | caaattgtaa | atatgacaca | aagtgtacta | 2100 |
| aagcagattg | tcccttcact | cacatgagta | aagagcctc | gatactgact | ccaaaaccag | 2160 |

```
tgtcgtcacc agcaccgtct tctaatggcc agctctgccg ttacttccct gcttgtaaga    2220
aaatggaatg tcccttctac cacccaaaac actgtaggtt taacactcag tgtacgagac    2280
ctgactgcac attttatcac cccaccatta ctgtgccacc aagacacgcc ttgaaatgga    2340
ttcgacctca gagcagtgag tgatgcccta gtcctacctg gcagaagatc atgcagtttg    2400
aaagcttcca tcttctgatg agagatgttc tacagaactt gtcacgtctt tgaaatttag    2460
aatatattgc tttcataata cgaattttac tgccccactg aagtgtctaa tttttcaagt    2520
ttgtaagttt attaagtggt ttcaacattt tttgtttgtt cgttttgact atgaaaaaga    2580
cagtttaaag aaaagccaaa ttctattaaa acatttgcgg catgtttgta cattgctgtt    2640
taatatcatt tttggtaatg gtacttgcag cttagggctg tagtgctgtg ggaaggccag    2700
tgtcctcaga gctgaagcac ttttcagctt ttcccaaagg taatgcagtg tctgtaaccc    2760
agcgtggtaa cagtggccag gctttgaaac tgaggcagct ttggaacaac tagtttaaat    2820 ttctttttt agtgtctaaa tgaatttgct ctgagaagca taatgcagac tttattttga    2880
gtgctacttt ggtagagtgg accgaggtcc tgtgcctttc tgaaagtgag cagagacatg    2940
gtcataaagg gtaagcatag ttggaatgac gatgtaaaaa tatatggaca gttctttgga    3000
atgctcccat ttactattag cttatcattt tataagtaat tttggaggga ctacattatc    3060
acaaaagtat acaaaaattt ttacaggcat atgtacagaa agtatcagaa aacagacttt    3120
gaactcacaa gaatataaat atacgtatat attcccatat tctgaaaaat atcatcagaa    3180
ataaccccac agaaaatata cttatgttat tactaaagat cattcttgaa atgtagaagt    3240
tgagatttaa gtggtatatt ttaaatgaca gaactatatt gcagagatag gaaggtaaac    3300
ttgacaatag gatgaaactt ggcctactgt actatggagt tttatgtgtg gtttttgaaa    3360
ctgttaaggc aagatgtgtc atgttttaga actaaataac agacaactga tttcaaaaac    3420
gtgttgtttt aaaaattaaa gtgtaaacgg tggttagcaa aggggataat aaaagctcaa    3480
acattttgag gaccaaattt aactgttaag atacaataaa gtcacatcta taaaagtctg    3540
tgtttaataa tgtgaa                                                    3556
```

<210> SEQ ID NO 27
<211> LENGTH: 18153
<212> TYPE: DNA
<213> ORGANISM: Homo sapiens

<400> SEQUENCE: 27

```
ggaggcggtg gtgtcccggc tgcggggtag gagtccgcgg cagcctccgg gtaagccaag      60
cgccgcgcag tgctgagttc ccgcacgccg cagagccatg gagatcggca ccgagatcag    120
ccgcaagatc cggagtgcca ttaaggggaa attacaagaa ttaggagctt atgttgatga    180
agaacttcct gattacatta tggtgatggt ggccaacaag aaaagtcagg accaaatgac    240
agaggatctg tccctgtttc tagggaacaa cacaattcga ttcaccgtat ggcttcatgg    300
tgtattagat aaacttcgct ctgttacaac tgaaccctct agtctgaagt cttctgatac    360
caacatcttt gatagtaacg tgccttcaaa caagagcaat ttcagtcggg gagatgagag    420
gaggcatgaa gctgcagtgc caccacttgc cattcctagc gcgagacctg aaaaaagaga    480
ttccagagtt tctacaagtt cgcaggagtc aaaaaccaca aatgtcagac agacttacga    540
tgatggagct gcaaccccgac taatgtcaac agtgaaacct tgagggagc cagcaccctc    600 tgaagatgtg attgatatta gccagaacc agatgatctc attgacgaag acctcaactt    660
tgtgcaggag aatcccttat ctcagaaaaa acctacagtg acacttacat atggttcttc    720
```

```
tcgcccttct attgaaattt atcgaccacc tgcaagtaga aatgcagata gtggtgttca    780
tttaaacagg ttgcaatttc aacagcagca gaatagtatt catgctgcca agcagcttga    840
tatgcagagt agttgggtat atgaaacagg acgtttgtgt gaaccagagg tgcttaacag    900
cttagaagaa acgtatagtc cgttctttag aaacaactcg gagaaaatga gtatggagga    960
tgaaaacttt cggaagagaa agttgcctgt ggtaagttca gttgttaaag taaaaaaatt   1020
caatcatgat ggagaagagg aggaagaaga tgatgattac gggtctcgaa caggaagcat   1080
ctccagcagt gtgtctgtgc ctgcaaagcc tgaaggagac ccttctcttc caccttctaa   1140
acaagctaac aagaatctga ttttgaaggc tatatctgaa gctcaagaat ccgtaacaaa   1200
aacaactaac tactctacag ttccacagaa acagacactt ccagttgctc ccagaactcg   1260
aacttctcaa gaagaattgc tagcagaagt ggtccaggga caaagtagga cccccagaat   1320
aagtcccccc attaaagaag aggaaacaaa aggagattct gtagaaaaaa atcaaggaac   1380
tcaacagagg caattattat cccgactgca aatcgaccca gtaatggcag aaactctgca   1440
gatgagtcaa gattactatg acatggaatc catggtccat gcagacacaa gatcatttat   1500
tctgaagaag ccaaagctgt ctgaggaagt agtagtggca ccaaaccaag agtcggggat   1560
gaagactgca gattcccttc gggtactttc aggacacctt atgcagacac gagatcttgt   1620
acaaccagat aaacctgcaa gtcccaagtt tatagtgacg ctggatggtg tccccagccc   1680
cccaggatac atgtcagatc aagaggagga catgtgcttt gaaggaatga acccgtaaa    1740
ccaaactgca gcctcaaaca agggactcag aggtctcctc cacccacagc agttgcactt   1800
gctgagcagg cagcttgagg acccaaatgg tagcttttct aacgctgaga tgagtgaact   1860
gagtgtggca cagaaaccag aaaaactttt ggagcgctgc aagtactggc ctgcttgtaa   1920
aaatggggat gagtgtgcct accatcaccc catctcaccc tgcaaagcct tccccaattg   1980
taaatttgct gaaaaatgtt tgtttgttca cccaaattgt aaatatgatg caaagtgtac   2040
taaaccagat tgtcccttca ctcatgtgag tagaagaatt ccagtactgt ctccaaaacc   2100
agcagttgca ccaccagcac caccttccag tagtcagctc tgccgttact ccctgcttg    2160
taagaagatg aatgtccct tctatcatcc aaaacattgt aggtttaaca ctcaatgtac    2220
aagaccggac tgcacattct accatcccac cattaatgtc ccaccacgac atgccttgaa   2280
atggattcga cctcaaacca gcgaatagca cccagtcctg cctggcagaa gatcatgcag   2340
tttggaagtt ttcatgtact gatgaaagat actctacaga acttgtcaaa tctttgaaac   2400
ttggaatata ttgctttcat aatatgaagt tttattgcct atctatctga agtgtctaat   2460
ttttcaagtt tgtaagttta ttatgtggtt ttaacattgg gtgttttgt tttgttttta    2520
ctatgaaaag acagcttaag gaagagctaa attctgttaa aatatttggg gcatgtttgt   2580
gcactgctgt tgtgaggatc agcatatgaa attgacatca tggttagtca tggtactgca   2640
gcttagggg ctacacggtt gctgtgtgag tggagagatg cagtgaggca gttgtcatta    2700
ttctaaaaat tgtactactt tcactttcc caaagattat ataatgttca taatccacca    2760
tgaaaacagc attggccaaa ggtactgagg ctgcttaaaa tattcaattc tgcttttaa    2820
tttttaagtg aatttagttt gaaaagcatg attatacagg cctctcaggc tgagtgctac   2880
tttggtaaag ttcccagttt tcctgccttc tgtgacagga tgaatgaggt gggtatggac   2940
agtggaggca gctggaatgg caagtgcaga aaataggaac agttctatac agtgctctca   3000
tttactaata acataatgcc ttctaaataa ttttttggg aaactacatt atcacaaaat    3060
tatacaaatt ttttacaag tatttacata ctgtatctga aaacagactt taaagtcaca    3120
```

```
agattataaa tgtacatata tattctcaca ttctgaaaaa taacattctc agaatccaca    3180
gaaaatatac ttagttacta ctgaagataa tttttgaaat gtaaaaatta gatttaaata    3240
gtatatttta aatgacagaa ctataattac agagatcaga tcagataggt aaactgcaag    3300
atagatagga tgaaactttt ggcctactgt attacttaca gagtttttt gtgtgtggtt     3360 tttaaaactg ttaaggcaag aagtgtcaaa tgctttagag ttaaataaca gatcactgat    3420
ttcaaagact tggtgtatag tgttaaaaat taaagcttaa aaggtggtta gaaaagtgga    3480
ttaatgcaaa agggtaata aagactgcaa cattctcagg accaaattaa actgctaaaa      3540
aaaaaaaaaa agttcattga cttgcttagt cgtatactca aatgatgata aacctacatg     3600
tgcaaaggct cacgtttaag attgtcaagc cagcagtcta ctgttgtgtt gccattgctt     3660
ttccattggg agaagaaaga attaccagt cattaaacca tttggtaagt tgcactttgc      3720
tgtgctgatc ccacaggaaa ggcttgaaac acgagaagca gcaaagacag agcacacaag    3780
tgcataaggc tgttgtcttc ggcttgggtg aaatgacagt tcctcttcat tctaaaggtt    3840
tactccattg aatttaaggc atttgttcat tccagtgttg agatgctttg catctctgca    3900
gaagaaattt attttaaatt gtttaaatat ctggaaatac ttttagctat catttataaa    3960
gatagttttg ttctcagttt cactataaat tatagaacaa atgggaaaca agggtttaat    4020
ttagttcagc catttacaa ggaaataata aaatactaaa atctgattgt tttttgctat      4080
ttaatagcca ctgcccagac acatatttaa gagtttaatc tttcagttgc tatggcttat    4140
gaacaagcta aggttgacca taaaacattt gttggatgac gtggtttaaa atgatcacca    4200
caaaaaggga ccacaaaaaa aggaaggaaa tgagcatggt tggcgattgg aagcaagggt    4260
accagagggc acagtgtgct ttggcatgca ttttatacat aaaatgaatg gaacaaaagg    4320
tgccagaagt cccaggttac acaatcagga gcttagatac tgcacacaaa ataattatc     4380 tgggttaaaa aagtaaacat agggcagatt ctatatggcc tatcatgttt cttcaccttc    4440
ccctcgttgc tggctgatac agcgaggtgg tcagctgatg actacttagt caatatgacc    4500
tttagtcgtg aaactgacag cagcagtgat taaggctgac ttaatcaggt tggccacttt     4560
gaaggacaga aatgcagtgg aaacagtttt attctatgta gtttacatgc ttaaggttac    4620
agagtttcta cctgcactgt aatggaaata taatttctct gtagccaaaa gctggcaaac    4680
ttgacccaga gggaaatttt aaaactgcag caggctcaaa tgtagagtat ttttcttttt    4740
atgggcaggt tgttcaggga tttttttcct cctttaattt attgactgac tgtaaataca    4800
tgagtagaaa cttaatagtc atgtatttca aaatttggct taatttagga gaatccactg    4860
atgaacaagt accaacttac gtttcaagct tcttagcccc ataatcagtc cttcagccac    4920
agctatttag agctttaaaa ctaccaggtt caatcactgg ttatgctttc tgtgatgtaa    4980
tttagtcatt tctatttta gtattaacca agtattagac acagaaaata ggtattaaga     5040
atcttcatat atcctgtcag accaaatggg attccaggaa cctaaagcga tctattatgc    5100
tataaagata attaacacat taaaaactca tagggtcaat acagcatctt aaacctcaca    5160
cttagaaaaa tatattttta aatagcagtc tacataattt tcaatcttca ggaaactaca    5220
gataggctag acagcgaatt cctgaatgat gagtagtgat ctttggcagc atttaaagtg    5280
aaagaaaata aggatctaag aattcagccc taatccacta aaaaaggaa ttctaactga     5340 caagttttta caaatggagt tgggctcatt cattttggaa ataaacctat ggagtggcac    5400
acatctaaac aaattttccc aatagaaaaa aggctataaa aatttattc caagagtgat     5460 taaattgtat aatgttgtat atgtgaattt aacacttttg tttacatgtt aaacaaatgt    5520
```

```
gtatatatta gactacatta aatatgcaat tctttcttcc agttaaatac tgttgctccc    5580
taaaacccctt acattgtaca ccattgggaa tgattgttca tcatactact tttccattag   5640
tgaggctaca gttatgtttt aaatgtgcga ttacagagat ggcatctgaa cataaactga    5700
tggctcgaaa atgaaaatgg aaatgtagca gccatatact gctaactttg gatctgttcc    5760
tgaattcaaa actactagga gaaaagtgtc ctttataaaa aaggacctta ttaatgccta    5820
aaaaacatca tattctctag gaaagcttgt gtctgtttcc ttagggaaaa tgtttgcctt    5880
ttaaaaactg tgatccttta ggatgatcat gactttccct ttccttatgg aaatgcaaga    5940
ataaaatatt tcattaaaca atgaaccttg aaaataaaat ataaacatta agaaaccatt    6000
ttgctaaaaa gataatgaaa attatccaaa ttgggttttt gagttcttct gtaaagagtg    6060
ctctacccta aattttccca gcaggtctgc cgaaatcaca cacttcccaa tacaggggga    6120
cttggccttt accatcaagt attcgatcct tccttgaaat ggcattatct ggcagtgtat    6180
ggattacgga ttatacccag tgcatatagc aaatattttg aacagatcag tctttcacta    6240
ttttgatgat tctgggcatt tctccctgtt acagtcttgg gttagcacca cttgaccatg    6300
cagggttggg ttttggtttt tcttctctgt aattctggtc tcaaagttaa tttctgtagt    6360
catctcagca tctctcagtg aggtgtatgt acacatttcc agacaaataa gctgcaatca    6420
gagaagaaaa ttgcagggag ttaattatgt ttttagattt tcataacagt ttaatatttt    6480
tcagttgtgc tttcaggtta catgtgtaat attttttcctc tttaactcct tttattctgt   6540
atttgcataa atatgagatt ctgaagagcc atctggttat actaccttct actaatgttg    6600
actagctgat ttcataaacc aaagctgtag gagttgttgt attaagtctc ttaactagta    6660
acatagtctg ctcttcatgg gctgagaaag ttactaacct gcagtcatca cctccagcac    6720
taacaacatg tcgatcacca ctggtaaatc gaatatttgt cacatggggc gaatgaccca    6780
agaacctttt gtgttttgcc taaaaaacaa tgacagacaa gctcagggca tttggtgcac    6840
acagaagtca aaggctctta ttaggaacta taatctctat gacaagagct gtggagagag    6900
tagggagtta gcaccgcagc cagtgattag aatgcttttc agcatgagta gtggatctgc    6960
aaaaccaggc tgtgtgggca gtcagatgtc tccaggtact ctgaccattt ttctctaagg    7020
aaaagcattt gaaatttgat aactgattat aggtttggtg aaaagctaat tacagctttt    7080
gtaggatggt tccaaagatg gtattactcg agggagagga tttgtttcta atagctttta    7140
tttcaaagta aatagattta gaaagtttgg ggaaaaattt agaaattagg acaaaacatt    7200
ttaaatatat ggggaaaagt gctgatgata agacatcaaa attaggagta aactgataat    7260
agtaaacaaa acacaaactt acaaattttt ctggacatgg gaagtcaaat aacttaacca    7320
tgccaaagtc atctcctgta acaagactga ttcctgaatg agatacacag gcacagttga    7380
catcagcttt ctcagcatgt ctggaccaga ttcccaaaac ctcatctcct agaatactag    7440
agggaaggaa caaagaaaaa ctcatcatgg caagtgcggg caggttgact atattccaaa    7500
agtttcttgg caattaatct ctaagtaccc tatcatgtta cttaaaatac aggaagtaaa    7560
ttatggtaag ttgtttggag acctgaattt catcaggata tcaactcctg ccttttaaaa    7620
atgacatttt ataatttgaa gggtttctag attaatcttt ttaagattaa agtagtactt    7680
tatgaaaact gatagaacta ttttttcttt tttttttttt gagacggagt tttcgctctt    7740
gttacccagg ctggagtgca atggcatgat ctcggctcac cgcaacctct gcctcctggg    7800
ttcaagcaat tctcctgcct cagcctcccg agtagctggg atcacaggca tgcgctaaca    7860
tgcccggctt attttgtatt tttagtagag acagggtttc tccatgttgg tcaggctagt    7920
```

```
ctcgaactcc cgacctcagg tgatcacccc cgctcggcct cccaaagtgc tgggattaca    7980
ggctgagcca ccgcgcctga ctgaaaactg atagaactat ttttcaaatt aaaagtgcta    8040
cttggctggg tccagcagca cataccagta atcccaacat tttgggaggc tgaggcagga    8100
ggactgcttg aggccaagag tttgagacca gcctgggcaa tattgtgaga tccctatctc    8160
tacaaaaata aaaatgactt atgacatagg aattaaaaaa atttcagaga tggggtcttg    8220
ctatgttgcc caggctggta tcaaaacttc taggctcaag tgatcctccc acctcggcct    8280
gctacatcag agattacagg catgagccac tatatgcctg gctgatacag gaatttgatg    8340
gcatttttca ttggccaaaa aaatggatag tcatggttac ctgtcataca gccaggaaat    8400
ttgaacaaat ttggaagctt tgacttctaa tagattcaag atagcattcc tttagataga    8460
gaattaataa cagttgctta acagcaccca ataccttttt gccagtcatt aaatttagca    8520
ttaagaaaaa tatcagggta tctttaaagt taaaactttg atttccttaa aaaaaaaact    8580
tgataaatca tggaaactga taaaacatgg aaatatattc aataaaaagg gtcccaaca    8640
tgaacatacc atttcaaaat atggtaacaa aaacttgaaa ctcaattact attccttatt    8700
ggaatggctc taacagttca gaaataggat tttctaactg gccttcaaag tcagttcttg    8760
ccttgtgaat atataagtat ttacctagtc catgtagccc aagtaattct gtcaatagcg    8820
gcatgatcca taagatgttt tcctgaaggc acttcataga catgccgttt atagcagcca    8880
ctagagacct ttttcatcag attaaaatgg acaagaatt ccattaggtg agagacaaaa    8940
tccacagggg gtttacagaa tactagcata ttgctacttg atttacatgt ctaacattat    9000
taagtatgca aaagatcact acaaaaactt aataggagaa aagctctgat aagtggggga    9060
ggaaagggga gctgtaggtc agaaggtaca aagggaggag ttgagaagct ggagctctgg    9120
agctcaggaa ctttaaatgc attcactaac acgaaatgta aaagcagaag aacttgccac    9180
ctgggtatac agtattggta ctgtacctgg agataactgc tatctgcaga gaagtccatt    9240
tgaatgacaa agcttggaat gtcttttgcag tagctgattc tgttaagagt ggggcccagc    9300
gttaggtcat aaaaatccac tgagttctca ctagaaccta ctgccagata ccgggaatcc    9360
ggactaaatc tgaatcaaaa caaaacgtaa aaagtattag accacatgaa gtattataaa    9420
tacttaagat cagtgacttt tcctttctag ttcttaaaag taacgtgtga taaggcctca    9480
aatagattta cctgtcagac acaactgatc atgtatactg agattgtctg ggttacatga    9540
aataaggaag ctttatattt tacttaaatt ttaaatattt ccccaattgt catctcccaa    9600
ttcctttaaa aacgtctaat ggcttaaaaa aactttctta ggccaggccc agtggctcac    9660
acctataatc ccagaacttt gggaagcgga ggcgggcaga tcacctgagg tcgagagttt    9720
gagaccagcc tgaccaacat agagaaaccc tgtctctact aaaaatacaa aattagccag    9780
gcatggtggt gcacgcctgt aatcccatct actcgggagg ctgaagcagg agaatcgctt    9840
gaacccagga ggcacaggtt gtggtgagct gagattgcac cattgcactt cagcatgggc    9900
aacaagagca aaactccaac tcaaacaaa acaaaacaaa atttaattt ttaaatagag    9960
gcggggtctc actatggtcc caaactcctg gcctcaagca atccttcccc cttggcctcc    10020
caaggtactg ggattacagg tgtgagccac aacacccagt cagaacatct cagcttttaa    10080
aagccattag cattacataa ttaataagct aacaattcat taagatagtt ttcttccatc    10140
tggaaaaaac gttgtcttaa tattaagcaa agaacacagc ccagcttaac taacctccag    10200
ttattaaggt gaaatgacac aacttgaatc ttggaagaag aattttttt ttttgagacg    10260
aagtctcgct cttgtctccc aggctggagt gcgatggcgc aacctccgcc tcccgggttc    10320
```

```
aagcgattct cctgtttcag cccctgagt agctgggatt acaggcgcct gccaccacgc   10380
ccggctgatt tttgtatttt tagttgagat ggggtttcac tatgttggcc aggctggtcg   10440
agtactcctg acttcaggtg atctgcctgc ctcggcctcc caaagtgctg ggattacagg   10500
catgagccac cgcgcccggc ctgaagaact tatttaaaag acaaagtgaa atgctatttg   10560
cctagcaatc tttggagtca tatgggacaa ttcagtctct tgaaatggcc catgagtctt   10620
actgaggtac gatagagaca tgtaaaagct aagggaagcc actgttacta ttttatatat   10680
tgaagttctg aggaaggttt catttgtaaa aggattttac tgatgaaaag tgtacaagct   10740
tttgacagac ctagattcaa taatcttatc tactgatcac acggaagtac tccgtaaatg   10800
gtagccactg ttgaaaaatg cttaagcact gaaaaacaaa ggtttaagaa acatttaaat   10860
taatttggat tctggaacat ttaatcaata ggtattgatt aaattaatga actacatatt   10920
cccaaactga ggttactaag agaagatatg tttgaaatca caactttagt tttccagggt   10980
gacaactttt gaagggcaga tagctctctt gtattacagt gggagatacc tcttggtggg   11040
atgaacttaa tggacatggc taagtgttaa catgaattca tcaaacatta cctactagta   11100
cttgctatta tagttggtgc ccagtgggtt tataatttag caagaagaat taagtagtat   11160
acaaacagcc atattttagc atacaattta taatacggga aatgctacag gccctgggga   11220 cctcttttg aaggcaaggc tatggaaaat tttacaaatg gaagttaaat caagtatata   11280
ctagaaactc tattccattt gttcactaac ctgatatcat ggattgcaca tctcctgtct   11340
ctcttctttc cccatatttt tagagaactc actagtaaaa tgataaattc tccattttc   11400 attccaatag ccaccatgtc cccttcaggg ctgtaacaca cagtacgagc agcatgtccc   11460
aaattcactt tgtttaacat cttctgcatt taaaaaaaaa aaaaaaaaga gtcataggaa   11520
acattaagtg aagtacttct aaattatacc agtttcccct caaatgctc aacagaattc   11580 tggcagttct ttaagtacta gcaatttaga acttccaact tttctttta gaagttgtaa   11640 cctctttaa aaaattatc tgtacttact ttatcagcaa tatcccaaag tctcactgtc   11700
ccatcttctg cagcagaaag gaaaaaatcc ctggaaggat gtgttgctag tccccagatt   11760
ggcccatcca catgaccgtt aactaaaata ttacaagctg catttttctc tccaacttcg   11820
attatttcag cattccttgt cccaacaagg atcttgccct gaaacacaag caggaccaat   11880
acagtgaatg taatacaaca gctgcttttc ttcttcataa tataaaaatg acctattga   11940 cctgctttca gagaacttt tgctttgagc taatctagta gcaaggcagt cattagctca   12000
tgcaaatttt tctatgacta caggcacaca tctatctgta agcacaatgg gctagattac   12060
atattagagt ccatgctaca gaatagaact tttctgtggc agtacacctg gattcttcaa   12120
taatcaaagt ttttattga taatcttagg atttccaaac tggggtcagt gcagtgggat   12180
ataggaaaaa ataatagaat ttatttttta gttaaaaagt aaaagcttaa ctacaattta   12240
atatgcaggc tgaagataat atccgtatga tttataaata cacttaataa gtacaaacac   12300
gctcaaaaat tttcatagga gttgtagttt tgaattttta ttttgaaatt gacacataat   12360
tatacatatc tataggggcat agggtaatac gcataaccat cacctcagac atttatcatt   12420
tctttgtgat ggaaacttc aaaatcctct cttgtaaata cctgaaaata cataaatacg   12480
tgattcttaa ctatagtcat cctacagtac tacagaatac taaaacatac tattcctatc   12540
tggctgtgta aacttgtatc ctttaaccag tccttcccta tccccctccc cctccccctt   12600
gtccgcctcc agtaaccact attctactct ccacctctgt gggatcaact tttttagttt   12660
ctgcacagga gtgagaacat gtatttatct ttctgtgcct ggcttatttc acttcacatc   12720
```

```
atgtcctcca gtctcatcca tgttgccacc aagaatgaca gaatttcatt attttttatg   12780
gctgagtagt atttcattgt ttgtttactg cacgttttat ctagggaatg tgtgtttttt   12840
taaaaaatgg agacagctgt cctaatatga gtcaactgcc aagggctttc aattatgtct   12900
actagagttg ttaaattggc agattctaga aaatattgga ggtttacata cagtatttag   12960
acagaatagc ttcctagctt atgcaccaca ctggtgctaa ctttggcaaa gaaagcagca   13020
aagacagagt aatgttggca agcaaatcca tcgttatgca ttattaagta ttgttcatta   13080
ggctgcaaag ggtgagggaa tcacagtaat aaccactttc tgttttctgc tgcactgtat   13140
cagctcatgg aacatcttac tttgcctctg cacacagaac gaacacaatc tgtggcttgt   13200
cctgtctcaa gcctgaaggc acggcaccgc ctcagttcct gatcccacag tttaaccgct   13260
cctccttctt ttgacctaag taaataacca agccagagta agtgttcatt attggctact   13320 ataatttta ttataaacaa ataccaagtt ataagcagaa tcttttttt ttaaaaggc     13380 cctgatattt ataatttacc tctaatattc ttgtaaactt tctatggcaa tttgaggata   13440
tactatatct cagtcaaaat aaacatccag tttcagtgaa ttttattttg agaaatactc   13500 ttttttctg acatgagcat aatttatttt agcctctaca atacattaca atacattatc    13560
ctctctcata atacttttt tttttttttt aagatgtagt ctcgctctgt ctcccaggct    13620
tgagtgcagt ggcatgatct aggcttattg caacctctgc ctcccaggtt caagcgattc    13680
tcctacctca gcctcccgag tagctagcat tacaggtgtg caccaccaca cccagctaat    13740
ttctgtattt ttagtagaga tggggtttca ccatgttggc caggctggtc tcaaatacct    13800
tgacctcagg tgatctgcct gcctcggcct cccaaagtgc tgggattcca ggtatgagcc    13860
actgtgcctg gcctcataat acttcttgat taggaagatg taaaaaaaca attttattaa    13920
aaggataatg gaaatgtaag gcaaaataat agaattacaa atgctatgct acagagttga    13980
tttatttatt tttttgagac agagtgtcgc tctgtcacct ggcctggagt gcagtggtgt    14040
gatctcggct cactgcaacc tgtgcctccc aggttcaagc gattcttctc cttcagcctc    14100
ccaagtagct gggattacag gcaccatgcc tggctaattt ttgtatttt agtagagatg     14160 gagtttcacc atattggcca ggctgatccc aaactcctga cctcgtgatc cgcccacctc    14220
ggcctcccaa agtgttggga ttacaggcgt gagccactgc aactggccca gagcttattt    14280
ttgaaggcca aaacagaagc atatttattc cctatcaggt gttaaaatat ctcactggaa    14340
cagtttagca ggcttctagt gagtgggggt gtgcaggagt aaatgacgtg ggaaatacaa    14400
gtgttggagg acgaaataga gcccatttat ggatttatt cctggaaggg ctgaaaaatg     14460
tattccttcc ttttctgcta gatgaattgc ttgtctgaaa gcatgcctat gtgcattctt    14520
cctttatgta aaaggcacaa attctgcgct tgtgtttaat taacatatgt gggttctttc    14580
aatcctgtat tgaaatgtac ttcttagtca actatatgtc acattttttt ttgttttgt     14640 ttttgttttt taaatggggt ctcactctgt cacccaggct ggagtgcagt ggcaccatca    14700
cagctcacta aagccttgac ctccccaggc tcaagtgatc ctcccacctc agcctcctga    14760
gtagcaggga ctacaggcat gtgccaccac acccggctaa ttgttgtttt ttatagcgat    14820
ggggtttcac catgttgccc aggctggtct gaactcctg ggctcaagcg atccacctgc     14880
ctcagcctcc caaagtgata agattacagg tgtgagccac tgtgcctggc ctacatgtca    14940
tgtttcaaca tgcatatgac tatgttggtg acaaatcaaa tcataagtat ctggttactg    15000
ttgggagatt tgaaaatcac tcagaagaga cctcttctca aatttgagg tcttgtataa     15060 aacagtttaa atttgcctca agcaaaagga aacaaggcag ttctctctag ttccctcatc    15120
```

```
cttttctaaa gcaacaatgt gcattctact ccttagaatc cattctgaac aaaaagagag    15180
caggcagtca aaatacaacc ctggctccag attcccccat gggcctccta ctcagcaaat    15240
catacacagg catacagaca ttaagaaaag taactcaact tgtaggacaa ctacctatcc    15300
acacctcaga aaaagtatca ccccaacatg aaaaaaattg gaagtgaatt aagaccagaa    15360
atgagaatca aatagaaggc acataaaagg taataaagga gaagcatatg aggaggaagg    15420
tcggagagga cactctgtgt agcctagaaa caactagaat aattaactgc aaacctcagg    15480
taggtcacaa atgcataaat attctgtgaa aagaaagagg actcacggcc tttccttcc    15540 cccagtcacg ataagtccat ctcgcagggt ggtgtacatg gcaaacacag gcccgttgtg    15600
agctctcgcc acgattctac acaatatgtg atctttccac acacagacat caccactgat    15660
ggtacctgta aacgtcaagt tattctgaaa aggagtgggg gaggggagga caaactcatc    15720
aaaagttcaa atagagttta aatagataat tttctatgta tgtgtaatgc tgtctcaccc    15780
ttgatacaaa gagcatgcat cgtgtagtgg cagcagcact gaattcacga gtcaggaaac    15840
ctgaacggga ggcttagctt tgtcaggacc ttttcctttc caagtctgtt gcttattagc    15900
tagaataacc ttagacaatt cttcccttcc aattctaaca tactataatt ctagggttta    15960
ttttttattt ttttgagacg gagtttcgct cttgttgcc caggctggag tgcaatggtg    16020
cgatctcagc tcaccacaac ctctgcttcc caggttcaag tgattctcct gtctcagcct    16080
cccaagtagc tgggattaca gcgccagcc accacgcccg gctaatttt gtattttag     16140 tagagacaga gtttcacctt gttagccagg ctggtcttga actcctgact tcaggtgatc    16200
ttccgccctt ggcctcccta agtgctggga ttataggtgt gagccactgt gcccggcctg    16260
agccacggtg cctggcctgg tcttatatta agaataccca aaatgttcaa ctgaaatttg    16320
acatggcaca aacatttcaa tagtcttttt ctcaaaaatg taagtgtact taaatattct    16380
aaaattataa cttttcctat aagtattgca taatcacaaa acaaaaaat gcacttagtt     16440 tttcgatgca ccaaaggatt tatacagcct agccaatgca ggatattaaa ggaaagagat    16500
gtggattgga agccacaggt ccagatgaga tggaataaag tgagaggaga gcaggtctcc    16560
tgaacaccct tctgtcaggg ccaggaattg tgctatttcc ttctgtctca ctacctcctt    16620
cttccctcga agtagagaca ctggcccaga gcacttccag ctgtatgata agcagtgtgt    16680
taaatgataa aaagcaaagg aaatcctaaa ccctagtacc accttaaatc atttgaaaat    16740
catgtttctt gatttacctt tctctctgac aaattttag gactatgaag aactactagg     16800
aagacagaaa ttttaggata tttagggtga caattagaag attaaggaag cttttgagt     16860 ataacagtag tccaaggaat caaatgttca tcagaatcct tattatggtg gctcatgcct    16920
gtaaacccag cactttggga ggtcaagatg ggaggatcac atagcttagg agcttgagac    16980
cacctaggca acatagcgaa accctgtctc tactaaaaat gaaagaaaaa ttagcctagc    17040
atggtggttc ctgccctgta gtcccagcta ctaaggaggc tgaggatcac ttgaacctgg    17100
gagatggagg ctacagtgag ctataatcgc accattgcac cccagcccag cgacagagt     17160 gagatactgt gtcaaaaaaa aaaaaaaatc cttttccccc tctcattaac attcttttca    17220
ctccctaatt tctgaaagaa ctagattttt gaaagatgaa atatatgctt gaccagggca    17280
tgtaatgatt agcagatcac agtatcatct caacaacatt catgtggctg atgatctaag    17340
gcaagagaat gtaaagtagt caagtcaca ctatgtgcat tttaagagac atactgcacc     17400
aaatgcaata gcgagcatgg tctgcatccg ggcatcttcc agtgtgctca gtagcccttt    17460
tttgctaaga agagctcttc ctgccagggt ccagaacttc acatgtttta ctcccactga    17520
```

```
gacaaactgg gtatctgaat ctggtcggaa ttctgccaca aaaatacgtt gattgtgacc   17580
agctctgctg gcaattttgg cacctgacaa gatacaacaa aattatctag gttattacaa   17640
gaaccaagct aatcaacagc atcaaacaaa tatgtaaaat acatagttca aaaaacaaag   17700
gcttagaaga gaggccaatg gcccctgctc tactacctag caatacatga tttacaatta   17760
tttgtgtatt gagtcctttt cacttatctt cgctccatta acttttcttt atataacgta   17820
aatgttttgt ctaaagtgtg gtaggtaata ttatcctgct gatctgccat tatcattaga   17880
aatatacata attttcataa gaatctccaa aaccaatcaa atcattaata ataaatacat   17940
agtttcttgc tggaagaaaa tagcagtgaa tcatttataa tgctaataat ggtttcatta   18000
atttatctgt tttgtgaggt tacagttcca ctgggctttt aaagtgaaat atacctacag   18060
taccactgtg tacagtatat tgcataggcc tccactgaat gattgtttca accaccaact   18120
ttaagacaaa tattaaatac agaattccta cta                                18153

<210> SEQ ID NO 28
<211> LENGTH: 22
<212> TYPE: RNA
<213> ORGANISM: Artificial Sequence
<220> FEATURE:
<223> OTHER INFORMATION: Synthetic construct

<400> SEQUENCE: 28
gaauuuaucg accaccugca ag                                            22

<210> SEQ ID NO 29
<211> LENGTH: 22
<212> TYPE: RNA
<213> ORGANISM: Artificial Sequence
<220> FEATURE:
<223> OTHER INFORMATION: Synthetic construct

<400> SEQUENCE: 29
guacuggccu gccuguaaaa au                                            22

<210> SEQ ID NO 30
<211> LENGTH: 21
<212> TYPE: RNA
<213> ORGANISM: Artificial Sequence
<220> FEATURE:
<223> OTHER INFORMATION: Synthetic construct

<400> SEQUENCE: 30
ggccugccug uaaaaauggg g                                             21

<210> SEQ ID NO 31
<211> LENGTH: 21
<212> TYPE: RNA
<213> ORGANISM: Artificial Sequence
<220> FEATURE:
<223> OTHER INFORMATION: Synthetic construct

<400> SEQUENCE: 31
gccaccaaga cacgccuuga a                                             21

<210> SEQ ID NO 32
<211> LENGTH: 20
<212> TYPE: RNA
<213> ORGANISM: Artificial Sequence
<220> FEATURE:
<223> OTHER INFORMATION: Synthetic construct
```

```
<400> SEQUENCE: 32
auuagacacu ucagauagau                                            20

<210> SEQ ID NO 33
<211> LENGTH: 107
<212> TYPE: RNA
<213> ORGANISM: Artificial Sequence
<220> FEATURE:
<223> OTHER INFORMATION: Synthetic construct

<400> SEQUENCE: 33
guacuggccu gccuguaaaa aucaaaguuu uaguacucug gaaacagaau cuacuaaaac    60
aaggcaaaau gccuguuuua ucucgucaac uuguuggcga gauuuuu                107
```

COMPOSITIONS AND METHODS FOR SUPPRESSING MSUT2

CROSS REFERENCE TO RELATED APPLICATIONS

This application claims the benefit of the filing date of U.S. Provisional Application 62/656,900, which was filed on Apr. 12, 2018. The content of this earlier filed application is hereby incorporated by reference herein in its entirety.

STATEMENT REGARDING FEDERALLY FUNDED RESEARCH

This invention was made with government support under grant number 5I01BX000877 awarded by the Department of Veterans Affairs and under grant number RF1AG055474 awarded by National Institutes of Health. The government has certain rights in the invention.

INCORPORATION OF THE SEQUENCE LISTING

The present application contains a sequence listing that is submitted in ASCII format via EFS-Web herewith, containing the file name "37759_0204U1_SL.txt" which is 36,864 bytes in size, created on Mar. 18, 2022", and is herein incorporated by reference in its entirety.

BACKGROUND

The molecular mechanisms underpinning neurodegenerative diseases include the cellular disruption of proteostasis. In Alzheimer's disease (AD), this disruption manifests as the deposition of amyloid plaques and neurofibrillary tangles (NFTs), the diagnostic pathological lesions of the disorder. While the mechanistic relationship between plaques and tangles remains unclear, abnormal tau and Aβ synergize to drive neurodegeneration in AD. A large body of evidence supports the idea of Aβ amyloid pathology initiating the disease process in AD. However, the discovery of tau mutations in frontotemporal lobar degeneration with tau inclusions (FTLD-tau) (P. Poorkaj, et al., *Ann. Neurol.* 43, 815-825 (1998); M. G. Spillantini, et al., *Proc. Natl. Acad. Sci. U.S.A.* 95, 7737-7741 (1998); L. N. Clark, et al., *Proc. Natl. Acad. Sci. U.S.A.* 95, 13103-13107 (1998); and M. Hutton, et al., *Nature* 393, 702-705 (1998)) demonstrates that tau pathology can cause neurodegeneration independent of amyloid plaques. Furthermore, tau pathology, not amyloid deposition, correlates with the severity of dementia in AD (L. M. Bierer, et al., *Arch Neurol* 52, 81-88 (1995). Thus, findings to date justify active investigation of the mechanistic underpinnings of both amyloid- and tau-mediated neurodegeneration in AD. Despite a diverse array of highly powered AD clinical trials targeting amyloid production, clearance, or deposition, none have been successful. Altogether, these observations suggest that tau-targeted therapies in conjunction with removal of amyloid may be required to achieve cognitive preservation when treating AD (M. R. Khanna, et al., *Alzheimers Dement* 12, 1051-1065 (2016); and C. Ballatore, et al., *Nat Rev Neurosci* 8, 663-672 (2007)).

SUMMARY

Disclosed herein are methods of treating Alzheimer's disease or dementia, the methods comprising: administering to a subject with Alzheimer's disease or dementia a therapeutically effective amount of a mammalian suppressor of tauopathy 2 (MSUT2) inhibitor, wherein the therapeutically effective amount reduces accumulation of phosphorylated and aggregated human tau.

Disclosed herein are methods of inhibiting expression of a MSUT2 polynucleotide in a subject, the methods comprising administering to a subject with Alzheimer's disease or dementia a therapeutically effective amount of a mammalian suppressor of tauopathy 2 (MSUT2) inhibitor.

Disclosed herein are methods of inhibiting expression of a MSUT2 polynucleotide, the methods comprising contacting a cell with a mammalian suppressor of tauopathy 2 (MSUT2) inhibitor, wherein the suppressor of tauopathy 2 (MSUT2) reduces accumulation of phosphorylated and aggregated tau.

Disclosed herein are methods of reducing phosphorylated and aggregated human tau protein in a subject, the methods comprising administering to a subject with Alzheimer's disease or dementia a therapeutically effective amount of a mammalian suppressor of tauopathy 2 (MSUT2) inhibitor.

Disclosed herein are methods of suppressing expression of a MSUT2 polynucleotide in a subject, the methods comprising administering to a subject with Alzheimer's disease or dementia a therapeutically effective amount of a mammalian suppressor of tauopathy 2 (MSUT2) inhibitor.

Disclosed herein are methods of suppressing expression of a MSUT2 polynucleotide, the methods comprising contacting a cell with a mammalian suppressor of tauopathy 2 (MSUT2) inhibitor, wherein the suppressor of tauopathy 2 (MSUT2) reduces accumulation of phosphorylated and aggregated tau.

Disclosed herein are methods of potentiating a neuroinflammatory response to a pathological tau protein in a subject, the methods comprising administering to a subject with Alzheimer's disease or dementia a therapeutically effective amount of a mammalian suppressor of tauopathy 2 (MSUT2) inhibitor.

Disclosed herein are methods of potentiating a neuroinflammatory response to a pathological tau protein, the methods comprising contacting a cell with a mammalian suppressor of tauopathy 2 (MSUT2) inhibitor, wherein the suppressor of tauopathy 2 (MSUT2) reduces accumulation of phosphorylated and aggregated tau.

Disclosed herein are methods of decreasing astrocytosis or microgliosis in a subject, the methods comprising administering to a subject with Alzheimer's disease or dementia a therapeutically effective amount of a mammalian suppressor of tauopathy 2 (MSUT2) inhibitor.

Disclosed herein are methods of decreasing astrocytosis or microgliosis, the methods comprising contacting a cell with a mammalian suppressor of tauopathy 2 (MSUT2) inhibitor, wherein the suppressor of tauopathy 2 (MSUT2) reduces accumulation of phosphorylated and aggregated tau.

Disclosed herein are methods of reducing neuroinflammation in a subject, the methods comprising administering to a subject with Alzheimer's disease or dementia a therapeutically effective amount of a mammalian suppressor of tauopathy 2 (MSUT2) inhibitor.

Disclosed herein are methods of reducing neuroinflammation, the methods comprising contacting a cell with a mammalian suppressor of tauopathy 2 (MSUT2) inhibitor wherein the suppressor of tauopathy 2 (MSUT2) reduces accumulation of phosphorylated and aggregated tau.

Disclosed herein are guide RNA (gRNA) molecules that target one or more nucleotides in a MSUT2 gene.

Disclosed herein are CRISPR-Cas systems comprising one or more vectors comprising: a) a promoter operably linked to one or more nucleotide sequences encoding a CRISPR-Cas system guide RNA (gRNA), wherein the gRNA hybridizes with a target sequence of a DNA locus in a cell; and b) a regulatory element operably linked to a nucleotide sequence encoding a RNA-directed nuclease, wherein components a) and b) are located on the same or different vectors of the same system, wherein the gRNA targets and hybridizes with the target sequence and directs the RNA-directed nuclease to the DNA locus; wherein the gRNA sequence is selected from the group consisting of SEQ ID NOs: 6, 7, 8, 9, 28, 29, 30, 31, 32 and 33. Disclosed herein are CRISPR-Cas systems comprising one or more vectors comprising: a) a promoter operably linked to one or more nucleotide sequences encoding a CRISPR-Cas system guide RNA (gRNA), wherein the gRNA hybridizes with a target sequence of a DNA locus in a cell; and b) a regulatory element operably linked to a nucleotide sequence encoding a RNA-directed nuclease, wherein components a) and b) are located on the same or different vectors of the same system, wherein the gRNA targets and hybridizes with the target sequence and directs the RNA-directed nuclease to the DNA locus; wherein the gRNA sequence comprises 10-30 bp, 15-25 bp, 17-24 bp or any other fragment of the sequences set forth in SEQ ID NOs: 6, 7, 8, 9, and 33. In some aspects, the gRNA sequence comprises a sequence having 80%, 85%, 90%, 95%, 96%, 97%, 98%, or 99% identity to the sequences set forth in SEQ ID NOs: 6, 7, 8, 9, 33 or a fragment thereof.

Disclosed herein are vectors comprising: a) a promoter operably linked to one or more nucleotide sequences encoding a CRISPR-Cas system guide RNA (gRNA); and b) a regulatory element operably linked to a nucleotide sequence encoding a RNA-directed nuclease; wherein the gRNA sequence is selected from the group consisting of SEQ ID NOs: 6, 7, 8, 9, 28, 29, 30, 31, 32 and 33.

Disclosed herein are methods of screening for compounds capable of inhibiting MSUT2 binding to poly(A) RNA, the methods comprising: (a) contacting at least one candidate compound, poly(A) RNA and PABPN1 under conditions in which PABPN1 is capable of stimulating RNA polyadenylation in the absence of the candidate compound; (b) determining whether the candidate compound inhibits MSUT2 binding to poly(A) RNA; and (c) selecting the candidate compound which inhibits MSUT2 binding to poly(A) RNA.

Disclosed herein are methods for screening compounds for pharmacological intervention in tauopathy disorders, the methods comprising: (a) providing an assay for MSUT2 to bind to poly(A) RNA and its modulation of RNA polyadenylation; (b) providing a purified or non-purified compound or purified or non purified mixture of compounds; (c) screening the purified or non-purified compound or purified or non-purified mixture of compounds in an environment that allow for inhibition of MSUT2 binding to poly(A) RNA by the purified or non-purified compound or purified or non-purified mixture of compounds in the assay; and (d) isolating the one or more compounds that inhibit MSUT2 binding to poly(A) RNA.

Disclosed herein are compositions comprising a small molecule consisting of

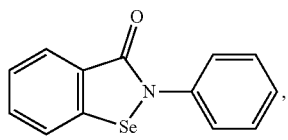

-continued

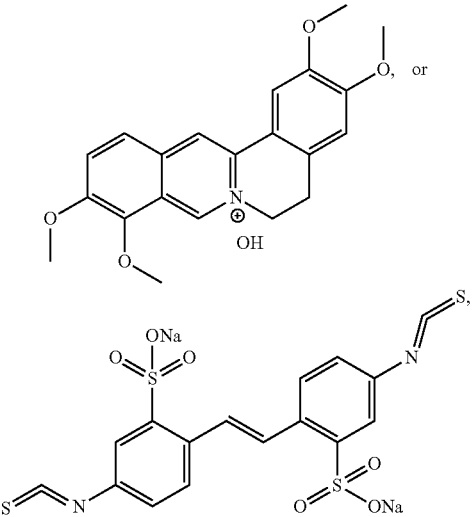

wherein the composition reduces accumulation of phosphorylated and aggregated human tau protein in a subject with Alzheimer's disease or dementia.

Disclosed herein are compositions comprising a gRNA sequence selected from the group consisting of GAAUUUAUCGACCACCUGCAAGCAAAGUUUU-AGUACUCUGGAAACAGAAUCU ACUAAAACAAGGCAAAAUGCCGUGUUUAUCUC-GUCAACUUGUUGGCGAGAUU UUU (SEQ ID NO: 6), GGCCUGCCUGUAAAAAUGGGGCAAAGUUUU-AGUACUCUGGAAACAGAAUCUA CUAAAACAAGGCAAAAUGCCGUGUUUAUCUCGU-CAACUUGUUGGCGAGAUUU UU (SEQ ID NO: 7), GCCACCAAGACACGCCUUGAACAAAGUUUU-AGUACUCUGGAAACAGAAUCUAC UAAAACAAGGCAAAAUGCCGUGUUUAUCUCGU-CAACUUGUUGGCGAGAUUUU U (SEQ ID NO: 8), AUUAGACACUUCAGAUAGAUCUGUUUUAGAGC-UAGAAAUAGCAAGUUAAAAU AAGGCUAGU-CCGUUAUCAACUUGAAAAAGUGGCACCGAGUCG-GUGCUUUU (SEQ ID NO: 9), GUACUGGCCUGCCUGUAAAAAUCAAAGUUUU-AGUACUCUGGAAACAGAAUCU ACUAAAACAAGGCAAAAUGCCGUGUUUAUCUC-GUCAACUUGUUGGCGAGAUU UUU (SEQ ID NO: 33), GAAUUUAUCGACCACCUGCAAG (SEQ ID NO: 28) GUACUGGCCUGCCUGUAAAAAU (SEQ ID NO: 29) GGCCUGCCUGUAAAAAUGGGG (SEQ ID NO: 30) GCCACCAAGACACGCCUUGAA (SEQ ID NO: 31), and AUUAGACACUUCAGAUAGAU (SEQ ID NO: 32).

Disclosed herein are compositions comprising AUGAUGCAAAGUGUACUAAACCAG (SEQ ID NO: 10), AUGAUGCAAAGUGUACUAAACCAGAUU (SEQ ID NO: 11, AUGAUGCAAAGUGUACUAAACCAGAU (SEQ ID NO: 12) AUGAUGCAAAGUGUACUAAACCA (SEQ ID NO: 13) AUAUGAUGCAAAGUGUAC-UAAACCAG (SEQ ID NO: 14), or UAUGAUGCAAAGU-GUACUAAACCAG (SEQ ID NO: 15).

Other features and advantages of the present compositions and methods are illustrated in the description below, the drawings, and the claims.

BRIEF DESCRIPTION OF THE DRAWINGS

FIGS. 1A-F show MSUT2 KO mouse characterization. FIG. 1A shows the genetrap insertion site on mouse chromosome 12. Vertical bars are exons, intervening lines represent introns. The position on chromosome 12 is at 49.88 cM, cytoband F1 or between bases 98746968-98787774. The triangle on the lower diagram indicates the position of the deleted exon 13 in MSUT2 (otherwise known as ZC3H14). FIG. 1B shows the protein domain structures of mouse MSUT2 and C. elegans sut-2 homologs. Below is the consequence of deleting MSUT2 exon 13 for protein coding potential of the gene. Namely, the CCCH finger domains are deleted and out of frame resulting in a non-functional protein. Arrows with bk741 and bk87 indicate the locations of mutations identified in C. elegans that result in early stop codons. FIG. 1C shows the Northern blot of MSUT2 mRNA with an exon 13 specific probe. Note missing specific transcripts in MSUT2 KO mice (marked by arrowheads). FIG. 1D shows MSUT2 immunoblot for MSUT2 protein reveals loss of full MSUT2 protein isoforms in MSUT2 KO mice. MSUT2/ZC3H14 antibody recognizes the N-terminal domain which is not deleted by elimination of Exon 13 (J. Rha, et al., Hum Mol Genet, (2017)). FIG. 1E shows that MSUT2 KO show no change in total tau protein levels by immunoblot in PS19 Tg mice. Actin is load control. FIG. 1F shows that MSUT2 KO decreases accumulation of NFTs in the entorhinal cortex (EC) of PS19 tauopathy mice. NFTs are detectable by Gallyas silver stain of 9 month old PS19 tauopathy mouse brain sections. Gallyas+ NFTs in MSUT2 KO/PS19 Tg (N=24) compared with PS19 Tg alone (N=24) demonstrated a significant reduction of ~73% (p=0.0145 by two-tailed t-test). Scale bar=100 µm.

FIGS. 2A-E show Genetic ablation of MSUT2 protects against tauopathy in mice. FIG. 2A shows that MSUT2 KO decreases accumulation of NFTs in the CA1 region of hippocampi of PS19 tauopathy mice. NFTs are detectable by Gallyas silver stain of 9 month old PS19 tauopathy mouse brain sections. Gallyas+ NFT counts in MSUT2 KO/PS19 Tg (N=24) compared with PS19 Tg alone (N=24) demonstrated a significant reduction of 85% (p=0.0129 by two-tailed t-test). Statistical significance indicated by asterisks throughout the figures; * denotes p<0.05,  denotes p<0.01, * denotes p<0.001. Scale bar=100 µm. FIG. 2B shows that MSUT2 KO decreases accumulation of hyperphosphorolated tau (pTau) in the stratum lacunosum moleculare (SLM) of PS19 tauopathy mice. pTau (T231) was detected by monoclonal antibody AT180 staining of 9 month old PS19 tauopathy mouse brain sections. Densitometry of AT180+ pathological tau deposits in MSUT2 KO/PS19 Tg (N=24) compared with PS19 Tg alone (N=24) demonstrated a significant reduction of 55% (p=0.0156 by two-tailed t-test). Scale bar=100 µm. FIG. 2C shows that MSUT2 KO decreases accumulation of pre-tangle tau species in the stratum oriens (SO) region of hippocampi of PS19 tauopathy mice. Pre-tangle pathological tau species were detected by conformation dependent tau monoclonal antibody MC1 staining of 9 month old PS19 tauopathy mouse brain sections. Densitometry of MC1+ lesions in MSUT2 KO/PS19 Tg (N=24) compared with PS19 Tg alone (N=24) demonstrated a significant reduction of 50% (p=0.0042 by two-tailed t-test). Scale bar=50 µm. FIG. 2D shows that MSUT2 KO decreases loss of CA1 region neurons of PS19 tauopathy mice. Neuronal cell bodies were detected by cresyl violet staining of 9 month old PS19 tauopathy mouse brain sections (arrows indicate pyramidal cell layer). Densitometry of pyramidal neuron density in MSUT2 KO/PS19 Tg (N=21) compared with PS19 Tg alone (N=19) demonstrated a significant increase in CA1 neurons of 53% (p=0.0062 by two-tailed t-test). FIG. 2E shows that MSUT2 KO enhances performance in Barnes maze training of 8 month old PS19 tauopathy mice. Although PS19 Tg+ animals perform poorly on the Barnes maze, taking longer to locate the escape hole compared to either WT or Msut2 KO animals (p<0.001), PS19 Tg+ animals that are homozygous for Msut2 KO perform much better (p<0.001), and are not significantly different from WT. Note normal spontaneous activity levels in both PS19 and MSUT2 KO/PS19 as measured in an open field (FIG. 4A), and normal locomotor coordination as measured on a rotorod (FIG. 4G).

FIG. 3A shows that MSUT2 KO decreases pTau in in the stratum oriens (SO) and entorhinal cortex (EC) of PS19 tauopathy mice. pTau (T231) was detected by phospho-dependent tau monoclonal antibody AT180 staining of 9 month old PS19 tauopathy mouse brain sections. Densitometry of AT180+ pathological tau deposits in MSUT2 KO/PS19 Tg (N=24) compared with PS19 Tg alone (N=24) demonstrated a significant reduction of 56% in the EC (p=0.01 by two-tailed t-test). The significant decrease in the SO was 56% (p=0.005 by two-tailed t-test). Scale bar=50 µm SO; 100 µm EC. FIG. 3B show that MSUT2 KO decreases accumulation of pre-tangle tau species in the stratum lacunosum moleculare (SLM) region of hippocampus and the entorhinal cortex (EC) of PS19 tauopathy mice. Pre-tangle pathological tau species were detected by conformation dependent tau monoclonal antibody MC1 staining of 9 month old PS19 tauopathy mouse brain sections. Densitometry of MC1+ lesions in MSUT2 KO/PS19 Tg (N=24) compared with PS19 Tg alone (N=24) demonstrated a significant reduction of 43% in the EC (p=0.03 by two-tailed t-test). The decrease of 38% in the SLM approached statistical significance (p=0.07 by two-tailed t-test). Scale bar=100 µm. FIG. 3C shows that WT and MSUT2 KO mouse brain have similar NeuN staining throughout the hippocampus. Scale bar=500 µm.

FIG. 4A shows that the animals at the time of Barnes testing remain active in an open field. The genotypes exhibit mild hyperactivity compared to wildtype when allowed to explore an open field for 10 minutes. Data are shown as mean+/−SEM. FIG. 4B shows that Msut2 KO mice have similar body weight compared to their wildtype littermates at 3 months (p=0.74). N=12 MSUT2 KO mice and N=7 WT controls. FIG. 4C shows that there is a strong effect of the PS19 transgene on body weight change from 6 to 9 months of age (p<0.001). FIG. 4D shows that there is not a significant main effect of MSUT2 genotype (p=0.18) on weight change from 6 to 9 months of age in PS19 animals, but there is a significant main effect of sex (p<0.0001) and an interaction between genotype and sex (p=0.05). Post-hoc analysis revealed a significant effect of MSUT2 genotype in males (p=0.02) but not in females (0.65). MSUT2 KO partially protects PS19 males against the weight loss associated with the tau transgene. PS19 females held approximately constant body weight from 6 to 9 months of age regardless of MSUT2 genotype. FIG. 4E shows that prior to progression to paralysis, PS19 Tg+ animals perform better than their non-Tg littermates on the rotorod task, in agreement with reports from other groups (p<0.001). FIG. 4F shows that Msut2 KO mice do not exhibit any locomotor defects during rotorod testing. (p=0.30). FIG. 4G shows that Msut2 KO did not have any significant effect on the locomotor coordination of PS19 Tg+ mice during rotorod testing. (p=0.54).

FIGS. 5A-E show that MSUT2 binds independently to both poly(A) tails and PABPN1. FIG. 5A shows the in vitro confirmation of the yeast two-hybrid interaction between MSUT2 CCCH finger domain and PABPN1. 35S radiolabeled PABPN1 was tested against immobilized recombinant GST-MSUT2 Zinc Finger (ZF) fusion protein or recombinant GST alone using GST pulldown assays. RNAse pre-treatment of samples does not prevent MSUT2 and PABPN1 protein-protein interactions. FIG. 5B shows that the Proximity Ligation Assay (PLA) detects MSUT2/PABPN1 interaction within intact HEK293 cell nuclei. Gray, DAPI staining. White, PLA detected interactions. Left, panel is high magnification stitched-panel image of a large field of PLA immunostained HEK293 cells. Scale bar=100 Rectangle represents a single image in the stitched panel. FIG. 5C shows the Surface Plasmon Resonance detection of MSUT2 and PABPN1 binding to poly(A) RNA. Dissociation constants were calculated for biotinylated poly(A)15 from the binding kinetics of each protein at five concentrations (1, 0.9, 0.8, 0.7, 0.6 1, 1M). MSUT2 KD=60±15 nM vs PABPN1 KD=237±21 nM for poly(A)15. FIG. 5D shows that MSUT2 and PABPN1 colocalize in splicing factor SC35-positive nuclear speckles in HEK293 cells (Pearson Coefficient of Correlation (PCC)=0.7976). Representative single channel image of nuclear MSUT2, PABPN1, and DAPI. Colocalization analysis of MSUT2 with SC35 (PCC=0.7578) and PABPN1 with SC35 (PCC=0.4347) are shown in FIGS. 6C-D. FIG. 5E shows that MSUT2 and PABPN1 colocalize at nuclear speckles in neuronal nuclei from human frontal cortex. Representative confocal image shows immunofluorescent staining for MSUT2 (upper panel with box), PABPN1 (light white), and DAPI (gray). Inset image is high magnification examination of a single nucleus displayed as split channels for MSUT2 and PABPN1 and merged channels. MSUT2 and PABPN1 colocalize with a PCC=0.88 in this image (see also FIG. 6). Scale bar=25 µm.

FIGS. 6A-D show that MSUT2, PABPN1, and poly(A) mRNA colocalize at nuclear speckles in HEK293 cells. Representative images are displayed as split channels, merged, the colocalization of the two species, and the plot of the PCC of the two species. FIG. 6A shows that MSUT2 colocalizes with poly(A) mRNA within the nucleus with a PCC=0.7644. FIG. 6B shows that PABPN1 colocalizes with poly(A) mRNA with a PCC=0.6241. FIG. 6C shows that MSUT2 colocalizes with SC35 with a PCC=0.7578. FIG. 6D shows that less PABPN1 colocalizes with SC35 when compared to MSUT2 with a PCC=0.4347.

FIGS. 7A-J show that MSUT2 mediates effects on tauopathy through poly(A) tail length but not gene expression. FIG. 7A show that synthetic siRNA treatment eliminates MSUT2 and PABPN1 protein in HEK293 cells. FIG. 7B shows HEK/tau cells overexpressing human tau. Immunofluorescent staining of nuclei (DAPI, dark gray) and pTau T231 (AT180, white) (M. Goedert, et al., *Biochem J* 301 (Pt 3), 871-877 (1994)); positive staining control, total tau (light gray). Scale bar=15 nm. FIG. 7C shows that MSUT2 knockdown by siRNA decreases pTau accumulation. Immunofluorescent staining of nuclei (DAPI, dark gray) and pTau T231 (AT180, white) ((M. Goedert, et al., *Biochem J* 301 (Pt 3), 871-877 (1994)); positive staining control, total tau (light gray). FIG. 7D shows that PABPN1 knockdown by siRNA increases pTau accumulation. Immunofluorescent staining of nuclei (DAPI, dark gray) and pTau T231 (AT180, white) ((M. Goedert, et al., *Biochem J* 301 (Pt 3), 871-877 (1994)); positive staining control, total tau (light gray). FIG. 7E shows quantitation of immuno staining for pTau T231 (AT180), conformation dependent tau (MC1) (C. L. Weaver, et al., *Neurobiology of Aging* 21, 719-727 (2000)), and tau oligomeric complex-1 monoclonal antibody (TOC1) (S. M. Ward, et al., *J Alzheimers Dis* 37, 593-602 (2013); and K. R. Patterson, et al., *Biochemistry* 50, 10300-10310 (2011)). Error bars are SEM. For comparisons of MSUT2 siRNA treated to untreated cells stained for AT180, $p<0.005$, for PABPN1 treated vs untreated $p<0.001$; for TOC1 staining, MSUT2 siRNA vs untreated gives $p<0.05$, for PABPN1 treated vs untreated $p<0.001$; for both PABPN1 and MSUT2 treatment MC1 staining comparison vs untreated gives $p<0.001$. FIG. 7F shows that modulating poly(A) tail length exacerbates tauopathy. The ccr-4 mutants have long poly(A) tails on bulk mRNA. 4-day-old tau Tg *C. elegans* with or without a strong loss of function mutation in ccr-4 were placed in liquid and their swimming activity recorded. Tau Tg animals exhibit significantly better locomotion relative to tau Tg; ccr-4 mutant animals ($p<0.0001$ by 2-tailed Student's t-test). FIG. 7G shows multidimensional scaling and principal component analysis of MSUT2 KO vs. C57BL/6J RNA sequencing data. Total brain RNA from MSUT2 KO and C57BL/6J was analyzed by RNAseq. Principal component analysis clearly distinguishes knockout (ko) from control (ctl) mice. FIG. 7H shows the transcriptomic changes of MSUT2 KO vs. C57BL/6J from RNA sequencing data (normalized mean read count by gene). Differentially regulated genes are depicted as red spots. See Table 1 for listing of the differentially expressed genes. FIG. 7I shows the alternative splicing changes of MSUT2 KO vs. C57BL/6J from RNA sequencing data (normalized mean read count by exon). 201 differentially spliced exons were detected (depicted by gray spots). See FIG. 16 for listing of differentially spliced exons. FIG. 7J shows the volcano plot of alternative polyadenylation site selection (APA) changes in MSUT2 KO vs. C57BL/6J from RNA sequencing data. Analysis of APA was conducted using Dynamic Analysis of Alternative Polyadenylation from RNAseq (DaPars). Ten genes exhibited a significant change in percentage of distal poly(A) site usage (PDUI) of greater than 20% (see gray spots). See FIG. 17 for listing of genes with significant alterations in APA.

FIG. 8A shows that tau protein was sequentially extracted to obtain detergent insoluble tau protein from HEK/tau cells with or without MSUT2 and PABPN1 siRNA knockdown. MSUT2 knockdown ameliorates aggregated tau accumulation while PABPN1 knockdown exacerbates tau aggregation. Knockdown of both MSUT2 and PABPN1 together has an intermediate effect on tau aggregation. The detergent insoluble fraction containing aggregated tau was probed with a pan-tau antibody as described (see ab17026 (68)). FIG. 8B shows that comparison of PABPN1 protein levels in PS19 Tg and PS19/MSUT2 KO mice as determined by immunoblotting. FIG. 8C shows the comparison of PABPN1 expression in wild type vs. MSUT2 KO mice by PABPN1 immunohistochemistry (IHC).

FIGS. 9A-F show MSUT2 overexpression in the hippocampus following AAV-MSUT2 injection. MSUT2 overexpression is seen throughout the hippocampal formation on the ipsilateral side (FIG. 9A) compared to the contralateral side (FIG. 9B) of the brain of Tau4RTg2652 mice injected with AAV-MSUT2. FIGS. 9C, D show higher magnification of the CA3 region of the hippocampus. Note that MSUT2 is normally expressed in the nucleus of CA3 neurons on the contralateral side (FIG. 9D) but is abnormally distributed to the cytoplasm and fibers on the ipsilateral side when overexpressed by AAV injection. FIG. 9E shows that MSUT2 overexpression does not impact tau abundance. Shown is the hippocampus of Tau4RTg2652 mice injected with AAV-MSUT2 or AAV-GFP and immunostained for total tau. FIG.

9F shows that MSUT2 overexpression increases microgliosis. Shown is the ipsilateral fimbria of the hippocampus of Tau4RTg2652 mice injected with AAV-MSUT2 or AAV-GFP. MSUT2 overexpression exacerbates reactive microglia as compared to AAV-GFP injection. Microgliosis was detected by IBA1 IHC of glia by staining of 4 month old Tau4RTg2652 tauopathy mouse brain sections. Densitometry of IBA1+ reactivity in MSUT2 AAV/Tg2652 (N=12) compared with GFP AAV/Tg2652 (N=5) demonstrated an increase of 1816% that approached statistical significance (p=0.06 by two-tailed t-test). Scale bars=500 µm (A, B) 50 µm (C, D) 100 µm (E).

Figures 10A, 10B, 10C, 10D, 10E:
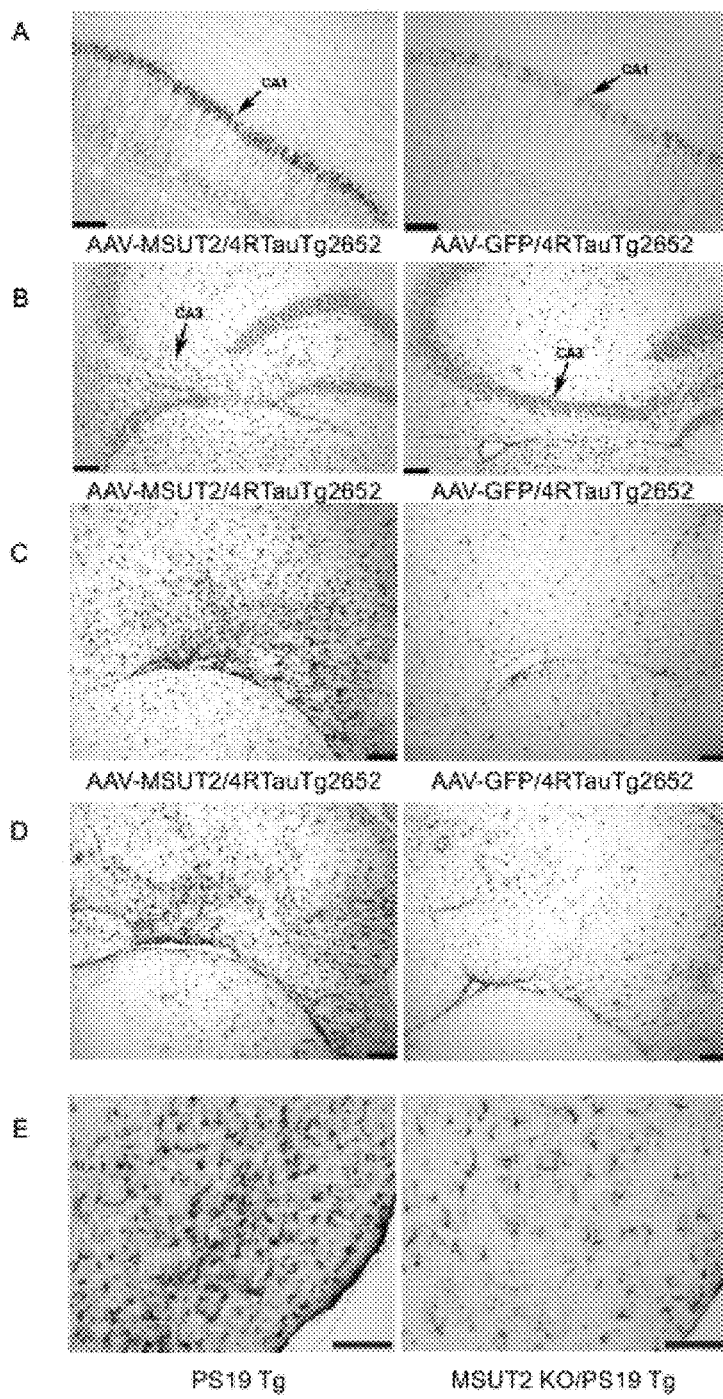

FIGS. 10A-E shows MSUT2 potentiates neuroinflammation, tau pathology and neurodegeneration. FIG. 10A shows that MSUT2 overexpression exacerbates pTau accumulation in hippocampus. Shown is the ipsilateral CA1 region of Tau4RTg2652 mice injected with AAV-MSUT2 or AAV-GFP. MSUT2 overexpression exacerbates pTau accumulation as compared to AAV-GFP injection. pTau (phospho-Thr231) was detected by phospho-dependent tau monoclonal antibody AT180 staining of 4 month old Tau4RTg2652 tauopathy mouse brain sections (arrows indicate CA1 pyramidal cell layer). Densitometry of AT180+ pathological tau deposits in MSUT2 AAV/Tau4RTg2652 (N=15) compared with GFP AAV/Tau4RTg2652 (N=5) demonstrated a significant increase of 294% (p=0.0044 by two-tailed t-test). Scale bar=100 µm. FIG. 10B shows that MSUT2 overexpression exacerbates neuronal loss in hippocampus. Shown is the ipsilateral CA3 region of Tau4RTg2652 mice injected with AAV-MSUT2 or AAV-GFP. MSUT2 overexpression exacerbates neuronal loss in CA3 as compared to AAV-GFP injection. Neuronal cell bodies were detected by cresyl violet staining (arrows indicate CA3 pyramidal cell layer). Densitometry of pyramidal layer staining in MSUT2 AAV/Tau4RTg2652 (N=15) compared with GFP AAV/Tau4RTg2652 (N=5) demonstrated a significant decrease of cresyl violet positive neuronal cell bodies in CA3 (33%, p=0.0001 by two-tailed t-test). Scale bar=100 µm. FIG. 10C shows that MSUT2 overexpression exacerbates microgliosis in hippocampus. Shown is the ipsilateral CA3 region of Tau4RTg2652 mice injected with AAV-MSUT2 or AAV-GFP. MSUT2 overexpression exacerbates reactive microglia as compared to AAV-GFP injection. Microgliosis was detected by IBA1 IHC of glia by staining of 4-month-old Tau4RTg2652 tauopathy mouse brain sections. Densitometry of IBA1+ reactivity in MSUT2 AAV/Tg2652 (N=13) compared with GFP AAV/Tau4RTg2652 (N=5) demonstrated a statistically significant 19-fold increase (p=0.024 by two-tailed t-test). Scale bar=100 µm. FIG. 10D shows that MSUT2 overexpression exacerbates astrocytosis in hippocampus. Shown is the ipsilateral CA3 region of Tau4RTg2652 mice injected with AAV-MSUT2 or AAV-GFP. MSUT2 overexpression exacerbates reactive astrocytes as compared to AAV GFP injection. Astrocytosis was detected as GFAP reactivity of astrocytes by immunostaining of 4 month old Tau4RTg2652 tauopathy mouse brain sections. Densitometry of GFAP+ reactivity in MSUT2 AAV/Tg2652 (N=14) compared with GFP AAV/Tau4RTg2652 (N=5) demonstrated a statistically significant 12-fold increase (p=0.022 by two-tailed t-test). Scale bar=100 µm. FIG. 10E shows that MSUT2 KO suppresses reactive astrocytosis in response to tau pathology in PS19 mice. Shown is the entorhinal cortex of PS19 Tg mice analyzed for astrocytosis by IHC for GFAP. Densitometry of GFAP+reactivity in the EC of MSUT2 KO/PS19 Tg (N=23) compared with PS19 Tg alone (N=23) demonstrated an approximately 2-fold decrease in astrocytosis (p=0.0104 by two-tailed t-test). Scale bar=100 µm.

Figure 11A:
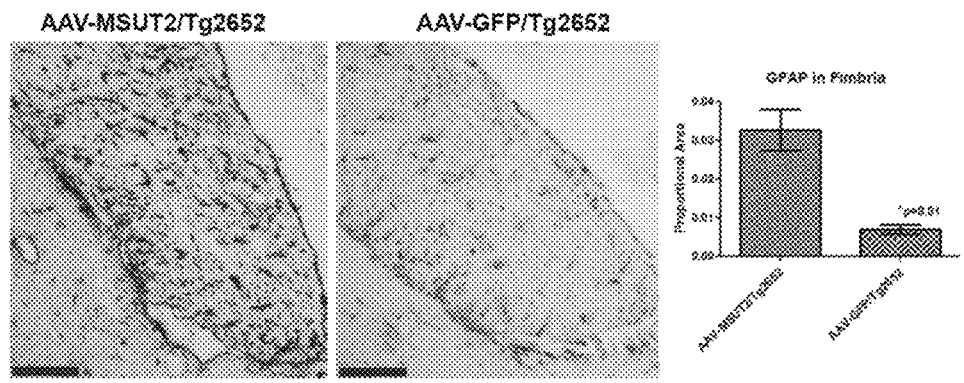
Figure 11B:
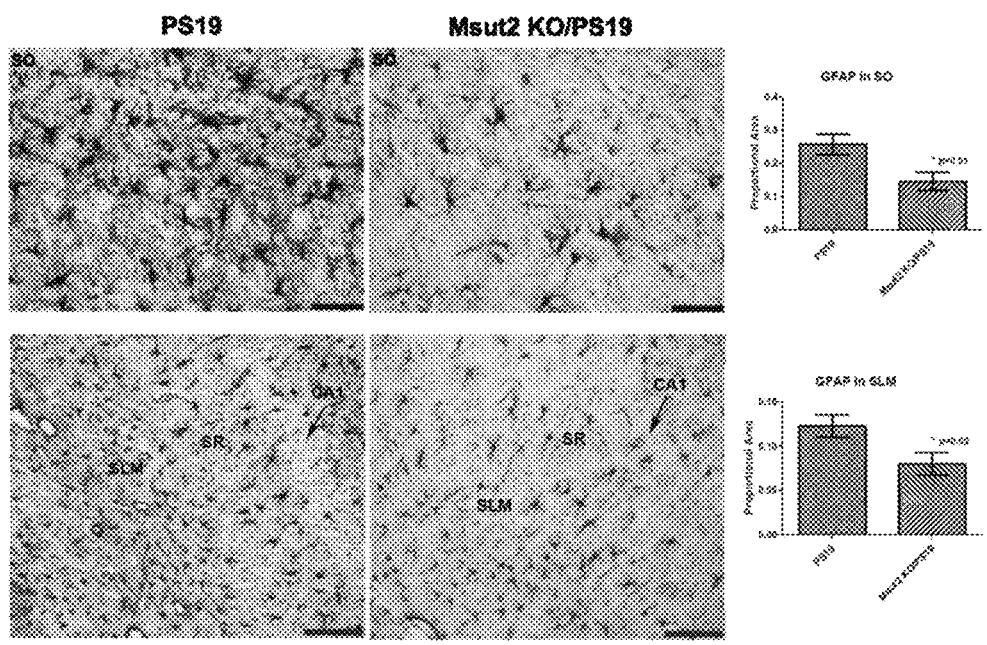

FIGS. 11A-B show the effect of MSUT2 expression on astrocytes in the hippocampus. FIG. 11A shows that MSUT2 overexpression increases astrocytosis. Shown is the ipsilateral fimbria of the hippocampus of Tau4RTg2652 mice injected with AAV-MSUT2 or AAV-GFP. MSUT2 overexpression exacerbates reactive astrocytes as compared to AAV-GFP injection. Astrocytosis was detected as GFAP reactivity of astrocytes by immunostaining of 4 month old Tau4RTg2652 tauopathy mouse brain sections. Densitometry of GFAP+ reactivity in MSUT2 AAV/Tg2652 (N=14) compared with GFP AAV/Tg2652 (N=5) demonstrated a significant increase of 468% (p=0.011 by two-tailed t-test). FIG. 11B shows that MSUT2 KO suppresses reactive astrocytosis in response to tau pathology in PS19 mice. Shown are the stratum oriens (SO) and stratum lacunosum moleculare (SLM) regions of the hippocampi of PS19 Tg mice analyzed for astrocytosis by IHC for GFAP. Densitometry of GFAP+ reactivity in the SO and SLM of MSUT2 KO/PS19 Tg (N=24) was compared with PS19 Tg alone (N=23), demonstrating a significant decrease in astrocytosis (~43% in SO, p=0.011 by two-tailed t-test; ~35% in SLM, p=0.021 by two-tailed t-test). CA1 and stratum radiatum (SR) are indicated for orientation. Scale bar=50 µm SO; 100 µm SLM and fimbria.

FIGS. 12A-D show that MSUT2 KO suppresses reactive microgliosis in response to tau pathology in PS19 mice. Shown are the (FIG. 12A) entorhinal cortex (EC), (FIG. 12B) stratum oriens (SO), and (FIG. 12C) stratum lacunosum moleculare (SLM) of PS19 Tg mice analyzed for microgliosis by IHC for Iba1. Densitometry of Iba1+ reactivity in MSUT2 KO/PS19 Tg (N=23) was compared with PS19 Tg alone (N=24) in microgliosis. While there was a trend for reduced microgliosis in the three regions, this difference did not reach statistical significance. Scale bar=50 µm SO; 100 µm SLM and EC. FIG. 12D shows that post mortem interval (PMI) in hours for AD cases analyzed are not significantly different (p=0.25 by unpaired two tailed t-test).

Figure 13:
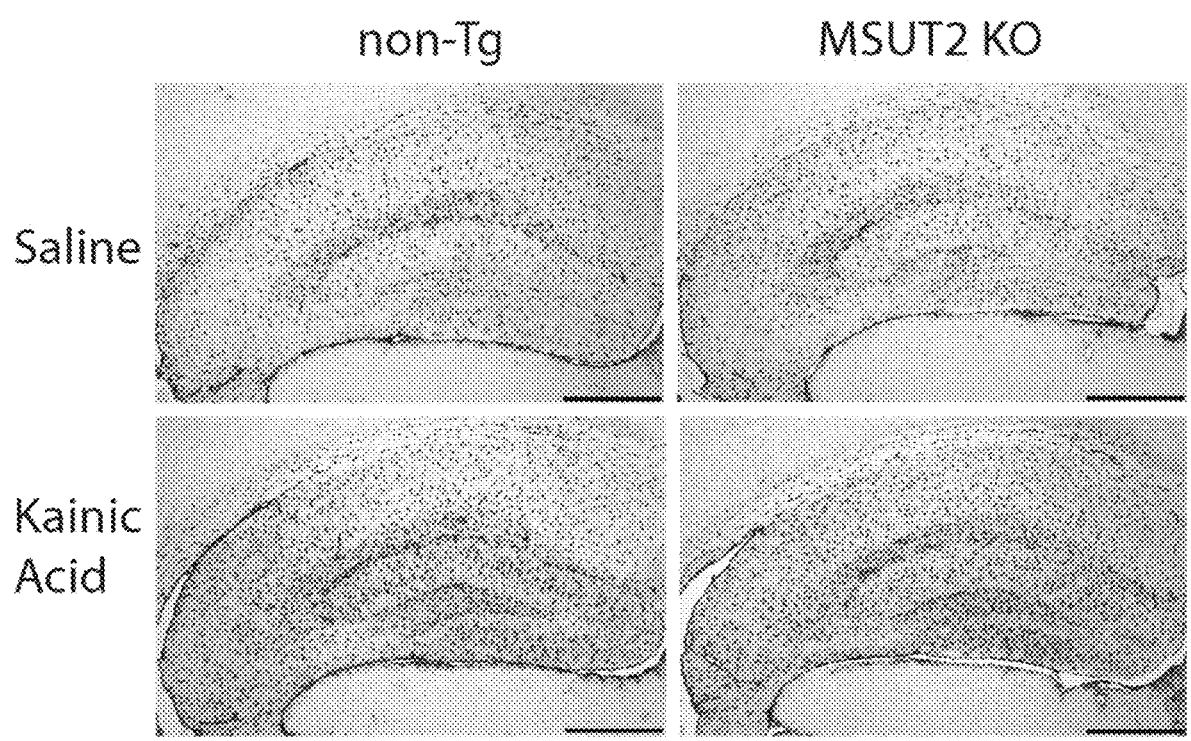

FIG. 13 shows that MSUT2 KO does not alter astrocytosis in response to Kainic Acid (KA) exposure. Shown are the hippocampi of wild type or MSUT2 KO mice 3 days after KA treatment (a single dose of 25 mg/kg KA administered i.p.). While KA treatment provoked an obvious and strong gliotic response, there is no obvious difference in MSUT2 KO relative to wildtype littermates in terms of astrocytosis (IHC for GFAP) in response to KA treatment. Scale bar=500 µm.

Figure 14A:
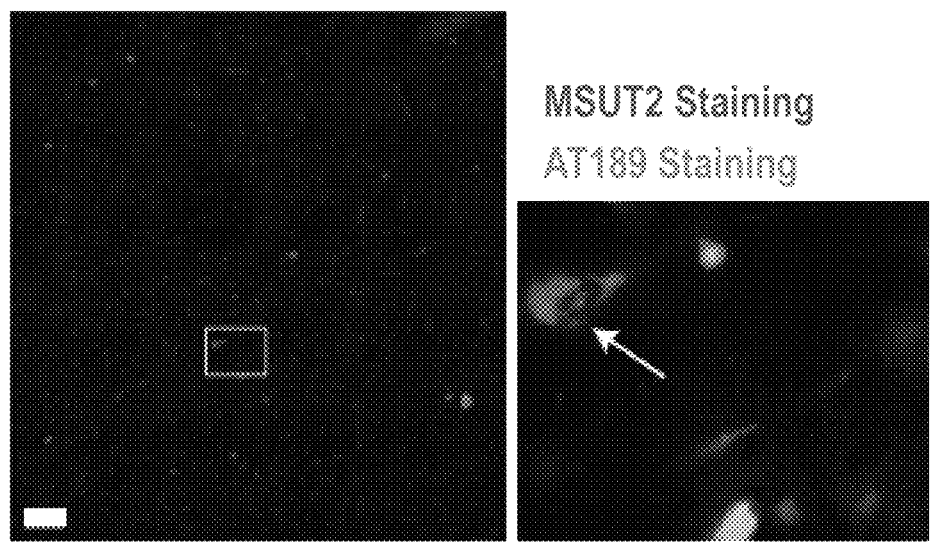
Figure 14B:
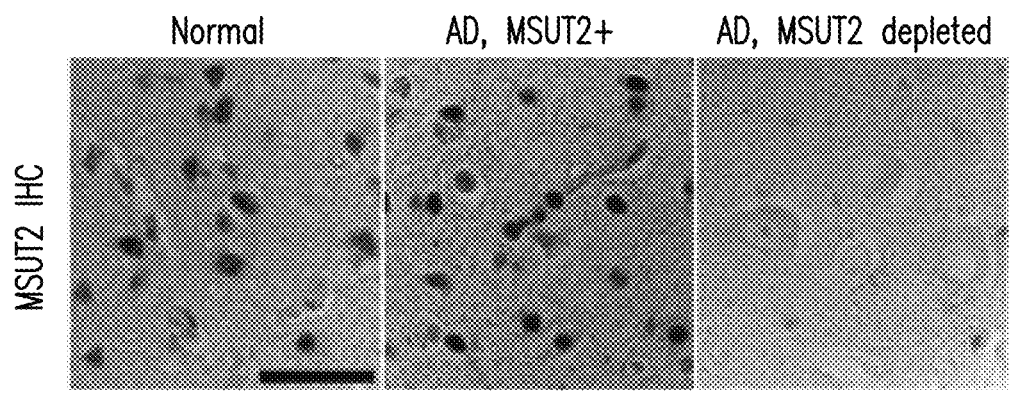
Figure 14C:
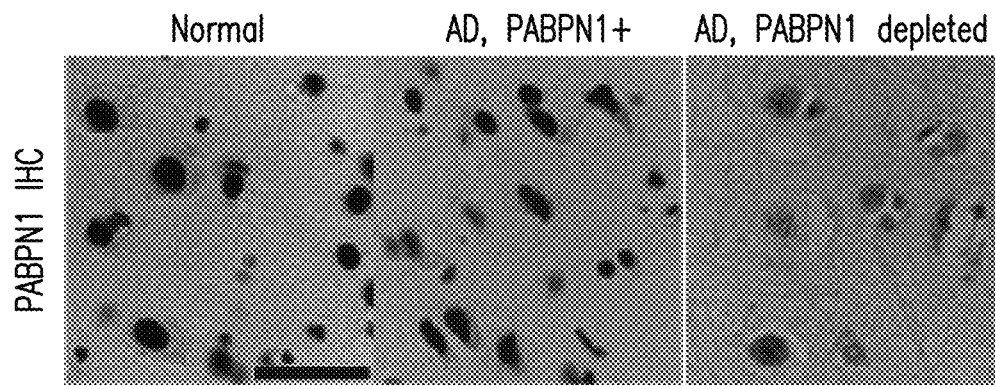
Figure 14D:
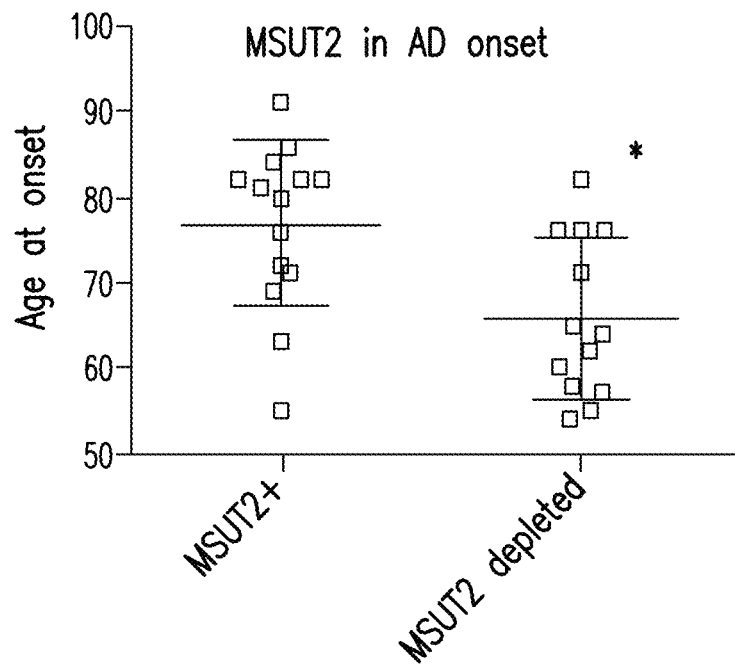
Figure 14E:
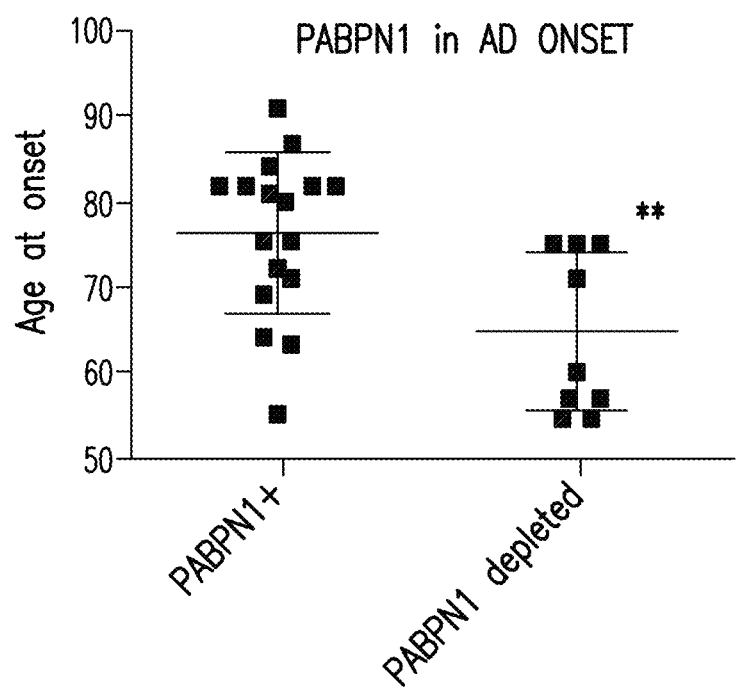
Figure 14F:
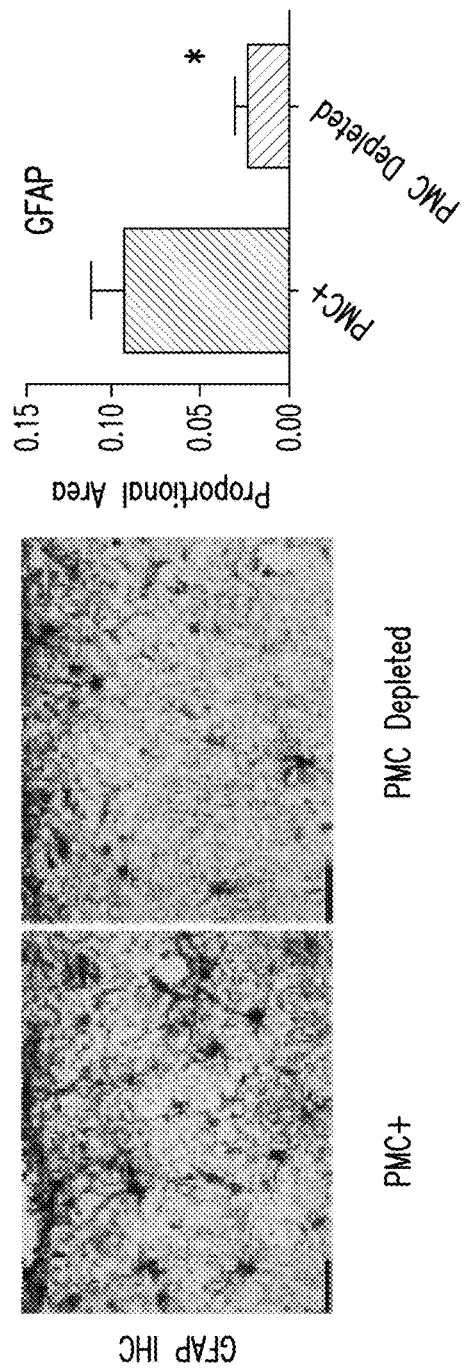
Figure 14G:
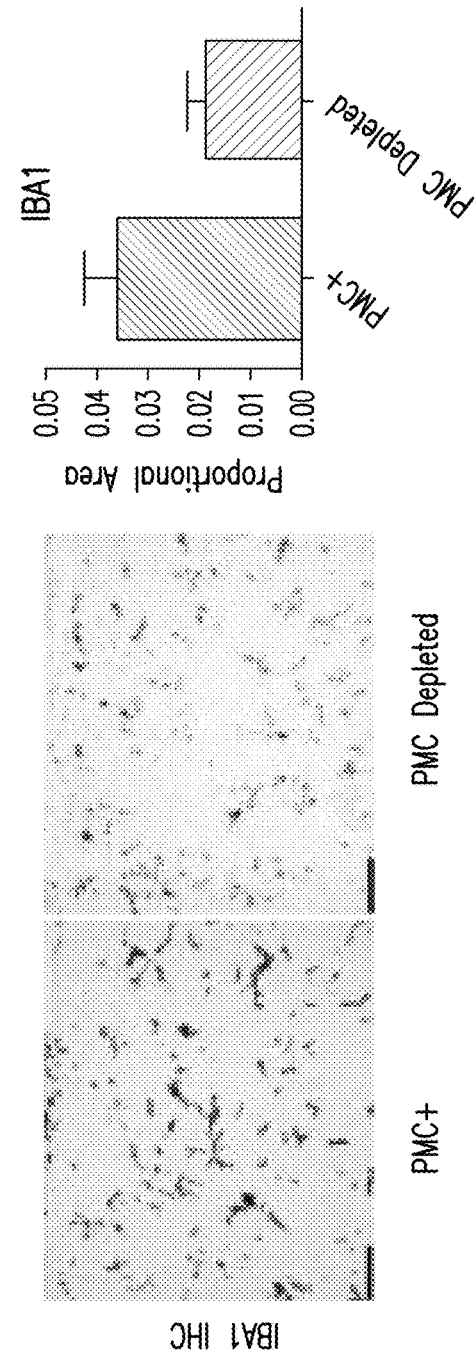
Figure 14H:
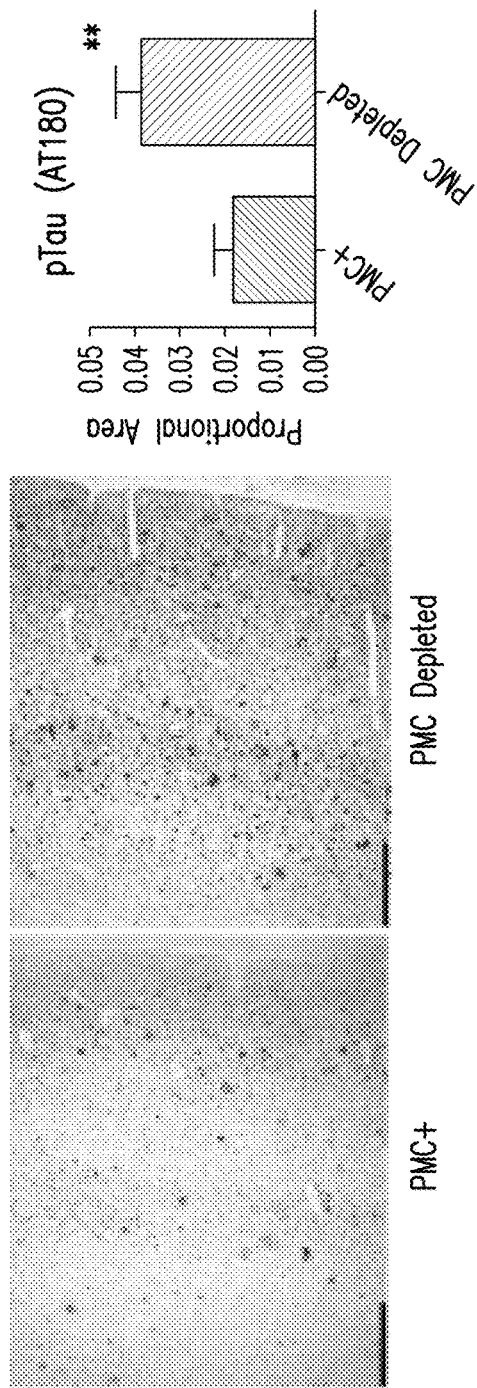
Figure 14I:
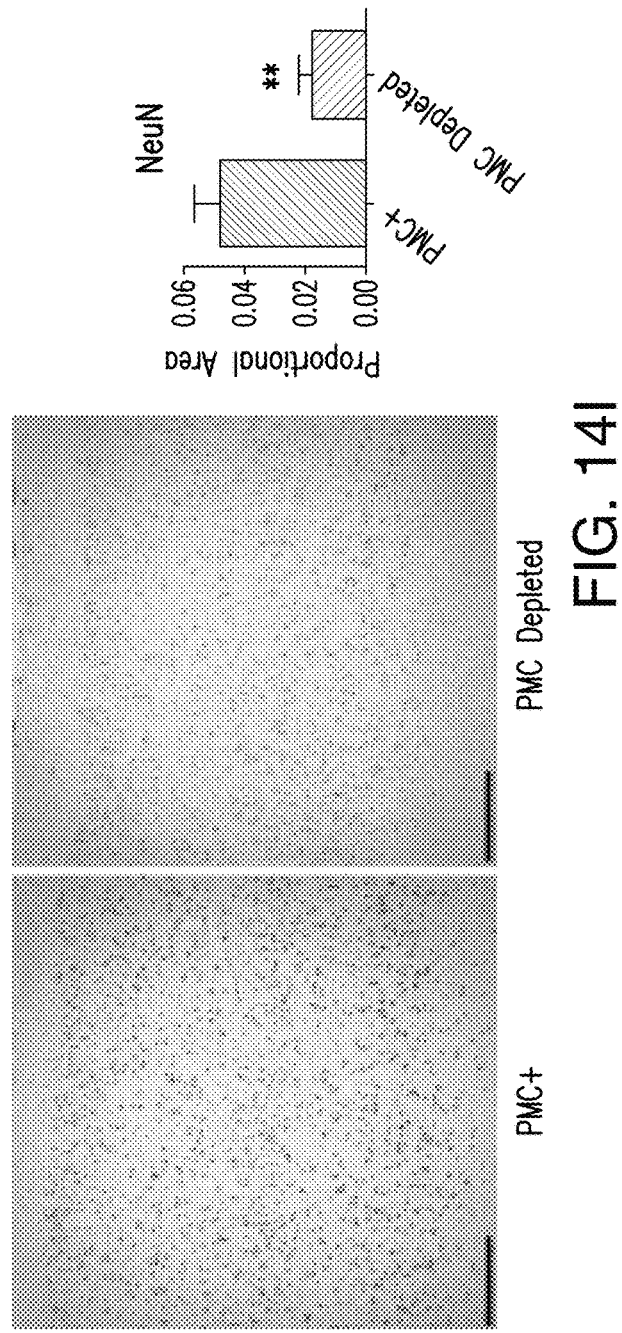

FIGS. 14A-I show that MSUT2 activity potentiates neuroinflammation induced by tauopathy. FIG. 14A shows that AD brain frontal cortex co-immunostained for pathological tau (gray) and MSUT2 (white) reveals MSUT2-positive neurons harboring tangles. Pathological tau is detected by immunofluorescence with mAb AT180 (M. Goedert, et al., *Biochem J* 301 (Pt 3), 871-877 (1994)) while MSUT2 is detected with a polyclonal MSUT2 antibody (C. R. Guthrie, et al., *Hum Mol Genet* 20, 1989-1999 (2011)). Arrow on inset panel indicates an MSUT2+ tangle bearing neuron. Scale bar=100 nm. FIG. 14B shows that MSUT2 immunostaining on normal control and AD cortex brain sections indicates MSUT2 protein is abundant in normal controls and some AD cases, while other AD cases have depleted or completely undetectable MSUT2 protein. See Table 4 for AD case series details. Scale bar=50 nm. FIG. 14C shows that PABPN1 immunostaining on normal control and AD cortex brain sections shows PABPN1 protein is abundant in normal controls and some AD cases, while other AD cases have greatly reduced PABPN1. Scale bar=50 nm. FIG. 14D shows that postmortem AD frontal cortex analysis of MSUT2 levels as a function of age at disease onset (see Table 4 for case details). AD cases with normal MSUT2 (N=14) have a later age of onset as compared with cases with depleted MSUT2 (N=13) (p=0.0306 by Student's t-test). FIG. 14E shows the analysis of PABPN1 levels as a function of age at onset of AD in postmortem tissue (see Table 4 for case details). AD cases with normal PABPN1 (N=16) have a later age of onset as compared with cases with depleted PABPN1 (N=11) (p=0.0084 by Student's t-test). FIG. 14F shows that PABPN1 and MSUT2 levels may influence severity of astrocytosis in AD. Evaluation of astrocytosis in the frontal cortex of AD cases with PABPN1 and MSUT2 complex normal (PMC+) vs. depleted (PMC Depleted) stained with GFAP specific antibody. Densitometry of GFAP-positive reactivity in PMC+ cases (N=9) compared with PMC depleted cases (N=6) demonstrated a significant decrease of over 400% (p=0.0139 by two-tailed t-test). Scale bar=50 nm. FIG. 14G show that PABPN1 and MSUT2 levels may influence severity of microgliosis in AD. Evaluation of microgliosis in the frontal cortex of AD cases with normal MSUT2 (PMC+) vs depleted MSUT2 (PMC Depleted) stained with IBA1 specific antibody. Densitometry of IBA1+ reactivity in PMC normal cases (N=9) compared with PMC depleted cases (N=6) demonstrated a trend towards decrease in PMC depleted cases of 51.9% (p=0.069 by two-tailed t-test). Scale bar=50 nm. FIG. 14H show that the PABPN1 and MSUT2 complex (PMC) depleted AD cases exhibit more pathological tau (AT180+ lesions) than PMC+ cases. Densitometry of AT180-positive reactivity in PMC normal cases (N=14) compared with PMC depleted cases (N=13) demonstrated a significant increase of over 218% (p=0.0089 by two-tailed t-test). Scale bar=500 nm. FIG. 14I shows that the PABPN1 and MSUT2 complex (PMC) depleted AD cases exhibit more neuronal loss (less NeuN positive neurons) than PMC+ cases. Densitometry of NeuN-positive reactivity in PMC normal cases (N=14) compared with PMC depleted cases (N=13) demonstrated a significant increase of over 272% (p=0.0039 by two-tailed t-test). Scale bar=500 nm.

Figure 15A:
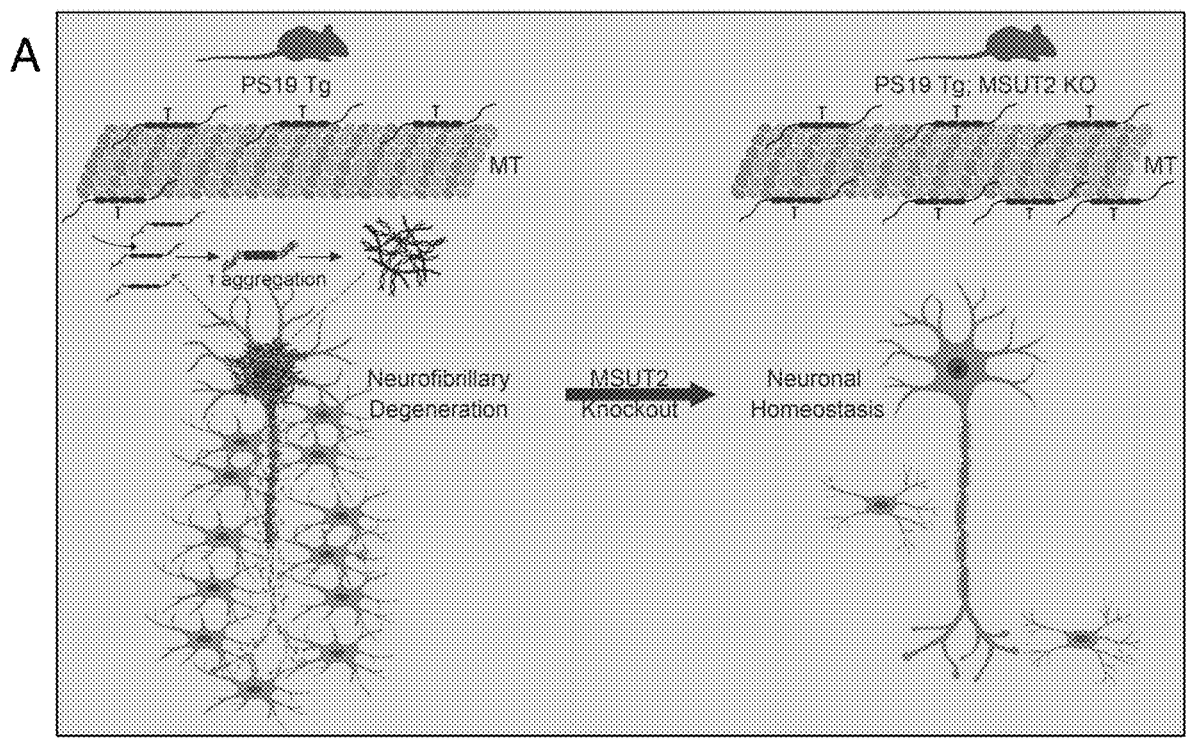
Figure 15B:
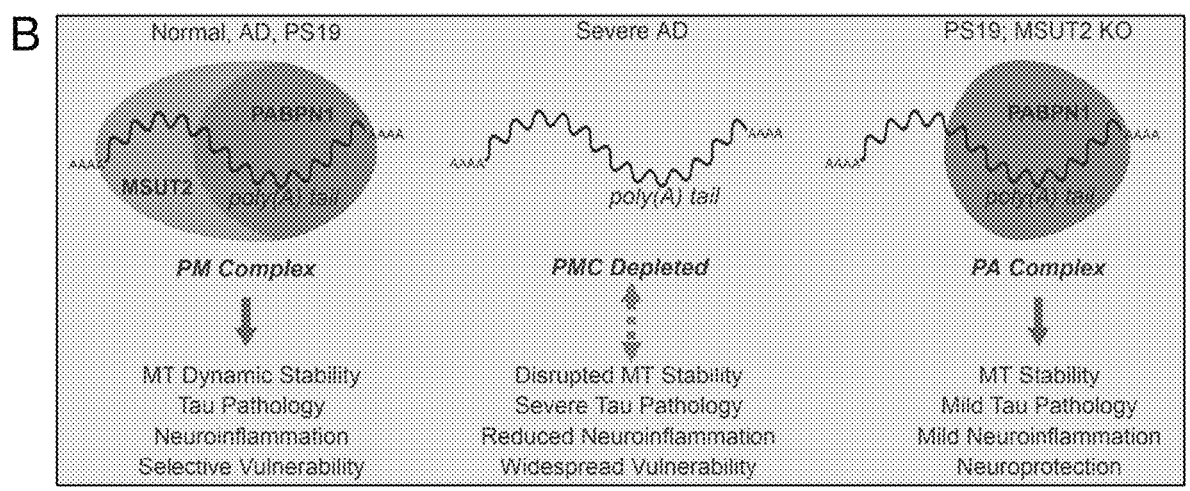

FIGS. 15A-B show the molecular hypothesis for MSUT2 activity. FIG. 15 shows a data summary. PS19 transgenic mice exhibit tau pathology in the form of misfolded tau and paired helical filaments. Tau pathology reduces tau binding to microtubules promoting microtubule destabilization and neurofibrillary degeneration. Pathological tau aggregation causes neurodegeneration driving gliosis and other neuroinflammatory changes. Knocking out MSUT2 in the PS19 tau transgenic mouse brain reduces pathological tau species, thereby protecting neurons and reducing consequent gliosis. Neurons (large cell), Microglia (small cell), Microtubules (MT labeled striated bundle), Paired helical filaments (PHFs black fibers), Tau (T). FIG. 15B shows a working hypothesis: MSUT2 and PABPN1 may act together in a complex and influence neuronal susceptibility to pathological tau. PABPN1 and MSUT2 form a complex binding to poly(A) in normal human brain, Alzheimer's disease, and PS19 Tg mice. The PABPN1/MSUT2 complex (PMC) could enable the development of tau pathology and the neuroinflammatory response to tau resulting in vulnerability of select neurons. Depletion of the PMC in severe AD accompanies more abundant tau pathology, disrupted MTs, and widespread neuronal loss with a paradoxical reduction in neuroinflammatory changes (dashed arrows indicate correlation not causation). Depletion of MSUT2 but sparing of PABPN1 in tau Tg mice promotes restoration of tau/microtubule homeostasis and neuroprotection resulting in suppression of neuroinflammation.

Figure 16:
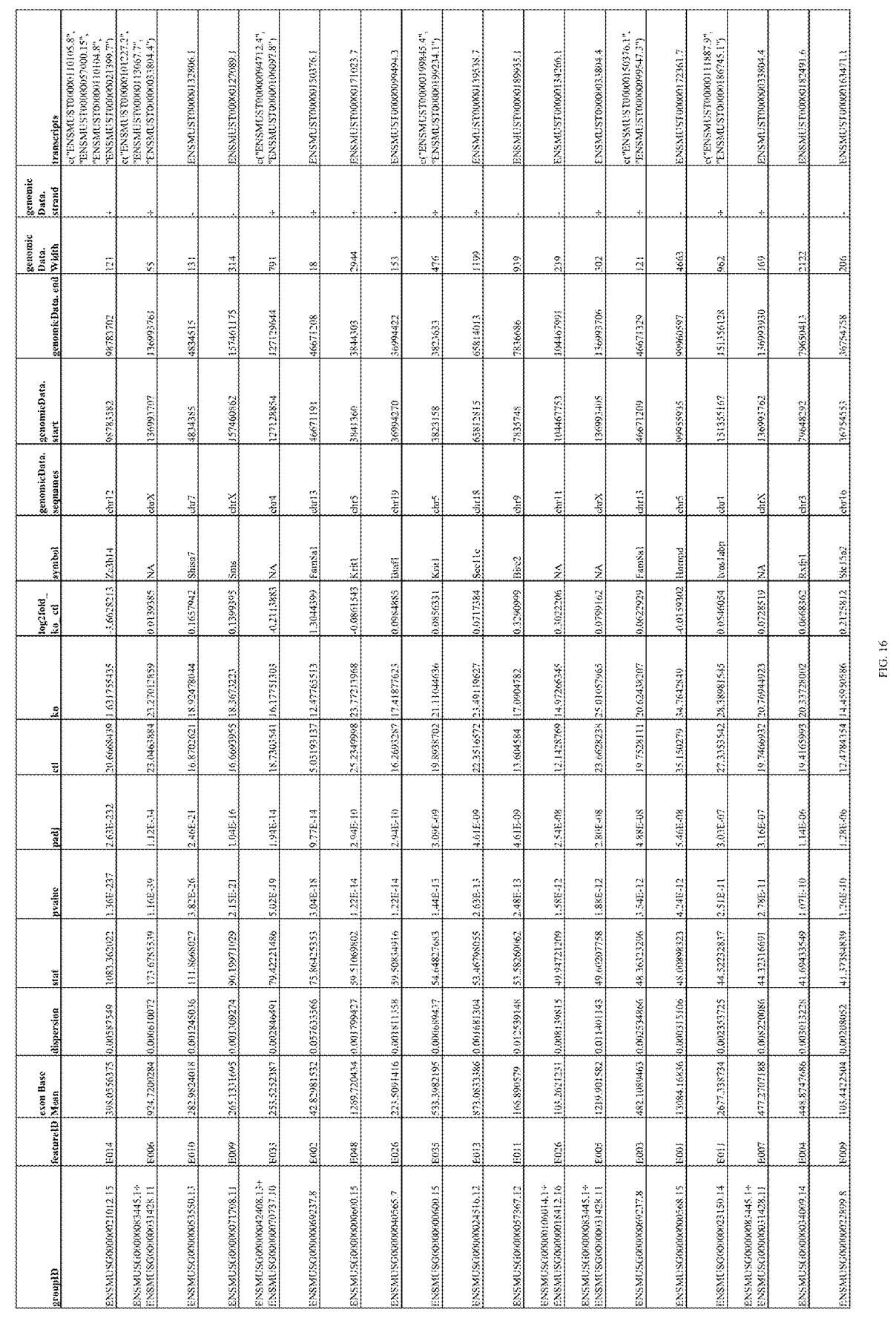
Figure 16:
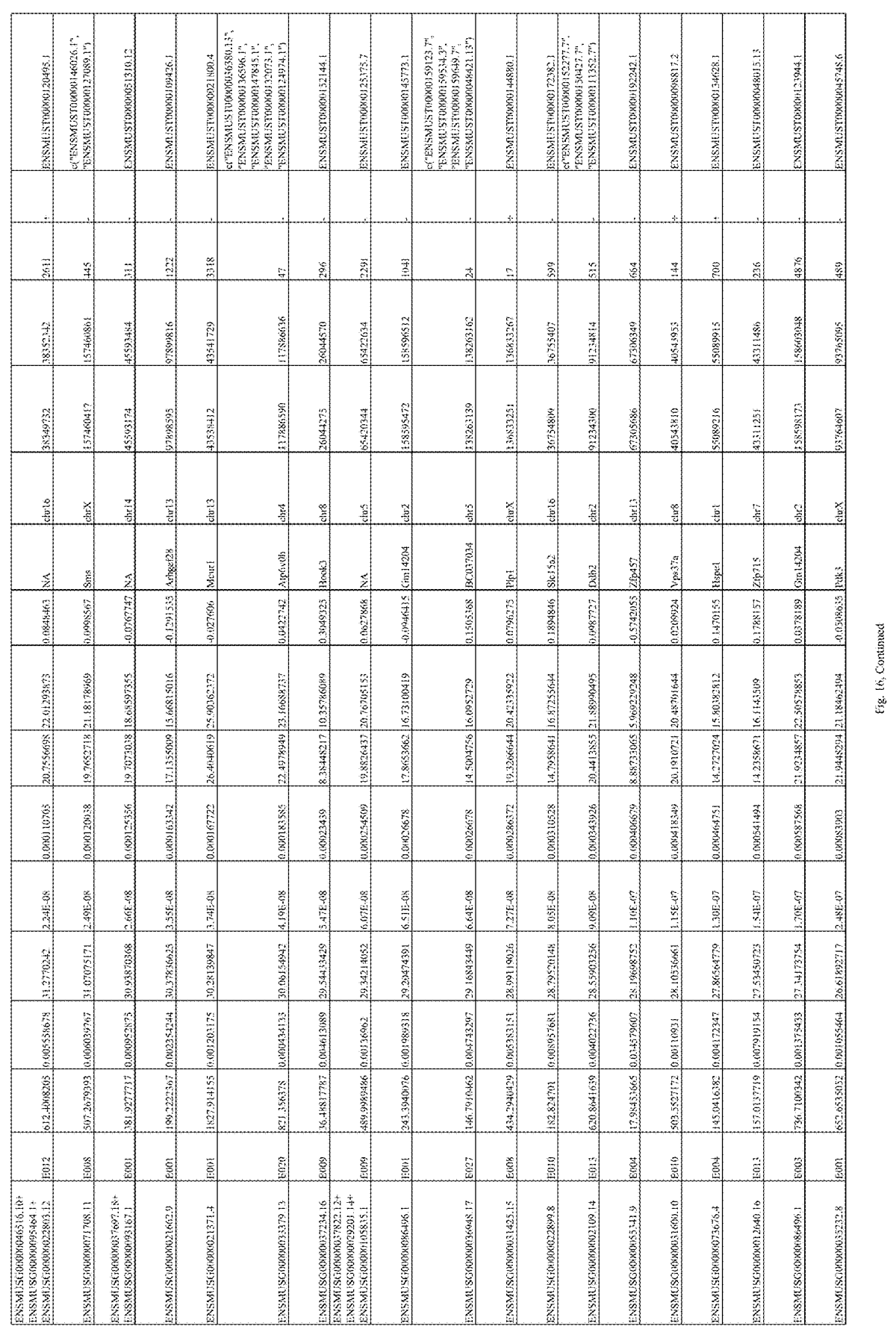
Figure 16:
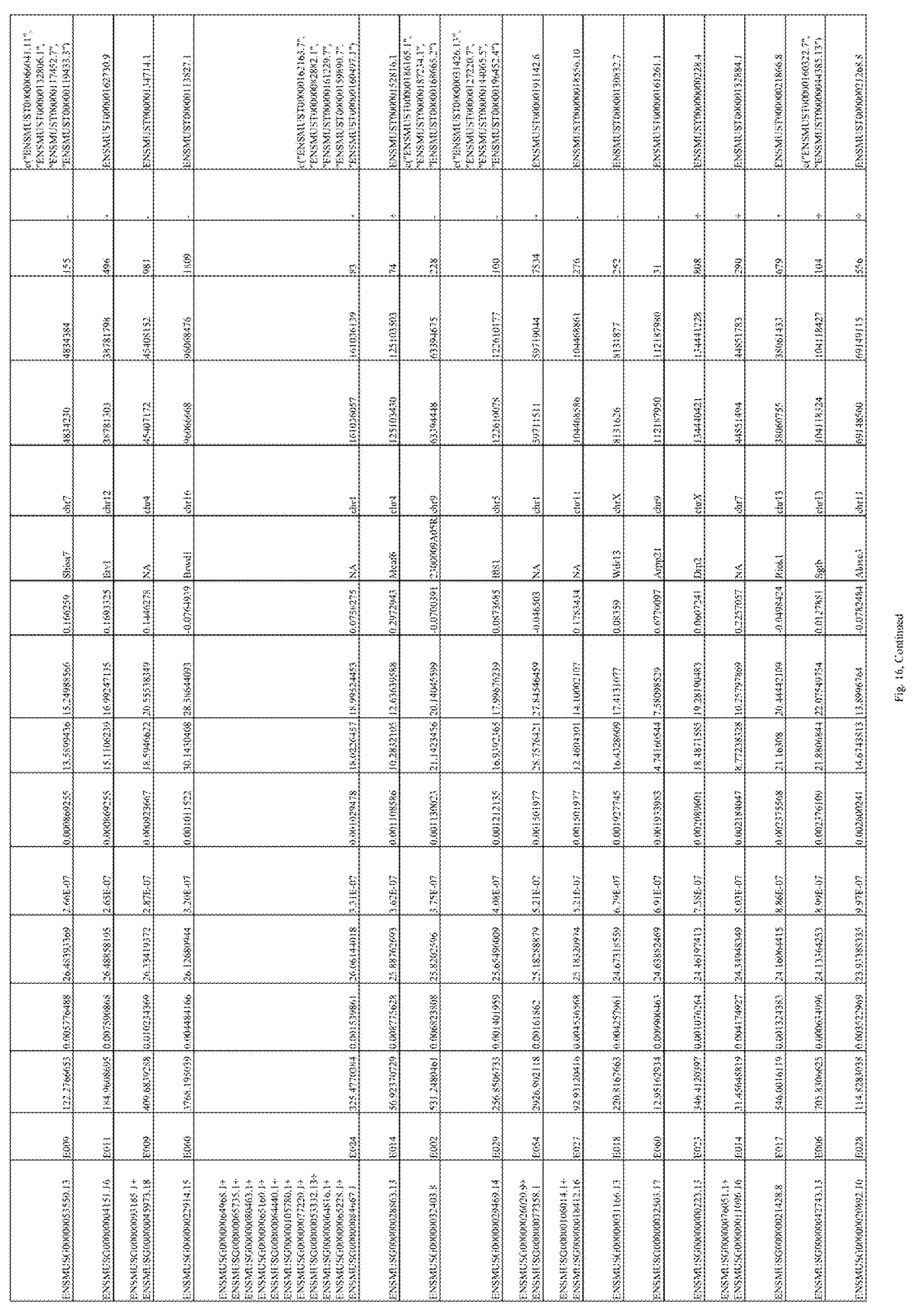
Figure 16:
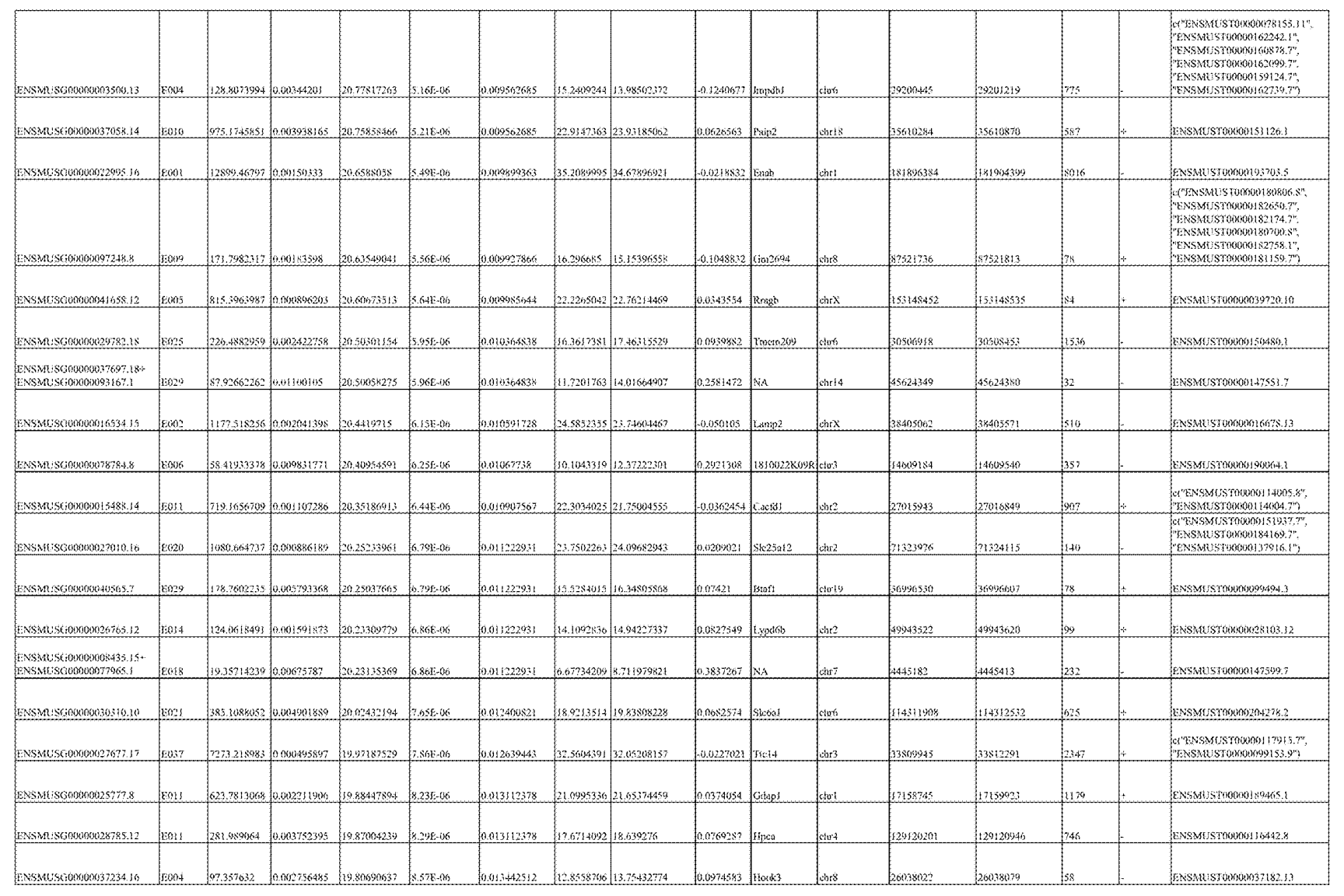
Figure 16:
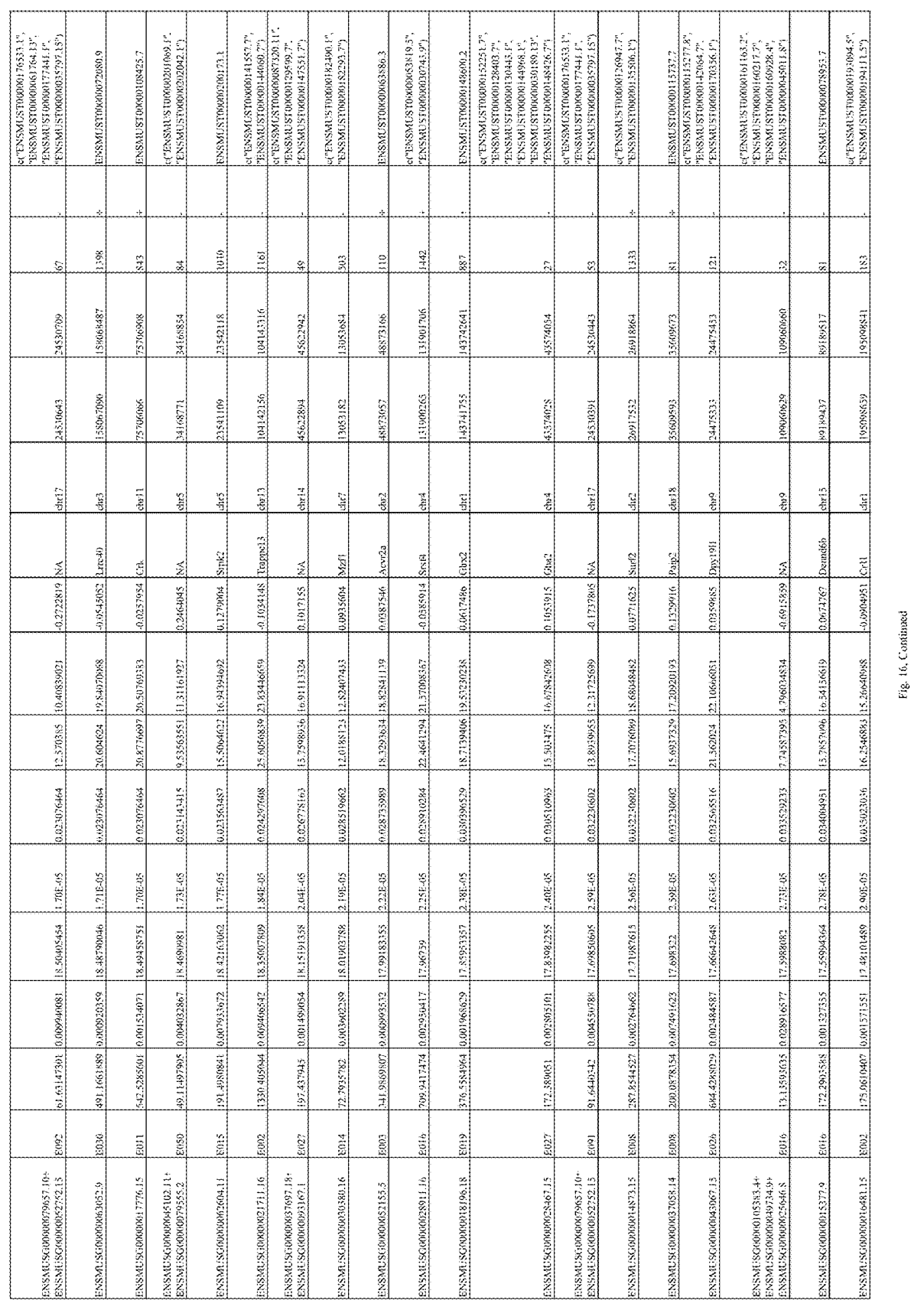
Figure 16:
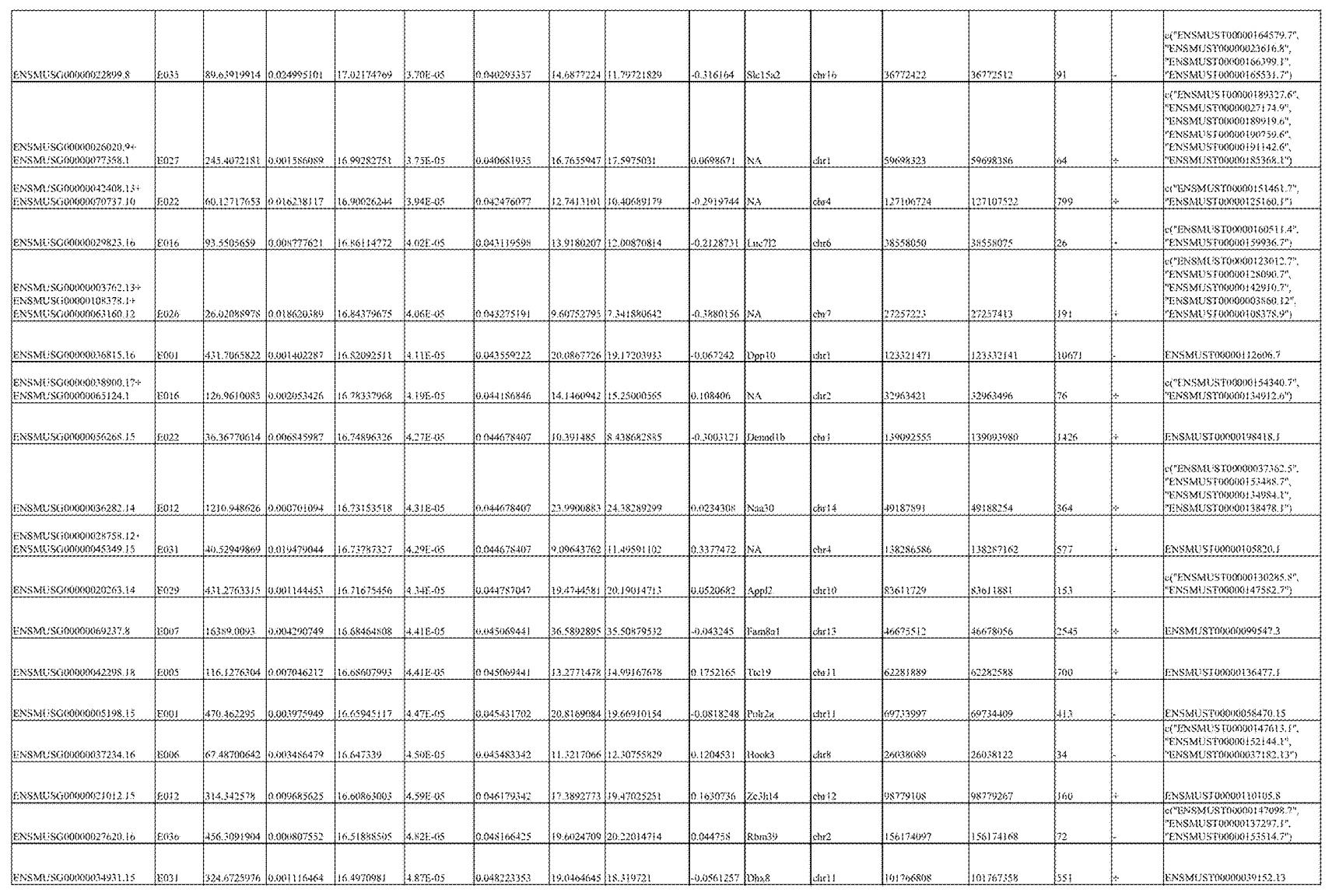

FIG. 16 shows MSUT2 KO vs C57BL/6 alternative exon inclusion changes.

FIG. 17 shows MSUT2 KO vs C57BL/6 alternative DaPars analysis of alternative polyadenylation usage.

Figure 18A:
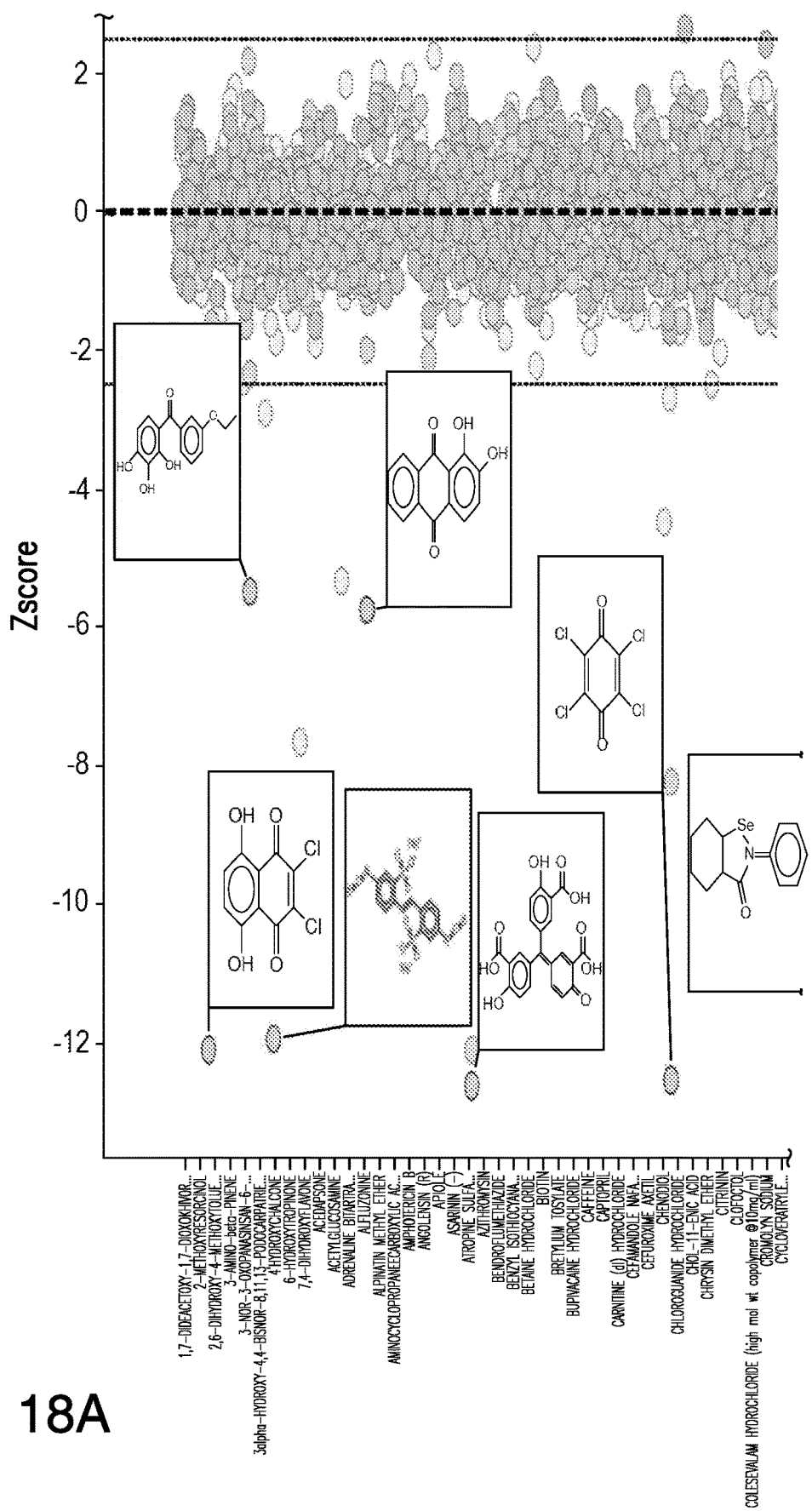
Figure 18B:
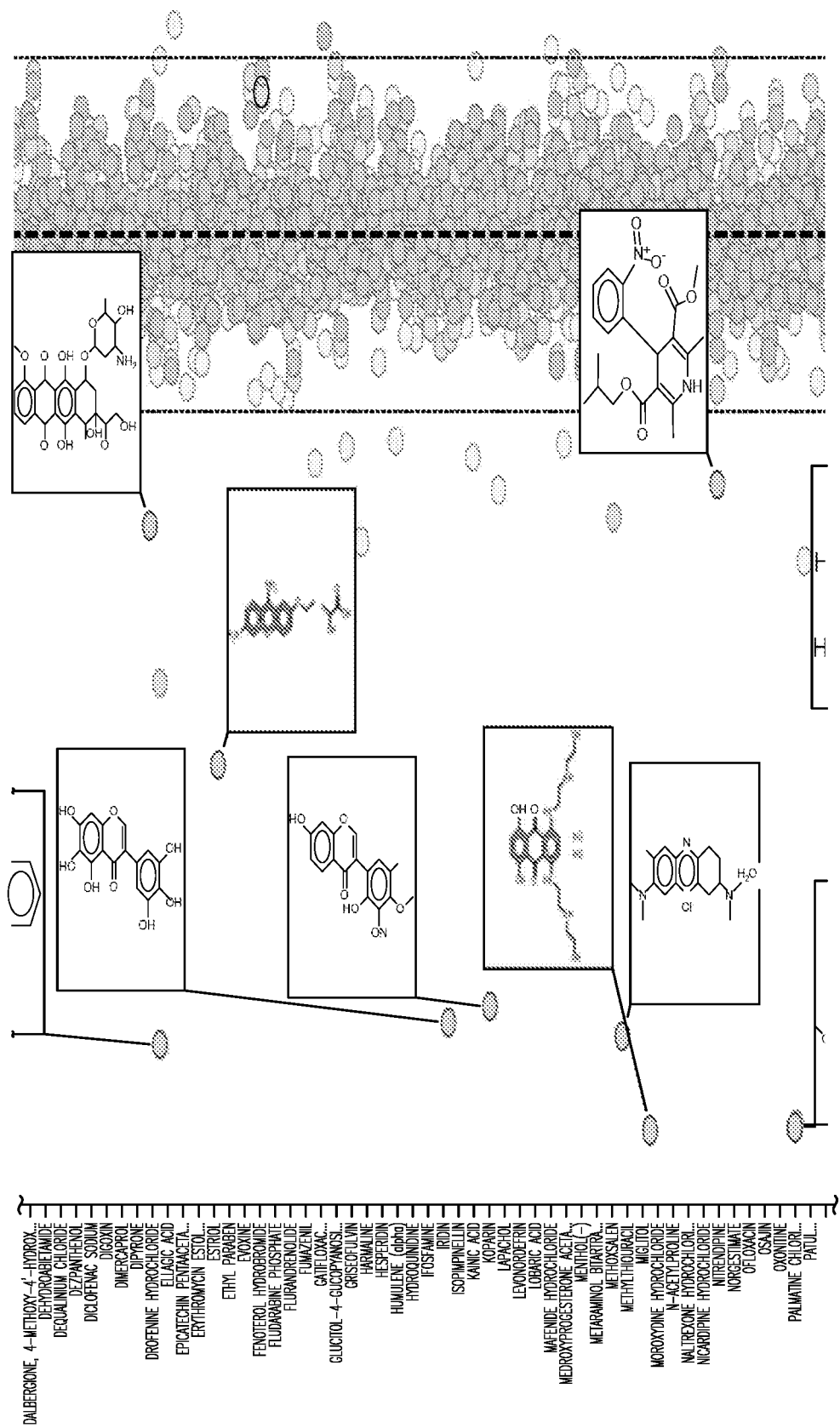
Figure 18C:
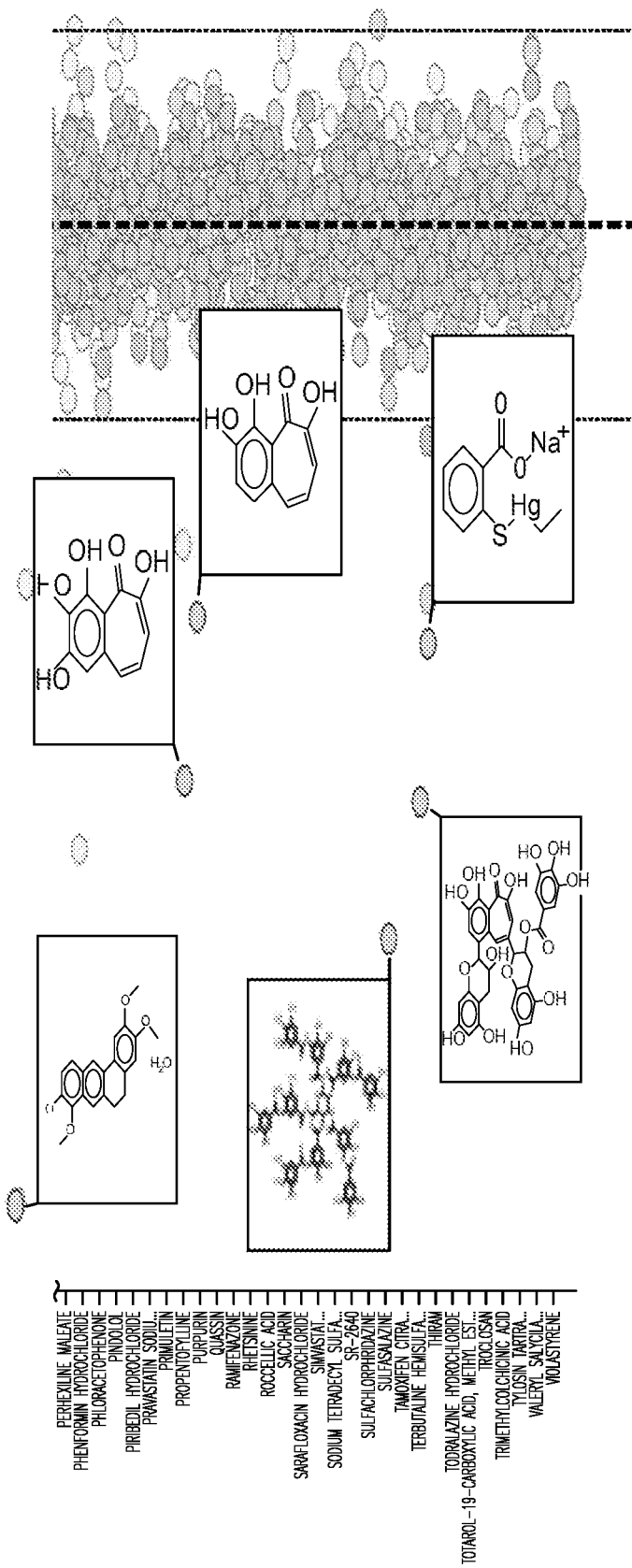

FIGS. 18A-C show the summary of pilot AlphaScreen for antagonists of polyA RNA/MSUT2 protein interaction (FIGS. 18A, 18B, and 18C).

Figure 19:
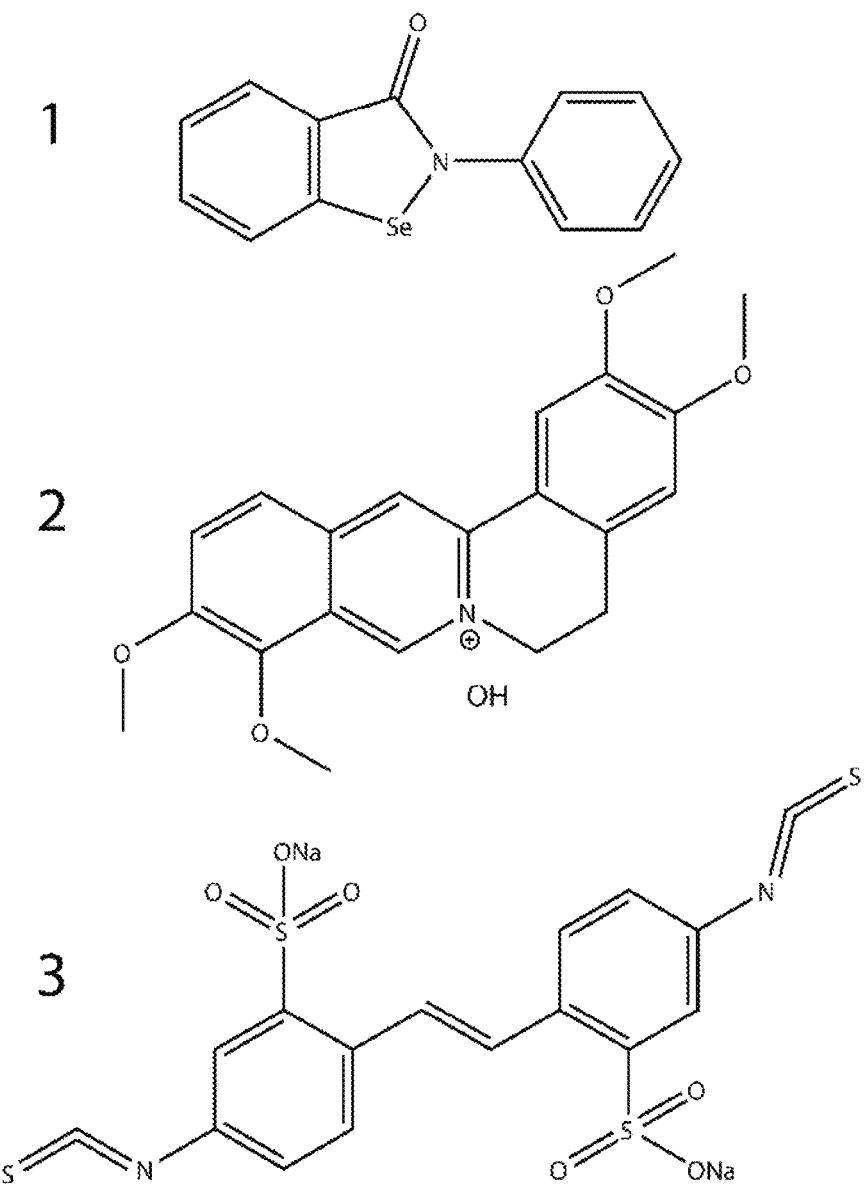

FIG. 19 shows dose validated hits identified by AlphaScreen Assay. 1. Ebselen (IC50=1.6 µM); 2. Palmatine (IC50=1.7 µM); and 3.4,4'-Diisothiocyano-stilbene-2,2' sulfonic acid (IC50=6.8 µM).

Figure 20:
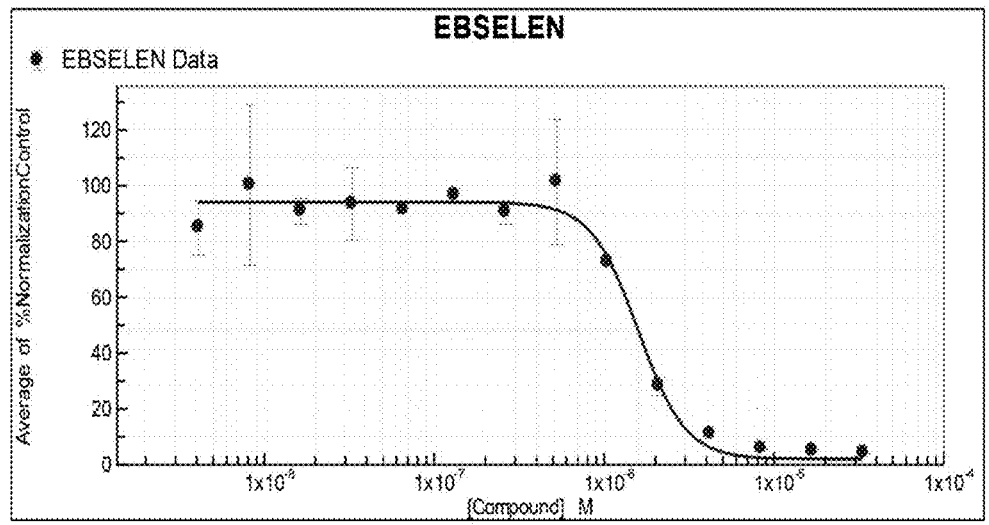

FIG. 20 shows Ebselen dose response in AlphaScreen Assay. (IC50=1.6 µM)

Figure 21:
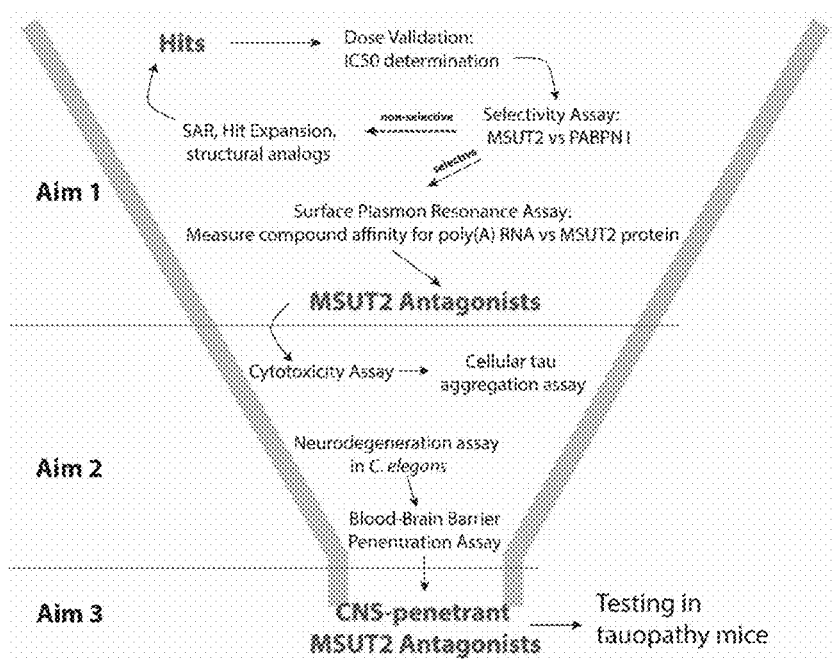

FIG. 21 shows validation funnel and secondary screening strategies.

Figure 22:
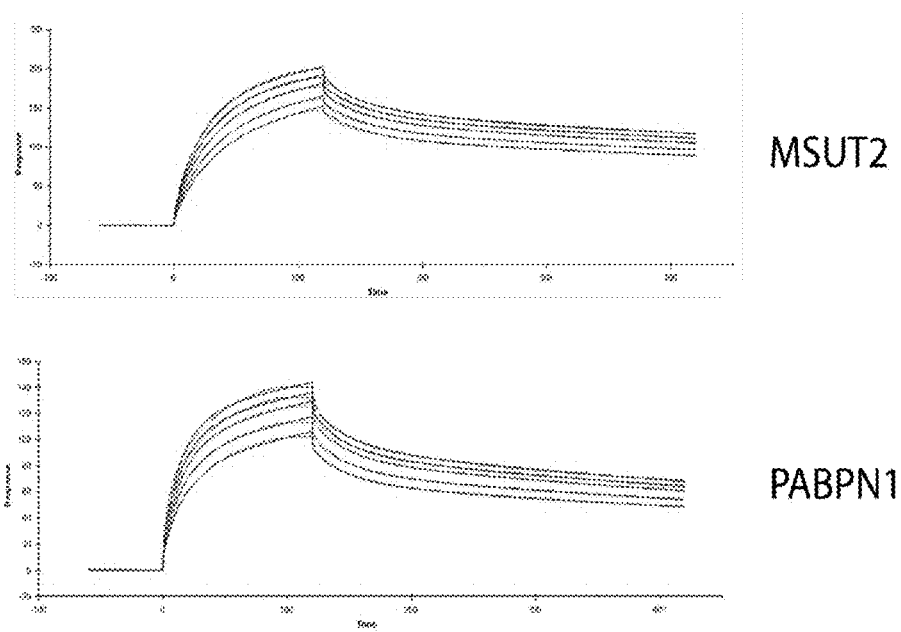

FIG. 22 shows that MSUT2 and PABPN1 bind poly(A) RNA. RNA-protein affinities measured by surface plasmon resonance (BIACORE). MSUT2 $K_D$ for poly(A) RNA=60±15 nM PABPN1 $K_D$ for poly(A) RNA=237±21 nM.

FIG. 23 is a schematic of fluorescence polarization assay. Polarized light excites fluorescein labeled RNA molecule (FAM-PolyA$_{15}$). When bound to MSUT2 protein, it results in slow tumbling and emits polarized fluorescence. However, if this interaction is inhibited by a compound (i), it results in rapid tumbling of the unbound FAM-PolyA$_{15}$ and subsequent low polarization signal.

Figure 24A:
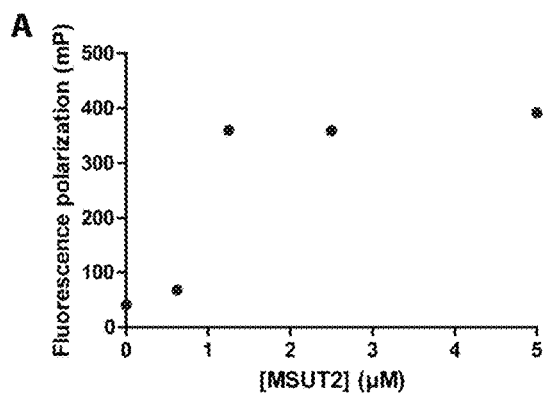
Figure 24B:
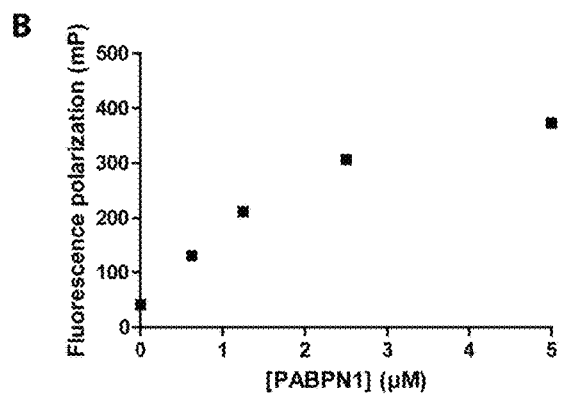
Figure 24C:
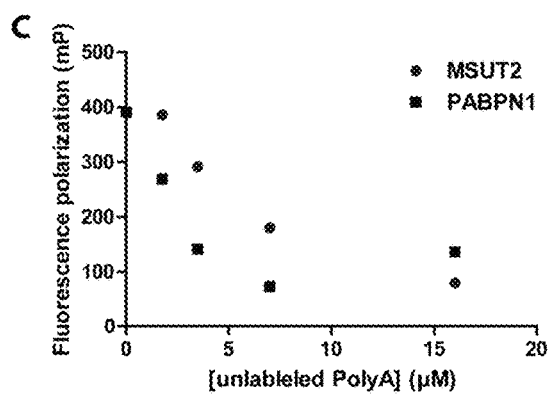
Figure 24D:
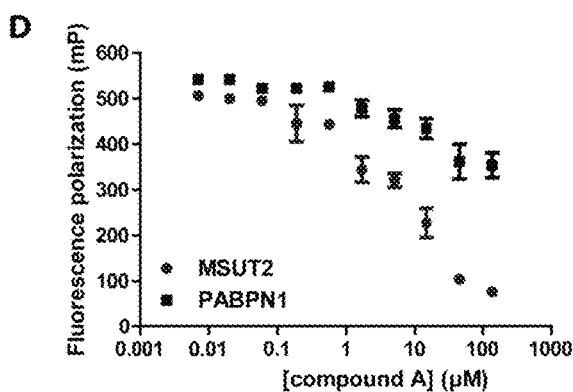

FIGS. 24A-D show the results of using the fluorescence polarization assay. FIG. 24A shows that increasing concentrations of MSUT2 protein result in increasing polarization signal. FIG. 24B shows that increasing concentrations of PABPN1 protein result in increased polarization signal. FIG. 24C shows that titration of unlabeled PolyA results in decrease of polarization signal. FIG. 24D shows that Compound A titration decreases fluorescence polarization signal.

DETAILED DESCRIPTION

Many modifications and other embodiments of the present disclosure set forth herein will come to mind to one skilled in the art to which this disclosure pertains having the benefit of the teachings presented in the foregoing descriptions and the associated drawings. Therefore, it is to be understood that the present disclosure is not to be limited to the specific embodiments disclosed and that modifications and other embodiments are intended to be included within the scope of the appended claims. Although specific terms are employed herein, they are used in a generic and descriptive sense only and not for purposes of limitation.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present disclosure, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present disclosure is not entitled to antedate such publication by virtue of prior disclosures. Further, the dates of publication provided herein can be different from the actual publication dates, which can require independent confirmation.

Definitions

As used in the specification and in the claims, the term "comprising" can include the aspects "consisting of" and "consisting essentially of." "Comprising" can also mean "including but not limited to."

As used in the specification and the appended claims, the singular forms "a," "an" and "the" can include plural referents unless the context clearly dictates otherwise. Thus, for example, reference to "a compound" includes mixtures of compounds; reference to "a pharmaceutical carrier" includes mixtures of two or more such carriers, and the like.

The word "or" as used herein means any one member of a particular list and also includes any combination of members of that list.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for Alzheimer's disease or dementia, such as, for example, prior to the administering step.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

"Modulate", "modulating" and "modulation" as used herein mean a change in activity or function or number. The change may be an increase or a decrease, an enhancement or an inhibition of the activity, function or number.

As used herein, the term "treating" refers to partially or completely alleviating, ameliorating, relieving, delaying onset of, inhibiting or slowing progression of, reducing severity of, and/or reducing incidence of one or more symptoms or features of a particular disease, disorder, and/or condition. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. Treatment can also be administered to a subject to ameliorate one more signs of symptoms of a disease, disorder, and/or condition. For example, the disease, disorder, and/or condition can be relating to Alzheimer's disease, Alzheimer's disease-related dementia or dementia.

The phrase "nucleic acid" as used herein refers to a naturally occurring or synthetic oligonucleotide or polynucleotide, whether DNA or RNA or a DNA-RNA hybrid, single-stranded or double-stranded, sense or antisense, which is capable of hybridization to a complementary nucleic acid by Watson-Crick base-pairing. Nucleic acids as disclosed herein can also include nucleotide analogs (e.g., BrdU), and non-phosphodiester internucleoside linkages (e.g., peptide nucleic acid or thiodiester linkages). In particular, nucleic acids can include, without limitation, DNA, RNA, cDNA, gDNA, ssDNA, dsDNA or any combination thereof.

As used herein, the term "complementary" refers to the ability of a nucleic acid to form hydrogen bond(s) with another nucleic acid sequence by either traditional Watson-Crick or other non-traditional types. A percent complementary indicates the percentage of residues in a nucleic acid molecule which can form hydrogen bonds (e.g., Wastson-Crick base pairing) with a second nucleic acid sequence (e.g., 5, 6, 7, 8, 9, 10 out of 10 being 50%, 60%, 70%, 80%, 90%, and 100% complementary).

As used herein, the term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element or regulatory element). The terms "plasmid" and "vector" can be used interchangeably, as a plasmid is a commonly used form of vector. Moreover, this disclosure is intended to include other vectors which serve equivalent functions.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

Abnormally aggregated highly phosphorylated tau becomes deposited as tangles or other lesions in tauopathy disorders. For Alzheimer's disease (AD) and many other tauopathies, the molecular role tau plays in disease initiation and progression remains unknown. However, in frontotemporal lobar degeneration-tau (FTLD-tau), mutations in the gene encoding tau (MAPT) cause the disease by reducing tau affinity for microtubules (MTs) and increasing tau aggregation propensity (M. Hong, et al., *Science* 282, 1914-1917 (1998); and S. Barghorn, et al., *Biochemistry* 39, 11714-11721 (2000)). Because tau binds MTs, abnormal tau may impair function of the cytoskeleton. The reduced affinity of tau for MTs caused by FTLD mutations may disrupt MT stability and axonal transport (M. Hong, et al., *Science* 282, 1914-1917 (1998)). Alternately, tau aggregation may reduce the amount of tau available for binding to microtubules (M. R. Khanna, et al., *Alzheimers Dement* 12, 1051-1065 (2016); and V. M. Lee, et al., *Neurobiol Aging* 15 Suppl 2, S87-89 (1994)). Evidence suggests toxic tau aggregates or oligomers can spread by a seeding mechanism following neuronal connectivity pathways (H. Braak, et al., *Neurobiol Aging* 16, 271-278; discussion 278-284 (1995); and F. Clavaguera, et al., *Nat Cell Biol* 11, 909-913 (2009)). The important neurotoxic species remain poorly defined, and dimers, low level tau oligomers, higher order assemblies of tau, and end-stage NFTs are candidate triggers of neurotoxicity. The phosphorylation state of tau likely contributes to toxicity as tau phosphorylation can drive tau from MTs and promote aggregation (reviewed in (Y. Wang, et al., *Nat Rev Neurosci* 17, 5-21 (2016); and C. Ballatore, et al., *Curr Top Med Chem* 11, 317-330 (2011)). Taken together, recent evidence suggests a diversity of related and varyingly neurotoxic species likely contribute to both the spreading of tau pathology and tau-mediated neurodegeneration (reviewed in N. Sahara, et al., *Curr Alzheimer Res* 5, 591-598 (2008); and M. Goedert, *Alzheimers Dement* 12, 1040-1050 (2016)).

How abnormal tau kills neurons remains unknown. The identification of genes mediating susceptibility or resistance to pathological tau may inform disease mechanisms in AD and related disorders. To date, genomic studies in AD patients implicate many genes in susceptibility, however the APOE2 allele is strongly protective against AD. Among the risk-causing genetic variants, genes involved in innate immune response and expressed in microglia are unusually common (reviewed in (A. C. Naj, et al., *Am J Med Genet B Neuropsychiatr Genet* 174, 5-26 (2017)). While glial tau pathology does not commonly occur in AD, it is a feature of some pure tauopathy disorders (T. Komori, *Brain Pathology* 9, 663-679 (1999)) occurring in astrocytes in progressive supranuclear palsy (PSP) and in oligodendrocytes in some forms of FTLD. Furthermore, reactive gliosis is a common feature of tauopathy disorders including AD. Neuroinflammation and tau pathology appear to be mutually reinforcing features of AD and related disorders (N. Maphis, et al., *Alzheimer's research & therapy* 8, 54 (2016); N. Maphis, et al., *Frontiers in neuroscience* 9, 196 (2015); and K. Bhaskar, et al., Regulation of tau pathology by the microglial fractalkine receptor. *Neuron* 68, 19-31 (2010)).

To identify genes controlling tau toxicity, a tauopathy model was generated by expressing human tau in *C. elegans* using a promoter that drives expression in neurons. The phenotype of this model includes uncoordinated locomotion, accumulation of insoluble tau, neurodegeneration, and a shortened life span (B. C. Kraemer, et al., *Proc Natl Acad Sci USA* 100, 9980-9985 (2003)). This model was used to identify loss-of-function mutations suppressing tau-induced neurodegenerative phenotypes (C. R. Guthrie, et al., *Hum Mol Genet* 18, 1825-1838 (2009); and B. C. Kraemer, et al., *Hum Mol Genet* 16, 1959-1971 (2007)). In this model, loss-of-function mutations in the suppressor of tauopathy 2 gene (sut-2) decrease tau aggregation and protect against neurodegeneration (C. R. Guthrie, B. C. Kraemer, Proteasome inhibition drives HDAC6-dependent recruitment of tau to aggresomes. *J Mol Neurosci* 45, 32-41 (2011)). The sut-2 gene encodes a CCCH (SEQ ID NO: 22) finger protein with conserved homologs in species from yeast to humans. MSUT2 (also known as ZC3H14) is the mammalian homolog of the *C. elegans* sut-2 gene. As described herein, the loss of function of MSUT2 in mammals would ameliorate neurodegenerative tauopathy by a previously unknown mechanism. As disclosed herein, the mechanistic role of MSUT2 in resistance to tauopathy in mice and humans was examined.

Compositions

The compositions disclosed herein include a CRISPR-Cas system. The CRISPR-Cas system can be non-naturally occurring. In some aspects, the CRISPR-Cas system comprises one or more vectors. In an aspect, the vector can be a repression vector.

In some aspects, the one or more vectors can comprise a promoter operably linked to one or more nucleotide sequences encoding a CRISPR-Cas system guide RNA (gRNA). In some aspects, the gRNA can hybridize with a target sequence of a DNA molecule or locus in a cell. In some aspects, the one or more vectors can also comprise a regulatory element operably linked to a nucleotide sequence encoding a RNA-directed nuclease. In some aspects, the promoter operably linked to one or more nucleotide sequences encoding a CRISPR-Cas system gRNA and the regulatory element operably linked to a nucleotide sequence encoding a RNA-directed nuclease can be located on the same or different vectors of the same system. The gRNA can target and hybridize with the target sequence. In some aspects, the gRNA can also direct the RNA-directed nuclease into the DNA molecule or locus. In some aspects, gRNA can be selected from the group consisting of SEQ ID NOs: 6, 7, 8, 9, 28, 29, 30, 31, 32 and 33.

As used herein, the term "regulatory element" refers to promoters, promoter enhancers, internal ribosomal entry sites (IRES) and other elements that are capable of controlling expression (e.g., transcription termination signals, including but not limited to polyadenylation signals and polyuridylic acid sequences). Regulatory elements can direct constitutive expression. Regulatory elements can be tissue-specific. Examples of tissue-specific promoters can direct expression in a desired tissue of interest (e.g., neuron), specific organs (e.g., brain, spinal cord, liver), or particular cell types (neurons, microglia, astrocytes, oligodendrocytes, hepatocytes). Regulatory elements can also direct expression in a temporal-dependent manner including but not limited to cell-cycle dependent or developmental stage-dependent. Temporal-dependent expression can be tissue or cell-type specific. Regulatory element can also refer to enhancer elements. Examples of enhancer elements include but are not limited to woodchuck hepatitis post-transcriptional regulatory element (WPRE), human cytomegalovirus (CMV) enhancers, and simian virus 40 (SV40) enhancers. In an aspect, the regulatory element can be human Ubiquitin C (hUbC) promoter. In an aspect, the hUbC promoter is operably linked to a nucleotide sequence encoding a RNA-directed nuclease. Generally, any constitutive promoter can be operably linked to a nucleotide sequence encoding a RNA-directed nuclease. Gene specific promoters can be used. Such promoters allow cell specific expression or expression tied to specific pathways. Any promoter that is active in mammalian cells can be used. In an aspect, the promoter can be an inducible promoter including, but not limited to, tetracycline/doxycycline-controlled activation systems (also known as Tet-on Tet-off systems). Such inducible promoters can be used to control the timing of the desired expression.

Disclosed herein, are vectors comprising a promoter operably linked to one or more nucleotide sequences encoding a CRISPR-Cas system gRNA and a regulatory element operably linked to a nucleotide sequence encoding a RNA-directed nuclease. In some aspects, the gRNA sequence can be selected from the group consisting of SEQ ID NOs: 6, 7, 8, 9, 28, 29, 30, 31, 32 and 33. In an aspect, the gRNA sequence can comprise 10-30 bp, 15-25 bp, 17-24 bp or any other fragment of the sequences set forth in SEQ ID NOs: 6, 7, 8, 9, and 33. In some aspects, the gRNA sequence can comprise a sequence having 80%, 85%, 90%, 95%, 96%, 97%, 98%, or 99% identity to the sequences set forth in SEQ ID NOs: 6, 7, 8, 9, 33 or a fragment thereof. In some aspects, the gRNA sequence can comprise a sequence having 90%, 95%, 96%, 97%, 98%, or 99% identity to the sequences set forth in SEQ ID NOs: 28, 29, 30, 31, 32 or a fragment thereof. In some aspects, any of the gRNA sequences or gRNA fragments disclosed herein can contain 1, 2, 3, or 4 or more nucleotide changes as compared to the parent or reference gRNA. Said sequences can share or improve biological function, specificity and/or activity of the parent or reference gRNA. In some aspects, any of gRNA sequences disclosed herein can include a single nucleotide change as compared to the parent or reference gRNA. In some aspects, any of the gRNA sequences disclosed herein can include at least two nucleotide changes as compared to the parent or reference gRNA. In some aspects, the gRNA fragment can include a deletion of at least one or at least two nucleotides at the 5' end, the 3' end, or at both the 5' and 3' end. In some aspects, the promoter operably linked to one or more nucleotide sequences encoding a CRISPR-Cas system gRNA and a regulatory element operably linked to a nucleotide sequence encoding a RNA-directed nuclease can be on the same or different vectors of the same system.

Vectors include, but are not limited to nucleic acid molecules that are single-stranded double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a viral vector, wherein virally-derived DNA or RNA sequences are present in the vector for packaging into a virus. Viral vectors can include polynucleotides carried by a virus for transfection into a host cell. In some aspects, the CRISPR-Cas system described herein can be packaged into a single lentiviral, adenoviral or adeno-associated virus particle. In an aspect, the CRISPR-Cas system can be packaged into a single adeno-associated virus particle.

The vectors disclosed herein can also include detectable labels. Such detectable labels can include a tag sequence designed for detection (e.g., purification or localization) of an expressed polypeptide. Tag sequences include, for example, green fluorescent protein, yellow fluorescent protein, red, fluorescent protein, mCherry, glutathione S-transferase, polyhistidine, c-myc, hemagglutinin, or Flag™ tag, and can be fused with the encoded nucleic acid. In some aspects, the vector can be pX601. In some aspects, the vector can be pX330. In some aspects, the vector can have a 3× hemagglutinin (HA) tag on the saCas9 (*Staphylococcus aureus* Cas9).

Some vectors are capable of autonomous replication in a host cell which they are introduced (e.g., bacterial vectors having a bacterial origin of replication and episomal mammalian vectors). Other vectors (e.g., non-episomal mammalian vectors) are integrated into the genome of a host cell upon introduction into the host cell, and are thereby replicated along with the host genome.

The term "expression vector" is used herein to refer to vectors that are capable of directing the expression of genes to which they are operatively-linked. Common expression vectors of utility in recombinant DNA techniques are often in the form of plasmids. Recombinant expression vectors can comprise a nucleic acid as disclosed herein in a form suitable for expression of the acid in a host cell. In other words, the recombinant expression vectors can include one or more regulatory elements or promoters, which can be selected based on the host cells used for expression that is operatively linked to the nucleic acid sequence to be expressed.

The term "operatively linked to" refers to the functional relationship of a nucleic acid with another nucleic acid sequence. Promoters, enhancers, transcriptional and translational stop sites, regulatory elements, regulatory control elements and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

One or more vectors can be introduced into a cell (e.g., a host cell) to produce transcripts, proteins, peptides including fusion proteins and peptides, encoded by nucleic acids as described herein (e.g., clustered regularly interspersed short palindromic repeats (CRISPR) transcripts, proteins, enzymes, mutant forms thereof, fusion proteins thereof, etc.). In some aspects, the vector is a viral vector. Examples of vectors include, but are not limited to lentiviruses, adenoviral, and adeno-associated viruses. The type of vector can also be selected for targeting a specific cell type.

The vectors disclosed herein can comprise one or more promoters or regulatory elements or the like. In an aspect, a vector comprises one or more polymerase (pol) promoters, one or more pol II promoters, one or more pol III promoters, or combinations thereof. Examples of pol II promoters include, but are not limited to the retroviral Rous sarcoma virus (RSV) long terminal repeat (LTR) promoter (optionally with the RSV enhancer), the cytomegalovirus (CMV) promoter (optionally with the CMV enhancer), the SV40 promoter, the dihydrofolate reductase promoter, the β-actin promoter, the phospho glycerol kinase (PGK) promoter, and the EF1α promoter. In some aspects, pol II promoters can be engineered to confer tissue specific and inducible regulation of gRNAs. Examples of pol III promoters include, but are not limited to, U6 and H1 promoters. In an aspect, any pol III promoter can be used. In an aspect, the promoter can be a U6 promoter. In an aspect, the promoter operably linked to the gRNA can be a pol III promoter, human u6, mouse U6, H1, or 7SK.

In some aspects, the compositions described herein (e.g., CRISPR-Cas systems, vectors) can comprise one or more promoters or regulatory elements. In the instance of two or more promoters or regulatory elements, said promoters or regulatory elements can be referred to as a first promoter, a second promoter and so on.

The vector or vector systems disclosed herein can comprise one or more vectors. Vectors can be designed for expression of CRISPR transcripts (e.g., nucleic acid transcripts, proteins, or enzymes) in prokaryotic or eukaryotic cells. CRISPR transcripts, for example, can be expressed in bacterial cells (e.g., *Escherichia coli*), insect cells (using baculovirus expression vectors), yeast cells, or mammalian cells. Alternatively, the recombinant expression vector can be transcribed and translated in vitro, for example, using T7 promoter regulatory sequences and T7 polymerase.

Vectors can be introduced in a prokaryote, amplified and then the amplified vector can be introduced into a eukaryotic cell. The vector can also be introduced in a prokaryote, amplified and serve as an intermediate vector to produce a vector that can be introduced into a eukaryotic cell (e.g., amplifying a plasmid as part of a viral vector packaging system). A prokaryote can be used to amplify copies of a vector and express one or more nucleic acids to provide a source of one or more proteins for delivery to a host cell or host organism. Expression of proteins in prokaryotes is often carried out in *Escherichia coli* with vectors containing constitutive or inducible promoters directing the expression of either fusion or non-fusion proteins. Vectors can also be a yeast expression vector (e.g., *Saccharomyces cerivisaie*).

In some aspects, the vector can be capable of driving expression of one or more sequences in mammalian cells using a mammalian expression vector. Examples of mammalian expression vectors include but are not limited to pCDM8 and pMT2PC. In mammalian cells, regulatory elements control the expression of the vector. Examples of promoters are those derived from polyoma, adenovirus 2, cytomegalovirus, simian virus 40, and others disclosed herein and known in the art.

In some aspects, the regulatory element can be operably linked to one or more elements of a CRISPR system to drive expression of the one or more elements of the CRISPR system. CRISPRs are a family of DNA loci that are generally specific to a particular species (e.g., bacterial species). The CRISPR locus comprises a distinct class of interspersed short sequence repeats (SSRs) that were identified in *E. coli*, and associated genes. The repeats can be short and occur in clusters that are regularly spaced by unique intervening sequences with a constant length.

As used herein, "CRISPR system" and "CRISPR-Cas system" refers to transcripts and other elements involved in the expression of or directing the activity of CRISPR-associated ("Cas") genes, including sequences encoding a Cas gene, a guide sequence (also referred to as a "spacer" in the context of an endogenous CRISPR system; e.g. guide RNA or gRNA), or other sequences and transcripts from a CRISPR locus. In some aspects, one or more elements of a CRISPR system can be derived from a type I, type II, or type III CRISPR system. In some aspects, one or more elements of a CRISPR system are derived from a particular organism comprising an endogenous CRISPR system, such as *Streptococcus pyogenes*. In some aspects, one or more elements of a CRISPR system are derived from *Staphylococcus aureus*. Generally, a CRISPR system can be characterized by elements that promote the formation of a CRISPR complex at the site of a target sequence (also referred to as a protospacer adjacent motif (PAM) in the context of an endogenous CRISPR system).

As used herein, the term "target sequence" refers to a sequence to which a guide sequence (e.g. gRNA) is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence can comprise any polynucleotide, such as DNA or RNA polynucleotides. In some aspects, a target sequence can be located in the nucleus or cytoplasm of a cell. In some aspects, the target sequence can be within an organelle of a eukaryotic cell (e.g., mitochondrion). A sequence or template that can be used for recombination into the targeted locus comprising the target sequences is referred to as an "editing template" or "editing polynucleotide" or "editing sequence." Disclosed herein are target sequences. In an aspect, the target sequence(s) can be selected from one or more of the sequences listed in Table 1. In an aspect, the target can be MSUT2 (also known as ZC3H14). The mouse MSUT2 gene ID is 75553. The human MSUT2 gene ID is 79882.

The mouse longest coding mRNA → protein is: NM_029334.2 → NP_083610.2
(SEQ ID NO: 26)

```
  1 ggggacgcgc acggcggagg cggagcggcg gcggcagcgg cggcagcggc agcggcagcg 61 gcgtaggggg cccaggctgc agggtggcag cccgcggcgg gctccaggta accgaggcgc 121 cgcgcagtgc cgagccggcc gcccgccgcc gagccatgga aatcggcacc gagatcagcc
```

-continued

```
 181  gcaagatccg gagtgccatt aagggaaat tacaagaatt aggagcttac gtagatgaag
 241  aacttcctga ttacattatg gtgatggtgg ccaacaagaa aagtcaggac caaatgacag
 301  aggacctgtc cctgtttcta gggaacaaca caattcgatt caccgtatgg ctccatggtg
 361  tattagataa actgcgctct gtcacgactg agccctctag tctaaagtct cctgacgcca
 421  gcatcttcga tagtcacgtg ccttcaaaca agagcagttt cagtcgggga gatgagagaa
 481  ggcacgaagc tgccgtccct ccccttgctg tttctagttc tagacctgaa agagggatt
 541  ccagagtttc tacaagttca caggagcaga atccactaa tgtcagacat tcatatgatg
 601  atggagcttc caccggcta atgtcaacag tgaaacctct gagggaacca gcaccctctg
 661  aagatgtgat tgatatcaag ccagaaccag atgatctcat tgatgaagac ctcaattttg
 721  tgcaggagaa tcccttatct cagaaaaaac ctacagtgac acttacatac ggttcttctc
 781  gcccttctat tgaaatttat cgaccacctg caagtagaaa tgcagacact ggtactcact
 841  taaacaggct gcaacttcat ccgcagcaaa gcagtgctca cgctgccaag cagctggatg
 901  tacaaagcag ccaggtatcc gaagcaggac ggttgtgtga ccaccagtg cttagcagcg
 961  tagaagacac ttatagcccc ttcttcagaa acaacttgga taaaatgagt attgaggacg
1021  aaaactttcg aaagagaaaa ttgcctgtgg taagttcggt tgttaaagta aaaagattta
1081  gccatgatgg agaagaggag gaagaagatg aggattatgg gaccccgcata ggaagcttgt
1141  ccagcagcgt gtcagtacca gcaaagcctg agaggagacc ttctcttcca ccttctaaac
1201  aagctaacaa gaatctaatt ttgaaggcta tctctgaagc tcaagagtct gtaacaaaga
1261  caactaacta ttctgcagtt ccacagaaac agacacttcc agttgctccc agaactcgaa
1321  cttctcaaga agaattgcta gcagaaatgg tccagggga aaacagggcc cccagaataa
1381  gtccccctgt taaagaagag gaagcaaaag gagataatac aggaaaaagt caaggaactc
1441  aacagaggca attgttatcc cgactgcaaa ttgatccagt aatggtagaa acaatggaga
1501  tgagtcaaga ttactatgac atggaatcca tggtccatgc agacacaaga tcatttattc
1561  tgaagaagcc aaagctgtct gaggaaatag tagtgacacc caaccaggat tcgggggatga
1621  agactgcaga tgcccttcgg gtcctttcag gacacccttat gcagacacga gatcttgtac
1681  aaccagataa acctgcaagt cccaagttta tagtgacgct ggatggtgtc ccccagccccc
1741  caggatacat gtcagatcaa gaggaggaga tgtgctttga aggaatgaaa cccgtaaacc
1801  aaacttcagc ctcaaacaag ggactcagag gtctcctcca cccacagcag ttgcatttgc
1861  tgagcaggca gcttgaggac ccagatggta gcttttccaa cgccgagatg actgacctga
1921  gtgtggcaca gaaaccagaa aaacttctgg agcgctgcaa gtactggcct gcctgtaaaa
1981  atggggatga gtgtgtatac catcatccca tttcacctta caagccttt cccaactgta
2041  aatttgctga gaaatgtttg tttgtgcatc caaattgtaa atatgacaca aagtgtacta
2101  aagcagattg tcccttcact cacatgagta gaagagcctc gatactgact ccaaaaccag
2161  tgtcgtcacc agcaccgtct tctaatggcc agctctgccg ttacttccct gcttgtaaga
2221  aaatggaatg tccccttctac cacccaaaac actgtaggtt taacactcag tgtacgagac
2281  ctgactgcac attttatcac cccaccatta ctgtgccacc aagcacgcc ttgaaatgga
2341  ttcgacctca gagcagtgag tgatgcccta gtcctacctg gcagaagatc atgcagtttg
2401  aaagcttcca tcttctgatg agagatgttc tacagaactt gtcacgtctt tgaaatttag
2461  aatatattgc tttcataata cgaatttttac tgccccactg aagtgtctaa ttttttcaagt
2521  ttgtaagttt attaagtggt tcaacatttt tttgtttgtt cgttttgact atgaaaaaga
2581  cagtttaaag aaaagccaaa ttctattaaa acatttgcgg catgtttgta cattgctgtt
```

-continued

```
2641 taatatcatt tttggtaatg gtacttgcag cttagggctg tagtgctgtg ggaaggccag
2701 tgtcctcaga gctgaagcac ttttcagctt ttcccaaagg taatgcagtg tctgtaaccc
2761 agcgtggtaa cagtggccag gctttgaaac tgaggcagct ttggaacaac tagtttaaat
2821 ttctttttt agtgtctaaa tgaatttgct ctgagaagca taatgcagac tttattttga
2881 gtgctacttt ggtagagtgg accgaggtcc tgtgcctttc tgaaagtgag cagagacatg
2941 gtcataaagg gtaagcatag ttggaatgac gatgtaaaaa tatatggaca gttctttgga
3001 atgctcccat ttactattag cttatcattt tataagtaat tttggaggga ctacattatc
3061 acaaaagtat acaaaaattt ttacaggcat atgtacagaa agtatcagaa aacagacttt
3121 gaactcacaa gaatataaat atacgtatat attcccatat tctgaaaaat atcatcagaa
3181 ataacccac agaaaatata cttatgttat tactaaagat cattccttgaa atgtagaagt
3241 tgagatttaa gtggtatatt ttaaatgaca gaactatatt gcagagatag aaggtaaac
3301 ttgacaatag gatgaaactt ggcctactgt actatggagt tttatgtgtg gtttttgaaa
3361 ctgttaaggc aagatgtgtc atgttttaga actaaataac agacaactga tttcaaaaac
3421 gtgttgtttt aaaaattaaa gtgtaaacgg tggttagcaa aggggataat aaaagctcaa
3481 acattttgag gaccaaattt aactgttaag atacaataaa gtcacatcta taaagtctg
3541 tgtttaataa tgtgaa.
```

The human longest coding mRNA is: NM_024824.5 → NP_079100.2

(SEQ ID NO: 27)

```
   1 ggaggcggtg gtgtcccggc tgcggggtag gagtccgcgg cagcctccgg gtaagccaag
  61 cgccgcgcag tgctgagttc ccgcacgccg cagagccatg agatcggca ccgagatcag
 121 ccgcaagatc cggagtgcca ttaaggggaa attacaagaa ttaggagctt atgttgatga
 181 agaacttcct gattacatta tggtgatggt ggccaacaag aaaagtcagg accaaatgac
 241 agaggatctg tccctgtttc tagggaacaa cacaattcga ttcaccgtat ggcttcatgg
 301 tgtattagat aaacttcgct ctgttacaac tgaaccctct agtctgaagt cttctgatac
 361 caacatcttt gatagtaacg tgccttcaaa caagagcaat ttcagtcggg gagatgagag
 421 gaggcatgaa gctgcagtgc caccacttgc cattcctagc gcgagacctg aaaaaagaga
 481 ttccagagtt tctacaagtt cgcaggagtc aaaaaccaca aatgtcagac agacttacga
 541 tgatggagct gcaacccgac taatgtcaac agtgaaacct ttgagggagc cagcacctc
 601 tgaagatgtg attgatatta agccagaacc agatgatctc attgacgaag acctcaactt
 661 tgtgcaggag aatcccttat ctcagaaaaa acctacagtg acacttacat atggttcttc
 721 tcgcccttct attgaaattt atcgaccacc tgcaagtaga atgcagata gtggtgttca
 781 tttaaacagg ttgcaatttc aacagcagca gaatagtatt catgctgcca agcagcttga
 841 tatgcagagt agttgggtat atgaaacagg acgtttgtgt gaaccagagg tgcttaacag
 901 cttagaagaa acgtatagtc cgttctttag aaacaactcg gagaaaatga gtatggagga
 961 tgaaaacttt cggaagagaa agttgcctgt ggtaagttca gttgttaaag taaaaaaatt
1021 caatcatgat ggagaagagg aggaagaaga tgatgattac gggtctcgaa caggaagcat
1081 ctccagcagt gtgtctgtgc ctgcaaagcc tgaaaggaga ccttctcttc caccttctaa
1141 acaagctaac aagaatctga ttttgaaggc tatatctgaa gctcaagaat ccgtaacaaa
1201 aacaactaac tactctacag ttccacagaa acagacactt ccagttgctc ccagaactcg
1261 aacttctcaa gaagaattgc tagcagaagt ggtccaggga caaagtagga cccccagaat
1321 aagtcccccc attaagaag aggaaacaaa aggagattct gtagaaaaaa atcaaggaac
1381 tcaacagagg caattattat cccgactgca aatcgaccca gtaatggcag aaactctgca
```

```
1441 gatgagtcaa gattactatg acatggaatc catggtccat gcagacacaa gatcatttat
1501 tctgaagaag ccaaagctgt ctgaggaagt agtagtggca ccaaaccaag agtcgggat
1561 gaagactgca gattcccttc gggtactttc aggacacctt atgcagacac gagatcttgt
1621 acaaccagat aaacctgcaa gtcccaagtt tatagtgacg ctggatggtg tccccagccc
1681 cccaggatac atgtcagatc aagaggagga catgtgcttt gaaggaatga aacccgtaaa
1741 ccaaactgca gcctcaaaca agggactcag aggtctcctc cacccacagc agttgcactt
1801 gctgagcagg cagcttgagg acccaaatgg tagcttttct aacgctgaga tgagtgaact
1861 gagtgtggca cagaaaccag aaaaactttt ggagcgctgc aagtactggc ctgcttgtaa
1921 aaatggggat gagtgtgcct accatcaccc catctcaccc tgcaaagcct tccccaattg
1981 taaatttgct gaaaaatgtt tgtttgttca cccaaattgt aaatatgatg caaagtgtac
2041 taaaccagat tgtcccttca ctcatgtgag tagaagaatt ccagtactgt ctccaaaacc
2101 agcagttgca ccaccagcac caccttccag tagtcagctc tgccgttact ccctgcttg
2161 taagaagatg gaatgtccct tctatcatcc aaaacattgt aggtttaaca ctcaatgtac
2221 aagaccggac tgcacattct accatcccac cattaatgtc ccaccacgac atgccttgaa
2281 atggattcga cctcaaacca gcgaatagca cccagtcctg cctggcagaa gatcatgcag
2341 tttggaagtt ttcatgtact gatgaaagat actctacaga acttgtcaaa tctttgaaac
2401 ttggaatata ttgctttcat aatatgaagt tttattgcct atctatctga agtgtctaat
2461 ttttcaagtt tgtaagttta ttatgtggtt ttaacattgg gtgtttttgt tttgttttta
2521 ctatgaaaag acagcttaag gaagagctaa attctgttaa aatatttggg gcatgtttgt
2581 gcactgctgt tgtgaggatc agcatatgaa attgacatca tggttagtca tggtactgca
2641 gcttaggggg ctacacggtt gctgtgtgag tggagagatg cagtgaggca gttgtcatta
2701 ttctaaaaat tgtactactt tcacttttcc caaagattat ataatgttca taatccacca
2761 tgaaaacagc attggccaaa ggtactgagg ctgcttaaaa tattcaattc tgcttttaa
2821 ttttaagtg aatttagttt gaaaagcatg attatacagg cctctcaggc tgagtgctac
2881 tttggtaaag ttcccagttt tcctgccttc tgtgacagga tgaatgaggt gggtatggac
2941 agtggaggca gctggaatgg caagtgcaga aaataggaac agttctatac agtgctctca
3001 tttactaata acataatgcc ttctaaataa ttttttgg aaactacatt atcacaaaat
3061 tatacaaatt ttttacaag tatttacata ctgtatctga aaacagactt taaagtcaca
3121 agattataaa tgtacatata tattctcaca ttctgaaaaa taacattctc agaatccaca
3181 gaaaatatac ttagttacta ctgaagataa ttttgaaat gtaaaaatta gatttaaata
3241 gtatatttta aatgacagaa ctataattac agagatcaga tcagataggt aaactgcaag
3301 atagatagga tgaaactttt ggcctactgt attacttaca gagttttttt gtgtgtggtt
3361 tttaaaactg ttaaggcaag aagtgtcaaa tgctttagag ttaaataaca gatcactgat
3421 ttcaaagact tggtgtatag tgttaaaaat taaagcttaa aaggtggtta gaaaagtgga
3481 ttaatgcaaa aggggtaata aagactgcaa cattctcagg accaaattaa actgctaaaa
3541 aaaaaaaaaa agttcattga cttgcttagt cgtatactca aatgatgata aacctacatg
3601 tgcaaaggct cacgtttaag attgtcaagc cagcagtcta ctgttgtgtt gccattgctt
3661 ttccattggg agaagaaaga attaaccagt cattaaacca tttggtaagt tgcactttgc
3721 tgtgctgatc ccacaggaaa ggcttgaaac acgagaagca gcaaagacag agcacacaag
3781 tgcataaggc tgttgtcttc ggcttgggtg aaatgacagt tcctcttcat tctaaaggtt
3841 tactccattg aatttaaggc atttgttcat tccagtgttg agatgctttg catctctgca
```

-continued

```
3901  gaagaaattt attttaaatt gtttaaatat ctggaaatac ttttagctat catttataaa
3961  gatagttttg ttctcagttt cactataaat tatagaacaa atgggaaaca aggggtttaat
4021  ttagttcagc cattttacaa ggaaataata aaatactaaa atctgattgt ttttttgctat
4081  ttaatagcca ctgcccagac acatatttaa gagtttaatc tttcagttgc tatggcttat
4141  gaacaagcta aggttgacca taaaacattt gttggatgac gtggtttaaa atgatcacca
4201  caaaagggga ccacaaaaaa aggaaggaaa tgagcatggt tggcgattgg aagcaagggt
4261  accagagggc acagtgtgct ttggcatgca ttttatacat aaaatgaatg gaacaaaagg
4321  tgccagaagt cccaggttac acaatcagga gcttagatac tgcacacaaa aataattatc
4381  tgggttaaaa aagtaaacat agggcagatt ctatatggcc tatcatgttt cttcaccttc
4441  ccctcgttgc tggctgatac agcgaggtgg tcagctgatg actacttagt caatatgacc
4501  tttagtcgtg aaactgacag cagcagtgat taaggctgac ttaatcaggt tggccacttt
4561  gaaggacaga atgcagtggg aaacagtttt attctatgta gtttacatgc ttaaggttac
4621  agagtttcta cctgcactgt aatggaaata taatttctct gtagccaaaa gctggcaaac
4681  ttgacccaga gggaaaattt aaaactgcag caggctcaaa tgtagagtat ttttcttttt
4741  atgggcaggt tgttcaggga tttttttcct cctttaattt attgactgac tgtaaataca
4801  tgagtagaaa cttaatagtc atgtatttca aaatttggct taatttagga gaatccactg
4861  atgaacaagt accaacttac gtttcaagct tcttagcccc ataatcagtc cttcagccac
4921  agctatttag agctttaaaa ctaccaggtt caatcactgg ttatgctttc tgtgatgtaa
4981  tttagtcatt tctattttta gtattaacca agtattagac acagaaaata ggtattaaga
5041  atcttcatat atcctgtcag accaaatggg attccaggaa cctaaagcga tctattatgc
5101  tataaagata attaacacat taaaaactca tagggtcaat acagcatctt aaacctcaca
5161  cttagaaaaa tatattttta aatagcagtc tacataattt tcaatcttca ggaaactaca
5221  gataggctag acagcgaatt cctgaatgat gagtagtgat ctttggcagc atttaaagtg
5281  aaaagaaata aggatctaag aattcagccc taatccacta aaaaaaggaa ttctaactga
5341  caagttttta caaatggagt tgggctcatt cattttggaa ataaacctat ggagtggcac
5401  acatctaaac aaattttccc aatagaaaaa aggctataaa aattttattc caagagtgat
5461  taaattgtat aatgttgtat atgtgaattt aacacttttg tttacatgtt aaacaaatgt
5521  gtatatatta gactacatta aatatgcaat tctttcttcc agttaaatac tgttgctccc
5581  taaaacccctt acattgtaca ccattgggaa tgattgttca tcatactact tttccattag
5641  tgaggctaca gttatgtttt aaatgtgcga ttacagagat ggcatctgaa cataaactga
5701  tggctcgaaa atgaaaatgg aaatgtagca gccatatact gctaactttg gatctgttcc
5761  tgaattcaaa actactagga gaaaagtgtc ctttataaaa aaggacctta ttaatgccta
5821  aaaaacatca tattctctag gaaagcttgt gtctgtttcc ttagggaaaa tgtttgcctt
5881  ttaaaaactg tgatcccttta ggatgatcat gactttccct ttccttatgg aaatgcaaga
5941  ataaaatatt tcattaaaca atgaaccttg aaaataaaat ataaacatta agaaaccatt
6001  ttgctaaaaa gataatgaaa attatccaaa ttgggttttt gagttcttct gtaaagagtg
6061  ctctacccta aattttccca gcaggtctgc cgaaatcaca cacttcccaa tacaggggga
6121  cttggccttt accatcaagt attcgatcct tccttgaaat ggcattatct ggcagtgtat
6181  ggattacgga ttatacccag tgcatatagc aaatattttg aacagatcag tctttcacta
6241  ttttgatgat tctgggcatt tctccctgtt acagtcttgg gttagcacca cttgaccatg
6301  cagggttggg ttttggtttt tcttctctgt aattctggtc tcaaagttaa tttctgtagt
```

-continued

```
6361 catctcagca tctctcagtg aggtgtatgt acacatttcc agacaaataa gctgcaatca
6421 gagaagaaaa ttgcagggag ttaattatgt ttttagattt tcataacagt ttaatatttt
6481 tcagttgtgc tttcaggtta catgtgtaat attttcctc tttaactcct tttattctgt
6541 atttgcataa atatgagatt ctgaagagcc atctggttat actaccttct actaatgttg
6601 actagctgat ttcataaacc aaagctgtag gagttgttgt attaagtctc ttaactagta
6661 acatagtctg ctcttcatgg gctgagaaag ttactaacct gcagtcatca cctccagcac
6721 taacaacatg tcgatcacca ctggtaaatc gaatatttgt cacatggggc gaatgaccca
6781 agaacctttt gtgttttgcc taaaaaacaa tgacagacaa gctcagggca tttggtgcac
6841 acagaagtca aaggctctta ttaggaacta taatctctat gacaagagct gtggagagag
6901 tagggagtta gcaccgcagc cagtgattag aatgcttttc agcatgagta gtggatctgc
6961 aaaaccaggc tgtgtgggca gtcagatgtc tccaggtact ctgaccattt ttctctaagg
7021 aaaagcattt gaaatttgat aactgattat aggtttggtg aaaagctaat tacagctttt
7081 gtaggatggt tccaaagatg gtattactcg agggagagga tttgtttcta atagctttta
7141 tttcaaagta aatagattta gaaagtttgg ggaaaaattt agaaattagg acaaaacatt
7201 ttaaatatat ggggaaaagt gctgatgata agacatcaaa attaggagta aactgataat
7261 agtaaacaaa acacaaactt acaaattttt ctggacatgg gaagtcaaat aacttaacca
7321 tgccaaagtc atctcctgta acaagactga ttcctgaatg agatacacag gcacagttga
7381 catcagcttt ctcagcatgt ctggaccaga ttcccaaaac ctcatctcct agaatactag
7441 agggaaggaa caaaagaaaa ctcatcatgg caagtgcggg caggttgact atattcaaaa
7501 agtttcttgg caattaatct ctaagtaccc tatcatgtta cttaaaatac aggaagtaaa
7561 ttatggtaag ttgtttggag acctgaattt catcaggata tcaactcctg cctttaaaa
7621 atgacatttt ataatttgaa gggtttctag attaatcttt ttaagattaa agtagtactt
7681 tatgaaaact gatagaacta ttttttcttt tttttttttt gagacggagt tttcgctctt
7741 gttacccagg ctggagtgca atggcatgat ctcggctcac cgcaacctct gcctcctggg
7801 ttcaagcaat tctcctgcct cagcctcccg agtagctggg atcacaggca tgcgctaaca
7861 tgcccggctt attttgtatt tttagtagag acagggtttc tccatgttgg tcaggctagt
7921 ctcgaactcc cgacctcagg tgatcacccc cgctcggcct cccaaagtgc tgggattaca
7981 ggctgagcca ccgcgcctga ctgaaaactg atagaactat ttttcaaatt aaaagtgcta
8041 cttggctggg tccagcagca cataccagta atcccaacat tttgggaggc tgaggcagga
8101 ggactgcttg aggccaagag tttgagacca gcctgggcaa tattgtgaga tccctatctc
8161 tacaaaaata aaaatgactt atgacatagg aattaaaaaa atttcagaga tggggtcttg
8221 ctatgttgcc caggctggta tcaaaacttc taggctcaag tgatcctccc acctcggcct
8281 gctacatcag agattacagg catgagccac tatatgcctg gctgatacag gaatttgatg
8341 gcatttttca ttggccaaaa aaatggatag tcatggttac ctgtcataca gccaggaaat
8401 ttgaacaaat ttggaagctt tgacttctaa tagattcaag atagcattcc tttagataga
8461 gaattaataa cagttgctta acagcaccca ataccttttt gccagtcatt aaatttagca
8521 ttaagaaaaa tatcagggta tctttaaagt taaaactttg atttccttaa aaaaaaaact
8581 tgataaatca tggaaactga taaaacatgg aaatatattc aataaaaagg ggtcccaaca
8641 tgaacatacc atttcaaaat atggtaacaa aaacttgaaa ctcaattact attccttatt
8701 ggaatggctc taacagttca gaaataggat tttctaactg gccttcaaag tcagttcttg
8761 ccttgtgaat atataagtat ttacctagtc catgtagccc aagtaattct gtcaatagcg
```

-continued

```
 8821  gcatgatcca taagatgttt tcctgaaggc acttcataga catgccgttt atagcagcca
 8881  ctagagacct ttttcatcag attaaaatgg gacaagaatt ccattaggtg agagacaaaa
 8941  tccacagggg gtttacagaa tactagcata ttgctacttg atttacatgt ctaacattat
 9001  taagtatgca aaagatcact acaaaaactt aataggagaa aagctctgat aagtggggga
 9061  ggaaagggga gctgtaggtc agaaggtaca aagggaggag ttgagaagct ggagctctgg
 9121  agctcaggaa ctttaaatgc attcactaac acgaaatgta aaagcagaag aacttgccac
 9181  ctgggtatac agtattggta ctgtacctgg agataactgc tatctgcaga gaagtccatt
 9241  tgaatgacaa agcttggaat gtctttgcag tagctgattc tgttaagagt ggggcccagc
 9301  gttaggtcat aaaaatccac tgagttctca ctagaaccta ctgccagata ccgggaatcc
 9361  ggactaaatc tgaatcaaaa caaaacgtaa aaagtattag accacatgaa gtattataaa
 9421  tacttaagat cagtgacttt tcctttctag ttcttaaaag taacgtgtga taaggcctca
 9481  aatagattta cctgtcagac acaactgatc atgtatactg agattgtctg ggttacatga
 9541  aataaggaag ctttatattt tacttaaatt ttaaatattt ccccaattgt catctcccaa
 9601  ttcctttaaa aacgtctaat ggcttaaaaa aactttctta ggccaggccc agtggctcac
 9661  acctataatc ccagaacttt gggaagcgga ggcgggcaga tcacctgagg tcgagagttt
 9721  gagaccagcc tgaccaacat agagaaaccc tgtctctact aaaaatacaa aattagccag
 9781  gcatggtggt gcacgcctgt aatcccatct actcgggagg ctgaagcagg agaatcgctt
 9841  gaacccagga ggcacaggtt gtggtgagct gagattgcac cattgcactt cagcatgggc
 9901  aacaagagca aaactccaac tcaaaacaaa acaaaacaaa atttaatttt ttaaatagag
 9961  gcggggtctc actatggtcc caaactcctg gcctcaagca atccttcccc cttggcctcc
10021  caaggtactg ggattacagg tgtgagccac aacacccagt cagaacatct cagcttttaa
10081  aagccattag cattacataa ttaataagct aacaattcat taagatagtt ttcttccatc
10141  tggaaaaaac gttgtcttaa tattaagcaa agaacacagc ccagcttaac taacctccag
10201  ttattaaggt gaaatgacac aacttgaatc ttggaagaag aattttttttt ttttgagacg
10261  aagtctcgct cttgtctccc aggctggagt gcgatggcgc aacctccgcc tcccgggttc
10321  aagcgattct cctgtttcag cccctgagt agctgggatt acaggcgcct gccaccacga
10381  ccggctgatt tttgtatttt tagttgagat ggggtttcac tatgttggcc aggctggtcg
10441  agtactcctg acttcaggtg atctgcctgc ctcggcctcc caaagtgctg ggattacagg
10501  catgagccac cgcgcccggc ctgaagaact tatttaaaag acaaagtgaa atgctatttg
10561  cctagcaatc tttggagtca tatgggacaa ttcagtctct tgaaatggcc catgagtctt
10621  actgaggtac gatagagaca tgtaaaagct aagggaagcc actgttacta ttttatatat
10681  tgaagttctg aggaaggttt catttgtaaa aggattttac tgatgaaaag tgtacaagct
10741  tttgacagac ctagattcaa taatcttatc tactgatcac acgaagtac tccgtaaatg
10801  gtagccactg ttgaaaaatg cttaagcact gaaaaacaaa ggtttaagaa acatttaaat
10861  taatttggat tctggaacat ttaatcaata ggtattgatt aaattaatga actacatatt
10921  cccaaactga ggttactaag agaagatatg tttgaaatca caactttagt tttccagggt
10981  gacaactttt gaagggcaga tagctctctt gtattacagt gggagatacc tcttggtggg
11041  atgaacttaa tggacatggc taagtgttaa catgaattca tcaaacatta cctactagta
11101  cttgctatta tagttggtgc ccagtgggtt tataatttag caagaagaat taagtagtat
11161  acaaacagcc atattttagc atacaattta taatcgggaa aatgctacag gccctgggga
11221  cctctttttg aaggcaaggc tatggaaaat tttacaaatg gaagttaaat caagtatata
```

-continued

```
11281  ctagaaactc tattccattt gttcactaac ctgatatcat ggattgcaca tctcctgtct
11341  ctcttctttc cccatatttt tagagaactc actagtaaaa tgataaattc tccatttttc
11401  attccaatag ccaccatgtc cccttcaggg ctgtaacaca cagtacgagc agcatgtccc
11461  aaattcactt tgtttaacat cttctgcatt taaaaaaaaa aaaaaaaaga gtcataggaa
11521  acattaagtg aagtacttct aaattatacc agtttcccct caaaatgctc aacagaattc
11581  tggcagttct ttaagtacta gcaatttaga acttccaact tttcttttta gaagttgtaa
11641  cctcttttaa aaaaattatc tgtacttact ttatcagcaa tatcccaaag tctcactgtc
11701  ccatcttctg cagcagaaag gaaaaaatcc ctggaaggat gtgttgctag tccccagatt
11761  ggcccatcca catgaccgtt aactaaaata ttacaagctg catttttctc tccaacttcg
11821  attatttcag cattccttgt cccaacaagg atcttgccct gaaacacaag caggaccaat
11881  acagtgaatg taatacaaca gctgcttttc ttcttcataa tataaaaatg accctattga
11941  cctgctttca gagaactttt tgctttgagc taatctagta gcaaggcagt cattagctca
12001  tgcaaatttt tctatgacta caggcacaca tctatctgta agcacaatgg gctagattac
12061  atattagagt ccatgctaca gaatagaact tttctgtggc agtacacctg gattcttcaa
12121  taatcaaagt ttttatttga taatcttagg atttccaaac tggggtcagt gcagtgggat
12181  ataggaaaaa ataatagaat ttattttta gttaaaaagt aaaagcttaa ctacaattta
12241  atatgcaggc tgaagataat atccgtatga tttataaata cacttaataa gtacaaacac
12301  gctcaaaaat tttcatagga gttgtagttt tgaattttta ttttgaaatt gacacataat
12361  tatacatatc tatagggcat agggtaatac gcataaccat cacctcagac atttatcatt
12421  tctttgtgat ggaaactttc aaaatcctct cttgtaaata cctgaaaata cataaatacg
12481  tgattcttaa ctatagtcat cctacagtac tacagaatac taaaacatac tattcctatc
12541  tggctgtgta aacttgtatc ctttaaccag tccttcccta tcccctccc cctccccctt
12601  gtccgcctcc agtaaccact attctactct ccacctctgt gggatcaact tttttagttt
12661  ctgcacagga gtgagaacat gtatttatct ttctgtgcct ggcttatttc acttcacatc
12721  atgtcctcca gtctcatcca tgttgccacc aagaatgaca gaatttcatt atttttatg
12781  gctgagtagt atttcattgt ttgtttactg cacgttttat ctagggaatg tgtgttttt
12841  taaaaaatgg agacagctgt cctaatatga gtcaactgcc aagggctttc aattatgtct
12901  actagagttg ttaaattggc agattctaga aaatattgga ggtttacata cagtatttag
12961  acagaatagc ttcctagctt atgcaccaca ctggtgctaa ctttggcaaa gaaagcagca
13021  aagacagagt aatgttggca agcaaatcca tcgttatgca ttattaagta ttgttcatta
13081  ggctgcaaag ggtgagggaa tcacagtaat aaccactttc tgttttctgc tgcactgtat
13141  cagctcatgg aacatcttac tttgcctctg cacacagaac gaacacaatc tgtggcttgt
13201  cctgtctcaa gcctgaaggc acggcaccgc ctcagttcct gatcccacag tttaaccgct
13261  cctccttctt ttgacctaag taaataacca agccagagta agtgttcatt attggctact
13321  ataatttta ttataaacaa ataccaagtt ataagcagaa tctttttttt ttaaaaaggc
13381  cctgatattt ataatttacc tctaatattc ttgtaaactt tctatggcaa tttgaggata
13441  tactatatct cagtcaaaat aaacatccag tttcagtgaa ttttattttg agaaatactc
13501  tttttttctg acatgagcat aatttttattt agcctctaca atacattaca atacattatc
13561  ctctctcata atactttttt ttttttttttt aagatgtagt ctcgctctgt ctcccaggct
13621  tgagtgcagt ggcatgatct aggcttattg caacctctgc ctcccaggtt caagcgattc
13681  tcctacctca gcctcccgag tagctagcat tacaggtgtg caccaccaca cccagctaat
```

-continued

```
13741  ttctgtattt ttagtagaga tggggtttca ccatgttggc caggctggtc tcaaatacct
13801  tgacctcagg tgatctgcct gcctcggcct cccaaagtgc tgggattcca ggtatgagcc
13861  actgtgcctg gcctcataat acttcttgat taggaagatg taaaaaaaca attttattaa
13921  aaggataatg gaaatgtaag gcaaaataat agaattacaa atgctatgct acagagttga
13981  tttatttatt tttttgagac agagtgtcgc tctgtcacct ggcctggagt gcagtggtgt
14041  gatctcggct cactgcaacc tgtgcctccc aggttcaagc gattcttctc cttcagcctc
14101  ccaagtagct gggattacag gcaccatgcc tggctaattt ttgtattttt agtagagatg
14161  gagtttcacc atattggcca ggctgatccc aaactcctga cctcgtgatc cgcccacctc
14221  ggcctcccaa agtgttggga ttacaggcgt gagccactgc aactggccca gagcttattt
14281  ttgaaggcca aaacagaagc atatttattc cctatcaggt gttaaaatat ctcactggaa
14341  cagtttagca ggcttctagt gagtgggggt gtgcaggagt aaatgacgtg ggaaatacaa
14401  gtgttggagg acgaaataga gcccatttat ggattttatt cctggaaggg ctgaaaaatg
14461  tattccttcc ttttctgcta gatgaattgc ttgtctgaaa gcatgcctat gtgcattctt
14521  cctttatgta aaaggcacaa attctgcgct tgtgtttaat taacatatgt gggttctttc
14581  aatcctgtat tgaaatgtac ttcttagtca actatatgtc acattttttt ttgttttgt
14641  ttttgttttt taaatggggt ctcactctgt cacccaggct ggagtgcagt ggcaccatca
14701  cagctcacta aagccttgac ctccccaggc tcaagtgatc ctcccacctc agcctcctga
14761  gtagcaggga ctacaggcat gtgccaccac acccggctaa ttgttgtttt ttatagcgat
14821  ggggtttcac catgttgccc aggctggtct tgaactcctg gctcaagcg atccacctgc
14881  ctcagcctcc caaagtgata agattacagg tgtgagccac tgtgcctggc ctacatgtca
14941  tgtttcaaca tgcatatgac tatgttggtg acaaatcaaa tcataagtat ctggttactg
15001  ttgggagatt tgaaaatcac tcagaagaga cctcttctca aatttttgagg tcttgtataa
15061  aacagtttaa atttgcctca agcaaaagga aacaaggcag ttctctctag ttccctcatc
15121  cttttctaaa gcaacaatgt gcattctact ccttagaatc cattctgaac aaaaagagag
15181  caggcagtca aaatacaacc ctggctccag attcccccat gggcctccta ctcagcaaat
15241  catacacagg catacagaca ttaagaaaag taactcaact tgtaggacaa ctacctatcc
15301  acacctcaga aaaagtatca ccccaacatg aaaaaaattg gaagtgaatt aagaccagaa
15361  atgagaatca aatagaaggc acataaaagg taataaagga gaagcatatg aggaggaagg
15421  tcggagagga cactctgtgt agcctagaaa caactagaat aattaactgc aaacctcagg
15481  taggtcacaa atgcataaat attctgtgaa aagaaagagg actcacggcc tttcctttcc
15541  cccagtcacg ataagtccat ctcgcagggt ggtgtacatg gcaaacacag gcccgttgtg
15601  agctctcgcc acgattctac acaatatgtg atctttccac acacagacat caccactgat
15661  ggtacctgta aacgtcaagt tattctgaaa aggagtgggg gaggggagac caaactcatc
15721  aaaagttcaa atagagttta aatagataat tttctatgta tgtgtaatgc tgtctcaccc
15781  ttgatacaaa gagcatgcat cgtgtagtgg cagcagcact gaattcacga gtcaggaaac
15841  ctgaacggga ggcttagctt tgtcaggacc ttttcctttc caagtctgtt gcttattagc
15901  tagaataacc ttagacaatt cttcccttcc aattctaaca tactataatt ctagggttta
15961  tttttattt ttttgagacg gagtttcgct ctttgttgcc caggctggag tgcaatggtg
16021  cgatctcagc tcaccacaac ctctgcttcc caggttcaag tgattctcct gtctcagcct
16081  cccaagtagc tgggattaca agcgccagcc accacgcccg gctaattttt gtatttttag
16141  tagagacaga gtttcacctt gttagccagg ctggtcttga actcctgact tcaggtgatc
```

```
-continued
16201  ttcccgcctt ggcctcccta agtgctggga ttataggtgt gagccactgt gcccggcctg
16261  agccacggtg cctggcctgg tcttatatta agaataccca aaatgttcaa ctgaaatttg
16321  acatggcaca aacatttcaa tagtcttttt ctcaaaaatg taagtgtact taaatattct
16381  aaaattataa cttttcctat aagtattgca taatcacaaa aacaaaaaat gcacttagtt
16441  tttcgatgca ccaaaggatt tatacagcct agccaatgca ggatattaaa ggaaagagat
16501  gtggattgga agccacaggt ccagatgaga tggaataaag tgagaggaga gcaggtctcc
16561  tgaacaccct tctgtcaggg ccaggaattg tgctatttcc ttctgtctca ctacctcctt
16621  cttccctcga agtagagaca ctggcccaga gcacttccag ctgtatgata agcagtgtgt
16681  taaatgataa aaagcaaagg aaatcctaaa ccctagtacc accttaaatc atttgaaaat
16741  catgtttctt gatttacctt tctctctgac aaattttag gactatgaag aactactagg
16801  aagacagaaa ttttaggata tttagggtga caattagaag attaaggaag gcttttgagt
16861  ataacagtag tccaaggaat caaatgttca tcagaatcct tattatggtg gctcatgcct
16921  gtaaaccag cactttggga ggtcaagatg ggaggatcac atagcttagg agcttgagac
16981  cacctaggca acatagcgaa accctgtctc tactaaaaat gaaagaaaaa ttagcctagc
17041  atggtggttc ctgccctgta gtcccagcta ctaaggaggc tgaggatcac ttgaacctgg
17101  gagatggagg ctacagtgag ctataatcgc accattgcac cccagcccag gcgacagagt
17161  gagatactgt gtcaaaaaaa aaaaaaaatc cttttccccc tctcattaac attcttttca
17221  ctccctaatt tctgaaagaa ctagattttt gaaagatgaa atatatgctt gaccagggca
17281  tgtaatgatt agcagatcac agtatcatct caacaacatt catgtggctg atgatctaag
17341  gcaagagaat gtaaagtagt caaagtcaca ctatgtgcat tttaagagac atactgcacc
17401  aaatgcaata gcgagcatgg tctgcatccg ggcatcttcc agtgtgctca gtagcccttt
17461  tttgctaaga agagctcttc ctgccagggt ccagaacttc acatgtttta ctcccactga
17521  gacaaactgg gtatctgaat ctggtcggaa ttctgccaca aaaatacgtt gattgtgacc
17581  agctctgctg gcaattttgg cacctgacaa gatacaacaa aattatctag gttattacaa
17641  gaaccaagct aatcaacagc atcaaacaaa tatgtaaaat acatagttca aaaaacaaag
17701  gcttagaaga gaggccaatg gcccctgctc tactacctag caatacatga tttacaatta
17761  tttgtgtatt gagtcctttt cacttatctt cgctccatta acttttcttt atataacgta
17821  aatgttttgt ctaaagtgtg gtaggtaata ttatcctgct gatctgccat tatcattaga
17881  aatatacata attttcataa gaatctccaa aaccaatcaa atcattaata ataaatacat
17941  agtttcttgc tggaagaaaa tagcagtgaa tcatttataa tgctaataat ggtttcatta
18001  attatctgt tttgtgaggt tacagttcca ctgggctttt aaagtgaaat atacctacag
18061  taccactgtg tacagtatat tgcataggcc tccactgaat gattgtttca accaccaact
18121  ttaagacaaa tattaaatac agaattccta cta.
```

A guide sequence (e.g. gRNA) can be any polynucleotide sequence having sufficient complementarity with a target polynucleotide sequence to hybridize with the target sequence and direct sequence-specific binding of a CRISPR-Cas system or CRISPR complex to the target sequence. In some aspects, the degree of complementarity between a guide sequence (e.g. gRNA) and its corresponding target sequence is about or more than about 50%, 60%, 70%, 75%, 80%, 85%, 90%, 95%, 99%, or more. In some aspects, a guide sequence can be about more than about 5, 10, 15, 20, 25, 30, 35, 40, 45, 50 or more nucleotides in length or any number in between.

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). It is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). A skilled person will be able to identify further PAM sequences for use with a given CRISPR enzyme. In an aspect, the PAM comprises NGG (where N is any nucleotide, (G)uanine, (G)uanine). The target sequence corresponds mammalian suppressor of taupathy 2 (MSUT2). In an aspect, the target sequence can be a MSUT2 gene sequence. In an aspect, the target sequence can be selected from one or more of the sequences listed in Table 1.

Disclosed herein, are gRNA sequences. Also disclosed herein, are gRNA molecules that can target one or more molecules in a MSUT2 gene. The disclosed gRNA sequences can be specific for one or more desired target sequences. In some aspects, the gRNA sequence can hybridize with a target sequence of a DNA molecule or locus in a cell. In an aspect, the gRNA sequence hybridizes to one or more target or targets sequences corresponding to a MSUT2 gene. In some aspects, the cell can be a eukaryotic cell. In some aspects, the target sequences can be selected from one or more of the sequences listed in Table 1. In some aspects, the cell can be a mammalian or human cell. In some aspects, the cell can be a mesenchymal stem cell. In some aspects, the cell can be a neuron. In some aspects, the cell can be a brain cell. In some aspects, the cell can be any cell that can be delivered therapeutically to the brain, including but not limited to stem cells. For direct gene therapy and delivery to the brain, the cell type can be any cell type in the brain, including but not limited to neurons, oligodendrocytes, microglia, and astrocytes. In an aspect, gRNA sequences target one or more cell type in the brain.

In some aspects, the gRNA targets and hybridizes with the target sequence and directs the RNA-directed nuclease to the DNA locus. In some aspects, the CRISPR-Cas system and vectors disclosed herein comprise one or more gRNA sequences. In some aspects, the gRNA sequences are listed in Table 2. In some aspects, the target sequences can be selected from one or more of the sequences listed in Table 1. In some aspects, the CRISPR-Cas system and vectors disclosed herein comprise 2, 3, 4 or more gRNA sequences. In some aspects, the CRISPR-Cas system and/or vector described herein comprises 4 gRNA sequences in a single system. In some aspects, the gRNA sequence can comprise 10-30 bp, 15-25 bp, 17-24 bp or any other fragment of the sequences set forth in SEQ ID NOs: 6, 7, 8, 9, and 33. In some aspects, the gRNA sequence comprises a sequence having 80%, 85%, 90%, 95%, 96%, 97%, 98%, or 99% identity to the sequences set forth in SEQ ID NOs: 6, 7, 8, 9, and 33 or a fragment thereof.

In some aspects, the gRNA molecule disclosed herein can target a nucleic acid sequence that can encode the MSUT2 gene. In some aspects, the nucleic acid sequence that can encode the MSUT2 gene can comprises one or more of: a sequence encoding an amino acid sequence of the MSUT2 gene, a sequence encoding the amino acid sequence of the MSUT2 gene comprising non-translated sequence, or a sequence encoding the amino acid sequence of the MSUT2 gene comprising non-transcribed sequence. In some aspects, the nucleic acid that encodes the MSUT2 gene can correspond to human gene ID: 79882 or mouse gene ID: 75553.

In some aspects, the gRNA molecule can be configured to provide a Cas9 molecule-mediated cleavage event in the nucleic acid that encodes the MSUT2 gene. In some aspects, the gRNA molecule can target the sequence encoding an amino acid sequence of the MSUT2 gene; can be configured to provide a Cas9 molecule-mediated cleavage event in the sequence encoding an amino acid sequence of the MSUT2 gene; or can comprise a targeting domain configured to provide a Cas9 molecule-mediated cleavage event in the sequence encoding an amino acid sequence of the MSUT2 gene.

The compositions described herein can include a nucleic acid encoding a RNA-directed nuclease. The RNA-directed nuclease can be a CRISPR-associated endonuclease. In some aspects, the RNA-directed nuclease can be a Cas9 nuclease or protein. In some aspects, the Cas9 nuclease or protein can have a sequence identical to the wild-type *Staphylococcus aureus* sequence. In some aspects, the Cas9 nuclease or protein can be a sequence for other species including, for example, *Streptococcus pyrogenes* or other *Streptococcus* species, such as *thermophilus; Psuedomona aeruginosa, Escherichia coli*, or other sequenced bacteria genomes and archaea, or other prokaryotic microogranisms. In some aspects, the wild-type *Staphylococcus aureus* sequence can be modified. In some aspects, the nucleic acid sequence can be codon optimized for efficient expression in eukaryotic cells.

Disclosed herein, are CRISPR-Cas systems, referred to as CRISPRi (CRISPR interference), that utilizes a nuclease-dead version of Cas9 (dCas9). In some aspects, the dCas9 can be used to repress expression of one or more target sequences (e.g., mammalian suppressor of tauopathy 2 (MSUT2)). In some aspects, the target sequences can be selected from one or more of the sequences listed in Table 1. Instead of inducing cleavage, dCas9 tightly binds to the DNA sequence, and when targeted inside an actively transcribed gene, sterically hinders RNA pol II progression leading to efficient transcriptional repression.

In some aspects, the CRISPR system can be used in which the nuclease has been deactivated. Further, a Krueppel-associated box (KRAB) or p300 core can be attached. In some aspects, the KRAB is attached to downregulate one or more genes in a cell. In some aspects, the p300 core is attached to upregulate one or more genes in a cell.

In some aspects, the CRISPR-Cas system described herein can be used to downregulate a gene in a cell. In an aspect, the expression of one or more genes (or gene products) can be decreased.

In some aspects, the vector can comprise a regulatory element operably linked to an enzyme-coding sequence encoding a CRISPR enzyme (e.g., a Cas protein). In some aspects, the CRISPR enzyme can be Cas9 and can be from *Streptococcus pyogenes, Streptococcus thermophiles, Treponema Centicola* or *Staphylococcus aureus*. In some aspects, the Cas9 can be dCas9. In some aspects, the Cas9 protein can be codon optimized for expression in the cell.

In some aspects, dCas9 can be used to silence or inhibit one or more target genes (e.g., MSUT2). For example, dCas9 can be used to silence one or more genes through steric hindrance with or without an attached domain, such as KRAB. dCas9 is the protein that interacts with gRNAs to place the desired editing proteins to specific sites. dCas9 can be used to silence (downregulate or turn off one or more genes). In some aspects, the dCas9 can be attached to KRAB to knockdown, silence or downregulate one or more genes Other proteins can be further attached to dCas9 or included in the CRISPR-Cas system and/or vectors described herein. For example, T2A, a self-cleaving peptide, can be included. T2A allows selection markers (e.g., GFP, fluorescent proteins, antibiotics) to also be attached. The attachment of such markers can be included to permit detection or selection of cells expressing the CRISPR-Cas system and/or vectors described herein.

TABLE 1

Examples of Target Sequences

| Target Gene | Name | Sequence | SEQ ID NO. |
|---|---|---|---|
| MSUT2/ZC3H14 | crRNA_human and mouse MSUT2 E6 | 5'-AATTTATCGACCACCTGCAAG-3' | 1 |
| MSUT2/ZC3H14 | crRNA_mouse MSUT2 E13 | 5'-TACTGGCCTGCCTGTAAAAAT-3' | 2 |
| MSUT2/ZC3H14 | crRNA_mouse MSUT2 E13 | 5'-GGCCTGCCTGTAAAAATGGGG-3' | 3 |
| MSUT2/ZC3H14 | crRNA_mouse MSUT2 E16 | 5'-GCCACCAAGACACGCCTTGAA-3' | 4 |
| MSUT2/ZC3H14 | MSUT2 sgRNA 3'UTR#1 | 5'-ATTAGACACTTCAGATAGAT-3' | 5 |

TABLE 2

Examples of Guide RNA Sequences (gRNAs)

| Target Gene | Name | Sequence | SEQ ID NO. |
|---|---|---|---|
| MSUT2/ZC3H14 | sgRNA_human and mouse MSUT2 E6 | 5'-GAAUUUAUCGACCACCUGCAAGCAAAG UUUUAGUACUCUGGAAACAGAAUCUACU AAAACAAGGCAAAAUGCCGUGUUUAUCU CGUCAACUUGUUGGCGAGAUUUUU-3' | 6 |
| MSUT2/ZC3H14 | sgRNA_human and mouse MSUT2 E6 | 5'-GAAUUUAUCGACCACCUGCAAG-3' | 28 |
| MSUT2/ZC3H14 | sgRNA_mouse MSUT2 E13 | 5'-GGCCUGCCUGUAAAAAUGGGGCAAAGU UUUAGUACUCUGGAAACAGAAUCUACUA AACAAGGCAAAAUGCCGUGUUUAUCUCG UCAACUUGUUGGCGAGAUUUUU-3' | 7 |
| MSUT2/ZC3H14 | sgRNA_mouse MSUT2 E13 | 5'-GGCCUGCCUGUAAAAAUGGGG-3' | 30 |
| MSUT2/ZC3H14 | sgRNA_mouse MSUT2 E16 | 5'-GCCACCAAGACACGCCUUGAACAAAGU UUUAGUACUCUGGAAACAGAAUCUACUA AAACAAGGCAAAAUGCCGUGUUUAUCUC GUCAACUUGUUGGCGAGAUUUUU-3' | 8 |
| MSUT2/ZC3H14 | sgRNA_mouse MSUT2 E16 | 5'-GCCACCAAGACACGCCUUGAA-3' | 31 |
| MSUT2/ZC3H14 | sgRNA MSUT2 UTR#1 | 5'-AUUAGACACUUCAGAUAGAUCUGUUU UAGAGCUAGAAAUAGCAAGUUAAAAUAA GGCUAGUCCGUUAUCAACUUGAAAAAGU GGCACCGAGUCGGUGCUUUU-3' | 9 |
| MSUT2/ZC3H14 | sgRNA MSUT2 UTR#1 | 5'-AUUAGACACUUCAGAUAGAU-3' | 32 |
| MSUT2/ZC3H14 | sgRNA_mouse MSUT2 E13 | 5'-GUACUGGCCUGCCUGUAAAAAUCAAAG UUUUAGUACUCUGGAAACAGAAUCUACU AAAACAAGGCAAAAUGCCGUGUUUAUCU CGUCAACUUGUUGGCGAGAUUUUU-3' | 33 |
| MSUT2/ZC3H14 | sgRNA_mouse MSUT2 E13 | 5'-GUACUGGCCUGCCUGUAAAAAU-3' | 29 |

Also, disclosed herein are small molecules. In some aspects, the composition can comprise a small molecule. In an aspect, the small molecule can be

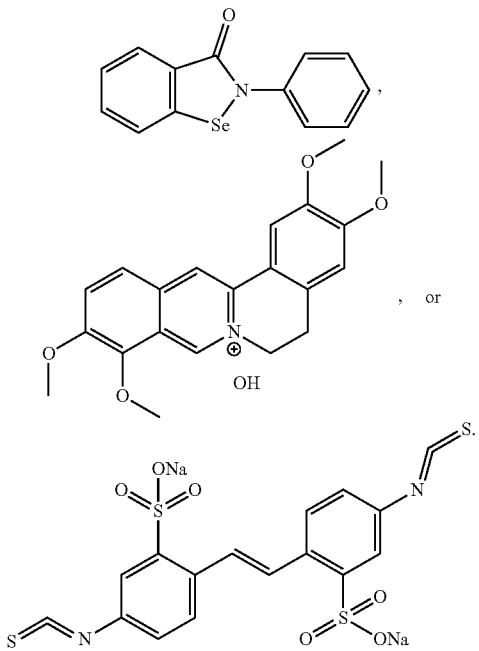

In an aspect, the small molecule (or composition comprising the small molecule) can reduce accumulation of phosphorylated and aggregated human tau protein in a subject. In an aspect, the subject has Alzheimer's disease or dementia. Disclosed herein are compositions comprising a guide RNA sequence selected from the group consisting of SEQ ID NOs: 6, 7, 8, 9, 28, 29, 30, 31, 32 and 33. Also, disclosed herein are compositions comprising an siRNA sequence. Disclosed herein are compositions comprising AUGAUGCAAAGUGUACUAAACCAG (SEQ ID NO: 10), AUGAUGCAAAGUGUACUAAACCAGAUU (SEQ ID NO: 11), AUGAUGCAAAGUGUACUAAACCAGAU (SEQ ID NO: 12), AUGAUGCAAAGUGUACUAAACCA (SEQ ID NO: 13), AUAUGAUGCAAAGUGUAC-UAAACCAG (SEQ ID NO: 14), or UAUGAUGCAAAGU-GUACUAAACCAG (SEQ ID NO: 15).

Any of the compositions disclosed herein can further comprise a pharmaceutically acceptable carrier. In some aspects, the pharmaceutically acceptable carrier for the siRNA molecule can be buffered saline. In some aspects, the pharmaceutically acceptable carrier for the small molecule can be water or DMSO. In an aspect, the pharmaceutically acceptable carrier can comprise a lipid-based or polymer-based colloid. In some aspects, the colliod can be a liposome, a hydrogel, a microparticle, a nanoparticle, or a block copolymer micelle. In some aspects, the compositions described herein can be formulated for intravenous, subcutaneous, intrathecal, intramuscular, oral or intraperitoneal administration.

Methods

Methods of designing gRNAs. In some aspects, a publically available tool, such as the UCSC genome browser (GRCh37/hg19), can be used to select sequences for the 5'-UTR and the promoter region, 1000 base pairs upstream that can be entered into the CRISPR design tool (crispr.mit.edu). The design tool outputs 20 base pair gRNAs that are followed on their 3' end by the PAM sequence NNGRRT, which is specific to the CRISPR-Cas9 system derived from *Streptococcus aureus*. The selected gRNAs can then be entered into the BLAT tool of the UCSC genome browser to inspect for overlap of gRNAs with DNAse hypersensitivity sites to ensure overlap. Any site that has DNAse hypersensitivity value above 0.01 can be targeted with a guide if one is available from the list of guides generated as described above. Additionally, any site that shows greater than 10 transcription factor binding sites within a region, as determined from ChiP-seq, can also be considered. Generally, the DNAse hypersensitivity data is consistent with these regions. Using the criteria described above, gRNAs (e.g., 4-7 gRNAs) that are spaced at least 100 base pairs apart can be selected for performing targeted gene repression and screening. In an aspect, MSUT2 gRNAs guides can be screened using the method disclosed herein. In an aspect, gRNA sequences from the promoter region and 5'-UTR (crispr.mit.edu) can be selected. In an aspect, gRNA sequences are 20 bp in length followed by a PAM sequence (e.g., NNGRRTNGG). In an aspect, gRNA sequences with the least off-target sequences and those that overlap with DNase sensitivity peaks can be selected.

In some aspects, the design tool outputs 20 base pair gRNAs that are followed on their 3' end by the PAM sequence NGG, which is specific to the CRISPR-Cas9 system derived from *Streptococcus pyogenes*. The selected gRNAs can then be entered into the BLAT tool of the UCSC genome browser to inspect for overlap of gRNAs with DNAse hypersensitivity sites to ensure overlap. Any site that has DNAse hypersensitivity value above 0.01 can be targeted with a guide if one is available from the list of guides generated as described above. Additionally, any site that shows greater than 10 transcription factor binding sites within a region, as determined from ChiP-seq, can also be considered. Generally, the DNAse hypersensitivity data is consistent with these regions. Using the criteria described above, gRNAs (e.g., 4-7 gRNAs) that are spaced at least 100 base pairs apart can be selected for performing targeted gene repression and screening. In an aspect, MSUT2 gRNAs guides can be screened using the method disclosed herein. In an aspect, gRNA sequences from the promoter region and 5'-UTR (crispr.mit.edu) can be selected. In an aspect, gRNA sequences are 20 bp in length followed by a PAM sequence (e.g., NGG). In an aspect, gRNA sequences with the least off-target sequences and those that overlap with DNase sensitivity peaks can be selected.

Disclosed herein are methods of modulating expression of a gene in a cell. The method can include one or more of the following steps. First, introducing into a cell, a first nucleic acid. The first nucleic acid can encode a guide RNA comprising a DNA-binding domain. The nucleic acid can be operably linked to a regulatory element. The guide RNA described herein can be complementary to a target nucleic acid sequence disclosed herein comprising the gene. Next, a second nucleic acid encoding a transcriptional regulator protein or domain that modulates the target nucleic acid expression can be introduced into the cell. The second nucleic acid can further include a gRNA-binding domain. The second nucleic acid can be operably linked to a regulatory element. A third nucleic acid encoding a Cas9 (e.g., a deactivated nuclease (dCas9)) protein can be introduced. In an aspect, nuclease function can be removed. The third nucleic acid can be operably linked to a regulatory element. The Cas9 protein (e.g., dCas9) can interact with the guide RNA, and can be fused to the transcriptional regulator protein. The cell can then produce the guide RNA. The guide RNA can bind to the dCas9 protein and the transcriptional regulator protein or domain fused to the DNA-binding domain, and direct the complex (e.g., gRNA/dCas9 complex; the combined product of the gRNA and dCas9 interacting) to the DNA regulatory element encoded in the DNA-binding domain. The guide RNA and the dCas9 protein, for example, can co-localize to the target nucleic acid sequence. The transcriptional regulator protein or domain can modulate (increase or decrease) expression of the gene. The gRNA sequence can selected from the group listed in Table 2.

Disclosed herein, are methods for introducing into a cell a CRISPR-Cas system. In some aspects, the CRISPR-Cas system can include one or more vectors described herein. In some aspects, the method can include one or more vectors. For example, the vector can comprise a promoter operably linked to one or more nucleotide sequences encoding a CRISPR-Cas system gRNA. In some aspects, the gRNA can hybridize with a target sequence of a DNA molecule in a cell. In some aspects, the vector can also include a regulatory element operably linked to a nucleotide sequence encoding a RNA-directed nuclease. In some aspects, the promoter operably linked to one or more nucleotide sequences encoding a CRISPR-Cas system gRNA and the regulatory element operably linked to a nucleotide sequence encoding a RNA-directed nuclease can be located on the same or different vectors of the same system. In some aspects, the method also includes a step wherein the gRNA targets and hybridizes with the target sequence and directs the RNA-directed nuclease to the DNA molecule. In some aspects, the gRNA sequence can be selected from the group listed in Table 2. In some aspects, the target sequence can be selected from one or more of the sequences listed in Table 1.

Disclosed herein, are methods for introducing into a cell a vector. In some aspects, the vector can include a promoter operably linked to one or more nucleotide sequences encoding a CRISPR-Cas system gRNA. In some aspects, the vector can also include a regulatory element operably linked to a nucleotide sequence encoding a RNA-directed nuclease. In some aspects, the gRNA sequence can be selected from the group listed in Table 2.

Disclosed herein, are methods for inducing site-specific DNA cleavage in a cell. The method can comprise contacting a cell with a guide RNA. The guide RNA can be selected from the group listed in Table 2. The guide RNA can include a sequence capable of binding to a target DNA. The method can further comprise the following step: contacting the cell with a Cas9 protein. In an aspect, the DNA can be in a cell. In an aspect, the cell can be a eukaryotic cell. In an aspect, the cell can be in an individual. In an aspect, the individual can be a human.

The method steps described herein can be carried out simultaneously or sequentially in any order. In some aspects, the DNA can be in a cell. In some aspects, the cell can be a eukaryotic cell. In some aspects, the cell can be in an individual. In some aspects, the individual can be a human.

Method of Treatment

The methods disclosed herein can be useful for the treatment of a subject with Alzheimer's disease or dementia. The method can comprise administering to a subject with Alzheimer's disease or dementia a therapeutically effective amount of a mammalian suppressor of tauopathy 2 (MSUT2) inhibitor. In an aspect, the therapeutically effective amount can reduce accumulation of phosphorylated and aggregated human tau The methods disclosed herein can be useful for inhibiting expression of a MSUT2 polynucleotide. In some aspects, the method can inhibit expression of a MSUT2 polynucleotide in a subject. The method can comprise administering to a subject with Alzheimer's disease or dementia a therapeutically effective amount of a mammalian suppressor of tauopathy 2 (MSUT2) inhibitor. In some aspects, the method can comprise contacting a cell with a MSUT2 inhibitor. In some aspects, the suppressor of MSUT2 can reduce accumulation of phosphorylated and aggregated tau. In some aspects, the expression of the MSUT2 polynucleotide can be inhibited or suppressed by a small molecule. In some aspects, the small molecule can inhibit the binding of poly(A) RNA to the MSUT2 polynucleotide. In some aspects, the cell can be a mammalian cell. In some aspects, the mammalian cell can be a brain cell.

The methods disclosed herein can be useful for reducing phosphorylated and aggregated human tau protein in a subject. The methods can comprise administering to a subject with Alzheimer's disease or dementia a therapeutically effective amount of a mammalian suppressor of tauopathy 2 (MSUT2) inhibitor.

The methods disclosed herein can be useful for suppressing expression of a MSUT2 polynucleotide. In some aspects, the method can suppress expression of a MSUT2 polynucleotide in a subject. The method can comprise administering to a subject with Alzheimer's disease or dementia a therapeutically effective amount of a mammalian suppressor of tauopathy 2 (MSUT2) inhibitor. In some aspects, the method can comprise contacting a cell with a mammalian suppressor of tauopathy 2 (MSUT2) inhibitor. In some aspects, the suppressor of tauopathy 2 (MSUT2) can reduce accumulation of phosphorylated and aggregated tau. In some aspects, the expression of the MSUT2 polynucleotide can be inhibited or suppressed by a small molecule. In some aspects, the small molecule can inhibit the binding of poly(A) RNA to the MSUT2 polynucleotide. In some aspects, the cell can be a mammalian cell. In some aspects, the mammalian cell can be a brain cell.

The methods disclosed herein can be useful for potentiating a neuroinflammatory response to a pathological tau protein. In some aspects, the method can potentiate a neuroinflammatory response to a pathological tau protein in a subject. The method can comprise administering to a subject with Alzheimer's disease or dementia a therapeutically effective amount of a mammalian suppressor of tauopathy 2 (MSUT2) inhibitor. In some aspects, the method can comprise contacting a cell with a mammalian suppressor of tauopathy 2 (MSUT2) inhibitor. In some aspects, the suppressor of tauopathy 2 (MSUT2) can reduce accumulation of phosphorylated and aggregated tau. In some aspects, the cell can be a mammalian cell. In some aspects, the mammalian cell can be a brain cell.

The methods disclosed herein can be useful for decreasing astrocytosis or microgliosis. In some aspects, the method can decrease astrocytosis or microgliosis in a subject. The method can comprise administering to a subject with Alzheimer's disease or dementia a therapeutically effective amount of a mammalian suppressor of tauopathy 2 (MSUT2) inhibitor. In some aspects, the method can comprise contacting a cell with a mammalian suppressor of tauopathy 2 (MSUT2) inhibitor. In some aspects, the suppressor of tauopathy 2 (MSUT2) can reduce accumulation of phosphorylated and aggregated tau. In some aspects, the cell can be a mammalian cell. In some aspects, the mammalian cell can be a brain cell.

The methods disclosed herein can be useful for reducing neuroinflammation. In some aspects, the method can reduce neuroinflammation in a subject. The method can comprise administering to a subject with Alzheimer's disease or dementia a therapeutically effective amount of a mammalian suppressor of tauopathy 2 (MSUT2) inhibitor. In some aspects, the method can comprise contacting a cell with a mammalian suppressor of tauopathy 2 (MSUT2) inhibitor. In some aspects, the suppressor of tauopathy 2 (MSUT2) can reduce accumulation of phosphorylated and aggregated tau. In some aspects, the expression of the MSUT2 polynucleotide can be inhibited or suppressed by a small molecule. In some aspects, the small molecule can inhibit the binding of poly(A) RNA to the MSUT2 polynucleotide. In some aspects, the cell can be a mammalian cell. In some aspects, the mammalian cell can be a brain cell.

In some aspects, the subject has Alzheimer's disease. In some aspects, the subject has dementia. In some aspects, the subject has mild-moderate Alzheimer's disease. In some aspects, the subject has moderate-severe Alzheimer's disease. Alzheimer's disease typically progresses slowly in three general stages, mild (early stage), moderate (middle stage) and severe (late stage). In mild Alzheimer's disease (early stage), subjects can still function independently but may notice that they are having memory lapses such as forgetting familiar words or the location of everyday objects. During moderate Alzheimer's disease (middle stage), subjects may have greater difficulty performing tasks (e.g., paying bills) and confusing words, but may still remember significant details about their life. In addition, subjects in this stage may feel moodly or withdrawn, are at an increased risk of wandering and becoming lost, and can exhibit personality and behavioral changes including suspiciousness and delusions or compulsive, repetitive behavior. In severe Alzheimer's disease (late stage), subjects lose the ability to respond to their environment, to carry on a conversation and eventually, to control movement. Also, during this severe stage, subjects need expensive help with daily activities and have increasing difficulty communicating. In some aspects, the subject has an Alzheimer's-related dementia. In an aspect, the Alzheimer's-related dementia can be progressive supranuclear palsy, chronic traumatic encephalopathy, frontotemporal lobar degeneration, or other tauopathy disorders. The methods disclosed herein can be effective for targeting one or more genes, including mammalian suppressor of tauopathy 2 (MSUT2). In some aspects, the methods also include the step of administering a therapeutic effective amount of a mammalian suppressor of tauopathy 2 (MSUT2) inhibitor. In some aspects, the MSUT2 inhibitor can be a small interfering RNA (siRNA), a guide RNA, a small molecule, an antisense oligonucleotide or an aptamer. In some aspects, the antisense oligonucleotide can be ATGATGCAAAGTGTACTAAACCAG (SEQ ID NO: 16), ATGATGCAAAGTGTACTAAACCAGA (SEQ ID NO: 17), ATGATGCAAAGTGTACTAAACCAGATT (SEQ ID NO: 18), ATGATGCAAAGTGTACTAAACCAG (SEQ ID NO: 19), AATATGATGCAAAGTGTACTAAAC (SEQ ID NO: 20), or ATATGATGCAAAGTGTACTAAACCAG (SEQ ID NO: 21).

In some aspects, the methods of treating a subject can comprise contacting a cell or a subject with an effective amount of a gRNA molecule. In some aspects, the methods can further comprise altering the sequence of the target nucleic acid. In some aspects, the cell can be a vertebrate, a mammalian or a human cell. In some aspects, the cell can be a brain cell.

In some aspects, the methods also include the step of administering a therapeutic effective amount of one or more of the compositions disclosed herein (e.g., a CRISPR-Cas system comprising one or more vectors comprising: a) a promoter operably linked to one or more nucleotide sequences encoding a CRISPR-Cas system guide RNA (gRNA), wherein the gRNA hybridizes with a target sequence of a DNA locus in a cell; and b) a regulatory element operably linked to a nucleotide sequence encoding a RNA-directed nuclease, wherein components a) and b) are located on the same or different vectors of the same system, wherein the gRNA targets and hybridizes with the target sequence and directs the RNA-directed nuclease to the DNA locus; wherein the gRNA sequence is selected from the group listed in Table 2. In some aspects, the gRNA sequence can comprise 10-30 bp, 15-25 bp, 17-24 bp or any other fragment of the sequences set forth in SEQ ID NOs: 6, 7, 8, 9 and 33. In some aspects, the gRNA sequence comprises a sequence having 80%, 85%, 90%, 95%, 96%, 97%, 98%, or 99% identity to the sequences set forth in SEQ ID NOs: 6, 7, 8, 9, and 33 or a fragment thereof. In some aspects, the therapeutically effective amount can reduce accumulation of phosphorylated and aggregated human tau. In some aspects, the subject can be identified as being in need of treatment before the administering step. In some aspects, the subject can be a human.

In some aspects, the MSUT2 inhibitor can potentiate the neuroinflammatory response to pathological tau. In some aspects, the MSUT2 inhibitor can decrease astrocytosis and microgliosis.

In some aspects, the gRNA can target and hybridize to a MSUT2 target sequence. In some aspects, the target sequences can be selected from one or more of the sequences found with the following identifier: mouse gene ID: 75553; Human gene ID is: 79882. In some aspects, the MSUT2 target sequence can be AATTTATCGACCACCTGCAAG (SEQ ID NO: 1), TACTGGCCTGCCTGTAAAAAT (SEQ ID NO: 2), GGCCTGCCTGTAAAAATGGGG (SEQ ID NO: 3), GCCACCAAGACACGCCTTGAA (SEQ ID NO: 4), or ATTAGACACTTCAGATAGAT (SEQ ID NO: 5).

In some aspects, the gRNA sequence can be selected from the group consisting of GAAUUUAUCGACCAC-CUGCAAGCAAAGUUUUAGUACUCUG-GAAACAGAAUCU ACUAAAACAAGGCAAAAUGCCGUGUUUAUCUC-GUCAACUUGUUGGCGAGAUU UUU (SEQ ID NO: 6), GGCCUGCCUGUAAAAAUGGGGCAAAGUUUU-AGUACUCUGGAAACAGAAUCUA CUAAAACAAGGCAAAAUGCCGUGUUUAUCUCGU-CAACUUGUUGGCGAGAUUU UU (SEQ ID NO: 7), GCCACCAAGACACGCCUUGAACAAAGUUUU-AGUACUCUGGAAACAGAAUCUAC UAAAACAAGGCAAAAUGCCGUGUUUAUCUCGU-CAACUUGUUGGCGAGAUUUU U (SEQ ID NO: 8), AUUAGACACUUCAGAUAGAUCUGUUUUAGAGC-UAGAAAUAGCAAGUUAAAAU AAGGCUAGU-CCGUUAUCAACUUGAAAAAGUGGCACCGAGUCG-GUGCUUUU (SEQ ID NO: 9), GUACUGGCCUGCCUGUAAAAAUCAAAGUUUU-AGUACUCUGGAAACAGAAUCU ACUAAAACAAGGCAAAAUGCCGUGUUUAUCUC-GUCAACUUGUUGGCGAGAUU UUU (SEQ ID NO: 33), GAAUUUAUCGACCACCUGCAAG (SEQ ID NO: 28) GUACUGGCCUGCCUGUAAAAAU (SEQ ID NO: 29) GGCCUGCCUGUAAAAAUGGGG (SEQ ID NO: 30) GCCACCAAGACACGCCUUGAA (SEQ ID NO: 31), and AUUAGACACUUCAGAUAGAU (SEQ ID NO: 32).

In some aspects, the siRNA can consist of AUGAUGCAAAGUGUACUAAACCAG (SEQ ID NO: 10), AUGAUGCAAAGUGUACUAAACCAGAUU (SEQ ID NO: 11), AUGAUGCAAAGUGUACUAAACCAGAU (SEQ ID NO: 12), AUGAUGCAAAGUGUACUAAACCA (SEQ ID NO: 13), AUAUGAUGCAAAGUGUAC-UAAACCAG (SEQ ID NO: 14), or UAUGAUGCAAAGU-GUACUAAACCAG (SEQ ID NO: 15).

In some aspects, the small molecule can be

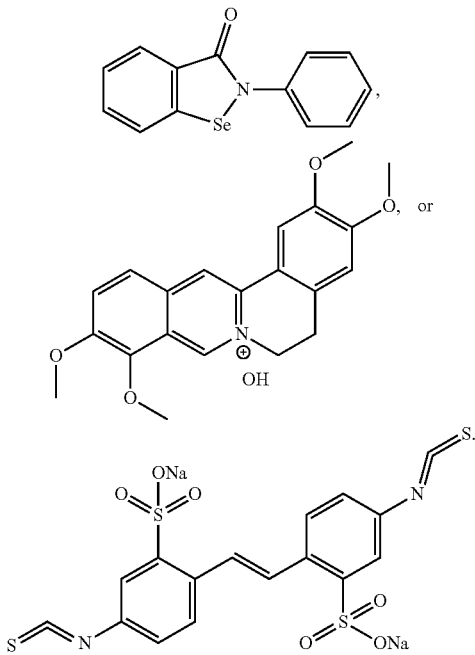

In some aspects, the methods can further include the step of identifying a subject (e.g., a human patient) who has Alzheimer's disease or dementia and then providing to the subject a composition comprising the CRISPR-Cas system or vector, or a MSUT2 inhibitor as disclosed herein. In some aspects, the subject has an Alzheimer's-related dementia. In an aspect, the Alzheimer's-related dementia can be progressive supranuclear palsy, chronic traumatic encephalopathy, frontotemporal lobar degeneration, or other tauopathy disorders. In some aspects, the subject can be identified using standard clinical tests known to those skilled in the art. While a definite AD diagnosis requires post-mortem examination, skilled clinicians can conduct an evaluation of cognitive function with over 95% accuracy. Examples of tests for diagnosing Alzheimer's disease or dementia include Mini-Mental State Examination (MMSE), Mini-cog© Score, Alzheimer's Disease Composite Score (ADCOMS), Alzheimer's Disease Assessment Scale-cognitive subscale (ADAS-Cog) and Clinical Dementia Rating Sum of Boxes (CDR-SB).

The therapeutically effective amount can be the amount of the composition administered to a subject that leads to a full resolution of the symptoms of the condition or disease, a reduction in the severity of the symptoms of the condition or disease, or a slowing of the progression of symptoms of the condition or disease. The methods described herein can also include a monitoring step to optimize dosing. The compositions described herein can be administered as a preventive treatment or to delay or slow the progression of degenerative changes.

The compositions disclosed herein can be used in a variety of ways. For instance, the compositions disclosed herein can be used for direct delivery of modified therapeutic cells, or adeno-associated virus. The compositions disclosed herein can be used or delivered or administered at any time during the treatment process. The compositions described herein including cells or a virus can be delivered to the one or more brain regions, one or more brain cells, or to brain regions or brain cells to stop or prevent one or more signs of symptoms of the disease or condition in an adjacent brain region or brain cell.

The dosage to be administered depends on many factors including, for example, the route of administration, the formulation, the severity of the patient's condition/disease, previous treatments, the patient's size, weight, surface area, age, and gender, other drugs being administered, and the overall general health of the patient including the presence or absence of other diseases, disorders or illnesses. Dosage levels can be adjusted using standard empirical methods for optimization known by one skilled in the art. Administrations of the compositions described herein can be single or multiple (e.g., 2- or 3-, 4-, 6-, 8-, 10-, 20-, 50-, 100-, 150-, or more fold). Further, encapsulation of the compositions in a suitable delivery vehicle (e.g., polymeric microparticles or implantable devices) can improve the efficiency of delivery.

The therapeutically effective amount of the compositions described herein can include a single treatment or a series of treatments (i.e., multiple treatments or administered multiple times). Treatment duration using any of compositions disclosed herein can be any length of time, such as, for example, one day to as long as the life span of the subject (e.g., many years). For instance, the composition can be administered daily, weekly, monthly, yearly for a period of 5 years, ten years, or longer. The frequency of treatment can vary. For example, the compositions described herein can be administered once (or twice, three times, etc.) daily, weekly, monthly, or yearly for a period of 5 years, ten years, or longer.

In some aspects, the compositions disclosed herein can also be co-administered with another therapeutic agent. In some aspects, the methods disclosed herein can further comprise administering a cholinesterase inhibitor to the subject. In some aspects, the cholinesterase inhibitor can be galantamine, rivastigmine or donepezil. In some aspects, the methods disclosed herein can further comprise administering an anti-inflammatory therapy to the subject.

In some aspects, the methods disclosed herein also include treating a subject having Alzheimer's disease or dementia. In some aspects, the methods disclosed herein can include the step of determining MSUT2 levels in a subject. In some aspects, the disclosed methods can further include the step of administering to the subject a pharmaceutical composition comprising a nucleic acid sequence encoding a CRISPR-associated endonuclease (e.g., deactivated endonuclease) and one or more guide RNAs, wherein the guide RNA is selected from the group listed in Table 2. In some aspects, the CRISPR-associated endonuclease is optimized for expression in a human cell.

Pharmaceutical Compositions

As disclosed herein, are pharmaceutical compositions, comprising the compositions disclosed herein. In an aspect, the pharmaceutical composition can comprise any of gRNA molecules disclosed herein. In an aspect, the pharmaceutical composition can comprise any of the small molecules, aptamers (e.g., DNA and RNA), antisense oligonucleotides or siRNAs disclosed herein. For example, disclosed are pharmaceutical compositions, comprising a vector or CRISPR-Cas system comprising one or more vectors comprising: a) a promoter operably linked to one or more nucleotide sequences encoding a CRISPR-Cas system guide RNA (gRNA), wherein the gRNA hybridizes with a target sequence of a DNA locus in a cell; and b) a regulatory element operably linked to a nucleotide sequence encoding a RNA-directed nuclease, wherein components a) and b) are located on the same or different vectors of the same system, wherein the gRNA targets and hybridizes with the target sequence and directs the RNA-directed nuclease to the DNA locus; wherein the gRNA sequence is selected from the group listed in Table 2. In some aspects, the gRNA sequence can comprise 10-30 bp, 15-25 bp, 17-24 bp or any other fragment of the sequences set forth in SEQ ID NOs: 6, 7, 8, 9, and 33. In some aspects, the gRNA sequence comprises a sequence having 80%, 85%, 90%, 95%, 96%, 97%, 98%, or 99% identity to the sequences set forth in SEQ ID NOs: 6, 7, 8, 9, and 33 or a fragment thereof. In some aspects, the target sequence can be selected from one or more of the sequences listed in Table 1. In some aspects, the pharmaceutical compositions comprise the any one of the CRISPR-Cas systems disclosed herein. In some aspects, the pharmaceutical composition comprises the nucleic acid sequence of any of the vectors or CRISPR-Cas systems disclosed herein. In some aspects, the pharmaceutical compositions further comprise a pharmaceutically acceptable carrier.

As used herein, the term "pharmaceutically acceptable carrier" refers to solvents, dispersion media, coatings, antibacterial, isotonic and absorption delaying agents, buffers, excipients, binders, lubricants, gels, surfactants that can be used as media for a pharmaceutically acceptable substance. The pharmaceutically acceptable carriers can be lipid-based or a polymer-based colloid. Examples of colloids include liposomes, hydrogels, microparticles, nanoparticles and micelles. The compositions can be formulated for administration by any of a variety of routes of administration, and can include one or more physiologically acceptable excipients, which can vary depending on the route of administration. Any of the nucleic acids, vectors, gRNAs, siRNAs, aptamers, antisense oligonucleotides and small molecules described herein can be administered in the form of a pharmaceutical composition.

As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed. The compositions can also include additional agents (e.g., preservatives).

The pharmaceutical compositions as disclosed herein can be prepared for oral or parenteral administration. Pharmaceutical compositions prepared for parenteral administration include those prepared for intravenous (or intra-arterial), intramuscular, subcutaneous, intrathecal or intraperitoneal administration. Paternal administration can be in the form of a single bolus dose, or may be, for example, by a continuous pump. In some aspects, the compositions can be prepared for parenteral administration that includes dissolving or suspending the CRISPR-Cas systems, nucleic acids, polynucleic sequences, vectors or small molecules in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

In some aspects, the compositions disclosed herein are formulated for oral, intramuscular, intravenous, subcutaneous or intraperitoneal administration.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment. The compositions can also be formulated as powders, elixirs, suspensions, emulsions, solutions, syrups, aerosols, lotions, creams, ointments, gels, suppositories, sterile injectable solutions and sterile packaged powders. The active ingredient can be nucleic acids or vectors described herein in combination with one or more pharmaceutically acceptable carriers. As used herein "pharmaceutically acceptable" means molecules and compositions that do not produce or lead to an untoward reaction (i.e., adverse, negative or allergic reaction) when administered to a subject as intended (i.e., as appropriate).

In some aspects, the CRISPR-Cas system, vectors, gRNAs and nucleic acid sequences as disclosed herein can be delivered to a cell of the subject. In some aspects, such action can be achieved, for example, by using polymeric, biodegradable microparticle or microcapsule delivery vehicle, sized to optimize phagocytosis by phagocytic cells (e.g., macrophages).

In some aspects, the formulations include any that are suitable for the delivery of a virus (e.g., adeno-associated virus) and cells. In an aspect, the route of administration includes but is not limited to direct injection into the brain. Such administration can be done without surgery, or with surgery.

Method of Screening

Disclosed herein are methods of screening compounds capable of inhibiting MSUT2 binding to poly(A) RNA. In some aspects, the method can comprise contacting at least one candidate compound, poly(A) RNA and polyadenylate-binding nuclear protein 1 (PABPN1) under conditions in which PABPN1 is capable of stimulating RNA polyadenylation in the absence of the candidate compound. In some aspects, the method can comprise determining whether the candidate compound inhibits MSUT2 binding to poly(A) RNA. In some aspects, the method can comprise selecting the candidate compound which inhibits MSUT2 binding to poly(A) RNA. In some aspects, the inhibition of MSUT2 binding to poly(A) RNA can be measured by RNA polyadenylation. In some aspects, the candidate compound selected can inhibit formation of a macromolecular complex, wherein the macromolecular complex can comprise MSUT2, PABPN1 and poly(A) RNA. In some aspects, the candidate compound can be purified. In some aspects, the candidate compound can be isolated.

Disclosed herein are methods for screening compounds for pharmacological intervention in tauopathy disorders. In some aspects, the method can comprise providing an assay for MSUT2 to bind to poly(A) RNA and its modulation of RNA polyadenylation. In some aspects, the method can comprise providing a purified or non-purified compound or purified or non purified mixture of compounds. In some aspects, the method can comprise screening the purified or non-purified compound or purified or non-purified mixture of compounds in an environment that can allow for inhibition of MSUT2 binding to poly(A) RNA by the purified or non-purified compound or purified or non-purified mixture of compounds in the assay. In some aspects, the method can comprise isolating the one or more compounds that inhibit MSUT2 binding to poly(A) RNA. In some aspects, the method can comprise the inhibition of MSUT2 binding to poly(A) RNA is measured by RNA polyadenylation. In some aspects, the assay can comprise forming a macromolecular complex that can comprise MSUT2, PABPN1, and poly(A) RNA.

In an aspect, the tauopathy disorder can be a degenerative disorder. Example of tauopathy disorders include but are not limited to primary tauopathies (e.g., Frontotemporal Lobar Degeneration Frontotemporal Dementia (FTLD), primary progressive aphasia, including atypical dopaminergic-resistant Parkinsonian syndromes with prominent extra-pyramidal symptoms and corticobasal syndrome; and secondary tauopathies.

Kits

The kits described herein can include any combination of the compositions (e.g., CRISPR-Cas system or vectors or siRNAs, gRNAs, aptamers, antisense oligonucleotides or small molecules) described above and suitable instructions (e.g., written and/or provided as audio-, visual-, or audio-visual material). In an aspect, the kit comprises a predetermined amount of a composition comprising any one compositions disclosed herein. The kit can further comprise one or more of the following: instructions, sterile fluid, syringes, a sterile container, delivery devices, and buffers or other control reagents.

EXAMPLES

Example 1: The Poly(A) Binding Protein MSUT2 Controls Resistance to Both Pathological Tau and Gliosis Abstract. Lesions composed of pathological tau drive neurodegeneration in Alzheimer's disease and related tauopathies. The mammalian suppressor of tauopathy 2 (MSUT2) gene was identified as a modifier of susceptibility to tau toxicity in multiple model systems. Tau transgenic MSUT2 knockout mice exhibit decreased learning and memory deficits, ameliorated neurodegeneration, and reduced accumulation of pathological tau. Conversely, MSUT2 overexpression in tau transgenic mice drives pathological tau deposition and promotes the neuroinflammatory response to pathological tau. MSUT2 functions as a poly(A) RNA binding protein that antagonizes the canonical nuclear poly(A) binding protein PABPN1. In Alzheimer's disease, MSUT2 abundance predicts age at disease onset and cases with normal levels of MSUT2 exhibit elevated neuroinflammation associated with tau pathology. Also, a similar co-depletion of PABPN1 was observed in the same subset of AD cases suggesting MSUT2 and PABPN1 act together in a macromolecular complex bound to poly(A) RNA. Although MSUT2 and PABPN1 have opposing effects on both tau aggregation and poly(A) tail length, it was found that increased poly(A) tail length does not ameliorate tauopathy, implicating other functions of MSUT2/PABPN1 in their role in tau proteostasis. These findings implicate poly(A) RNA binding proteins as both modulators of pathological tau toxicity in AD and as potential molecular targets for intervention in neurodegeneration in tauopathies.

Results.

Figure 1A:
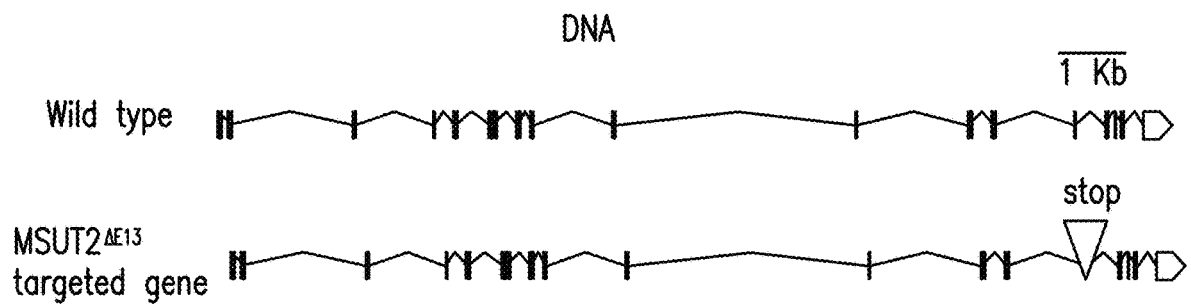
Figure 1B:
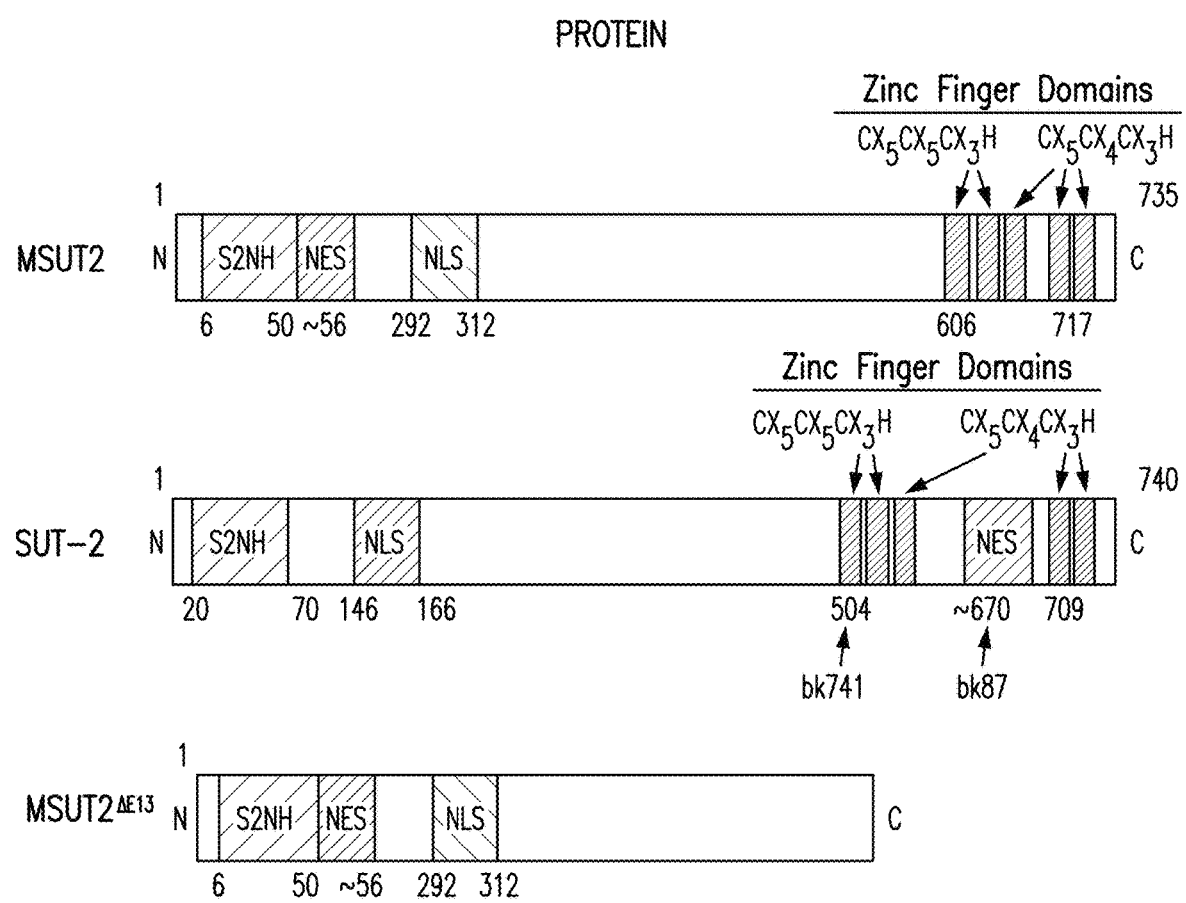
Figure 2A:
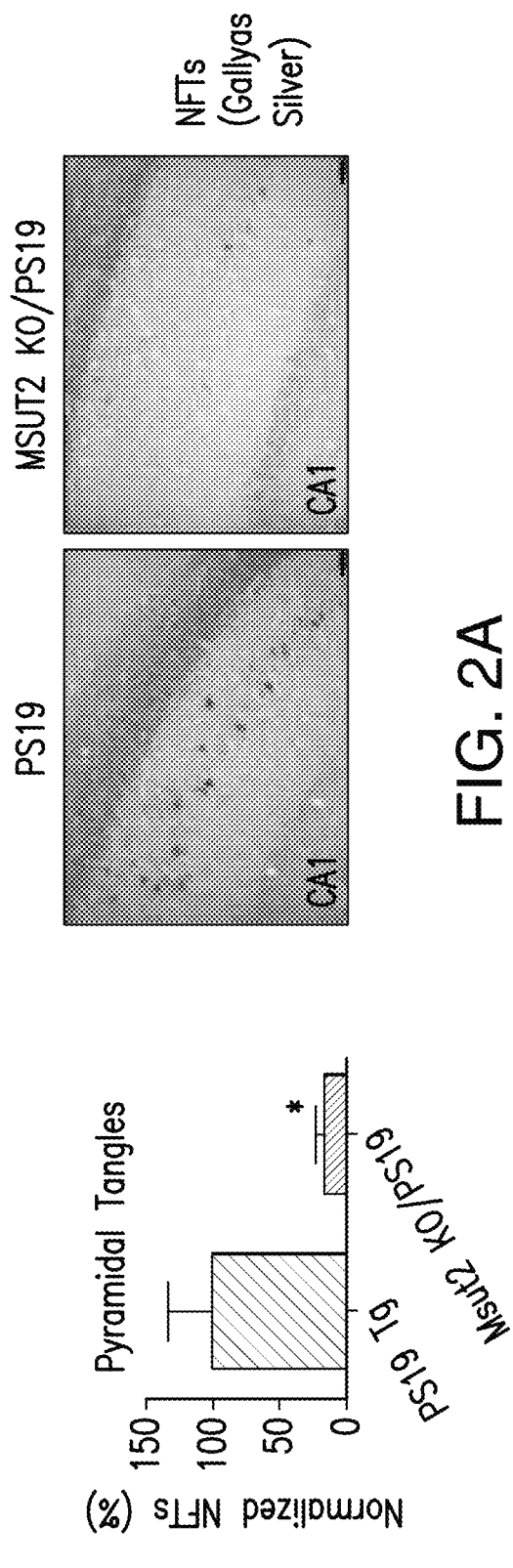
Figure 2B:
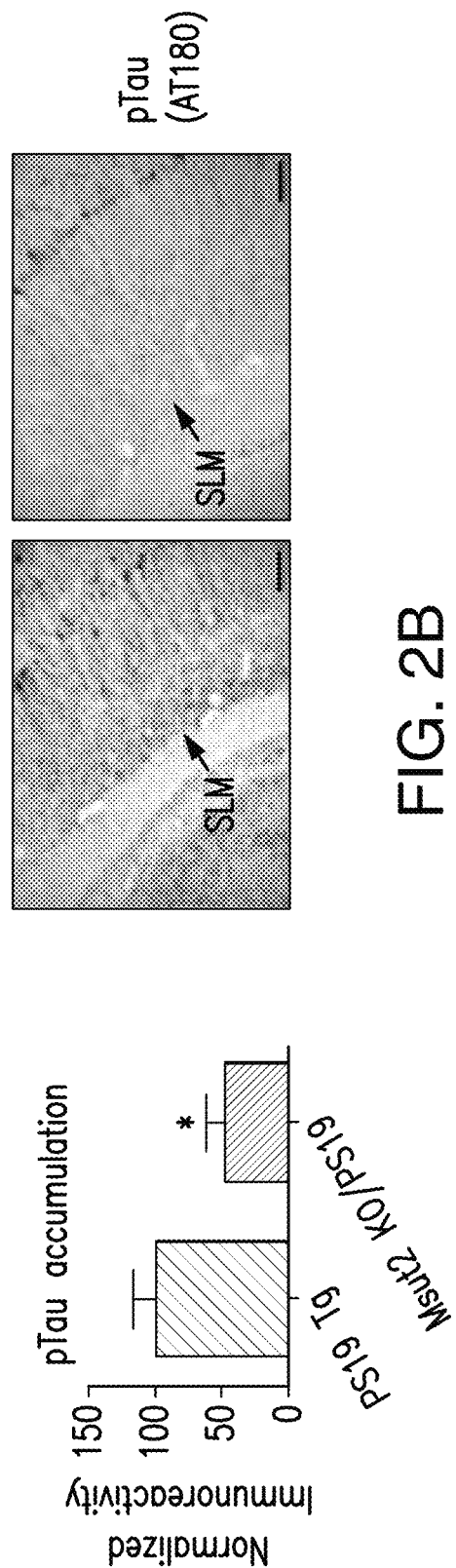
Figure 3A:
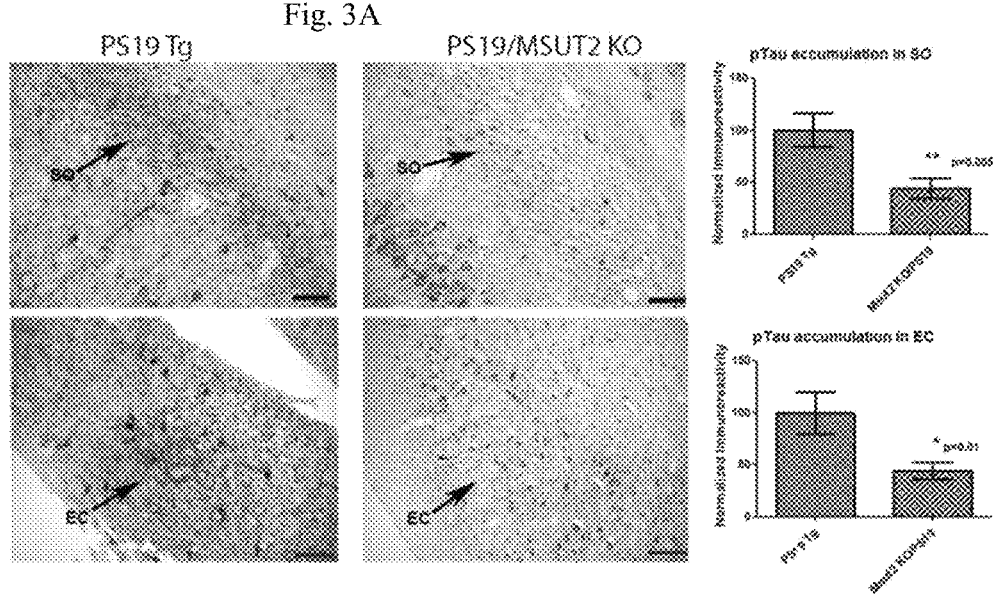
FIGS. 3A-C show that MSUT2 KO decreases accumulation of pathological tau.
Figure 3B:
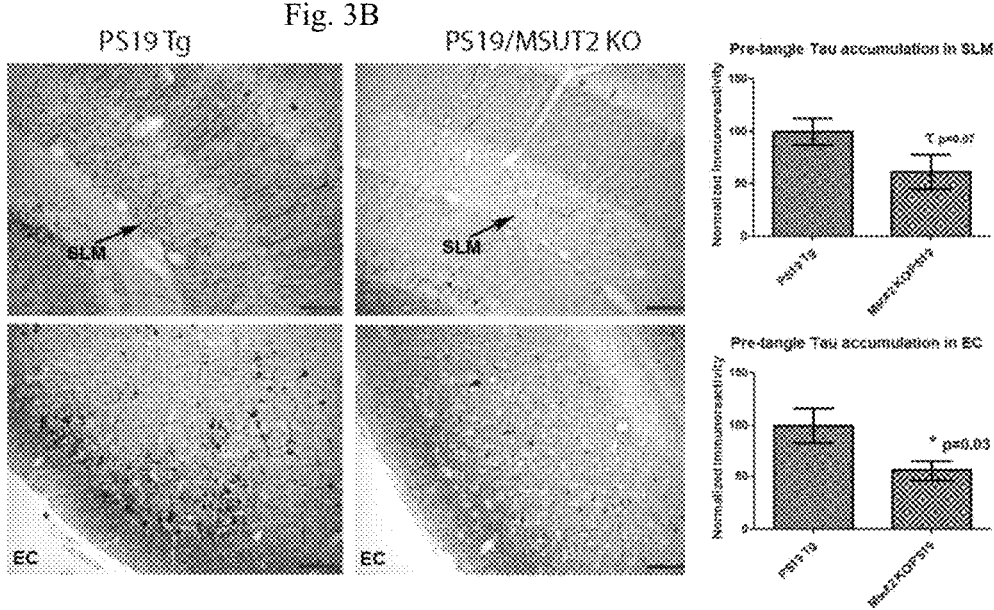
Figure 3C:
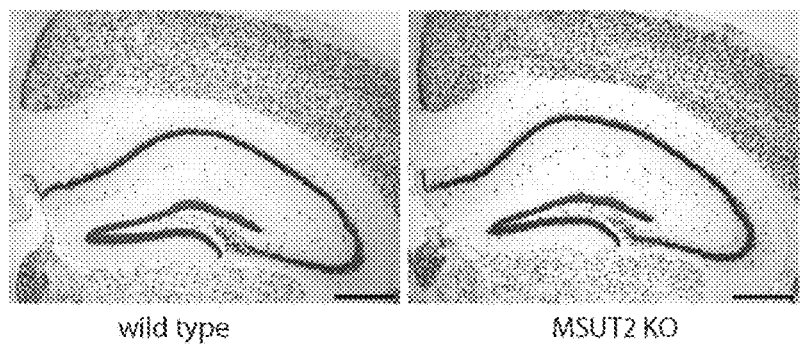

Removal of MSUT2 drives neuronal resistance to pathological tau. To test whether MSUT2 function impacts tauopathy in the intact mammalian brain, mice lacking the MSUT2 CCCH finger domains important for SUT-2 function in C. elegans was generated (FIGS. 1A-E). Mice homozygous for this disruption (henceforth, MSUT2 KO mice) are fully viable, grossly normal, exhibit no visible phenotypes, and appear neurologically intact. These mice were crossed with PS19, a well-characterized mouse tauopathy model transgenic for human tau carrying the P301S FTLD mutation (Y. Yoshiyama, et al., Neuron 53, 337-351 (2007)). PS19 mice homozygous for the MSUT2 KO allele were generated and the abundance of tau positive pathological lesions in PS19 mice with or without functional MSUT2 were compared. Since PS19 mice exhibit significant deficits in hippocampal dependent memory tasks (H. Takeuchi, et al., PLoS ONE 6, e21050 (2011)), the neuropathological analysis focused on the hippocampal formation and projecting regions. PS19 mice develop age-dependent neurofibrillary degeneration with a progression of pathological tau deposition similar to that seen in human patients with AD or other tauopathy disorders (Y. Yoshiyama, et al., Neuron 53, 337-351 (2007)). PS19 mice have an abundance of NFT-like inclusions in hippocampal CA1 pyramidal neurons and the entorhinal cortex. In contrast, PS19 mice that are homozygous null for MSUT2 have dramatically reduced numbers of hippocampal NFTs (FIG. 2A and FIG. 1F). Formation of pathological tau progresses from monomeric normal tau, to phosphorylated tau (pTau), to oligomeric and pre-tangle conformations of tau, to fibrillary tau culminating in deposition of mature NFTs. Both pTau and mis-folded tau (MC1 positive) are dramatically reduced in MSUT2 KO/PS19 relative to PS19 animals, especially in neuronal processes of hippocampal subfields stratum lacunosum moleculare (SLM) and stratum oriens (SO), as well as in the entorhinal cortex (FIGS. 2B-C, and FIG. S2A-B). When MSUT2 is absent, the overall decrease in pTau and MC1+ tau parallels the decrease of NFTs in the hippocampus and entorhinal cortex. Likewise, the MSUT2 KO/PS19 mice do not show the neuronal loss in the CA1 region of the hippocampus that is observed in PS19 mice with intact MSUT2 (FIG. 2D) while loss of MSUT2 alone does not obviously change neuronal abundance in the hippocampus (FIG. 3C). These findings demonstrate that loss of MSUT2 reduces accumulation of pathologic tau and protects against neuronal loss.

Figure 2E:
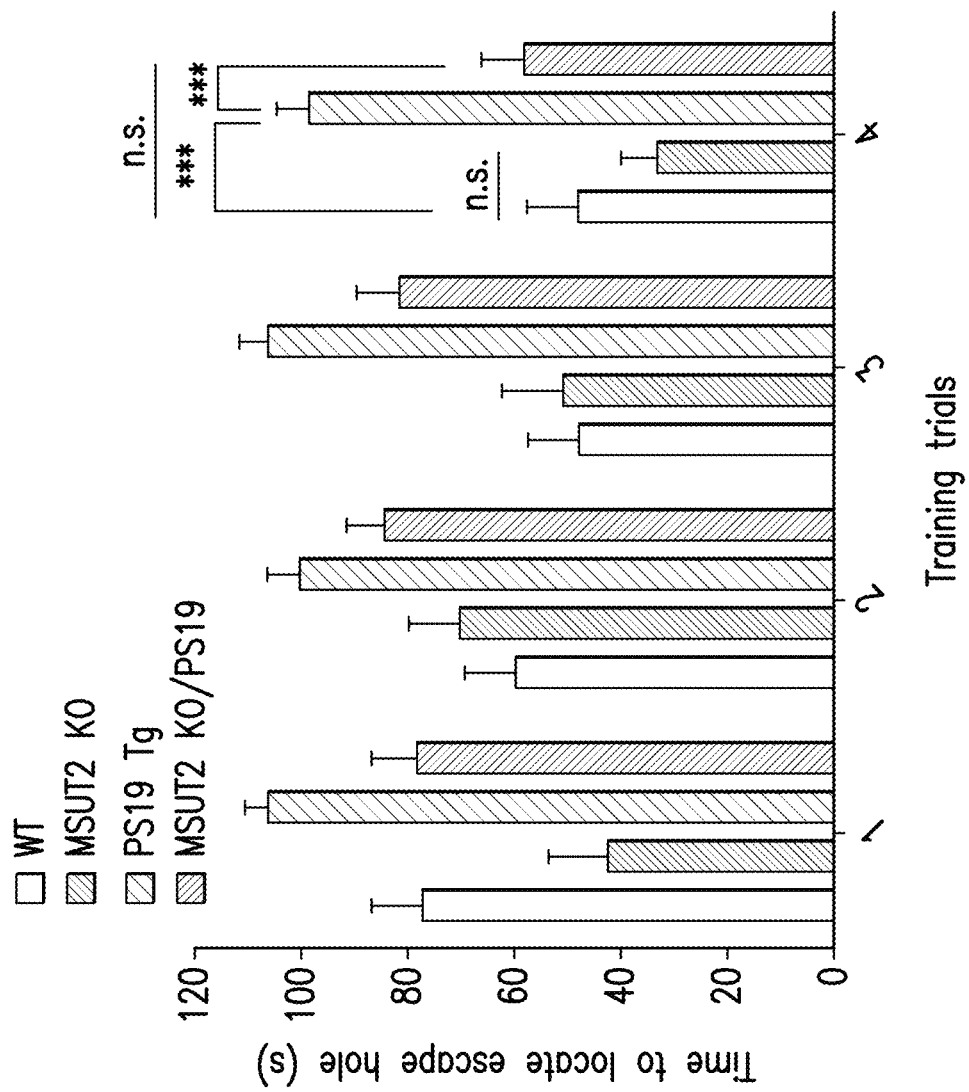
Figure 4A:
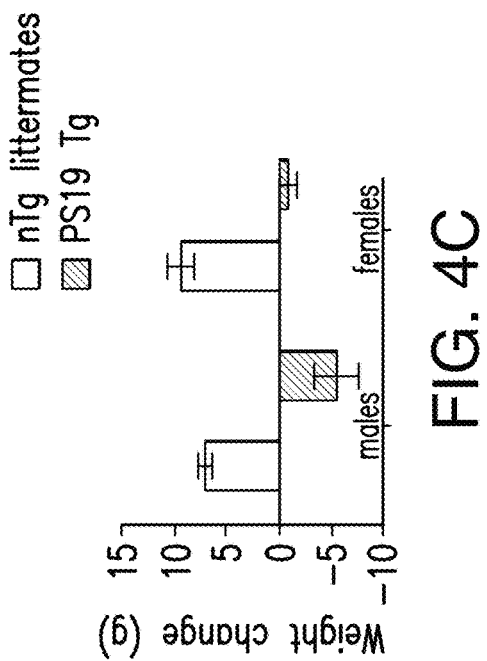
FIGS. 4A-G show that MSUT2 KO mice have grossly normal cognitive and locomotor abilities.
Figure 4B:
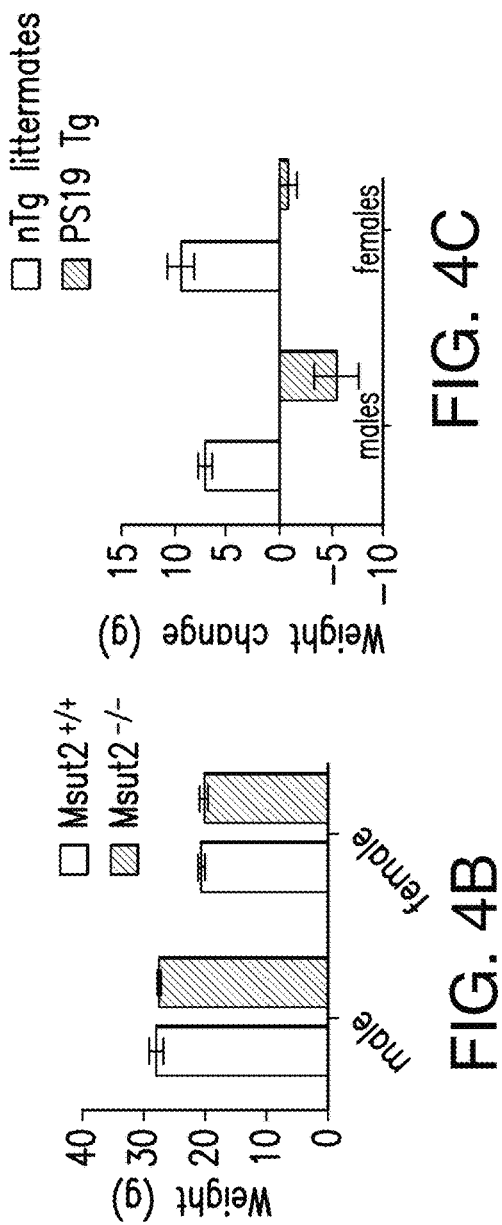
Figure 4C:
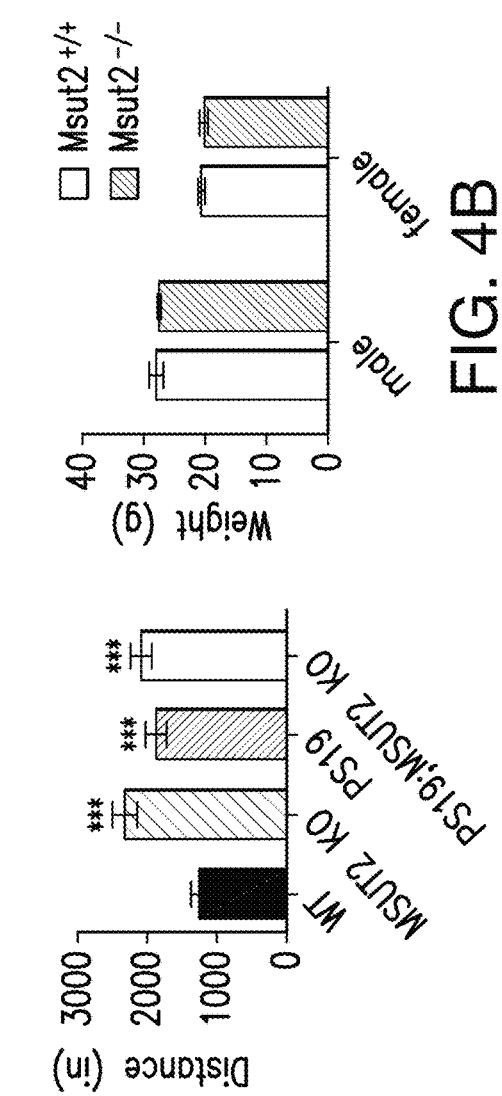
Figure 4D:
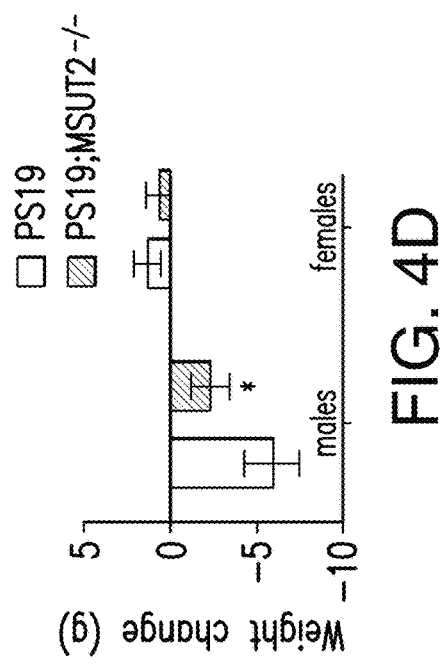
Figure 4E:
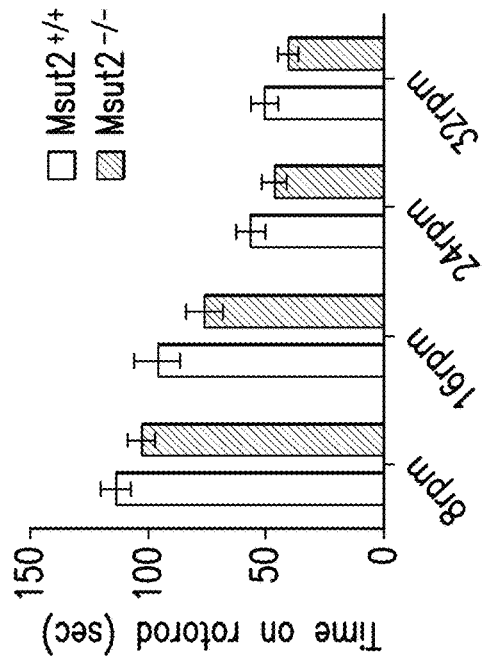
Figure 4F:
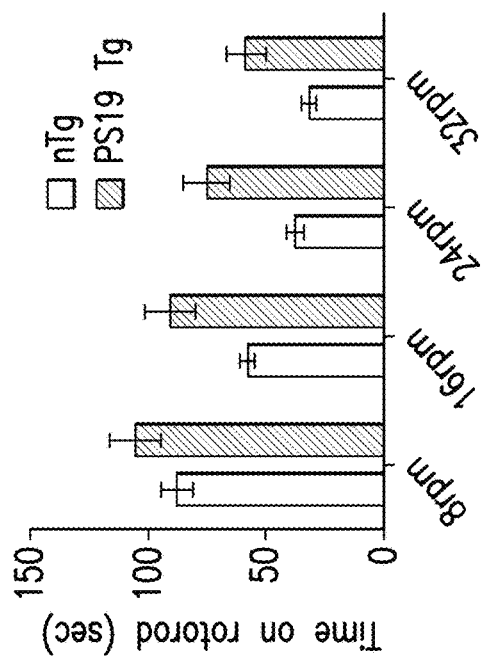
Figure 4G:
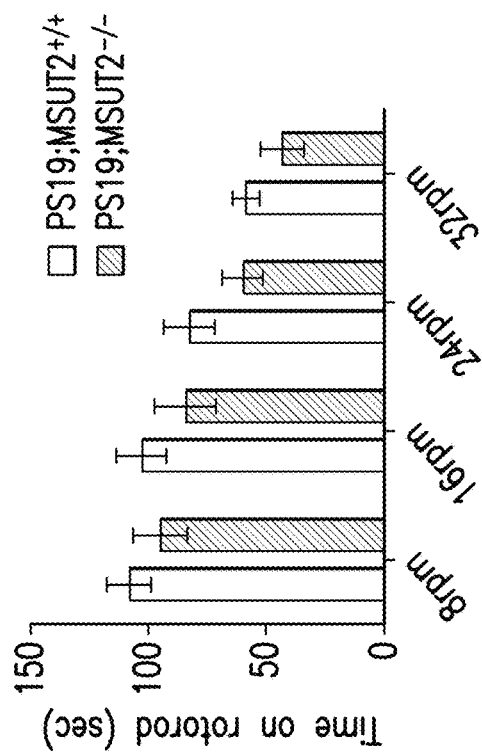

Knockout of MSUT2 improves cognitive function in tauopathy mice. MSUT2 KO mice exhibit typical motor function, and appear cognitively similar to wild type mice (FIG. 4 and FIG. 2E). To assess the effect of MSUT2 on PS19 motor activity and behavior, PS19 mice with or without a functional MSUT2 gene (PS19 vs MSUT2 KO/PS19) at 8 months of age (N=32-33 per genotype) were characterized. As in a wild type background, loss of MSUT2 does not alter gross physical parameters, motor function, or spontaneous activity levels of PS19 mice (FIGS. 4B-G), although MSUT2 KO does protect against age related weight loss in PS19 males (FIG. 4D). The cognitive performance of these mice was examined using the Barnes maze assay of hippocampal dependent learning and memory (C. A. Barnes, Journal of comparative and physiological psychology 93, 74-104 (1979), a task at which PS19 animals have a significant and reproducible impairment (FIG. 2E and K. R. Brunden, et al., *J Neurosci* 30, 13861-13866 (2010); and B. Zhang, et al., *J Neurosci* 32, 3601-3611 (2012)). MSUT2 KO/PS19 exhibit better performance during the training trials (as measured by time to locate the escape hole), and learn the Barnes maze task faster than their PS19 siblings (FIG. 2E). These data show that loss of MSUT2 function improves cognitive function caused by the mutant tau transgene in PS19 mice.

Figure 5B:
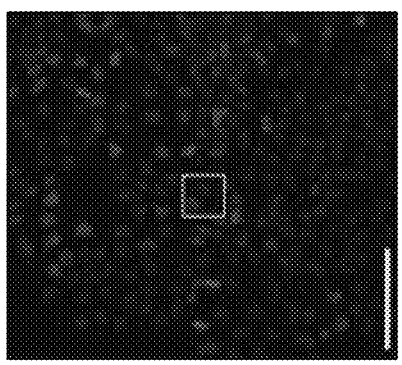
Figure 5A:
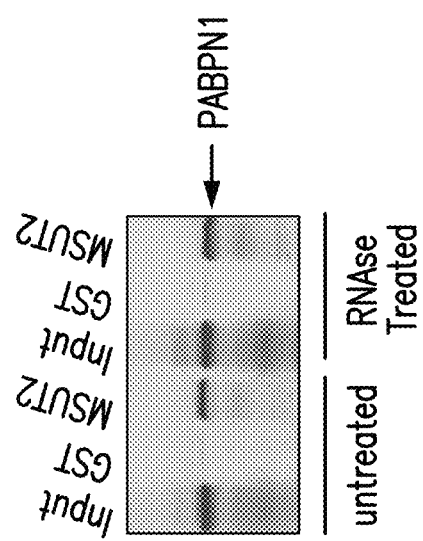
Figure 5C:
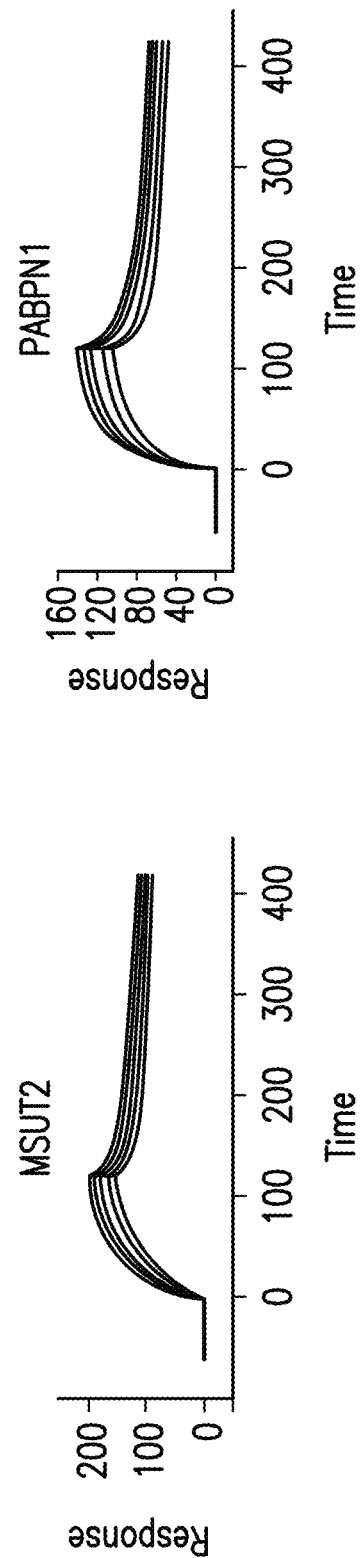

MSUT2 binds the poly(A) binding protein PABPN1 through multifunctional CCCH domains. To explore the mechanism of MSUT2 function, the C-terminus of MSUT2 and SUT-2 was the focus as this region appears to be an important functional domain for suppressing tauopathy phenotypes (C. R. Guthrie, et al., *Hum Mol Genet* 18, 1825-1838 (2009); and C. R. Guthrie, et al., *Hum Mol Genet* 20, 1989-1999 (2011)). To explore the functional partners of SUT-2 protein, a yeast two-hybrid screen was conducted using the sut-2 CCCH domains as bait. The major SUT-2 binding protein identified representing over 90% of the cDNAs recovered was the homolog of nuclear polyadenylate binding protein PABPN1. PABPN1 binds to the poly(A) tail on mRNAs through its RNA recognition motif (RRM) domain and regulates poly(A) tail length in both yeasts and mammals (U. Kuhn, et al., *J Biol Chem* 278, 16916-16925 (2003); and A. Banerjee, et al., *FEBS J* 280, 4230-4250 (2013)). It was demonstrated that a conserved protein-protein interaction between human PABPN1 and MSUT2 proteins using purified recombinant human proteins in an in vitro GST-pulldown assay and showed that the interaction can occur in the absence of detectable RNA (FIG. 5A). The binding of MSUT2 to PABPN1 was validated in a cellular context in situ using a proximity ligation assay on human HEK293 cells (O. Soderberg, et al., *Methods* 45, 227-232 (2008)) and found MSUT2 binds to PABPN1 predominantly in the nuclear compartment and to a lesser extent the cytoplasm (FIG. 5B). Since CCCH domains can bind both RNA and protein, MSUT2 association with poly (A) RNA was measured using a Surface Plasmon Resonance assay. MSUT2 affinity for poly(A) is approximately 4-fold greater than PABPN1 for a single poly(A) binding site (MSUT2 $K_D$=60±15 nM vs PABPN1 $K_D$=237±21 nM for poly(A)$_{15}$) (FIG. 5C).

MSUT2 co-localizes with PABPN1 and poly(A) RNA within nuclear speckles. Since MSUT2 binds PABPN1 and poly(A) independently in vitro, the relationship between MSUT2, PABPN1, and poly(A) RNA was examined in cultured human cells. HEK293 cells were immunostained for MSUT2 and PABPN1 and hybridized with poly(A)-specific fluorescent probes. Analysis showed that MSUT2 protein significantly co-localizes with PABPN1 and poly(A) RNA in the nucleus (FIG. 5D, FIGS. 6A-B). To explore whether the speckle-like appearance of MSUT2 and PABPN1 immunostaining represents authentic nuclear speckle localization, MSUT2 and PABPN1 were co-stained with antibodies against SC35, a nuclear splicing factor labeling nuclear speckles and significant co-localization of both MSUT2 and PABPN1 with SC35 within nuclear speckles were observed (FIGS. 6C, D). Also, the localization of MSUT2 and PABPN1 was investigated in normal human brain. Co-immunostaining for MSUT2 and PABPN1 revealed clear nuclear co-localization of PABPN1 and MSUT2 in frontal cortex neurons (FIG. 5E). Taken together, these data support the cellular co-localization of MSUT2 and PABPN1 to poly(A)+ RNA in nuclear speckles consistent with their demonstrated physical interaction with each other and RNA.

Figure 7G:
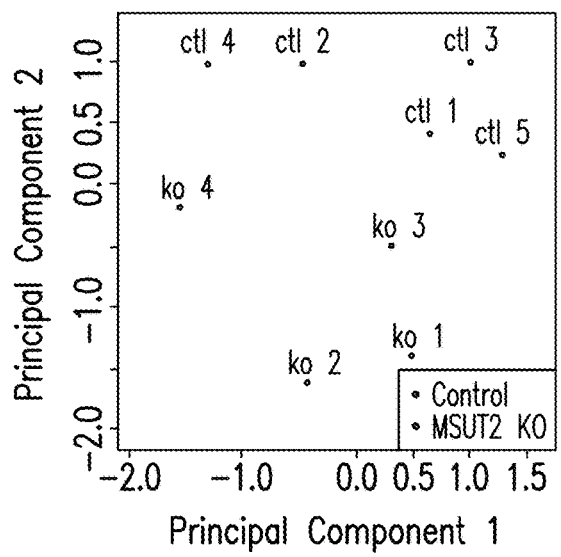
Figure 8A:
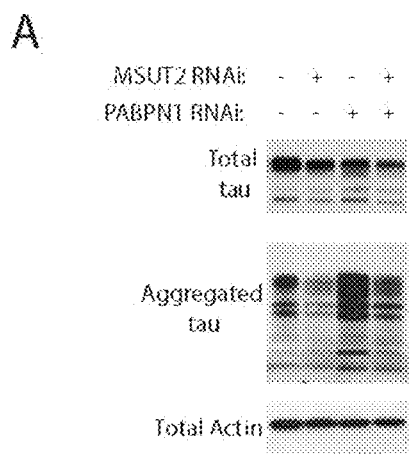
FIGS. 8A-C show that MSUT2 and PABPN1 have opposing impacts on tau aggregation, but MSUT2 KO in mice does not influence PABPN1 levels.
Figure 8B:
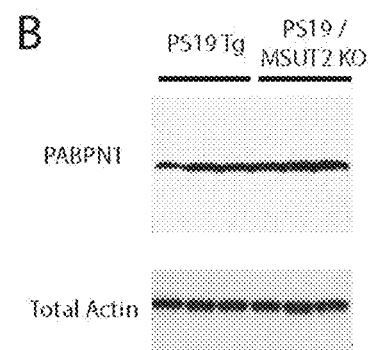
Figure 8C:
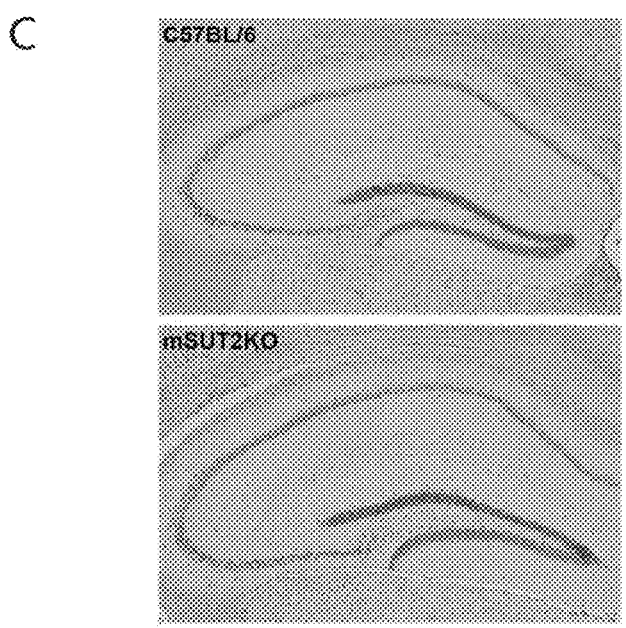

MSUT2 and PABPN1 reciprocally regulate tau aggregation. Recent work demonstrated that siRNA knockdown of PABPN1 decreases the poly(A) tail length on bulk mRNAs while knockdown of MSUT2 increases poly(A) tail length, indicating opposing functions of PABPN1 and MSUT2 in polyadenylation (S. M. Kelly, et al., *RNA* 20, 681-688 (2014); and S. Soucek, et al., *Biochim Biophys Acta* 1819, 546-554 (2012)). To explore whether the PABPN1/MSUT2 interaction mediates changes in accumulation of pathological tau, tau aggregation was analyzed in cultured human cells (HEK293/tau) constitutively overexpressing human tau in which MSUT2 or PABPN1 were knocked down by gene specific siRNA treatment (FIG. 7A). pTau species in MSUT2 knockdown was decreased as assessed by immunostaining with AT180 monoclonal antibody (Thr231, FIG. 7B vs 7C). Similar quantitative measures show MSUT2 siRNA-mediated knockdown decreases both pTau and tau oligomeric species accumulation as detected by quantitative immunofluorescence with TOC1 (S. M. Ward, et al., *J Alzheimers Dis* 37, 593-602 (2013)) and MC1 (G. A. Jicha, et al., *J Neurosci Res* 48, 128-132 (1997) conformation specific monoclonal antibodies (FIG. 7E). In contrast, PABPN1 knockdown exacerbates accumulation of aggregated tau in both assays (FIG. 7B vs 7D, and 7E). Thus, MSUT2 and PABPN1 have reciprocal effects on tau aggregation with MSUT2 promoting tau aggregation while PABPN1 inhibits tau aggregation. Likewise, knockdown of MSUT2 and PABPN1 together has an intermediate tau aggregation phenotype (FIG. 8A). However, knockout of MSUT2 does not alter PABPN1 protein expression level (FIG. 8B) or expression pattern (FIG. 8C). To investigate whether PABPN1 and MSUT2 effects on tau related phenotypes can be attributed to effects on mRNA poly(A) tail length, mRNA poly(A) tail lengths were directly manipulated using mutations in the gene encoding CCR-4, the major mRNA poly(A) deadenylase in *C. elegans*. Mutations in ccr-4 cause dramatic lengthening of bulk mRNA poly(A) tails in *C. elegans* (M. Nousch, et al., *J Cell Sci* 126, 4274-4285 (2013)), similar to what is seen for human MSUT2 knockdown in human cells (S. M. Kelly, et al., *RNA* 20, 681-688 (2014)). Analysis of tau Tg *C. elegans* carrying a strong loss of function mutation in ccr-4 demonstrate an enhancement of tauopathy related behavioral deficits (FIG. 7F). In contrast, loss of function mutations in sut-2 strongly suppress accumulation of pathological tau and tau mediated neurodegeneration (C. R. Guthrie, et al., SUT-2 potentiates tau-induced neurotoxicity in *Caenorhabditis elegans*. *Hum Mol Genet* 18, 1825-1838 (2009); and C. R. Guthrie, et al., *Hum Mol Genet* 20, 1989-1999 (2011)). These data suggest changes in bulk polyadenylation do not underpin the molecular mechanisms by which MSUT2 and PABPN1 modulate tauopathy phenotypes.

Figure 7H:
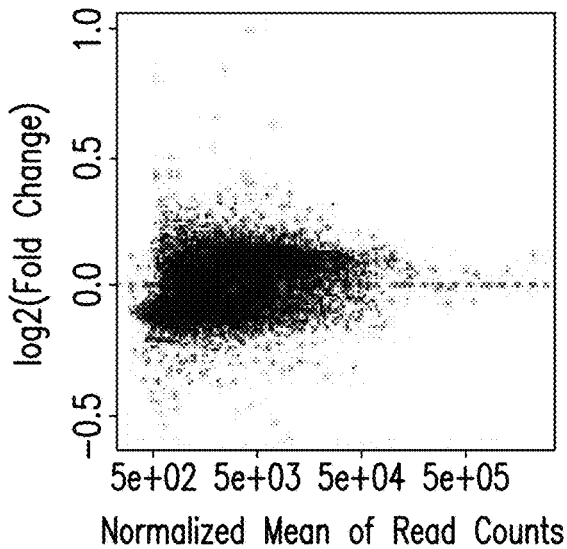
Figure 7I:
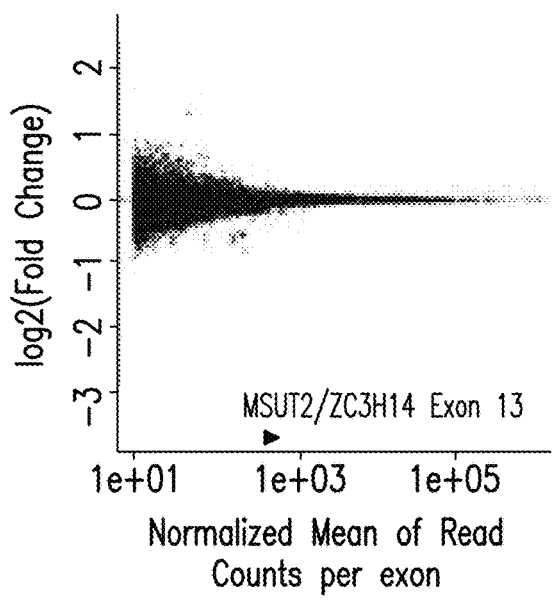
Figure 7J:
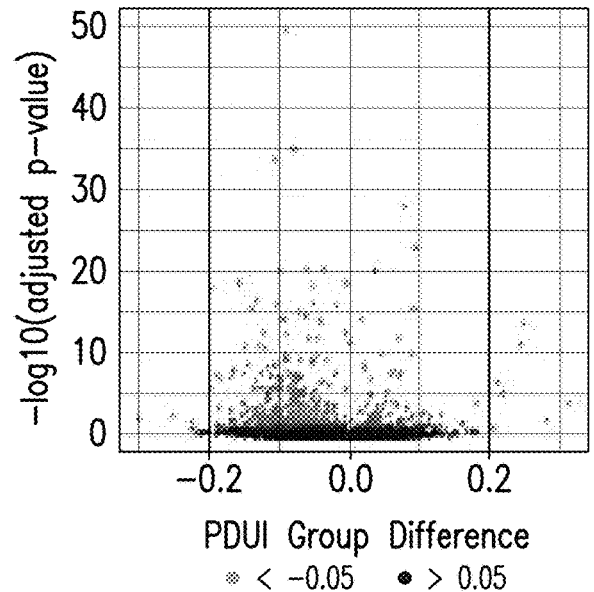

Since poly(A) tails may influence specific mRNA stability, the consequences of knocking out MSUT2 on the mouse brain transcriptome by sequencing total RNA isolated from 2.5-month-old mouse brains was examined. Multidimensional scaling and principal component analysis revealed clustering of control and MSUT2 KO transcriptomic profiles (FIG. 7G). Overall, few transcripts exhibited robust changes in abundance with few mRNAs exhibiting significant changes in expression (n<70) and none greater than 2-fold except for MSUT2 (FIG. 7H, and Table 3). Likewise, surprisingly few genes exhibited differential exon inclusion with 201 significantly differentially spliced exons detected (FIG. 7I and FIG. 16). These data suggest MSUT2 mediates its effects on tau by mechanisms other than regulation of mRNA levels and certainly not through global changes in mRNA processing/stability as might have been expected for a bulk poly(A) binding protein. Because PABPN1 has been shown to have dramatic effects on alternative polyadenylation site selection (APA) during mRNA processing (M. Jenal, R. et al., Cell 149, 538-553 (2012)), APA was analyzed in the MSUT2 KO RNAseq data set using the Dynamic Analysis of Polyadenylation site by RNAseq (DaPars) (Z. Xia, et al., Nat Commun 5, 5274 (2014)) (FIG. 7J and FIG. 17). Unlike with PABPN1, depletion of MSUT2 has modest consequences for alternative PAS utilization with 10 mRNAs showing a significant change greater than the 20% threshold. By contrast PABPN1 knockdown caused significant changes in PAS utilization for 500 mRNAs over the 20% threshold with more than 200 mRNAs exhibiting greater than 2 fold changes in PAS utilization (M. Jenal, et al., Cell 149, 538-553 (2012)).

TABLE 3

MSUT2KO vs B6 RNAseq gene expression changes.

| baseMean | log2Fold Change | lfcSE | pvalue | padj | symbol | qvalue |
|---|---|---|---|---|---|---|
| 7424.280841 | −0.539509641 | 0.095463119 | 1.59E−08 | 1.44E−05 | Zc3h14 | 9.03E−06 |
| 599.5610828 | −0.478783463 | 0.098806015 | 1.26E−06 | 0.000589059 | Col24a1 | 0.0003684 |
| 570.7311519 | −0.432272958 | 0.10387244 | 3.16E−05 | 0.007716042 | Fut10 | 0.004825644 |
| 2205.614241 | −0.414000115 | 0.078574924 | 1.37E−07 | 9.14E−05 | Ccnd1 | 5.71E−05 |
| 827.5027793 | −0.401547526 | 0.106153071 | 0.000155123 | 0.029777616 | Col5a1 | 0.018623044 |
| 497.8976194 | −0.401488262 | 0.096534127 | 3.20E−05 | 0.007716042 | Gm14169 | 0.004825644 |
| 4382.090393 | −0.397366539 | 0.107393008 | 0.000215501 | 0.03708852 | Tmem181b-ps | 0.023195314 |
| 513.8788067 | −0.394476199 | 0.106106486 | 0.000201014 | 0.035830738 | Echdc2 | 0.022408692 |
| 6024.122224 | −0.37875677 | 0.061798073 | 8.85E−10 | 9.93E−07 | Insig1 | 6.21E−07 |
| 664.2482456 | −0.375255184 | 0.10117301 | 0.000208043 | 0.03643307 | Hist1h1c | 0.022785393 |
| 2104.005103 | −0.368895577 | 0.101403365 | 0.000274867 | 0.042590249 | Col11a1 | 0.026636118 |
| 577.3146581 | −0.367585083 | 0.095542921 | 0.000119412 | 0.023839492 | Rlbp1 | 0.014909317 |
| 3549.896679 | −0.326519332 | 0.061198781 | 9.53E−05 | 6.80E−05 | Ints7 | 4.25E−05 |
| 1134.13249 | −0.320968783 | 0.068423287 | 2.72E−06 | 0.001085911 | Sdccag8 | 0.000679133 |
| 596.0447332 | −0.319937836 | 0.08196146 | 9.48E−05 | 0.019313224 | Col4a5 | 0.012078571 |
| 2965.307706 | −0.309050733 | 0.048576371 | 1.99E−10 | 2.84E−07 | 0610037L13Rik | 1.77E−07 |
| 1532.908809 | −0.295691528 | 0.067343534 | 1.13E−05 | 0.003522958 | Fam101b | 0.002203272 |
| 1001.76825 | −0.270718349 | 0.057149661 | 2.17E−06 | 0.000941335 | Park2 | 0.000588715 |
| 1385.402801 | −0.261612142 | 0.062956501 | 3.25E−05 | 0.007716042 | Tek | 0.004825644 |
| 1146.673265 | −0.25969436 | 0.070528789 | 0.000231317 | 0.037241991 | Mrps27 | 0.023291296 |
| 848.9705216 | −0.257755122 | 0.052227209 | 8.00E−07 | 0.000443877 | Gm43737 | 0.000277603 |
| 1187.938667 | −0.243085618 | 0.054797471 | 9.16E−06 | 0.003153434 | Zfp143 | 0.001972171 |
| 1607.541126 | −0.232663608 | 0.046501601 | 5.63E−07 | 0.000330836 | Slc18b1 | 0.000206907 |
| 1407.588104 | −0.230537253 | 0.056966132 | 5.19E−05 | 0.011511787 | Commd10 | 0.007199519 |
| 26282.21204 | −0.174483573 | 0.046326692 | 0.000160698 | 0.030265712 | Hsph1 | 0.018928302 |
| 2275.109515 | −0.145509577 | 0.04057085 | 0.000335076 | 0.048474273 | Sh3gl3 | 0.030316011 |
| 9143.676477 | −0.141794486 | 0.032220265 | 1.08E−05 | 0.003473078 | Epdr1 | 0.002172077 |
| 13031.79421 | −0.099174239 | 0.027278654 | 0.000277336 | 0.042590249 | Ankrd46 | 0.026636118 |
| 4692.67823 | 0.098919895 | 0.026588503 | 0.000198907 | 0.035830738 | Tbcel | 0.022408692 |
| 5413.94015 | 0.121018007 | 0.028856396 | 2.74E−05 | 0.007205889 | Exoc1 | 0.004506593 |
| 7145.204705 | 0.166703703 | 0.037037584 | 6.77E−06 | 0.002501256 | Dzip1 | 0.001564296 |
| 2687.409477 | 0.171621735 | 0.041724249 | 3.90E−05 | 0.009056902 | Ercc5 | 0.005664224 |
| 2406.413066 | 0.176606375 | 0.047808256 | 0.000220705 | 0.037241991 | Poc5 | 0.023291296 |
| 1104.737265 | 0.193779853 | 0.052594832 | 0.000229251 | 0.037241991 | Wdhd1 | 0.023291296 |
| 1571.206192 | 0.207487449 | 0.057744095 | 0.000326612 | 0.047944717 | Hmgb3 | 0.029984825 |
| 12423.89053 | 0.218133154 | 0.055001394 | 7.31E−05 | 0.015863157 | Usp48 | 0.009920884 |
| 1924.774799 | 0.222966446 | 0.043733302 | 3.43E−07 | 0.000213788 | Pus7 | 0.000133704 |
| 2859.833203 | 0.235787524 | 0.049963641 | 2.37E−06 | 0.000984786 | Rrnad1 | 0.00061589 |
| 4193.643163 | 0.236063411 | 0.059913933 | 8.15E−05 | 0.016941816 | Slc25a37 | 0.010595482 |
| 1222.660309 | 0.237198292 | 0.056295502 | 2.51E−05 | 0.006785039 | Gsap | 0.004243391 |
| 3070.5244 | 0.239698676 | 0.066134597 | 0.000289626 | 0.043803677 | Grm3 | 0.027395001 |
| 4034.4514 | 0.239833331 | 0.049507075 | 1.27E−06 | 0.000589059 | Narf | 0.0003684 |
| 14377.96886 | 0.242869581 | 0.059842055 | 4.94E−05 | 0.011204071 | Luc7l | 0.007007072 |
| 2980.928589 | 0.251412239 | 0.046379413 | 5.93E−08 | 4.56E−05 | Galnt11 | 2.85E−05 |
| 5407.856259 | 0.254967501 | 0.057447958 | 9.07E−06 | 0.003153434 | Uba5 | 0.001972171 |
| 4639.736409 | 0.255130896 | 0.058271412 | 1.20E−05 | 0.003617646 | Ncbp1 | 0.002262491 |
| 8456.080682 | 0.290539077 | 0.06816236 | 2.02E−05 | 0.005606337 | Ddhd1 | 0.003506226 |
| 807.6112815 | 0.305268331 | 0.077225601 | 7.72E−05 | 0.01639514 | Mtrr | 0.010253589 |
| 2176.111327 | 0.333123305 | 0.046361834 | 6.71E−13 | 1.34E−09 | Dtymk | 8.37E−10 |
| 708.98509 | 0.335344396 | 0.076577293 | 1.25E−05 | 0.00366627 | Mcm8 | 0.0022929 |
| 4140.058098 | 0.335749763 | 0.080220403 | 2.85E−05 | 0.007287832 | Bhlhe41 | 0.00455784 |
| 2618.686344 | 0.343633478 | 0.093516538 | 0.000238246 | 0.03774879 | Msantd2 | 0.02360825 |
| 4094.385388 | 0.351413417 | 0.063055696 | 2.50E−08 | 2.08E−05 | Per3 | 1.30E−05 |
| 7437.394197 | 0.355381709 | 0.092892105 | 0.000130376 | 0.025517912 | Zkscan2 | 0.015959008 |
| 4468.287414 | 0.377263518 | 0.077946702 | 1.30E−06 | 0.000589059 | Sgk1 | 0.0003684 |
| 746.9202893 | 0.38103927 | 0.103256116 | 0.000224048 | 0.037241991 | F2r | 0.023291296 |
| 550.9681612 | 0.391402382 | 0.086432071 | 5.94E−06 | 0.002281308 | Aaed1 | 0.001426739 |
| 849.9385594 | 0.398222191 | 0.092342156 | 1.61E−05 | 0.004604424 | Fzd4 | 0.002879626 |
| 1882.609448 | 0.483551341 | 0.052828693 | 5.53E−20 | 2.76E−16 | Atp13a4 | 1.73E−16 |
| 7196.4107 | 0.576432167 | 0.099806459 | 7.67E−09 | 7.66E−06 | Zmym6 | 4.79E−06 |
| 2007.764341 | 0.590285711 | 0.096341969 | 8.96E−10 | 9.93E−07 | Per2 | 6.21E−07 |
| 529.7213291 | 0.701047964 | 0.106387082 | 4.41E−11 | 7.34E−08 | Mid1 | 4.59E−08 |
| 4077.552062 | 0.80115702 | 0.106038692 | 4.18E−14 | 1.04E−10 | Zfp729a | 6.52E−11 |
| 2408.607482 | 0.82297539 | 0.056874573 | 1.87E−47 | 1.87E−43 | Ddb2 | 1.17E−43 |

MSUT2 overexpression synergizes with pathological tau causing premature death. To test whether MSUT2 overexpression can provoke tau pathology in the mammalian brain, human MSUT2 was expressed in the brains of tau transgenic mice using an adeno-associated virus (AAV) vector. An existing transgenic mouse line with mild and non-progressive tauopathy driven by high level pan-neuronal expression of wild type human tau (Tau4RTg2652) was used (J. M. Wheeler, et al., *Acta neuropathologica communications* 3, 33 (2015)). AAV serotype 9 encoded human MSUT2 was stereotaxically injected into the hippocampus of the mouse brain. The MSUT2 vector drives strong expression of MSUT2 throughout the hippocampus that includes both the normal nuclear distribution as well as abnormal distribution in the cytoplasm and within the neuronal processes (FIG. 9A-D). By one month post injection, sites with MSUT2 overexpression exhibit dramatic exacerbation of tau neuropathology, while injection of GFP encoding AAV does not exacerbate tauopathy (FIG. 10A). In contrast to pTau, MSUT2 overexpression does not impact total Tau abundance (FIG. 9E). Accumulation of pTau+ lesions in the CA1 is also accompanied by clear evidence of neuronal loss in associated projection regions, which is lacking in GFP AAV injected mice (FIG. 10B).

Neuroinflammation, as evidenced by activated microglia and reactive astrocytes, occurs in association with pathological tau in tauopathies including AD. It was examined whether MSUT2 overexpression exacerbates gliosis in response to pathological tau in the mild non-progressive Tau4RTg2652 mouse model of tauopathy. Profound neuroinflammatory changes in the hippocampi of MSUT2-overexpressing Tau4RTg2652 mice, including dramatically increased microgliosis as detected by IBA1 immunostaining was observed (FIG. 10C, FIG. 9F). Likewise, increased astrocytosis as detected by GFAP immunostaining occurs in MSUT2 overexpressing Tau4RTg2652 mice (FIG. 10D, FIG. 11A). To explore whether MSUT2 KO prevents the neuroinflammatory responses to tauopathy in the more severe PS19 mouse model, brain tissue was immunostained for markers of astrocytosis and microgliosis. Significantly decreased astrocytosis in MSUT2 KO/PS19 mice compared to PS19 mice with normal MSUT2 was observed (FIG. 10E, FIG. 11B). Furthermore, a trend towards decreased microgliosis as detected by IBA1 staining was also observed (FIG. 12A-C). However, MSUT2 KO mice appear to not be resistant to neuroinflammatory changes induced by an exogenous chemical trigger such as kainic acid (FIG. 13).

Neuronal depletion of the MSUT2/PABPN1 complex occurs in AD and predicts age at disease onset. To investigate the involvement of MSUT2 in a human disease, MSUT2 protein levels in postmortem human brain from normal and AD cases was examined. It was observed that in the frontal cortex of AD patients, MSUT2-positive neurons harbor pathological tau species without overt co-localization of nuclear MSUT2 protein and cytoplasmic tau deposits (FIG. 14A). To investigate how MSUT2 expression may influence tau pathology in AD, MSUT2 expression was characterized in a cohort of 32 AD cases by immunostaining (Table 4). In approximately half of the AD cases, dramatically diminished MSUT2 expression was observed compared to controls while the remainder exhibited control levels of MSUT2 expression (FIG. 14B). This difference is not due to differences in postmortem intervals (FIG. 12D, and Table 2). Next, the AD cases were classified into two groups: MSUT2 normal and MSUT2 depleted, on the basis of MSUT2 immunostaining. In the subset of AD cases with depleted MSUT2 protein, the number of MSUT2-positive neurons was dramatically lower.

TABLE 4

MSUT2 table of AD case information.

| Case ID | NPDX | AGE | SEX | ONS | DU | PMI | CERAD | Braak | MSUT2 | PABPN1 |
|---|---|---|---|---|---|---|---|---|---|---|
| UWA244 | AD | 78 | M | 72 | 6 | 7:00 | 3 | 3 | High | High |
| UWA447 | AD | 93 | F | 84 | 9 | 6:30 | 1 | 3 | High | High |
| UWA536 | AD | 78 | F | 69 | 9 | 2:20 | 2 | 3 | High | High |
| UWA650 | AD | 94 | M | 91 | 3 | 3:05 | 3 | 3 | High | High |
| UWA677 | AD | 86 | M | 80 | 6 | 2:40 | 3 | 3 | High | High |
| UWA730 | AD | 100 | F | 82 | 18 | 3:08 | 2 | 3 | High | High |
| UWA763 | AD | 91 | M | 82 | 9 | 7:00 | 2 | 3 | High | High |
| UWA771 | AD | 86 | M | 81 | 5 | 4:25 | 3 | 3 | High | High |
| UWA797 | AD | 62 | M | 55 | 7 | 4:32 | 3 | 3 | High | High |
| UWA1501 | AD | 77 | M | 71 | 6 | 6:32 | 3 | 3 | High | High |
| UWA1518 | AD | 77 | M | 63 | 14 | 5:20 | 3 | 2 | High | High |
| UWA1550 | AD | 94 | M | 82 | 12 | 4:25 | 3 | 3 | High | Low |
| UWA2385 | AD | 86 | F | 76 | 10 | 8:32 | 3 | 3 | High | High |
| UWA3556 | AD | 89 | M | 86 | 3 | 6:25 | 3 | 3 | High | High |
| CNDR2045 | AD | 71 | F | 60 | 11 | 5:00 | 3 | 3 | Low | Low |
| CNDR2142 | AD | 81 | F | 71 | 10 | 4:00 | 3 | 3 | Low | Low |
| UWA342 | AD | 60 | F | 54 | 6 | 7:30 | 2 | 2 | Low | Low |
| UWA343 | AD | 82 | M | 76 | 6 | 8:00 | 3 | 2 | Low | Low |
| UWA450 | AD | 76 | M | 65 | 11 | 4:30 | 3 | 3 | Low | Low |
| UWA519 | AD | 82 | F | 55 | 27 | 8:00 | 3 | 3 | Low | Low |
| UWA681 | AD | 75 | M | 64 | 11 | 4:30 | 3 | 3 | Low | High |
| UWA732 | AD | 89 | F | 82 | 7 | 5:23 | 2 | 3 | Low | High |
| UWA1443 | AD | 84 | F | 76 | 8 | 4:47 | 3 | 3 | Low | Low |
| UWA3554 | AD | 77 | M | 57 | 20 | 7:25 | 3 | 3 | Low | Low |
| UWA6511 | AD | 90 | F | 76 | 14 | 6:23 | 3 | 3 | Low | High |
| UWA6542 | AD | 70 | F | 76 | 8 | 5:00 | 3 | 3 | Low | Low |
| UWA6589 | AD | 68 | M | 57 | 10 | 9:25 | 3 | 3 | Low | Low |

To explore whether PABPN1 also varies in AD, PABPN1 expression was examined and depleted PABPN1 in neuronal nuclei from a subset of AD cases was observed (FIG. 14C, Table 2). Depletion of PABPN1 is significantly correlated with depletion of MSUT2 (Spearman correlation coefficient=0.71, p=0.0003, Table 2). These findings suggest depletion of the molecular complex containing PABPN1 and MSUT2 proteins bound to poly(A) RNA. To explore whether the co-depletion of PABPN1 and MSUT2 might influence clinical AD, the relationship between AD cases' age at onset and either MSUT2 or PABPN1 depletion from neuronal nuclei was examined. It was observed that AD cases with depleted brain MSUT2 protein levels exhibit a relatively younger age at AD onset (FIG. 14D). Likewise, AD cases exhibiting nuclear depletion of PABPN1 also exhibit a significantly earlier age of disease onset (FIG. 14E).

PABPN1 and MSUT2 complex (PMC) depletion exacerbates disease severity in AD. Previous investigations from others have demonstrated a clear relationship between pathological tau burden and severity of dementia (T. Gomez-Isla, et al., *Ann Neurol* 41, 17-24 (1997); and P. T. Nelson, et al., *J Neuropathol Exp Neurol* 71, 362-381 (2012)). However, it is unknown whether PMC depletion correlates with pathological neurodegenerative changes in AD. To further explore the relationship between PMC and severity of neuroinflammation, frontal cortex in the AD case collection was examined for markers of astrocytosis and microgliosis. A dramatic and significant decrease in astrocytosis in the cortex of PMC depleted AD cases was observed (FIG. 14F), consistent with the observations in MSUT2 KO/PS19 mice above (FIG. 10E, FIG. 11B). A parallel trend for decreased microgliosis is also evident in PMC depleted AD cases (FIG. 14G) and in MSUT2 KO/PS19 mice (FIG. 12A-C). Likewise, an increase in pTau burden in the PMC depleted cases (FIG. 14H) and increased neuronal loss detected by NeuN staining (FIG. 14I) was also observed. Note that loss of MSUT2 alone does not provoke neurodegeneration in the mouse brain (FIG. 3C), rather it may be the loss of the PMC as a complex with poly(A) RNA that exacerbates AD severity.

DISCUSSION

Pathological accumulation of abnormal tau occurs in normal aging, and to a much greater extent in AD and other related tauopathies. Abnormal assembly of tau and other aggregating proteins represent a toxic gain of function disrupting neuronal proteostasis in neurodegenerative disease. In AD specifically, accumulation of tau-positive lesions drives cognitive decline and neuronal loss (T. Gomez-Isla, et al., *Ann Neurol* 41, 17-24 (1997); and P. T. Nelson, et al., *J Neuropathol Exp Neurol* 71, 362-381 (2012)). As described herein, it was tested whether MSUT2, the mammalian homolog of sut-2, plays a role in tauopathy disorders by determining neuronal susceptibility to pathological tau accumulation.

It was demonstrated that MSUT2 does influence tauopathy related phenotypes in mammals. MSUT2 knockout mice exhibit reduced accumulation of phosphorylated and aggregated human tau driven by a human tau transgene. Likewise, MSUT2 KO mice are protected from the cognitive impairment and neuronal loss caused by neuropathological tau species. MSUT2 KO mice are also protected from neuroinflammatory changes in response to tauopathy as indicated by reduced astrocytosis. In contrast, introduction of excess MSUT2 exacerbates normally mild and non-progressive tauopathy phenotypes caused by a wild type human tau encoding transgene. MSUT2 overexpression in both nucleus and cytoplasm causes significant elevation of pTau accumulation and drives loss of neurons. While MSUT2 possesses a nuclear export signal, it is not normally seen in the cytoplasm, suggesting MSUT2 mislocalization may drive pathological tau by a direct but possibly supraphysiological mechanism. Regardless, MSUT2 overexpression also exacerbates neuroinflammation, as markers of both microgliosis and astrocytosis are elevated in regions with increased MSUT2 protein. These findings in tauopathy mouse models reveal neuronal MSUT2 levels determine both accumulation of pathological tau species and neuronal vulnerability (FIG. 15A).

In the model systems described herein, the mechanism of MSUT2 modulation of tauopathy involves the nuclear RNA binding functions of MSUT2. It was demonstrated herein that MSUT2 binds both to poly(A) RNA and to another nuclear poly(A) binding protein, PABPN1. The results showed that MSUT2 and PABPN1 co-occupy poly(A) RNA localized to nuclear speckles, forming a macromolecular complex. Furthermore, the constituents of this complex become co-depleted in AD cases with earlier onset or more extensive tau pathology. Others showed that PABPN1 and MSUT2 have opposing effects on poly(A) tail length (S. M. Kelly, et al., *RNA* 20, 681-688 (2014); and S. M. Kelly, et al., *Dev Neurobiol* 76, 93-106 (2016)). The results show that MSUT2 and PABPN1 also function together to influence tauopathy. MSUT2 normally promotes tau aggregation while PABPN1 normally promotes clearance of aggregated tau. To test the linkage between RNA polyadenylation state and susceptibility to tauopathy, the predominant poly(A) nuclease in the *C. elegans* model of tauopathy was inhibited and the results show that increasing the poly(A) tail length does not ameliorate tauopathy. These findings implicate functions of MSUT2 and PABPN1 other than mediation of poly(A) tail length as an important control point in tau proteostasis.

How does the RNA binding function of MSUT2 impact tau pathology? It was initially thought that the loss of MSUT2 function ameliorated tauopathy via changes in gene expression. However, RNAseq analysis of MSUT2 knockout brain revealed limited changes in gene expression, alternative splices, or alternative polyadenylation site selection. Another hypothesis implicates RNA stress granules in the process of pathological protein aggregation whereby poly(A)+ mRNA becomes recruited to stress granules containing poly(A) binding proteins (N. Kedersha, et al., *J Cell Biol* 169, 871-884 (2005)). In AD, RNA stress granule assembly factors TIA1 and G3BP overlap with tau positive lesions in neurons (T. Vanderweyde, et al., *Cell reports* 15, 1455-1466 (2016); and T. Vanderweyde, et al., *J Neurosci* 32, 8270-8283 (2012)). TIA1 participates in RNA stress granule assembly, binds poly(A) RNA, and has similarity to other poly(A) binding proteins (Q. Tian, et al., *Cell* 67, 629-639 (1991); and A. Kawakami, et al., *Proc Natl Acad Sci USA* 89, 8681-8685 (1992)). Thus, one possible mechanism of MSUT2 action could be through promotion of stress granule formation leading to increased tau aggregation. Formation of tau/RNA coacervates or tau liquid-liquid phase separation, properties of known aggregation-prone RNA binding proteins, has recently been suggested as a mechanism for initiating tau fibrillization (S. Wegmann, et al., *EMBO J* 37, (2018); and X. Zhang, et al., *PLoS Biol* 15, e2002183 (2017)). Another possible mechanism could involve a direct tau-RNA interaction whereby RNA, as a polyanion, can both sequester tau from its function as a tubulin binding protein and potentially promote pathological aggregation (X. Zhang, et al., *PLoS Biol* 15, e2002183 (2017); and J. B. Bryan, et al., *Proc Natl Acad Sci USA* 72, 3570-3574 (1975)). An alternative hypothesis incorporates the relationship between microtubule dynamics and polyadenylation. Previous work demonstrated that pathological tau causes microtubule hyper-dynamicity in tau transgenic mice (D. M. Barten, et al., *J Neurosci* 32, 7137-7145 (2012)). Tau pathology and consequent neurocognitive deficits can be ameliorated by stabilization of microtubules (K. R. Brunden, et al., *J Neurosci* 30, 13861-13866 (2010); B. Zhang, et al., *J Neurosci* 32, 3601-3611 (2012); and D. M. Barten, et al., *J Neurosci* 32, 7137-7145 (2012)). Previous investigation of the role of mRNA polyadenylation showed that defects in any one of several polyadenylation factors limits polyadenylation and causes MT destabilization or hyper-dynamicity (K. M. Cappell, et al., *Mol Cell Biol* 30, 5135-5144 (2010)). Thus, these data suggest that MSUT2 KO effects on polyadenylation may restore MT stability, thereby modulating tauopathy phenotypes (FIG. 15B).

While investigation of the molecular and cellular functions of MSUT2 has received attention in the context of RNA metabolism, investigation of its overall importance in brain function remains underdeveloped. However, its abundant expression in neurons suggests it may play a role in brain function. Recent reports implicate MSUT2 in learning and cognitive function in flies and mice (S. M. Kelly, et al., *RNA* 20, 681-688 (2014); S. M. Kelly, et al., *Dev Neurobiol* 76, 93-106 (2016); and J. Rha, et al., *Hum Mol Genet*, (2017)). Furthermore, the data described herein suggest MSUT2 may play an important role in mediating tauopathy-induced cognitive dysfunction. Nevertheless, the relationship between MSUT2 function, poly(A) RNA, and cognition remains unclear. The nuclear polyadenylation machinery and regulators of cytoplasmic mRNA polyadenylation also regulate synaptic function and memory (L. Du, et al., *RNA* 11, 1340-1347 (2005); and J. E. Kwak, et al., *Proc Natl Acad Sci USA* 105, 14644-14649 (2008)). For instance, the cytoplasmic polyadenylation element RNA binding protein (CPEB) possesses prion-like protein aggregation properties and influences poly(A) abundance and learning (K. Si, et al., *Cell* 115, 893-904 (2003)). Likewise, the RNA binding protein Cst-64 binds RNA and can influence learning and behavior in mice (J. C. Harris, et al., *PLoS One* 11, e0165976 (2016)). Collectively, poly(A) binding proteins and regulatory factors affect cognition and the co-depletion of MSUT2 and PABPN1 in AD suggests poly(A) binding protein homeostasis becomes disrupted in a substantial subset of AD cases.

In the human brain, MSUT2 protein occurs primarily in neurons. In AD cases, many tangle bearing neurons that are MSUT2 positive were observed. Extensive characterization of MSUT2 expression revealed that in about half of AD cases examined, MSUT2 protein becomes dramatically reduced. MSUT2 depletion occurs more often in AD cases with earlier onset and more extensive tau pathology, suggesting the possible loss of MSUT2+ neurons. In the same AD cases with depleted MSUT2, PABPN1 is also reduced suggesting depletion of the MSUT2/PABPN1 complex (PMC) occurs in earlier onset AD. While it is difficult to discern functional relationships between postmortem examination of pathological tau and underlying disease mechanisms, the data disclosed herein suggest that MSUT2+ neurons may die when challenged with pathological tau. Thus, cases with earlier onset AD could exhibit more extensive pathological tau and loss of MSUT2+ neurons while cases with later disease onset and milder tauopathy show a sparing of MSUT2+ neurons. The experiments overexpressing MSUT2 in mouse neurons demonstrated a dramatic exacerbation of tau pathology consistent with the notion that MSUT2 activity determines sensitivity to neuronal challenge by pathological tau.

While the relationship between tau pathology and neuroinflammation remains poorly understood, pathological tau clearly provokes neuroinflammation. Likewise, increasing neuroinflammation frequently exacerbates tauopathy. It remains less clear whether an adaptive form of neuroinflammation can mediate clearance of pathological tau and promote neuronal survival. Here, the data show that MSUT2 function promotes the brain's neuroinflammatory response to pathological tau. In mice, knockout of MSUT2 leads to a decrease in astrocytosis and microgliosis in tauopathy mice. Overexpression of MSUT2 in neurons provokes additional astrocytosis and microgliosis in tauopathy mice. Previous work showed that poly(A) can modulate inflammatory pathways (K. M. Rose, et al., *Nature* 267, 178-180 (1977)). Thus, MSUT2 function may drive susceptibility to tauopathy and gliosis by changing the neuroinflammatory response to tau pathology. Regardless, in AD patients, PMC+ cases exhibit a later disease onset in the face of a more robust neuroinflammatory response. Conversely, AD PMC-depleted cases exhibit an earlier disease onset but a weak neuroinflammatory response. Taken together, these observations suggest MSUT2 through the PMC could promote an adaptive neuroinflammatory response to AD neuropathology.

The work with MSUT2 demonstrates the molecular disease mechanisms of tauopathy remain conserved from *C. elegans* to humans. In mice, hypoactivity of MSUT2 protects neurons against abnormal tau while MSUT2 hyperactivity exacerbates tauopathy. Analysis of MSUT2 function implicates RNA polyadenylation machinery as an important node of cellular function in tauopathy. Likewise, the data presented here provides evidence that MSUT2 activity potentiates the neuroinflammatory response to pathological tau. Given the current dearth of success therapeutically targeting tauopathy, approaches targeting RNA processing warrant further investigation. Although how loss of MSUT2 protects against neurodegeneration requires further investigation, reducing MSUT2 function has potential as a therapeutic approach for treating tauopathies because complete loss of this protein appears to have little effect on mouse development or function. Described herein is MSUT2 as a therapeutic target for the development of small molecule inhibitors or specific reduction of gene expression by newly developed antisense oligonucleotide or CRISPR-based modulation of gene expression. Since tau accumulation in AD appears to occur concomitant with amyloid plaque deposition, it may be possible to stop the progression of neurodegeneration even after the Aβ-initiated AD process has begun by targeting tau through MSUT2.

Materials and Methods

Study design. The objective in conducting this study was to investigate the genetic and molecular involvement of MSUT2 in tauopathy. Previous work has suggested that MSUT2 expression modulates susceptibility to pathological tau in simple model organisms (C. R. Guthrie, et al., *Hum Mol Genet* 18, 1825-1838 (2009); C. R. Guthrie, et al., *Hum Mol Genet* 20, 1989-1999 (2011); and J. M. Wheeler, et al., *Biochem Soc Trans* 38, 973-976 (2010)). This work evaluated the impact of MSUT2 levels of pathological tau deposition in rodents and human AD patients. The mice (131 total mice) were on the C57BL/6J genetic background. MSUT2 KO mice were generated by KOMP using standard knockout mouse technologies (K. C. Lloyd, *Ann N Y Acad Sci* 1245, 24-26 (2011)). The PS19 transgenic mouse model expressing human P301S mutant human tau was utilized for its well characterized and highly progressive tauopathy related phenotypes (Y. Yoshiyama, et al., *Neuron* 53, 337-351 (2007)). A second, less severe tauopathy model was also chosen on the basis of its mild, consistent, and non-progressive tauopathy phenotype driven by wild type human tau (J. M. Wheeler, et al., *Acta neuropathologica communications* 3, 33 (2015)). Animals were assigned to experimental (MSUT2 KO) and control (MSUT2+/+) groups based on genotype. Experimental group sample sizes for neuropathology were based on previous pathological findings (Y. Yoshiyama, et al., *Neuron* 53, 337-351 (2007); and J. M. Wheeler, et al., *Acta neuropathologica communications* 3, 33 (2015)). FFPE tissue sections from each brain were collected using standard histological techniques (see below). For each experiment shown for mice, representative sections from each experimental animal were immunostained and visualized by standard light microscopy. Histology was analyzed under identical conditions for both experimental and control sections. Except where indicated, analyses were performed non-blinded using identical experimental procedures for both imaging and analysis. Where necessary, image adjustments applied linear contrast and brightness changes. For behavioral analysis, group sizes were based on previously published findings with these models (H. Takeuchi, et al., *PLoS ONE* 6, e21050 (2011); and J. M. Wheeler, et al., *Acta neuropathologica communications* 3, 33 (2015)). For RNAseq analysis, RNA isolated from brains of MSUT2 KO mice were compared with C57BL/6 mice. Brain specimens from a total of 27 Alzheimer's patients were subjected to histological and neuropathological analysis. AD autopsy cases were obtained from the UW ADRC and UPENN CNDR brain banks after standard neuropathological evaluation per NIAA criteria (T. J. Montine, et al., *Acta Neuropathol* 123, 1-11 (2012)). Evaluation of tissue specimens was conducted using the same workflows outlined for the rodent experiments above.

Construction of knockout mice. B6-Zc3h14$^{tm1a(KOMP)Wtsi}$ mice were generated from a KOMP ES cell line (K. C. Lloyd, *Ann N Y Acad Sci* 1245, 24-26 (2011)). B6-Zc3h14$^{tm1a}$ animals were crossed with strains carrying the Flp and Cre recombinases (12954/SvJaeSor-Gt(ROSA) 26Sor$^{tm1(FLP1)Dym/J}$ and $^{B}$6.129S4-Meox2$^{tm1(cre)Sor}$/J, respectively) to remove exon 13 of the Msut2 gene as well as the inserted transgene sequences. PS19 animals (B6-Tg (Prnp-MAPT*P301S)PS19Vle) were backcrossed to C57BL/6 for >10 generations. Tau4RTg2652 tauopathy model mice were generated (J. M. Wheeler, et al., *Acta neuropathologica communications* 3, 33 (2015)). Briefly, the cDNA encoding the most abundant brain isoform (1N4R) of tau was cloned into a mouse neuron specific expression vector, pThy1.2 (T. Seki, et al., *Proc Natl Acad Sci USA* 82, 6657-6661 (1985)). Transgenic mice were generated by pronuclear microinjection of the Thy1.2::Tau (1N4R) transgene at the University of Washington Nathan Shock Center Transgenic Animal Model Core (Warren Ladiges, PI). Founder mice were intercrossed with C57BL/6J mice to establish lines. The Tau4RTg2652 line was the focus of characterization due to its high level tau expression and robust phenotype. Mice from the Tau4RTg2652 line used in these studies were backcrossed 10 generations (incipient congenic) with the C57BL/6J strain. This mouse strain has been deposited with the Mutant Mouse Regional Resource Centers (MMRRC) and is available under the stock number MMRRC: 036717 and the strain name of B6.Cg-Tg(Thy1-MAPT*)2652Gds.

Immunohistochemistry and histological stains. Immunohistochemistry was performed on paraffin embedded frontal cortex sections from over 30 AD cases. In addition, the following transgenic mouse lines were examined by immunohistochemistry: 9 month-old PS19 Tg mice (n=24), MSUT2 KO/PS19 Tg mice (n=24), 4 month old Tau4RTg2652 mice injected with AAV-MSUT2 (n=15) or AAV-GFP (n=5). Mice were anesthetized and fixed by transcardial perfusion with 4% paraformaldehyde. Brains were removed and paraffin embedded for sectioning. Coronal sections from the hippocampus were cut and stored at 4° C. until use. Human and mouse brain sections were deparaffinized and rehydrated through alcohols and an antigen retrieval step consisting of heat pretreatment by microwave or autoclave in citrate buffer was used when necessary. Sections were treated for endogenous peroxidases with 3% hydrogen peroxide in PBS (pH 7.4), blocked in 5% non-fat milk in PBS, and incubated with one of the following primary antibodies overnight at 4° C.: MC1 (G. Carmel, et al., *J Biol Chem* 271, 32789-32795 (1996)), AT180 (ThermoScientific, catalog MN1040), GFAP (Dako Cytomation Z0334), Iba1 (Wako 019-19741), MSUT2 (C. R. Guthrie, et al., *Hum Mol Genet* 18, 1825-1838 (2009)), PABPN1 (Abcam ab81224), tau (Rb17025, (T. Ishihara, et al., *American Journal of Pathology* 158, 555-562 (2001)), or NeuN (Millipore MAB377). Biotinylated secondary antibody was applied for 45 min at room temperature. Finally, sections were incubated in an avidin-biotin complex (Vector's Vectastain Elite ABC kit, Burlingame, Calif.) and the reaction product was visualized with 0.05% diaminobenzidine (DAB)/0.01% hydrogen peroxide in PBS. Negative controls with secondary antibody alone did not immunostain tissue sections. The presence of NFTs was assessed by Gallyas silver staining (A. Y. Sun, et al., *Journal of Histochemistry & Cytochemistry* 50, 463-472 (2002)). In addition, cresyl violet staining was performed to assess neuronal loss.

For double label immunofluorescence of AT180 and MSUT2 in human AD brain, AlexaFluor 488 goat anti-rabbit and AlexaFluor 594 goat anti-mouse secondary antibodies (Molecular Probes) were used and autofluorescence was quenched with 0.1% Sudan Black.

For quantitation, stained sections were analyzed using the computerized image analysis system, MicroComputer Imaging Device (MCID, Imaging Research, St. Catherines, Ontario, Canada). Blinded assessment of optical density measurements were obtained relative to the proportional area for AT180, MC1, GFAP, Iba1, NeuN and cresyl violet staining in frontal cortex and hippocampus. Data were averaged and are represented as mean+/−SEM. A two tailed Student's t-test was used to assess differences in staining intensity between experimental groups.

Photomicrography and figure preparation. Immunohistochemistry photomicrographs were taken with a digital camera and imported into Adobe Photoshop. To optimize visualization of staining, photomicrographs were modified when necessary by adjusting brightness and contrast. Fluorescent and immunofluorescent microscopy was performed on a Delta Vision microscope (GE, Inc.) using a 60× oil immersion objective, a sCMOS camera, and 2×2 binning. Image analysis was performed using softWoRx 6.0 Beta software (GE, Inc.).

Rodent behavioral analysis. Mice were bred and housed at the VAPSHCS animal facility, and all experiments were approved by the IACUC committee. Mice were housed on a 12:12 light cycle in static microisolator cages, with rodent chow and water available ad libitum. Environmental enrichment was added at every cage change. The behavioral experiments were conducted during the light phase.

Open field testing was conducted in a 30 inch diameter circular plastic arena. The animals were moved into the testing room approximately 1 hour prior to start of testing. The arena was cleaned with 70% ethanol between animals.

Total locomotor activity was measured for 10 min using SMART behavioral tracking system (San Diego Instruments).

The Barnes maze is a circular white plastic platform 36 inches in diameter with 20 holes around the perimeter. One hole leads to a dark target escape box containing clean bedding material. Latencies to locate and to enter the escape box were recorded. Spatial cues (blue circle, yellow triangle, black/white striped square) were placed around the maze to be used as landmarks to find the escape box. Mice are placed in a clear box in the center of the maze for 30 sec at the beginning of each trial, so the direction each mouse faces at the trial start is random. When the start box is removed, each animal has a maximum of 2 min to locate the escape box. If the animal locates the hole, it is allowed to shelter there for 1 min before being returned to the home cage. If the animal fails the task, it is gently guided to the escape box by the investigator and allowed to shelter there for 1 min. The animals were moved into the testing room approximately 1 hour prior to start of testing, and the maze was cleaned with 70% ethanol between animals. Training trials were conducted twice daily on two consecutive days.

Rotorod testing was conducted using an accelerating UGO Basile Rota Rod. The rod surface is covered with ridged plastic, located 18 inches above a padded floor. The mice were transferred to the testing room approximately 1 hour prior to the start of testing, and were tested on four consecutive days. On the first three days, the mice received three training trials separated by a minimum of 30 min rest time. Animals were placed onto a stationary rotorod and allowed to acclimate for a minimum of 10 seconds before accelerating the rod up to 8 rpm over 2 minutes on all training trials. On the final test day, the animals were tested in four trials with acceleration up to 8, 16, 24, and 32 rpm.

Cell Culture, RNA interference, & transient transfections. HEK293 and HEK/tau cells (100 µg/ml Zeocin) were cultured under standard tissue culture conditions (DMEM, 10% defined fetal bovine serum, Penicillin (1000 IU/mL) Streptomycin (1000 µg/mL) (C. R. Guthrie, et al., *J Mol Neurosci* 45, 32-41 (2011); and C. R. Guthrie, et al., *Hum Mol Genet* 20, 1989-1999 (2011)). RNA interference and plasmid transient transfections were conducted following manufacture's protocol (RNAiMAX, Invitrogen).

Immunofluorescent staining and fluorescent in situ hybridization. Cells were grown on poly-D-lysine coated 12 mm round coverslips and fixed in 4% formaldehyde solution. Cells were washed 3×5 min in PBS/$Ca^{2+}$/$Mg^{2+}$, then blocked in antibody buffer (PBS, 0.5% Triton X-100, 1 mM EDTA, 0.1% BSA, 0.05% $NaN_3$) with 10% normal goat serum. Primary antibodies were applied and incubated for 1 hour at room temperature. Primary antibodies used were: PABPN1=Proteintech Group (Catalog #10782-2-AP), MSUT2=Rabbit 9857-2-AP (C. R. Guthrie, et al., *Hum Mol Genet* 20, 1989-1999 (2011)), oligomeric tau=TOC1 (S. M. Ward, et al., *Biochem Soc Trans* 40, 667-671 (2012)), SC35=Sigma Aldrich (Catalog #S4045). Cells were washed 3×5 min in PBS/$Ca^{2+}$/$Mg^{2+}$, then re-blocked for 10 min. Appropriate Alexa dye-labeled secondary antibodies (Invitrogen) were applied and incubated for 20 min at room temperature. Cells were again washed 3×5 min in PBS/$Ca^{2+}$/$Mg^{2+}$, counterstained with 300 nM DAPI and mounted with ProLong Gold antifade (Molecular Probes). TOC1 staining was conducted with 10% rabbit serum in antibody buffer. Rabbit anti-mouse secondary antibody used for TOC1 was FITC labeled (Invitrogen). Fluorescence In Situ Hybridization was conducted prior to counterstaining with DAPI as per the following: After secondary antibody staining, cells were washed 3×5 min in PBS/$Ca^{2+}$/$Mg^{2+}$, 100 pg/µl 5' Alexa-647 labeled Poly(T) oligonucleotide (sequence=TTTTT TTTTT TTTTT TTTTT TTTTT TTTTT TTTTT TTT (SEQ ID NO: 23); IDT), and incubated in the dark for 2 hrs at 37° C. Following hybridization, the samples were washed once in PBS/$Ca^{2+}$/$Mg^{2+}$ in the dark for 30 min at 37° C. Proximity Ligation assays were preformed using Duolink PLA technology (Sigma Aldrich Catalog #DU092101). Human brain samples stained for MSUT2 and PABPN1 were imaged on a Leica TCS SP5 II confocal microscope using a 63x oil immersion objective. Colocalization analysis of confocal images were conducted in ImageJ 1.51n using Coloc 2 (J. Schindelin, et al., *Nat Methods* 9, 676-682 (2012)).

Recombinant protein purification & in vitro binding assays. The MSUT2 ZF and PABPN1 protein expression constructs were prepared by inserting the MSUT2 ZF or PABPN1 cDNA into the pGEX6P-1 expression vector (Pharmacia) to generate a construct encoding a Glutathione S-Transferase (GST)-MSUT2 ZF or GST-PABPN1 fusion protein. The GST moiety allows one step affinity purification of recombinant protein on Glutathione coupled sepharose beads. A log phase culture of BL21 (DE3) cells carrying the pGEX-MSUT2 or PABPN1 vector was induced for 3 hours at 37° C. with shaking. *E. coli* lysates were treated with benzonase nuclease which degrades both RNA and DNA prior to clearing and purification. Glutathione sepharose (Pharmacia) was used as the affinity resin and purified (J. V. Frangioni, et al., *Anal Biochem* 210, 179-187 (1993)). In vitro protein-binding assays were performed using $^{35}S$ labeled PABPN1 protein generated with TNT reticulocyte lysates (Promega, Inc.); labeled PABPN1 was pretreated with RNAse (B. Kraemer, et al., *Curr Biol* 9, 1009-1018 (1999)). Briefly, GST beads coupled to MSUT2 were blocked and then incubated with labeled PABPN1 both of which had been pretreated with nucleases to remove RNA. Unbound protein was repeatedly washed away and then labeled proteins were eluted by boiling and analysis on SDS-PAGE.

Behavioral assay in *C. elegans*. Cultures were maintained at 20° C. on standard 60 mm NGM plates containing OP50 *Escherichia coli* (S. Brenner, *Genetics* 77, 71-94 (1974)). A timed egg lay using 10-20 gravid adults was performed and worms grown for 4 days at 20° C. To assess swimming behavior, a plate containing a synchronized population of worms was flooded with 1 mL of M9 buffer. The M9 solution containing *C. elegans* was pipetted onto an unseeded 35 mm NGM plate. One minute after the addition of M9 buffer, swimming worms were recorded using WormLab (MBF Bioscience) for 1 minute at 14 frames per second. Videos of swimming worms were analyzed using WormLab 2017 software. Swimming behavior was quantified by measuring the number of turns made by a worm during the video. A turn was calculated using Bending Angles-Multiple and setting the sample angles to 3, the amplitude threshold to 20°, and the duration threshold to 2 frames (0.14 seconds). Data from the angle 2 (the angle made from the body quarterpoints and midpoint) was used. The number of turns a worm made was divided by the time a worm was tracked by the software to calculate turns per minute. Only worms that were analyzed for at least 20 seconds were kept in the analysis. At least 100 worms were analyzed per strain.

RNAseq analysis. Raw reads from RNAseq experiments had their 3' Illumina TruSeq Indexed adaptors (AGATCG-GAAGAGCACACGTCTGAACTCCAGTCAC; SEQ ID NO: 24) trimmed using cutadapt v1.8.3 with parameters "-e 0.06 -O 6 -m 14 -n 2 --length-tag "length="" (M. Martin, Cutadapt Removes Adapter Sequences From High-Throughput Sequencing Reads. http://dx.doi.org/10.14806/ej.17.1.20017). Reads were then mapped to the mm10 *Mus musculus* genome build using STAR version 2.4.1d with parameters "--outFilterMultimapNmax 1 --outFilterMismatchNmax 2 --outFilterMismatchNoverReadLmax 0.06" (A. Dobin, et al., *Bioinformatics* 29, 15-21 (2013)) and were further filtered to mapping reads with a maximum mismatch rate of 0.06. The mapped reads from the RNA sequencing pipeline were analyzed for differential expression by using HTSeq with parameters "-s reverse -t exon -i gene_id" (S. Anders, et al., *Bioinformatics* 31, 166-169 (2015)) to compute the number of reads mapping to each gene using Ensembl mm10 gene annotations (F. Cunningham, et al., *Nucleic Acids Res* 43, D662-669 (2015)). Gene counts were then analyzed for differential expression with the DESeq2 R package v1.0.19 (M. I. Love, et al., *Genome Biol* 15, 550 (2014)). Splicing analysis was performed using the DEXSeq R package (S. Anders, et al., *Genome Res* 22, 2008-2017 (2012)). Briefly, exon reads were counted using the dexseq_count.py script and read into R v3.0.1 (R. D. C. Team, R: a language and environment for statistical computing. *R Development Core Team* (2011), *R: A Language and Environment for Statistical Computing. Vienna, Austria: the R Foundation for Statistical Computing*. ISBN: 3-900051-07-0. Available online at http://www.R-project.org/), where the DEXSeq analysis pipeline was followed using the GENCODE mm10 genome annotation. For both the differential expression and the differential splicing analyses, significantly differentially expressed genes/exons were defined as having an adjusted p-value of less than 0.05 using the Benjamini-Hochberg multiple testing correction (Y. B. a. Y. Hochberg, *Journal of the Royal Statistical Society. Series B (Methodological)* 57, 289-300 (1995)).

Alternative polyadenylation pnalysis. To perform alternative polyadenylation analysis, the DaPars tool was used (Z. Xia, et al., *Nat Commun* 5, 5274 (2014)). Ensembl gene annotations for the mm10 *Mus musculus* genome were downloaded from the UCSC Table Browser (W. J. Kent, et al., *Genome Res* 12, 996-1006 (2002)) and the DaPars_Extract_Anno.py script was used to generate 3' UTR annotations. Then, the RNA-seq data was converted to BedGraph format using the bedtools genomecov command (A. R. Quinlan, et al., *Bioinformatics* 26, 841-842 (2010)). Finally, the DaPars_main.py script was used to perform the alternative polyadenylation analysis.

Surface plasmon pesonance. SPR experiments were conducted on a Biacore T200 using the Biotin Capture Kit Series S following the manufacturer's instructions (GE). Biotin capture reagent was applied to the sensor chip at a flow rate of 2 µl/minute for 300 seconds. 1 nM biotinylated RNA (BiotinTEG-AAAAAAAAAAAAAAA; SEQ ID NO: 25) was captured at a flow rate of 10 µl/minute for 180 seconds. Samples were flowed across the sensor chip at 50 µl/minute for 120 seconds and the chip was regenerated for 120 seconds at a flow rate of 10 µl/minute. $K_D$ values for binding and disassociation were calculated from the binding kinetics of each protein at five concentrations using the Biacore T200 Software v3.1 application package (GE; 1, 0.9, 0.8, 0.7, 0.6 µM).

Immunoblotting. Tau fractions were obtained (B. C. Kraemer, et al., *Proc Natl Acad Sci USA* 100, 9980-9985 (2003)). Protein samples were brought to 10 mM Tris, pH 6.8, 1 mM EDTA, 40 mM DTT, 1% SDS, 10% sucrose by addition of 5× sample buffer boiled 5 minutes and loaded onto 4-15% pre-cast criterion SDS-PAGE gradient gels (Bio-Rad). For immunoblotting, human tau was detected using antibody 17025 at a dilution of 1:6000 (C. R. Guthrie, et al., *Hum Mol Genet* 18, 1825-1838 (2009)). Anti-tubulin antibody was used at a dilution of 1:1000 (Developmental Studies Hybridoma Bank, catalog E7). MSUT2 antibody Rbt9857 was prepared as described herein and used at a dilution of 1:1000. Secondary goat anti-mouse or goat anti-rabbit IgG were the secondary antibody reagents used at a dilution of 1:1000 (GE Lifesciences). Signals were measured by densitometry using Adobe Photoshop.

Stereotaxic injections of AAV viral vector. AAV viral vector preparations expressing either MSUT2 or GFP under control of the chicken beta actin promoter were obtained from Dr. Ronald Klein at Louisiana State University. Intracerebral injections were performed using a stereotaxic apparatus (Parkland Scientific) (P. Szot, et al., *Frontiers in pharmacology* 3, 184 (2012)). Three month old male and female Tau4RTg2652 mice were anesthetized with isoflurane and received a single injection of buprenorphine SR (0.3 mg/kg) during surgery for extended pain relief support. The animals received a single unilateral injection of 1.0 µl AAV9 (containing approx. 5×10E11 viral vectors) into the right ventral hippocampus delivered over an 8 minute period at the following coordinates: AP: −2.92 mm from bregma: ML: +2.80 mm; DV −3.50 mm from the surface of the skull. The needle was left in place for an additional 4 min after the injection and then the needle was slowly withdrawn. Animals were sutured, removed from the stereotaxic apparatus and allowed to recover. Animals were sacrificed 1 month later for analysis of neuropathological changes.

Human Tissue.

Samples of postmortem tissue from the University of Washington Alzheimer's Disease Research Center (ADRC) Neuropathology Core was used. AD cases were selected on the basis of having an autopsy-confirmed diagnosis of AD (Braak stages V or VI with CERAD score of moderate or frequent). Control samples were from neurologically healthy control participants, who were of a similar age with low levels of AD pathology (Braak stage III or less and CERAD scores of none or sparse).

Statistical analysis. Standard ANOVAs or t tests were used (two-tailed) for statistical analysis. Statistical analysis was performed using the Statistica software package (StatSoft). For measures, sex was included as a factor in the ANOVA. If sex did not have a significant effect on a particular measure, then the analysis was repeated without that factor. For repeated measures (Rotorod and Barnes testing), ANOVA was followed up with planned comparisons of the two genotypes on each testing day.

Example 2: High-Throughput AlphaScreen Assay

To identify small-molecule inhibitors of the MSUT2 protein/poly(A) RNA interaction, a high-throughput AlphaScreen assay optimized for detecting recombinant GST-MSUT2 binding to synthetic poly(A) RNA. The MSUT2 AlphaScreen assay has been well optimized during its development for 384-well screening (z-score=0.96). Two high throughput AlphaScreens of 53,400 distinct small molecules have been completed. A multi-point dose analysis pilot screen of the Spectrum Collection was performed. From this screen of 2,400 compounds, 20 preliminary hits with activity against MSUT2 were identified (FIG. 18) and showed robust dose validation for several (FIG. 19). Both the pilot screen and the screening approaches disclosed herein use the Quellos High-Throughput Screening Core at the University of Washington (UW).

Assay of inhibitor dose dependence. Hits identified in the pilot screen were validated by retesting resynthesized compounds over a wide concentration range. FIG. 20 shows a representative-dose response curve for Ebselen, which was one of the top hits in the pilot screen. These hits will be validated by conducting a 14-point dose-response analysis with a drug concentration range from 100 μM down to 1.4 nM; the MSUT2/poly(A) RNA AlphaScreen Assay will be used to produce a readout. From this dose-response analysis, IC50 values will be calculated for dose-responsive hits. For the full scale screen 64 primary hits were identified and will be subject to dose validation as described for pilot screen compounds (and Ebselen, shown in FIG. 20). It is expected that approximately one third of compounds from the primary screen will be validated based on the results from the pilot screen (6/20 hits showed robust dose validation and an IC50 below 20 μm).

Rigorous assessment of compound selectivity for MSUT2 over PABPN1. Hits identified in the primary screen will be validated by being retested over a 14-point dose range of drug concentrations from 100 μM to 1.4 nM; these methods will be identical to the dose validation of hit compounds in the pilot screen except using recombinant PABPN1 instead of MSUT2 (i.e., via a PABPN1/poly(A) RNA AlphaScreen assay). From this dose-response analysis, IC50s against both MSUT2 and PABPN1 binding to poly(A) RNA will be calculated. Although PABPN1 does not exhibit as robust a poly(A) RNA binding response by AlphaScreen or affinity (as measured by SPR), it will give a sufficient signal in the AlphaScreen assay to be measured in the same way as MSUT2/poly(A) RNA. Compounds that specifically inhibit MSUT2 but not PABPN1 RNA binding and that exhibit an IC50 <504 against MSUT2 will be given preference for characterization (FIG. 21).

Evaluation of inhibitor affinity for MSUT2 and poly(A) using surface plasmon resonance (SPR). Given that poly(A) performs many important functions in the cell, the goal is to disrupt the binding of MSUT2 to poly(A) RNA without interrupting the poly(A) interactions with PABPN1 or other poly(A)-binding proteins. Because CCCH domains can bind both RNA and protein, the MSUT2 association with poly(A) RNA was measured using a SPR assay; this demonstrated that MSUT2 affinity for poly(A) is about 4-fold greater than the affinity of PABPN1 for poly(A) (FIG. 22). Compounds will be tested to determine whether they directly associate with poly(A) RNA, PABPN1, or MSUT2. Hits that exhibit a high affinity for MSUT2, but not poly(A) RNA or PABPN1, will be advanced for further study.

Example 3: ALPHA Assay for MSUT2 Binding to Poly(A)

The steps and set up for performing the ALPHA assay for MSUT2 binding to polyA are as follows:
1. Dilutions are in assay buffer (1×PAMA final concentration).
2. Scale is for 96 well assay in PE 06 well ½ area plate (total volume/well is 50 μL).
3. Assays set up in low light conditions
4. Add 20 μL of diluted donor bead (10 ug/mL) to well bringing well volume to 20 μL
5. Add 10 μL diluted biotin RNA (15 nM)) bringing well volume to 30 μL
6. Add 10 μL diluted GST-MSUT2 Protein (125 nM)) bringing well volume to 40 μL
7. Incubate at room temp for 30 minutes in the dark
8. Add 10 μl of diluted Acceptor bead (2.5 μg/mL) to well bringing well volume to 50
9. Incubate at room temp for 60 minutes in the dark
10. Read Plate using standard AlphaAssay settings on Perkin Elmer EnSpire® Alpha microplate reader Table 5 provides the reagents useful for carrying out the ALPHA assay for MSUT2 binding to polyA.

TABLE 5

Reagents.

| Reagent | Composition and Final Concentration in Assay | Amount Supplied | Storage |
| --- | --- | --- | --- |
| Assay Buffer | 1x PAMA: 25 mM HEPES, 100 mM NaCl, 0.04% Casein, 1 mg/mL Dextran-500, 0.2% Triton X-100, pH 7.4 | 400 mL of 10x stock | −20° C. |
| Donor Bead | PE Avidin AlphaScreen Donor (catalog 6760002) at 4 ug/mL | ~3 mL (@ 5 mg/mL) | 4° C.- do not freeze |
| Biotin-RNA | 5' TEG-Biotin-Poly(A)20 RNA, 100 uM (660 ug/mL)-from IDT | ~200 uL, 100 uM | −70° C.- Freeze/thaw OK |
| MSUT2 Protein | GST-MSUT2 protein 50 nM (2.1 mg/mL)-brownish | ~2 mL (2 × 1 mL, 1 × 0.5 mL, 1 × 0.1 mL aliquots) (@ ~2 mg/mL) | −70° C.- Freeze/thaw decreases activity |
| Acceptor Bead | PE Glutathione AlphaLISA Acceptor(catalog AL109C) at 0.5 μg/mL | ~1 mL (@ 5 mg/mL) | 4° C.- do not freeze |

Example 4: Fluorescence Polarization/Anisotropy to Measure Binding

Fluorescence polarization/anisotropy (FP) is a technique used to measure binding between two biological molecules, often protein and ligand. As disclosed herein, are methods of using an FP screen capable of detecting mammalian SUT-2 (MSUT2) protein and fluorescein labeled 15-repeat polyadenylic RNA (FAM-polyA$_{15}$) interaction for the discovery of inhibitors. Briefly, FP assays rely on the fact that an excited fluorophore will emit polarized light inversely proportional to its rotational velocity. In terms of this assay, unbound FAM-PolyA$_{15}$ will emit depolarized light, however, when bound to MSUT2, the apparent molecular weight of the complex increases, lowering rotational velocity and increasing polarized light emission. Inhibitors blocking this interaction will cause rapid tumbling of FAM-PolyA$_{15}$ and subsequent decrease in polarized light emission (FIG. 23).

The results described herein show that bound MSUT2: FAM-PolyA$_{15}$ indeed emits polarized light in a dose dependent manner (FIG. 24A). Because the focus is screening for inhibitors of MSUT:FAM-PolyA$_{15}$ interactions, and not the important partner RNA-binding protein PABPN1, compounds were counter-screened for specificity against PABPN1:FAM-PolyA$_{15}$ interactions. A proof-of-concept experiment shows that FP is suitable to measure PABPN1: FAM-PolyA$_{15}$ interaction (FIG. 24B). Interactions between both MSUT2 and PABPN1 with PolyA can be inhibited by titrating unlabeled-PolyA, subsequently showing a decrease in emitted polarized light (FIG. 24C). Finally, results indicate that FP can be used to detect inhibitor specificity as compound A disrupts MSUT2: FAM-PolyA$_{15}$ binding, but not PABPN1: FAM-PolyA$_{15}$ (FIG. 24D).

What is claimed is:

1. A method of inhibiting expression of a MSUT2 polynucleotide in a subject in need thereof, the method comprising administering to the subject a mammalian suppressor of tauopathy 2 (MSUT2) inhibitor, wherein the MSUT2 inhibitor is a double stranded small interfering RNA (siRNA) consisting of first and second strands, wherein the first strand comprises AUGAUGCAAAGUGUACUAAACCAG (SEQ ID NO: 10), AUGAUGCAAAGUGUACUAAACCAGAUU (SEQ ID NO: 11), AUGAUGCAAAGUGUACUAAACCAGAU (SEQ ID NO: 12), AUGAUGCAAAGUGUACUAAACCA (SEQ ID NO: 13), AUAUGAUGCAAAGUGUACUAAACCAG (SEQ ID NO: 14), or UAUGAUGCAAAGUGUACUAAACCAG (SEQ ID NO: 15) and the second strand is sufficiently complementary to the first strand and to MSUT2 mRNA to mediate RNA interference of MSUT2, and wherein the MSUT2 inhibitor is administered intravenously or intrathecally.

2. A method of reducing phosphorylated and aggregated human tau protein in a subject in need thereof, the method comprising administering to the subject a mammalian suppressor of tauopathy 2 (MSUT2) inhibitor, wherein the MSUT2 inhibitor is a double stranded small interfering RNA (siRNA) consisting of first and second strands, wherein the first strand comprises AUGAUGCAAAGUGUACUAAACCAG (SEQ ID NO: 10), AUGAUGCAAAGUGUACUAAACCAGAUU (SEQ ID NO: 11), AUGAUGCAAAGUGUACUAAACCAGAU (SEQ ID NO: 12), AUGAUGCAAAGUGUACUAAACCA (SEQ ID NO: 13), AUAUGAUGCAAAGUGUACUAAACCAG (SEQ ID NO: 14), or UAUGAUGCAAAGUGUACUAAACCAG (SEQ ID NO: 15) and the second strand is sufficiently complementary to the first strand and to MSUT2 mRNA to mediate RNA interference of MSUT2, and wherein the MSUT2 inhibitor is administered intravenously or intrathecally.

3. A method of potentiating a neuroinflammatory response to a pathological tau protein in a subject in need thereof, the method comprising administering to the subject a mammalian suppressor of tauopathy 2 (MSUT2) inhibitor, wherein the MSUT2 inhibitor is a double stranded small interfering RNA (siRNA) consisting of first and second strands, wherein the first strand comprises AUGAUGCAAAGUGUACUAAACCAG (SEQ ID NO: 10), AUGAUGCAAAGUGUACUAAACCAGAUU (SEQ ID NO: 11), AUGAUGCAAAGUGUACUAAACCAGAU (SEQ ID NO: 12), AUGAUGCAAAGUGUACUAAACCA (SEQ ID NO: 13), AUAUGAUGCAAAGUGUACUAAACCAG (SEQ ID NO: 14), or UAUGAUGCAAAGUGUACUAAACCAG (SEQ ID NO: 15) and the second strand is sufficiently complementary to the first strand and to MSUT2 mRNA to mediate RNA interference of MSUT2, and wherein the MSUT2 inhibitor is administered intravenously or intrathecally.

4. A method of decreasing astrocytosis or microgliosis in a subject in need thereof, the method comprising administering to the subject a mammalian suppressor of tauopathy 2 (MSUT2) inhibitor, wherein the MSUT2 inhibitor is a double stranded small interfering RNA (siRNA) consisting of first and second strands, wherein the first strand comprises AUGAUGCAAAGUGUACUAAACCAG (SEQ ID NO: 10), AUGAUGCAAAGUGUACUAAACCAGAUU (SEQ ID NO: 11), AUGAUGCAAAGUGUACUAAACCAGAU (SEQ ID NO: 12), AUGAUGCAAAGUGUACUAAACCA (SEQ ID NO: 13), AUAUGAUGCAAAGUGUACUAAACCAG (SEQ ID NO: 14), or UAUGAUGCAAAGUGUACUAAACCAG (SEQ ID NO: 15) and the second strand is sufficiently complementary to the first strand and to MSUT2 mRNA to mediate RNA interference of MSUT2, and wherein the MSUT2 inhibitor is administered intravenously or intrathecally.

5. A method of reducing neuroinflammation in a subject in need thereof, the method comprising administering to the subject a mammalian suppressor of tauopathy 2 (MSUT2) inhibitor, wherein the MSUT2 inhibitor is a double stranded small interfering RNA (siRNA) consisting of first and second strands, wherein the first strand comprises AUGAUGCAAAGUGUACUAAACCAG (SEQ ID NO: 10), AUGAUGCAAAGUGUACUAAACCAGAUU (SEQ ID NO: 11), AUGAUGCAAAGUGUACUAAACCAGAU (SEQ ID NO: 12), AUGAUGCAAAGUGUACUAAACCA (SEQ ID NO: 13), AUAUGAUGCAAAGUGUACUAAACCAG (SEQ ID NO: 14), or UAUGAUGCAAAGUGUACUAAACCAG (SEQ ID NO: 15) and the second strand is sufficiently complementary to the first strand and to MSUT2 mRNA to mediate RNA interference of MSUT2, and wherein the MSUT2 inhibitor is administered intravenously or intrathecally.

* * * * *